US011696945B2

(12) United States Patent
Carver, III et al.

(10) Patent No.: US 11,696,945 B2
(45) Date of Patent: *Jul. 11, 2023

(54) PROTEINS AND IMMUNIZING COMPOSITIONS CONTAINING *PASTEURELLA* PROTEINS AND METHODS OF USE

(71) Applicant: EPITOPIX, LLC, Willmar, MN (US)

(72) Inventors: Charles Nelson Carver, III, Willmar, MN (US); Daryll Emery, Willmar, MN (US)

(73) Assignee: Epitopix, LLC, Willmar, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/191,913

(22) Filed: Mar. 4, 2021

(65) Prior Publication Data

US 2021/0205432 A1 Jul. 8, 2021

Related U.S. Application Data

(63) Continuation of application No. 16/484,332, filed as application No. PCT/US2018/017682 on Feb. 9, 2018, now Pat. No. 10,967,056.

(60) Provisional application No. 62/457,599, filed on Feb. 10, 2017.

(51) Int. Cl.

| | |
|---|---|
| ***A61K 39/102*** | (2006.01) |
| ***A61K 39/39*** | (2006.01) |
| ***C07K 14/285*** | (2006.01) |
| ***C07K 16/12*** | (2006.01) |
| ***G01N 33/569*** | (2006.01) |
| *A61K 39/00* | (2006.01) |

(52) U.S. Cl.

CPC ............ *A61K 39/102* (2013.01); *A61K 39/39* (2013.01); *C07K 14/285* (2013.01); *C07K 16/1242* (2013.01); *G01N 33/56911* (2013.01); *A61K 2039/552* (2013.01); *A61K 2039/55566* (2013.01); *G01N 2333/285* (2013.01)

(58) Field of Classification Search

None

See application file for complete search history.

(56) References Cited

U.S. PATENT DOCUMENTS

| | | | |
|---|---|---|---|
| 5,587,166 | A | 12/1996 | Donachie |
| 6,027,736 | A | 2/2000 | Emery et al. |
| 9,308,247 | B2 | 4/2016 | Narayanan et al. |
| 2009/0123500 | A1 | 5/2009 | Emery et al. |

FOREIGN PATENT DOCUMENTS

| | | | |
|---|---|---|---|
| EP | 0694560 A2 | 1/1996 | |
| EP | 2431382 A1 | 3/2012 | |
| JP | 9-505085 | 5/1997 | |
| JP | 2002-541790 | 12/2002 | |
| WO | WO 95/25742 | 9/1995 | |
| WO | WO 1996/01620 A1 | 1/1996 | |
| WO | WO 00/61724 | 10/2000 | |
| WO | WO 2000/61724 A2 | 10/2000 | |
| WO | WO 2001/37810 A2 | 5/2001 | |
| WO | WO 2007/006101 A1 | 1/2007 | |
| WO | WO 2011/125015 A2 | 10/2011 | |
| WO | WO 2017/011340 A2 | 1/2017 | |

OTHER PUBLICATIONS

Mikayama et al. (Nov. 1993. Proc.Natl.Acad.Sci. USA, vol. 90 : 10056-10060).*

Rudinger et al. (Jun. 1976. Peptide Hormones. Biol.Council, pp. 5-7).*

American Type Culture Collection, Budapest Treaty on the International Recognition of the Deposit of Microorganisms for the Purposes of Patent Procedure., Deposited on Behalf of : Willmar Poultry Co., Inc., Serotype A: 3,4.

Angen et al., "Taxonomic relationships of the [*Pasteurella*] *haemolytica* complex as evaluated by DNA-DNA hybridizations and 16s rRNA sequencing with proposal of *Mannheimia haemolytica* gen. nov., comb. Nov., *Mannheimia granulomatis* comb. Nov., *Mannheimia glucosida* sp. Nov., *Mannheimia ruminalis* sp. Nov. and *Mannheimia varigena* sp. Nov." 1999, *Int'l J. Systematic Bacteriology* 49:67-86.

Arnold et al., "The SWISS-MODEL workspace: a web-based environment for protein structure homology modelling", 2006, *Bioinformatics Original Paper* 22(2):195-201.

Bagos et al., "A hidden Markov Model method, capable of predicting and discriminating β-barrel outer membrane proteins", 2004, *BMC Bioinformatics* 5:29.

Boulianne et al., "Production of functional chimaeric mouse/human antibody", Dec. 13, 1984, *Nature* 312:643-646.

Brüggemann et al., "Production of human antibody repertoires in transgenic mice", 1997, *Current Opinion in Biotechnology* 8:455-458.

Carver, "Vaccination with Siderophore Receptors and Porins Protects against Fowl Cholera Challenge by Heterologous Serotypes," Western Poultry Disease Conference. Sacramento, California, Mar. 20-22, 2017.

"Chapter 2.3.9. Fowl Cholera," in *OIE Terrestrial Manual 2015*, pp. 1-11.

Confer et al., "Intranasal Vaccination of Rabbits with Pasteurella multocida A:3 Outer Membranes that Express Iron-Regulated Proteins" Mar. 2013 *AJVR*, 62(5):697-703.

Database Geneseq [Online] Feb. 2, 2012 (Feb. 2, 2012), "Drug delivery related pore-forming protein, SEQ 10 2985." XP055474131,retrieved from EBI accession No. GSP:AZQ49682 Database accession No. AZQ49682.

Database JPO Proteins [Online] Sep. 26, 2013 (Sep. 26, 2013), "JP 2013121347-A/107: Anti-Bacterial Vaccine Compositions.", XP055474134, retrieved from EBI accession No. JPOP:DL676647 Database accession No. DL676647.

(Continued)

*Primary Examiner* — Jennifer E Graser

(74) *Attorney, Agent, or Firm* — Mueting Raasch Group

(57) ABSTRACT

The present invention provides isolated proteins isolatable from a *Pasteurella* spp. such as *P. multocida*. Also provided by the present invention are compositions that include one or more of the proteins, and methods for making and methods for using the proteins.

11 Claims, 41 Drawing Sheets

Specification includes a Sequence Listing.

(56) References Cited

OTHER PUBLICATIONS

Daugelerty et al., "Polymerase chain reaction facilitates the cloning, CDR-grafting, and rapid expression of a murine monoclonal antibody directed against the CD18 component of leukocyte integrins", Mar. 1991, *Nucleic Acids Research*, 19(9):2471-2476.
Glisson et al, "Cross-Protection Studies with Pasteurella multocida Bacterins Prepared from Bacteria Propagated in Iron-Depleted Medium" Apr. 1993 *Avian Diseases*, 37(4):1074-1079.
Jones et al., "Replacing the complementarity-determining regions in a human antibody with those from a mouse", May 1986, *Nature* 321:522-525.
Ikeda et al, "Antigenically Related Iron-Regulated Outer Membrane Proteins Produced by Different Somatic Serotypes of Pasteurella multocida" Sep. 1988 *Infection and Immunity*, 56(9):2499-2502.
Keler et al., "Metachromatic Assay for the Quantitative Determinationof Bacterial Endotoxins", Oct. 1985, *Analytical Biochemistry* 156:189-193.
Liu et al., "Zinc Sequestration by the Neutrophil Protein Calprotectin Enhances *Salmonella* Growth in the Inflamed Gut", 11:227-239.
Lomize et al., "OPM database and PPM web server: resources for positioning of proteins in membranes", Sep. 2011, *Nucleic Acids Research*, 40: Database issue; D370-D376.
Lonberg et al., "Antigen-specific human antibodies from mice comprising four distinct genetic modifications", Apr. 1994, *Nature* 368:856-859.
Lobuglio et al., "Mouse/human chimeric monoclonal antibody in man: Kinetics and immune response", Jun. 1989, *Proc. Natl. Acad. Sci.*, 86:4220-4224.
Mietinen, "Proportion of Disease Caused or Prevented by a Given Exposure, Trait or intervention", 1974, *Am. J. Epidemiology*, 99(5):325-332.
Morrison et al., "Chimeric human antibody molecules: Mouse antigen-binding domains with human constant region domains", 1984, *Proc. Natl. Acad. Sci.* 81:6851-6855.
Petersen et al., "SignalP 4.0: discriminating signal peptides from transmembrane regions", Oct. 2011, *Nature Methods*, 8(10):785-786.
Patent Application No. PCT/US2018/017682, filed Feb. 9, 2018; [International Search Report / Written Opinion] dated Aug. 16, 2018; 21pages.
Patent Application No. PCT/US2018/017682, filed Feb. 9, 2018; [International Preliminary Report on Patentability] dated Aug. 22, 2019; 14 pages.
Queen et al., "A humanized antibody that binds to the interleukin 2 receptor", Dec. 1989, *Proc. Natl. Acad. Sci.*, 86:10029-10033.
Rice et al., "EMBOSS: The European Molecular Biology Open Software Suite" Jun. 2000, *TIG* 16(6).
Riechmann et al., "Reshaping human antibodies for therapy" Mar. 1988, *Nature*, 332:323-327.
Roier et al., "Immunogenicity of Pasteurella multocida and Mannheimia haemolytica outer membrane vesicles" Jul. 2013 *International Journal of Medical Microbiology*, 303(5):247-256.
Stork et al., "An Outer Membrane Receptor of *Neisseria meningitidis* Involved in Zinc Acquisition with Vaccine Potential", Jul. 2010, *PLoS Pathogens*, 6(7).
"Supplemental Assay Method for Potency Testing of Fowl Cholera (*Pasteurella multocida*) Bacterins, Type 1," in *United States Department of Agriculture Center for Veterinary Biologies Testing Protocal*. SAM 607.03, p. 1-11.
Tatusova et al., "BLAST 2 Sequences, a new tool for comparing protein and nucleotide sequences", 1999, *FEMS Microbiology Letters* 174:247-250.
Taylor et al., "A transgenic mouse that expresses a diversity of human sequence heavy and light chain immunoglobulins" 1992, *Nucleic Acids Research*, 20:23):6287-6295.
Wilson et al., "Comparison of DNA Fingerprinting and serotyping for Identification of Avian *Pasteurella multocida* Isolates", Feb. 1993, *J. Clin. Microbiology*, 31(2):255-259.
Office Action issued in Japan for Application No. 2019-543050 dated Jan. 19, 2022 (15 pages). English translation included.
Office Action issued in Europe for Application No. 18708005.6-1112 dated Jul. 30, 2020 (8 pages).
Office Action issued in Europe for Application No. 18708005.6-1112 dated Mar. 25, 2021 (4 pages).

* cited by examiner

FIG. 3

| Protein ID | MW | Description | Vaccine Strain MS061130 type A: 3x4 | X73: type A:1 | p1059 type A:3 |
|---|---|---|---|---|---|
| 1 | 128,216 | Putative Ton-B dependent hemine receptor | Present | Present | Present |
| 2 | 114,216 | Outer membrane receptor protein, mostly Fe transport | Present | Present | Absent |
| 3 | 109,900 | Outer membrane receptor protein, mostly Fe transport | Absent | Present | Absent |
| 4 | 109,863 | Outer membrane receptor protein, mostly Fe transport | Present | Absent | Present |
| 5 | 104,901 | Outer membrane receptor protein, mostly Fe transport | Absent | Present | Present |
| 6 | 91,308 | Outer membrane receptor protein, mostly Fe transport | Absent | Present | Absent |
| 7 | 90,917 | Outer membrane receptor protein, mostly Fe transport | Absent | Present | Present |
| 8 | 90,887 | Outer membrane receptor protein, mostly Fe transport | Absent | Present | Absent |
| 9 | 90,601 | Outer membrane receptor protein, mostly Fe transport | Present | Absent | Present |
| 10 | 89,635 | TonB-dependent hemoglobin receptor | Present | Present | Present |
| 11 | 88,107 | Outer membrane receptor protein, mostly Fe transport | Absent | Present | Absent |
| 12 | 84,792 | Outer membrane receptor protein, mostly Fe transport, HemR | Absent | Absent | Present |
| 13 | 81,394 | PfhR | Present | Present | Present |
| 14 | 59,543 | Heme binding protein A HbpA | Absent | Present | Present |

FIG. 6

| MW | % Identity | MS | x-73 | p1059 | p1662 | 1121 | 1135 | 1138 | 1558 | 1696 | gonz2 | gonz4 | gonz5 | gonz6 |
|---|---|---|---|---|---|---|---|---|---|---|---|---|---|---|
| 109,862 | | (+) | (-) | (+) | (+) | (+) | (-) | (+) | (-) | (-) | (-) | (+) | (+) | (-) |
| 109,900 | 97% | (-) | (+) | (-) | (-) | (-) | (+) | (-) | (+) | (+) | (-) | (-) | (-) | (+) |
| 92,670 | | (-) | (-) | (-) | (-) | (-) | (+) | (-) | (-) | (-) | (+) | (+) | (-) | (-) |
| 91,308 | >93% | (+) | (+) | (-) | (+) | (+) | (-) | (+) | (+) | (+) | (-) | (-) | (+) | (+) |
| 89,631 | 99% | (+) | (-) | (-) | (-) | (-) | (+) | (-) | (-) | (-) | (+) | (+) | (-) | (+) |
| 84,910 | 99% | (-) | (-) | (+) | (-) | (-) | (+) | (-) | (+) | (+) | (-) | (-) | (-) | (-) |
| 81,332 | 99% | (-) | (+) | (-) | (-) | (+) | (-) | (+) | (-) | (-) | (-) | (+) | (-) | (+) |

FIG.8-1.

SEQ ID NO:1

ATGCGTACAACAACAATAAAATTTTCTGCAATTACATTGGCATTATTGAGTTATTGTGGGGCTAT
TTTGGCGGATAGTCATCAAGAGGCGACTGAACTTGATACGATTACCGTTTCTTCTCAACAAGATG
AGATGAATATTAAAGAGAAAAAAGTCGGTGAAACTGTGAAAACGGCGAGTCAATTGAAACGCCAG
CAAGTACAGGATAGTCGTGATCTTGTGCGCTATGAAACCGGTGTGACTGTGGTAGAAGCTGGACG
TTTTGGGTCGAGCGGTTATGCCATTCGTGGTGTGGATGAGAACCGAGTGGCAATTACAGTAGATG
GCTTACATCAAGCAGAAACCCTTTCTTCTCAAGGTTTTAAAGAATTATTTGAAGGTTACGGCAAT
TTTAACAATACCCGAAATAGTGTGGAAATTGAGACGTTGAAAGTCGCTAAAATCGCGAAAGGTGC
TGATTCTGTAAAAGTGGGTAGTGGTTCTTTGGGAGGCGCTGTACTTTTTGAAACAAAAGATGCCA
GAGATTTCCTGACTGAAAAAGATTGGCATATCGGCTATAAAGCGGGCTACTCAACGGCAGATAAT
CAGGGATTAAATGCAGTGACTCTTGCAGGTCGCTATCAAATGTTTGATGCATTGATTATGCATTC
TAAGCGACATGGACATGAATTAGAAAATTATGACTATAAAAATGGCAGAGATATTCAAGGGAAAG
AAAGAGAGAAAGCGGATCCTTATACGATTACGAAAGAAAGTACATTAGTGAAATTCTCTTTTTCG
CCAACAGAAAATCATCGTTTTACAGTCGCTTCTGATACTTATCTTCAGCATTCCCGCGGACATGA
TCTTTCATACAATCTTGTTGCAACAACACATATTCAGTTAGATGAGAAAGAATCTCGTCATGCAA
ATGATCTGACAAAACGTAAAAATGTTTCCTTTACTTATGAAAATTATACTGTTACGCCATTTTGG
GATACGCTCAAGTTAAGCTATTCACAACAAAGAATTACAACAAGAGCAAGAACAGAAGATTACTG
TGATGGTAATGAAAAATGTGACTCTTATAAGAATCCTTTAGGGCTTCAATTAAAAGAGGGAAAAA
TCGTTGATCGTAATGGCGATCCTGTTAATTTGAAGCTTGTTGATGGTAAACATCAAGTTGTAGAT
AAAGCTGGTAAGCCTTTTGATGTAGCCTCTGGAACTAATTATGCGGCTTTCTCAGGTAAAGAATT
AAGTCCTTCTTCTTTTTGGTTAGATTGCTCTATTTTTGATTGTTCTAAGCCTATCAATACTTATA
AATATCGCTATACCTCTTCGGAGCCAACTTTGCAGCAAATTACTTTAAATAAAACCATGGAAATT
AATGGAAAGACATTTGCTACTTATGATGGGCGTGGACACTATATTATTTTACCAAATTCTAAAGG
TTACTTGCCTTTGGATTATAAAGAGCGTGATTTAAATACAAAGACGAAACAAATTAATTTAGATT
TAACAAAAGCATTTACTCTCTTTGAGATTGAAAATGAACTTTCCTATGGTGGTGTTTACGCGAAA
ACGACCAAGGAAATGGTGAATAAAGCAGGATATTATGGGCGTAATCCTACTTGGTGGGCGGAGAG
AACGTTAGGGCAATCATGGGGAAAATTGAGAGAGTGTAAGACAAGTTCTTCATATAATGGGATGC
TATGTCCTCGTCATGAACCATTAACCTCCTTCTTAATTCCGGTAGAAGCAACAACTAAGTCTTTA
TATTTTGCAGACAATATCAAGTTGCACAATATGTTAAGTGTAGATTTAGGTTATCGTTATGATGA
TATTAAATATCAGCCAGAATATATTCCTGGTGTGACACCTAAAATTGCAGATGATATGGTAAAAG
GGTTATTTATTCCATTACCTGAAGGTGAAAAAGTAACTGTAGGGACAATGGTATTCACAAAACCA
CTCACTCAGGCGCAAATTCGTAAGAATGCGGAGGAAAATATTGCTTATATTGCACAAGAAAAACG
CTTTAAGAAACATTCTTATTCTCTTGGTGCAACGTTCGATCCTCTGAATTTTTTACGAGTACAAG
TAAAATATTCAAAAGGGTTTAGGGCCCCGACTTCGGATGAACTTTATTTTACCTTTAAGCATCCA
GATTTTACGATTTTACCGAACCCCGTGTTGAAACCAGAGGAAGCAAAAAATCAAGAGATTGCATT
AACAGTGCACGATAATTGGGGATTTGTTAGCACAAGTGTTTTCCAAACAAAGTATCGTCATTTTA
TTGATTTAGCGTATTTAGGTTCAAGAAATTTATCGAATTCCGTGGGAGGGCAGGCACAAGCAAGA
GATTTCCAAGTTTATCAAAATGTCAATGTCGATAATGCCAAGGTTAAAGGACTTGAAATTAATGC
ACGTTTGAATTTGGGATATTTCTGGCATGTGTTGGATGGATTTAATACGAGCTATAAATTCACTT
ACCAACGTGGTCGTTTGGATGGCGATCGTCCAATGAATGCGATTCAGCCTAAAGCTTCTGTTTTT
GGTTTAGGCTATGATCATAAAGAAAATAAATTTGGCGCTGATTTATATATCACACGTGTGAGTGA

FIG.8-2.

AAAAAAGCGAAAGACACTTATAATATGTTCTATAAAGAACAGGGATATAAAGATAGTGCTGTTCG
TTGGAGAAGTGATGACTATACGCTAGTTGATGCGGTTGGTTATATTAAACCGATTAAGAATTTAA
CGTTACAGTTTGGCGTTTATAATTTGACAGACCGTAAATACTTGACATGGGAATCTGCTCGTTCG
ATTAAACCATTTGGTACAAGTAATTTAATTAATCAGAAAACAGGCGCAGGAATTAATCGTTTTTA
CTCACCAGGTCGTAATTTTAAATTTAGTGCCGAAATTACCTTCTAA

SEQ ID NO:2

MRTTTIKFSAITLALLSYCGAILADSHQEATELDTITVSSQQDEMNIKEKKVGETVKTASQLKRQ
QVQDSRDLVRYETGVTVVEAGRFGSSGYAIRGVDENRVAITVDGLHQAETLSSQGFKELFEGYGN
FNNTRNSVEIETLKVAKIAKGADSVKVGSGSLGGAVLFETKDARDFLTEKDWHIGYKAGYSTADN
QGLNAVTLAGRYQMFDALIMHSKRHGHELENYDYKNGRDIQGKEREKADPYTITKESTLVKFSFS
PTENHRFTVASDTYLQHSRGHDLSYNLVATTHIQLDEKESRHANDLTKRKNVSFTYENYTVTPFW
DTLKLSYSQQRITTRARTEDYCDGNEKCDSYKNPLGLQLKEGKIVDRNGDPVNLKLVDGKHQVVD
KAGKPFDVASGTNYAAFSGKELSPSSFWLDCSIFDCSKPINTYKYRYTSSEPTLQQITLNKTMEI
NGKTFATYDGRGHYIILPNSKGYLPLDYKERDLNTKTKQINLDLTKAFTLFEIENELSYGGVYAK
TTKEMVNKAGYYGRNPTWWAERTLGQSWGKLRECKTSSSYNGMLCPRHEPLTSFLIPVEATTKSL
YFADNIKLHNMLSVDLGYRYDDIKYQPEYIPGVTPKIADDMVKGLFIPLPEGEKVTVGTMVFTKP
LTQAQIRKNAEENIAYIAQEKRFKKHSYSLGATFDPLNFLRVQVKYSKGFRAPTSDELYFTFKHP
DFTILPNPVLKPEEAKNQEIALTVHDNWGFVSTSVFQTKYRHFIDLAYLGSRNLSNSVGGQAQAR
DFQVYQNVNVDNAKVKGLEINARLNLGYFWHVLDGFNTSYKFTYQRGRLDGDRPMNAIQPKASVF
GLGYDHKENKFGADLYITRVSEKKAKDTYNMFYKEQGYKDSAVRWRSDDYTLVDAVGYIKPIKNL
TLQFGVYNLTDRKYLTWESARSIKPFGTSNLINQKTGAGINRFYSPGRNFKFSAEITF*

FIG. 9-1.

SEQ ID NO:3

ATGGAATCCGCAAAAAATCCACTCAAAAAGACGACACTTGCACTCCTCTGTTGTTCTACCGCCTT
CTCGCTTTCCGCAAAAACCGATACGAACGCCGATAAAAATCACTTTCTGACGGAAATTGTCGTGT
ATGCGGATCAAAATAAATCAATGAGTTCAACACAGAGTGTCACTCAAGATGACATGAAAAAAAGC
CCTGTCACAAATGGTAATATTACTGACTATTTACGTTCAAATCCGCATGTGCGTTATGAGAATAG
CGATCAAAATGGATTGCAACGAGGTGAAATTAAACCCGAAAACATTTCAATTAATGGTGCAGATT
ATCAGCAGACCACTTTTTTTGTCGATAATGTAAATATCAATAATGATATGGGATTTGGTAGTGAT
CTTTTTGACGGCACCATGGCAACAGTCCCCTTTGCCAATCATTCTCAAGGCTACTTTTTTGATGC
CAATCTGCTCTCTTCAATTGTAGTGCATGACAGTAATGTTTCTGCCAGCTTAGGAGGATTTGCGG
GGGGAGCCGTCGTGGCGAAAACCAAACAATATGATGGGAAAGATCGGTTAAAATTTAGTTATCGT
ACAACTGATGCCTCATGGGCAAAATTTAAAGTAGAAGACAAAGATCTTGAACGTTTTAAAAATGC
GATTCCTGAAGGATCGGTCGCCGAATTTCAACCTAAGTATTCTAAACACTTTTTCAATATCACGG
CAGAAAAAGGGTTAAGTGAAAATTTAGGTATGGTGATCGGATTAAGTCGTAGAACATCAAGTATC
CAACAATCACGTCAAATTAATCCACAAGGTGATCGTGATAAACAAACACATACAAGACGTTCAGA
CAATGCGTTACTGAATTTTAATCTGACACCAAACGACAAACACCGTTTCGAACTCGGTTTCAGAT
ACTCAAATTATCGTGAGCGTAAATTCTTTAATACTAATATAGACAGTAATGTTTTTGACTATCAC
CGTGCTTATGGTGTGACTTTCTCTTGGATAAACGCCCTTCAGTCTGGCATTCTCACGACGACACT
CGCCTATGATAACTTTGATGACACGAGAAAATCAGCGTCAACTTATATGAAAACGACGCTCACTG
AAGAGGGTGAGGAATATACCGAAGGTGGAATGGGTAACAGTCAATTGAACCAAAAAAATTTACAT
ACGTCACTTGAATATGCGATGAATCCTTTTAATTTAGGTTCAATAGAACACTCTGTATCATTAGG
CGGTATTTATCAAGCAACGAAATATCGCTTTACGCGACATTCAGATGCAGTCGGTGAATTGTATA
CTCCTGATTGGTTAAATGGTAATACAGATAAACTTATATTGACGCAACGTAACATAGCCAAAAAA
GGGACCGTAAAAACACGTTATCAAAATATCGCACTTTACGTGGAAGATTTAATGACGTGGAAAAA
TCTCGAATTTCGGGCGGGACTTCGTCTTGAACGTGATGATTATTTAAAAAACACGAATTTGGCGC
CAAGAACCGTTTTTCGTTATAAACCATTTGAAGACACCGCATTCAGTGTGGGTTGGAACCGTTAC
TACGGACGTTCCTTTGCCTCAATGAAATTATCTGAAGGTATCTTCAAATTAGATGGTCATGATAC
CTTCCGTTACAAAGACCTTAGCCAATTTAAAACCCCTTATTCAGACGAACTGAGCTTTGGTGTAG
AACAATATGTTGCTAATCTCGCCTTTCACTTGAAATACATTTTACGTGATAACAAACAACGTATT
GTTTTACAAGAAGAAGAGGTCATGTTAAATGGAGAAAGGAAAAAACTCCGCTATTACCAACGAGG
AAAAGACTACAAAACGAATGTGTTAACCTTCCAAATTAACACACAAGCGCCTTGGGAGCTTGGTC
CAACACGCTGGACAAGTGCAGTGGCATTTGATTGGTTAGATAGCAAAGCTATCGATCATGGCAGG
GGCTATAACGGTTCGACACCTGTGATTTTAGACGGGAAATTAATGACTTATGAGCAAATGTTGAA
AAAAGTCAATGCTTACAAAGAAACATGGGGTCTACGTTTAAATCTTGACATGTTTGTTCCAATAT
TTGATCTTTCTTGGGCTAATACAATCTATGTCAAACCACCAACAACCTTAACCGAACGCGTTAGC
AGTAATACACCTGAGGTATATCGTAGCTATGATTATGGTACTTATACACAATGGGATACCAGTCT
TCGCTGGCAGCCAACTTTCGCAGAAAAACACCGTCCTTATATTAAATTAGATGTACTTAATGTGT
TAAATAAAACACGTAAAGGCGCGGGTCCAAATGGACAAGATCTCGGCATCTACACCCCCGGTCGT
GAGTTCTGGCTTGAAGTTGGTTACGAATTCTAA

FIG. 9-2.

SEQ ID NO:4

MESAKNPLKKTTLALLCCSTAFSLSAKTDTNADKNHFLTEIVVYADQNKSMSSTQSVTQDDMKKS
PVTNGNITDYLRSNPHVRYENSDQNGLQRGEIKPENISINGADYQQTTFFVDNVNINNDMGFGSD
LFDGTMATVPFANHSQGYFFDANLLSSIVVHDSNVSASLGGFAGGAVVAKTKQYDGKDRLKFSYR
TTDASWAKFKVEDKDLERFKNAIPEGSVAEFQPKYSKHFFNITAEKGLSENLGMVIGLSRRTSSI
QQSRQINPQGDRDKQTHTRRSDNALLNFNLTPNDKHRFELGFRYSNYRERKFFNTNIDSNVFDYH
RAYGVTFSWINALQSGILTTTLAYDNFDDTRKSASTYMKTTLTEEGEEYTEGGMGNSQLNQKNLH
TSLEYAMNPFNLGSIEHSVSLGGIYQATKYRFTRHSDAVGELYTPDWLNGNTDKLILTQRNIAKK
GTVKTRYQNIALYVEDLMTWKNLEFRAGLRLERDDYLKNTNLAPRTVFRYKPFEDTAFSVGWNRY
YGRSFASMKLSEGIFKLDGHDTFRYKDLSQFKTPYSDELSFGVEQYVANLAFHLKYILRDNKQRI
VLQEEEVMLNGERKKLRYYQRGKDYKTNVLTFQINTQAPWELGPTRWTSAVAFDWLDSKAIDHGR
GYNGSTPVILDGKLMTYEQMLKKVNAYKETWGLRLNLDMFVPIFDLSWANTIYVKPPTTLTERVS
SNTPEVYRSYDYGTYTQWDTSLRWQPTFAEKHRPYIKLDVLNVLNKTRKGAGPNGQDLGIYTPGR
EFWLEVGYEF*

FIG. 10-1.

SEQ ID NO:5

ATGTCATTCAAACATAAAACACTGGCGCTTTTTGTCGCACATGCTTGCTGCACTTCTGCCTTAGC
AGAAAACGTGGCTACCACGTTAGAACCCATCGTGGTTTCTGATCTCAGTCATACCACGCTGAACC
TTGATCAAAATAAGCTTGAAAAAGAAAGTCCAAAAGATTTAAAAGCTATTTTTGCCACAACGCCA
AATATTAATGTTATCCATACGGGACATGCACAATTAGGCGATATTGAAATTCGCGGTATGGGAAG
CAGCCGAGAAATCTTTGCTACCGGCGCAAACCGCGTCACAATGGAATTAGACGGTATGGACATTA
GCCCGAGTTTTTATTTTGGACACAGCTCACGCCATGGTCGGCAATATTTTGATCCCAGTGATCTA
AAACGTGTTGAGATTCATAAAGGTCCAAACAGTCAAGGCGTGGCAGGGCATGTTCGTTTCCAAAC
GAAAGATCCTCGTGATTATCTCTTGCCTAACCAACGTACAGGTGCACAACTTCGTGCTGGCTATT
TAGGCGATAGTGATGCTTATTATGTTGGGATAACTGGTGCCACTTTATTGGATGAACACAGTAGT
GCTTTAGTGAGCTATACACGACGCTGGTTTAATGAATTTAATAATAAGGGAGGCTTGGATGTCAC
AGGTAGTCAACGTACTAAAAGCAATCCTTCCAGTGGTTATAGTAATGCAGTGAACAGTAAATTAC
GCTATTCACCAAATGACCGCCATAAATTTACGCTGAATTTGCAACATTATGATTTAAAACGCACC
GCCTATTTAGAAGATAGCTTAGGAACAACGACAACACGACGTGGCACAAAAACAGTTCATCATAA
TACCAACATTCAGAAAAATCAGCGTCATGCTATTGCTTTCAGTCATGACATGCAACAAACCACGG
CATTTTTTGATCACCTGCACTGGCAAATTGCGTTACAACAAACGAAAAGCACGAGCCGTAATACA
GGGGCAGTCACGAATACATCAGCATCTCCTCCCCCAAGTACGCCAAAATTTAGCCAAGAGCGTTC
ACTTGATGGCTTTAAAACCAAAACCATCAGCTTAAAAACGGAATTCAATAAAAGCATTGGGCAAC
ATGTCGTACATGAACTTCACTATGGACTAAAATTACAATATAGCCAAATGCAAGCTTTACGCCAA
ACACAATCCCTAAACGAACAAGGGAGTAACACTCGAACCAGCGCCTTTTTCCCGACACAGCAACA
ATGGCAAAGTAAACTCCATCTTTCCGATCGGATCAGTTTTGGTAAATCTGGTTTAAGCTTGACAC
CATCCATACATCTCACACAGATTAGAATCAAACCGAAAACAGAAAATGTATCGAAGAAAAACCGT
GAACAATTATTTACTTACAAGGATACCGCCATTGGTTACGGTCTGCGTGTTGATTATGCACTCAA
TGAAGCGAATTTACTGAGTCTGAACTATCAGCACGCCACTCGCTTACCCGGCTATGGTGAAAACA
ATGCGCAAAGCTATGGACACTGGCCAGCAAAACCGAACCCTCATCTACAGCCAGAAACCTCAGAT
GGTATTGAATTAAGTTGGCGTAGTGCGGGGGCGATTGGTCAACAAACCACGACCTTGTTCTATAA
CCGTTACAATGACTTAATTTATCTCGATACCACGGCATGTTATGCTGACCGAACAGGTCAAGTGC
CTTGTGATTTAGCAAATGAAAAAGGACGTAGTTATAGCTATGGAATAGAATTCGACGGTAAACTC
AATCTTGATACGATCGGCTTCGCTCAAGGAACATATTTAAATGCTGGCTTCGCTTACAGCAAAGG
GAAGACCGCGAACAAGCAACCACAAGGACGTCTTGATCCCCTAACAGGCTTTGTCGGTCTTGGCT
ACCAACAGCCAATGGATGTTTGGGGCATTGAAGGTAAACTGAAATTTGCCGCGAAGAAAAAAACT
AAAGACTTACCCGCCAATCAAGGTTTTGAAGGCTTACCGGGCTATGCTGTAGTTGATCTTACCGC
CTATTATAATGTGACGAAACAGCTTTATCTTGGCATCGGCATCTATAATGTGCTAGATAAAAAAT
ATGCTCGCTGGGCAATGGCAAGAGGCGACATTAAACATGGTAACTATGACAAGCACACTGAAGCA
GGTCGTCATTTTGGTGCCAATATTCGTTACCACTTTTAA

SEQ ID NO:6

MSFKHKTLALFVAHACCTSALAENVATTLEPIVVSDLSHTTLNLDQNKLEKESPKDLKAIFATTP
NINVIHTGHAQLGDIEIRGMGSSREIFATGANRVTMELDGMDISPSFYFGHSSRHGRQYFDPSDL
KRVEIHKGPNSQGVAGHVRFQTKDPRDYLLPNQRTGAQLRAGYLGDSDAYYVGITGATLLDEHSS
ALVSYTRRWFNEFNNKGGLDVTGSQRTKSNPSSGYSNAVNSKLRYSPNDRHKFTLNLQHYDLKRT

FIG. 10-2.

AYLEDSLGTTTTRRGTKTVHHNTNIQKNQRHAIAFSHDMQQTTAFFDHLHWQIALQQTKSTSRNT
GAVTNTSASPPPSTPKFSQERSLDGFKTKTISLKTEFNKSIGQHVVHELHYGLKLQYSQMQALRQ
TQSLNEQGSNTRTSAFFPTQQQWQSKLHLSDRISFGKSGLSLTPSIHLTQIRIKPKTENVSKKNR
EQLFTYKDTAIGYGLRVDYALNEANLLSLNYQHATRLPGYGENNAQSYGHWPAKPNPHLQPETSD
GIELSWRSAGAIGQQTTTLFYNRYNDLIYLDTTACYADRTGQVPCDLANEKGRSYSYGIEFDGKL
NLDTIGFAQGTYLNAGFAYSKGKTANKQPQGRLDPLTGFVGLGYQQPMDVWGIEGKLKFAAKKKT
KDLPANQGFEGLPGYAVVDLTAYYNVTKQLYLGIGIYNVLDKKYARWAMARGDIKHGNYDKHTEA
GRHFGANIRYHF*

FIG. 11-1.

SEQ ID NO:7

ATGCGTACAACAACAATAAAATTTTCTGCAATTACATTGGCATTATTGAGTTATTGTGGGGTCAT
TTTGGCGGATAGTCATCAAGAGGCGACTGAACTTGATACGATTACCGTTTCTTCTCAACAAGATG
AGATGAATATTAAAGAGAAAAAAGTCGGTGAAACTGTGAAAACGGCGAGTCAATTGAAACGCCAG
CAAGTACAGGATAGTCGTGATCTTGTGCGCTATGAAACCGGTGTGACTGTGGTAGAAGCTGGACG
TTTTGGGTCGAGCGGTTATGCCATTCGTGGTGTGGATGAGAACCGAGTGGCAATTACAGTAGATG
GCTTACATCAAGCAGAAACCCTTTCTTCTCAAGGTTTTAAAGAATTATTCGAAGGTTACGGCAAT
TTTAACAATACCCGAAATAGTGTGGAAATTGAGACGTTGAAAGTCGCTAAAATCGCGAAAGGTGC
TGATTCTGTAAAAGTGGGTAGTGGTTCTTTGGGAGGCGCTGTACTTTTTGAAACAAAAGATGCCA
GAGATTTCCTGACTGAAAAAGATTGGCATATCGGCTATAAAGCGGGCTACTCAACGGCAGATAAT
CAGGGATTAAATGCAGTGACTCTTGCAGGTCGCTATCAAATGTTTGATGCATTGATTATGCATTC
TAAGCGACATGGACATGAATTAGAAAATTATGACTATAAAAATGGCAGAGATATTCAAGGGAAAG
AAAGAGAGAAAGCGGATCCTTATACGATTACGAAAGAAAGTACATTAGTGAAATTCTCTTTTTCG
CCAACAGAAAATCATCGTTTTACAGTCGCTTCTGATACTTATATACAACGTTCTCGTGGCCATGA
TCGCTCTTATTCTTTACAGCCTCAATCTAATTATTTCACATATGACGAGAAAGAATCGCGTCATG
CAAATGATTTGACAAAACGTAAAAATGTTTCTTTTACTTATGAAAACTATAGCGTAACTCCATTT
TGGGATACGCTAAAATTGAGTTATTCACAACAAAAGATCAGAACAAGAGCAAGAACAGAAGATTA
TTGTGATGGTAATGAAAAATGTGATTCTTATAAAAATCCATTAGGGCTTCAGTTGAAAGATGGCA
AAATTGTTGATCCAGAGGGAAATCAGATTACTTTAAAAGGAACAGGATTTAATACAGAAATAGTT
GATAAAAATGGTAACCCATTTCCTACGACATCTGGTACTAATAATGCAGCATTTAGTAATAATAT
TCAGTTAGGACCTAAAGAATTTTGGTTAGATTGTTCTCTTTTTGATTGTACTCAGCCATTTACTG
TTTATAACTATCAAAATGGTCAATATACGCCAAAACAAGTTGAGTTATCTGAAGAAATCACTGTC
AATGGTAAATTATATAAAACAGCTAAAGAAGAAAGAGGTGTTAGGAACTATTTAATTTTACCTAA
TTCAAAAGGTTATTTACCATATGATTACAAAGAAAGAGATCTTGATTCAAATACAAAACAAATCA
ATTTGGATTTAACAAAAACATTTTCGACTTTTAATATAGAAAATGAATTATTATACGGTGCCATT
TATTCACGTACAGAGAAGAAAATGGTTAATAAAGCAGGTTACGATGGGAGAAATCCTACATGGTG
GGCTGATAGAATTTTAGGGAAGAGTACGAATTGTAACTATAATGGACTGAAATGTCCTCGTCATG
AACCTTTAACTTCTTTCTTAATTCCAGTAGAAGCGACAACCAAGTCTCTATATTTTTCAGATAAT
ATCAAATTACACAACATGTTGAGTGTAGATTTAGGTTATCGTTATGACGATATTAAATATCAACC
AGAATATATTCCTGGTGTAACACCTAAAATTGCAGATGATATGGTGAAAGGTATTTTTATTCCAT
TACCTAAGGGAGAAAAAGTAACAACACCTTGGGGGGCCGAATATACAAAACCACTCACACAGGAA
CAAATTCGTAAGAATGCGGAGGAAAATATTGCTTATATTGCACAAGAAAAACGCTTTAAAAAACA
TTCTTATTCTCTTGGTGCAACGTTCGATCCTCTGAATTTTTTACGAGTACAAGTAAAATATTCAA
AAGGGTTTAGAGCCCCGACTTCGGATGAACTTTATTTTACCTTTAAGCATCCAGATTTTACGATT
TTACCGAACCCCGTGTTGAAACCAGAGGAAGCAAAAAATCAAGAGATTGCATTAACAGTGCACGA
TAATTGGGGATTTGTTAGCACAAGTGTTTTCCAAACAAAGTATCGTCATTTTATTGATTTAGCGT
ATTTAGGTTCAAGAAATTTATCGAATTCCGTGGGAGGGCAGGCACAAGCAAGAGATTTCCAAGTT
TATCAAAATGTCAATGTCGATAATGCCAAGGTTAAAGGACTTGAAATTAATGCACGTTTGAATTT
GGGATATTTCTGGCATGTGTTGGATGGATTTAATACGAGCTATAAATTCACTTACCAATGTGGTC
GTTTGGATGGCGATCGTCCAATGAATGCGATTCAGCCTAAAGCTTCTGTTTTTGGTTTAGGCTAT
GATCATAAAGAAAATAAATTTGGCGCTGATTTATATATCACACGTGTGAGTGAGAAAAAAGCGAA
AGACACCTATAATATGTTCTATAAAGAACAGGGGTATAAAGATAGTGCTATTCGTTGGAGAAGTG
ATGACTATACGCTAGTTGATGCGGTTGGTTATATTAAACCGATTAAGAATTTAACGTTACAGTTT

FIG. 11-2.

GGCGTTTATAATTTGACAGACCGTAAATACTTGACATGGGAATCTGCTCGTTCGATTAAACCATT
TGGTACAAGTAATTTAATTAATCAGAAAACAGGCGCAGGAATTAATCGTTTTTACTCACCAGGTC
GTAATTTTAAATTTAGTGCCGAAATTACCTTCTAA

SEQ ID NO:8

MRTTTIKFSAITLALLSYCGVILADSHQEATELDTITVSSQQDEMNIKEKKVGETVKTASQLKRQ
QVQDSRDLVRYETGVTVVEAGRFGSSGYAIRGVDENRVAITVDGLHQAETLSSQGFKELFEGYGN
FNNTRNSVEIETLKVAKIAKGADSVKVGSGSLGGAVLFETKDARDFLTEKDWHIGYKAGYSTADN
QGLNAVTLAGRYQMFDALIMHSKRHGHELENYDYKNGRDIQGKEREKADPYTITKESTLVKFSFS
PTENHRFTVASDTYIQRSRGHDRSYSLQPQSNYFTYDEKESRHANDLTKRKNVSFTYENYSVTPF
WDTLKLSYSQQKIRTRARTEDYCDGNEKCDSYKNPLGLQLKDGKIVDPEGNQITLKGTGFNTEIV
DKNGNPFPTTSGTNNAAFSNNIQLGPKEFWLDCSLFDCTQPFTVYNYQNGQYTPKQVELSEEITV
NGKLYKTAKEERGVRNYLILPNSKGYLPYDYKERDLDSNTKQINLDLTKTFSTFNIENELLYGAI
YSRTEKKMVNKAGYDGRNPTWWADRILGKSTNCNYNGLKCPRHEPLTSFLIPVEATTKSLYFSDN
IKLHNMLSVDLGYRYDDIKYQPEYIPGVTPKIADDMVKGIFIPLPKGEKVTTPWGAEYTKPLTQE
QIRKNAEENIAYIAQEKRFKKHSYSLGATFDPLNFLRVQVKYSKGFRAPTSDELYFTFKHPDFTI
LPNPVLKPEEAKNQEIALTVHDNWGFVSTSVFQTKYRHFIDLAYLGSRNLSNSVGGQAQARDFQV
YQNVNVDNAKVKGLEINARLNLGYFWHVLDGFNTSYKFTYQCGRLDGDRPMNAIQPKASVFGLGY
DHKENKFGADLYITRVSEKKAKDTYNMFYKEQGYKDSAIRWRSDDYTLVDAVGYIKPIKNLTLQF
GVYNLTDRKYLTWESARSIKPFGTSNLINQKTGAGINRFYSPGRNFKFSAEITF*

FIG. 12-1.

SEQ ID NO:9

ATGCAAAAACAGCAACCTTATCCCATTCACCTTGGGATTTTTTTGATGTTGGGTTTACCAACATG
GGCGTTCAGTCAAGCTAATTTAGAGAAATCAACAATCAATAAATTGGAAACGATTTTGGTCAATG
AGAGTGAAGAGAAAAATAAATTCGATGAGAATTTGATCAAAACTTATCTGTCTTCGGGTTCTTAT
TCTTATTTATCGCAATCGGATATCAGTACGTTCAGAGGTAGCTCGGTAGGGGATTTCCTCTCTGG
TGTACCAGGAGTTATTGTGGGAAATAAGCGTAATAGCGGCGCTTTATCCGTTAATATTCGAGGAA
TTGCGAATGAAAATCGTGTGCCTGTTTGGATAGATAAAGGTCTACAATCGGTACCCTCTTACCAA
GGTTATGCAGGTTCTTCAACTCGAACCTATTTAGATCCCGATTTGATCAGCCAAGTCGAGATTGA
AAAAGGTCCCTCTTTGCAAATGGACGCAACAGGCGCGACGGGAGGGGTAGTGAGAGTAGAGACTT
TACGTTGGCAAGATATTATTCCTCAAGGGAAAAATTGGGGCGTGCGTTTGAAACTAGGGACGATG
ACTAACACCGTATCACCTCCCCCTTATTATACAAGAGGAGGATATCAAACTAAGTATATTAGTAA
ATGTCTTTCTAATGATACTGGTTTATGTCAAACACAAACATATGCACCAAATGCACGCTATTCTT
CTCATGGCTTTGATTTGAATGCATACAATTATAGCCTGGCTTTTGCTAATAAATGGCAAAATGCT
GATCTTGTACTTGCGTATGCAAAACGTAAACAGGGCAACTATTTTGTTGGGCGTCATGGACAAAC
CCCAGTGATTGAATCCATTGAATTTGAGGAAGATTCAGTAGAAGTCAAAGAGCCTCGCGTTCATG
AAGAGGTTGAAATTGGTTCATTAACATTTAAAGAAAATCGCAGCACCTTATATCGACCGGGTGAA
GAAGCCCTGAATACCTCACAAGATAATACCTCTTATCTCGCTAAAATAAATGTCTACAATGATGT
TCATCGTTTAGGGTTAGCGTATCGCCATTATCATAGCCGTTTTGGTGAGATTATGAGCTCAATTT
TGAATTTCAGAGCGTATGGCGCATTGCAAGGTGAAGGGACAGAAGTCAAAGTCGATAGCTATCAT
GCAAATTATAGCTATAACCCAACGACACCTTATGTGAATTTGAATGTTAATGCATATTTTACTGA
CAGTGATTCGTCTAATTTTACCCCATTTATTGAAGAATATGGTTACTCTTTATCCAGTCGTCATG
CCCATTTTCTGGTTTCTAAGCAGAAAGGGTTAAGTATTGAAAATACTAGCATTTTCCAGCTTAAC
GACAAACCGTTTAGTTTAAAATATGGTCTTGCGCATAGTTATGAACGGATTTATCAACCACGTAA
TGCTCAAGCACGTGTGAGAGCTAAAGGGTATCCAGAAGATGCGATTGGTCCACTTTATATTCGAG
ATGGTAAGCGTAAAGAATGGAGCGCTTTTGTTGCTGCGAACTATCCAATCACTTCGTGGTTAAAA
GCCGACATCGGGCTACGTTATCTTCAATCTACTATTTATGATTATATTGTGAGAACGGAAAGAGT
GAATATTGGAGGGGCACTTGTGCCTAATCCAAATGGATCCGGTAATATTTGGGTGGAAAAATATA
AAGATGTTGTGCATAAACAGGCGCCAGTGAAAAATAAAGGCATGTCGCCAATTGTGATGCTCACA
TTTGAACCTATTAACGGAGTACAAATTTATACGAAATATGCAGAAGCATTGCGTTCGCCAAGTTT
ATTCCAAGCAACTAAAGGCTGGTCCATGAGTGCGACGGCAGATAATCTAGAACAATTGAGACCTG
AACGAGCCCAAAATTGGGAGGCGGGTATTAACTTGTTTTATGAAAATCTAGGTGGTAAGGACAAT
ATTCTTGGTTTTAAATTGGCGTATTTTAATAATAGGATAAAAGATTATTTGACGCGGAGTTATTC
GCCTAAAGATAAGGTGACGCAGACAATTAATATACAAAGTGCACAATTTAAAGGAATTGAGTTAT
CAGCGTATTATGATATGGGGAAATTTTACGCAAAATTAGCTGGTACATATTACACAAAAACGAAA
TTTTGTTTAACAGCAGAACAAGCAGGCAAAGGAGAGCAATGTAATTCAGGTTATGTATATCGTAG
TAATTTAAATAATGCCGTTCCTCCGCGTTTAAATTTACATGCGACTTTAGGAACCCGTTTGTTTG
AACAAAAACTCGATATTGGTGCGCGCTATAGTTACTACAGTAAGCGATTAGTACCAGTGCTTTCT
GCAGAACGTTTTGTTAACACATCAAGTATTGAGTGGGCGCCTTATTCCTTAGTAGATTTATATGC
CAATTACAATGTGTCTAATAACCTAAAACTTACGATGACCATGGATAATGTGTTTAATCGCTATT
ATTTAGATATCAATAATATGGGATTAAATACCGCACCGGGTAGAACATTGCATTTAGGATTAGAA
TATCGGTTTTAG

Fig. 12-2.

SEQ ID NO:10

MQKQQPYPIHLGIFLMLGLPTWAFSQANLEKSTINKLETILVNESEEKNKFDENLIKTYLSSGSY
SYLSQSDISTFRGSSVGDFLSGVPGVIVGNKRNSGALSVNIRGIANENRVPVWIDKGLQSVPSYQ
GYAGSSTRTYLDPDLISQVEIEKGPSLQMDATGATGGVVRVETLRWQDIIPQGKNWGVRLKLGTM
TNTVSPPPYYTRGGYQTKYISKCLSNDTGLCQTQTYAPNARYSSHGFDLNAYNYSLAFANKWQNA
DLVLAYAKRKQGNYFVGRHGQTPVIESIEFEEDSVEVKEPRVHEEVEIGSLTFKENRSTLYRPGE
EALNTSQDNTSYLAKINVYNDVHRLGLAYRHYHSRFGEIMSSILNFRAYGALQGEGTEVKVDSYH
ANYSYNPTTPYVNLNVNAYFTDSDSSNFTPFIEEYGYSLSSRHAHFLVSKQKGLSIENTSIFQLN
DKPFSLKYGLAHSYERIYQPRNAQARVRAKGYPEDAIGPLYIRDGKRKEWSAFVAANYPITSWLK
ADIGLRYLQSTIYDYIVRTERVNIGGALVPNPNGSGNIWVEKYKDVVHKQAPVKNKGMSPIVMLT
FEPINGVQIYTKYAEALRSPSLFQATKGWSMSATADNLEQLRPERAQNWEAGINLFYENLGGKDN
ILGFKLAYFNNRIKDYLTRSYSPKDKVTQTINIQSAQFKGIELSAYYDMGKFYAKLAGTYYTKTK
FCLTAEQAGKGEQCNSGYVYRSNLNNAVPPRLNLHATLGTRLFEQKLDIGARYSYYSKRLVPVLS
AERFVNTSSIEWAPYSLVDLYANYNVSNNLKLTMTMDNVFNRYYLDINNMGLNTAPGRTLHLGLE
YRF*

FIG. 13-1.

SEQ ID NO:11

ATGAAATATCCCTTAAGCTATAAAAATATAGCAAGGTCCATTCCTTTTCTCTCATTCATTGCGTT
TCCTCTGTATGCGCAAGAAACGACTGAATTAGAACAAATTACAGTACAAGAAAGCGCAACCGCTG
AAGTGAACAAAACCTCACCAACAGTGATCAGCAAAAGCGCCACGACCATTCAAAACGAAATGATT
CGAGACACCAGAGATTTAGTCCGCTACACAACGGATGTAGGGATTAGCGATAATGGGCGTTTTTT
GAAAGGCTTTGCGATGCGAGGCGTTGAAGATAACCGCGTTGGTATCAGTATTGATGGTGTTTCTT
TGCCTGATTCAGAAGAAAACTCACTGTATGCGCGTTATGGTAACTTTAATAATTCCCGCCTAAGC
ATTGATCCTGAATTAATTCAAACCATTGATATTGTACGCGGCTCAGATTCCTTTAATGCAGGCAG
CGGTTCATTAGGTGGCGGTGTGAATTATAACACTTTAGATCCACAACATATTGTTAAAACAGGTA
ATTCCGTTGGTGCTTTACTACGAGGCAGTTATGCCAGTAAAAATCGTGAATGGGTTCGTACTTTA
GGGATAGGCTATGTTGGCGAAAAATTTGATGCCTTATTGATGTATTCACAACGCACAGGGCACGA
GTTTAAAAGTCGTGGTTCAGGTCCTGAATTTCGGTATTCCAGTAGCCAGCATCCCGATCCTGTGA
CACAACGCTTCCACAATTATCTCGCTAAAATGAATTATCAAATTAATGACAAACAACGTATTGGT
TTAACGCTGAATGGGCAAACAGGGGGGCGTTACATTGATGAGCGTTCTTATACGTTAATGGGCTC
ACAATGGCGTGAAGCCGATGATCAAAACGAACGGTTGAATGCAAACTTATATTATATTTATGCAC
CAAGCACGGGATGGTTAGCCTACAGTAAATTTGATTTAGATTATCAAAAGACCGATCTAGCAGCA
GTTAACTATAAAGGCGGACGCCATTTCACGACAGATGCTAAAGAGCTGAACGAAATTTATGATCG
CCGTATGAAAACCGTGTTTACGCGCGGCAGTGTAGAACTCAATGCACAACCTGTACATTTCTATG
GTGAACATACTTTAACCATCAAAGGCTATGTTAGTCAGCGTGATTTCAAAAATATCAATCAAGAT
CGTATCGGTATTGGCACAAACTACGACACACAATACCACTATACGATTCAATATCCTATTAGAAC
CAAGCAGTACGGGCTTTCTTTGAAAGATCATGTGCGCTGGAATGATACCTTCTCAAGCCATTTAG
GTTTACGTTATGACCATACAAAACTAAAACCAAAGGAACTCAATGCACCTTGTAGCAAAGCCTGT
TTAGAAGAAGGAAAACCTAAACCGACCCGTTTCTCTACCGTTAGCACATTTGCGGGATTTGAGGC
ACAACTCAGCCCCTCATGGATGTTAGGCTACAATATTAGCACCGGTTATCGTGTACCAACGGCTT
CAGAAATGTTCTTCAGCTTTACCAATGCGTATGGCACGTGGAAATCTAACCCGAGCTTGAAACCC
GAAAAAAGTATTAACCATACACTCTCTTTGAAAGGCAATAGTGAAAAAGGCTTGCTTGATCTCAC
CCTCTATCAAACAAACTATCGTCATTTCTTATTTGAACAAGAAAGTTTAATTCAACGTACCGAAA
TGCGCTATGGACGCCCTTATACTTACCAAAGCCAAGAACAACAAATGGTGAACTTAGATAAAGCA
AAAATTTATGGTGTGGAATTGAAAACCCATGTCAATTTAGATCAGATGATCGCTGTGATACCACA
AGGCTTTAAGTTCTACGCCGCGCTCGGTTATAGCAAAGGTAAACTCTCGAATAACGCCAGCCTAC
TTTCCATTCAACCGCTTAAAATTATTCTGGGGTTGGATTATGAAGCAACAAACGGCAAATGGGCT
ATTTTCAACCGCCTAACCTATTTGGGTGAAAAAAGAGCTAGTGATGCGAAAGTGTATGAAATTAA
ACGTCGCTGTACTGAATTTGTGACAGAAACAGATCCTTGGACTGGTCAACAAATTACTCGCTGTA
AAAAACGGGAATTGTATCCAGATTTATCTACTTATAAACACTTAAATAAATCTGCTTTTGTGTTT
GATACTTTTGGTTATTACAAGATCACGGACGATATCACGTTCCGAGCTGGCATTTATAATCTGTT
TAATAAAAAATACCACACTTGGGATGCCTTACGTGGTATTAATGCCAATAGTACGTTAAATTCAG
TTGACCGTGAAGGGAAAGGGTTACAACGCTTCTATGCGCCCGGACGTAACTATGCGGCTTCCCTT
GAAATCCGTTTCTAA

FIG. 13-2.

SEQ ID NO:12

MKYPLSYKNIARSIPFLSFIAFPLYAQETTELEQITVQESATAEVNKTSPTVISKSATTIQNEMI
RDTRDLVRYTTDVGISDNGRFLKGFAMRGVEDNRVGISIDGVSLPDSEENSLYARYGNFNNSRLS
IDPELIQTIDIVRGSDSFNAGSGSLGGGVNYNTLDPQHIVKTGNSVGALLRGSYASKNREWVRTL
GIGYVGEKFDALLMYSQRTGHEFKSRGSGPEFRYSSSQHPDPVTQRFHNYLAKMNYQINDKQRIG
LTLNGQTGGRYIDERSYTLMGSQWREADDQNERLNANLYYIYAPSTGWLAYSKFDLDYQKTDLAA
VNYKGGRHFTTDAKELNEIYDRRMKTVFTRGSVELNAQPVHFYGEHTLTIKGYVSQRDFKNINQD
RIGIGTNYDTQYHYTIQYPIRTKQYGLSLKDHVRWNDTFSSHLGLRYDHTKLKPKELNAPCSKAC
LEEGKPKPTRFSTVSTFAGFEAQLSPSWMLGYNISTGYRVPTASEMFFSFTNAYGTWKSNPSLKP
EKSINHTLSLKGNSEKGLLDLTLYQTNYRHFLFEQESLIQRTEMRYGRPYTYQSQEQQMVNLDKA
KIYGVELKTHVNLDQMIAVIPQGFKFYAALGYSKGKLSNNASLLSIQPLKIILGLDYEATNGKWA
IFNRLTYLGEKRASDAKVYEIKRRCTEFVTETDPWTGQQITRCKKRELYPDLSTYKHLNKSAFVF
DTFGYYKITDDITFRAGIYNLFNKKYHTWDALRGINANSTLNSVDREGKGLQRFYAPGRNYAASL
EIRF*

FIG. 14-1.

SEQ ID NO:13

ATGGATAAAAATTTAATGAAGGGATGTGTATTCTTATCAATAGTCGGTTGCGGTATCCAAATAGG
GCTAGCATCAAATCCAAATCCTCCAGATGTGGATGAGTTATTACCTATTATTGTGAATGCTGATG
AAGATAATAAATTACCAGGTCGTTCTGTATTAAAACAGAAAAATATCGATCAACAACAAGCAGAT
AATGCTGCTGACTTAATAAATATTTTGCCTGGTGTAAATATGGCGGGAGGATTTCGCCCTAGTGG
TCAAACATTAAATATTAATGGAATGGGTGATGCTGAAGATGTTAGAGTTCAACTAGACGGCGCAA
CAAAAAGTTTCGAAAAATATCAACAAGGCTCTATTTTTATTGAACCTGAGTTATTAAGAAAGGTG
ACAGTAGACAAAGGAAATTATTCTCCTCAATATGGCAATGGTGGCTTTGCTGGTACTGTAAAATT
TGAAACAAAAGATGCAACTGATTTTTTGAAAGAAAATCAGAAAATAGGTGGATTATTTAAATATG
GAAATAATAGCAATAATAACCAAAAAACTTATAGTACAGCCCTAGTTTTACAGAATGAACAAAAA
AATATTGATTTGTTATTATTTGGTTCTGTAAGAAATGCAAGCAATTATACAAGACCTGATAAAAG
TAAAATTCTTTTTTCAAAAAACAATCAAAAAAGTGGATTAATAAAAGTAAATTGGCAAATTACTC
CTGAACATTTATTAACTTTATCCAGTGTTTATGGCATTCATAAAGGGTGGGAACCTTGGGCAGCA
AAAAGAGATGTGATGTCGAGACCAACAGAAACAGAAATAAAACACTATGGGATTGATGTTGCGTG
GAAACGTAAACTTGTTTATCGAGATCAAAAAGATGAAAGTTATTCATTGAAATATCGCTATTTAC
CTGAAAATAATAAGTGGATTAATTTATCTGTTCAGCTGAGTTATAGTAAAACAGAACAGAATGAT
ACTCGCCATGAGAAAGTCACTTCTTCATTCCTAGGTACATTAGGAAATAAAAGTTGGATAACTTA
TTCAGATCTTACTTTTGATATAAGTAACACAAGTACTCTAAATATTGGGCGTGCTGAGCATGAAC
TACTATTTGGTTTACAGTGGTTAAAAAATAAAAGAAATACCCTTATGTATCATAAAGGGGGAGTC
AAGAAGGCAGACTATAATTATGGCTATTTTCAGCCTTATTATATGCCTTCTGGACGCCAGTATAC
ACAAGCATTTTATTTACAAGATCAAATAAAATGGCAGAATTTCCTCTTTACAGGAGGGATAAGAT
ATGACCATATCAATAATATAGGGCAGAAAAATTTAGCGCCACGATATAATGATATCTCTGCAGGA
CATGATTATAGCCAGAAAAATTATAATGGTTGGTCTTATTATTTAGGTCTTAAGTATGATGTAAA
TCATTATTTAAGTTTATTTACGAATTTTAGTAAAACTTGGCGAGCCCCTGTTATTGATGAACAGT
ATGAGACACAATATAGTCAAGCTTCTGTATCTGCGACTTCTTTAAATTTAGAAAAAGAAATGATT
AATCAAACCAGAGTGGGTGGAATTATTACTCTCAATCATCTATTTCAGGAAAATGATGCTTTTCA
ATTTAGAACTACTTATTTTTACAATCGCGGCAAGAATGAAATCTTCAAAACGAGAGGAGTTAATT
GCGTAGAAAATGCTTTAGATGTTGATAATAGTGTTTGTCCTAAAATTATTAGTAATTACCGTAAT
TTACCTGGTTATGTTATTCAAGGAGCGGAATTAGAAGCTTATTATCAATCATCGTATTTATTTGG
TGGACTGACATATTCTTATGTAAAAGGAAAACGCGATACTTCACCAAGAAATCCATGGAGTAAAA
CATCTACATGGATCGCAGAAACATCACCTAGAAAAGCAATCGCTACTTTAGGTTTTAATATTCCG
GAATATTATTTTACGGCAGGTTGGCGTGCTGAGTTTGTGAGAAAGCAAGATAGATCACCACTATC
TAATGATTCTAAAGCATCATATTGGGCATTACCTTCTTCAAAAGGATATAGCCTACATAGTGTAT
TCTTCTCTTGGAGTCCTACAAAGATTAAAGGAATGAATTTCAAAGTTACTGTTGATAATTTATTT
AACCGACCCTATTATCCTTACTTAGGAGAATTAGCTTCAGGAACAGGTAGGAATGTCAAATTTAG
CCTGACTCAGCAATTTTAA

FIG. 14-2.

SEQ ID NO:14

MDKNLMKGCVFLSIVGCGIQIGLASNPNPPDVDELLPIIVNADEDNKLPGRSVLKQKNIDQQQAD
NAADLINILPGVNMAGGFRPSGQTLNINGMGDAEDVRVQLDGATKSFEKYQQGSIFIEPELLRKV
TVDKGNYSPQYGNGGFAGTVKFETKDATDFLKENQKIGGLFKYGNNSNNNQKTYSTALVLQNEQK
NIDLLLFGSVRNASNYTRPDKSKILFSKNNQKSGLIKVNWQITPEHLLTLSSVYGIHKGWEPWAA
KRDVMSRPTETEIKHYGIDVAWKRKLVYRDQKDESYSLKYRYLPENNKWINLSVQLSYSKTEQND
TRHEKVTSSFLGTLGNKSWITYSDLTFDISNTSTLNIGRAEHELLFGLQWLKNKRNTLMYHKGGV
KKADYNYGYFQPYYMPSGRQYTQAFYLQDQIKWQNFLFTGGIRYDHINNIGQKNLAPRYNDISAG
HDYSQKNYNGWSYYLGLKYDVNHYLSLFTNFSKTWRAPVIDEQYETQYSQASVSATSLNLEKEMI
NQTRVGGIITLNHLFQENDAFQFRTTYFYNRGKNEIFKTRGVNCVENALDVDNSVCPKIISNYRN
LPGYVIQGAELEAYYQSSYLFGGLTYSYVKGKRDTSPRNPWSKTSTWIAETSPRKAIATLGFNIP
EYYFTAGWRAEFVRKQDRSPLSNDSKASYWALPSSKGYSLHSVFFSWSPTKIKGMNFKVTVDNLF
NRPYYPYLGELASGTGRNVKFSLTQQF*

FIG. 15-1.

```
WP_053521090.1        -----------VLLMLSQPTNQPTNQPTNQNSNASEQLEQINVLGSDNNNDNTPPKIAET
1121_HgbA_968aa       MRTTTIKFSAITLALLSYCGA-----ILADSHQEATELDTITVSSQQDEMNIKEKKVGET
WP_005756141.1        MRTTTIKFSAITLALLSYCGA-----ILADSHQEATELDTITVSSQQDEMNIKEKKVGET
AAQ14873.1            MRTTTIKFSAITLALLSYCGV-----ILADSHQEATELDTITVSSQQDEMNIKEKKVGET
WP_061405928.1        MRTTTIKFSAITLALLSYCGA-----ILADSHQEATELDTITVSSQQDEMNIKEKKVGET
                                 .* :**            :. : : :*: *.* ..::: : .  *:.**

WP_053521090.1        VKTASQLKRQQVQDSRDLVRYETGVTVVEAGRFGSSGYAIRGVDENRVAITVDGLHQAET
1121_HgbA_968aa       VKTASQLKRQQVQDSRDLVRYETGVTVVEAGRFGSSGYAIRGVDENRVAITVDGLHQAET
WP_005756141.1        VKTASQLKRQQVQDSRDLVRYETGVTVVEAGRFGSSGYAIRGVDENRVAITVDGLHQAET
AAQ14873.1            VKTASQLKRQQVQDSRDLVRYETGVTVVEAGRFGSSGYAIRGVDENRVAITVDGLHQAET
WP_061405928.1        VKTASQLKRQQVQDSRDLVRYETGVTVVEAGRFGSSGYAIRGVDENRVAITVDGLHQAET
                      ************************************************************

WP_053521090.1        LSSQGFKELFEGYGNFNNTRNSVEIETLKVAKIAKGADSVKVGSGSLGGAVLFETKDARD
1121_HgbA_968aa       LSSQGFKELFEGYGNFNNTRNSVEIETLKVAKIAKGADSVKVGSGSLGGAVLFETKDARD
WP_005756141.1        LSSQGFKELFEGYGNFNNTRNSVEIETLKVAKIAKGADSVKVGSGSLGGAVLFETKDARD
AAQ14873.1            LSSQGFKELFEGYGNFNNTRNSVEIETLKVAKIAKGADSVKVGSGSLGGAVLFETKDARD
WP_061405928.1        LSSQGFKELFEGYGNFNNTRNSVEIETLKVAKIAKGADSVKVGSGSLGGAVLFETKDARD
                      ************************************************************

WP_053521090.1        FLTEKDWHIGYKAGYSTADNQGLNAVTLAGRYQMFDALIMHSKRHGHELENYDYKNGRDI
1121_HgbA_968aa       FLTEKDWHIGYKAGYSTADNQGLNAVTLAGRYQMFDALIMHSKRHGHELENYDYKNGRDI
WP_005756141.1        FLTEKDWHIGYKAGYSTADNQGLNAVTLAGRYQMFDALIMHSKRHGHELENYDYKNGRDI
AAQ14873.1            FLTEKDWHIGYKAGYSTADNQGLNAVTLAGRYQMFDALIMHSKRHGHELEIYDYKNGRDI
WP_061405928.1        FLTEKDWHIGYKAGYSTADNQGLNAVTLAGRYQMFDALIMHSKRHGHELENYDYKNGRDI
                      ************************************************** *********

WP_053521090.1        QGKEREKADPYTITKESTLVKFSFSPTENHRFTVASDTYLQHSRGHDFSYNLVKTTYINK
1121_HgbA_968aa       QGKEREKADPYTITKESTLVKFSFSPTENHRFTVASDTYLQHSRGHDLSYNLVATTHIQL
WP_005756141.1        QGKEREKADPYTITKESTLVKFSFSPTENHRFTVASDTYLQHSRGHDLSYNLVATTHIQL
AAQ14873.1            QGKEREKADPYTITKESTLVKFSFSPTENHRFTVASDTYLQHSRGHDLSYNLVATTYIQL
WP_061405928.1        QGKEREKADPYTITKESTLVKFSFSPTENHRFTVASDTYLQHSRGHDLSYNLVATTHIQL
                      ***********************************************:***** **:*:

WP_053521090.1        DEEELRHTNDLTKRKNVSFTYENYTVTPFWDTLKLSYSQQRITTRARTEDYCDGNEKCDS
1121_HgbA_968aa       DEKESRHANDLTKRKNVSFTYENYTVTPFWDTLKLSYSQQRITTRARTEDYCDGNEKCDS
WP_005756141.1        DEKESRHANDLTKRKNVSFTYENYTVTPFWDTLKLSYSQQRITTRARTEDYCDGNEKCDS
AAQ14873.1            DEKESRHANDLTKRKNVSFTYENYTVTPFWDTLKLSYSQQRITTRARTEDYCDGNEKCDS
WP_061405928.1        DEKESRHANDLTKRKNVSFTYENYTVTPFWDTLKLSYSQQRITTRARTEDYCDGNEKCDS
                      **:* **:****************************************************

WP_053521090.1        YKNPLGLQLKNGQIVDRDGNPVNLKLINGRHKVVDKNNKLFGLTDEDNNAAFDGKQLGLS
1121_HgbA_968aa       YKNPLGLQLKEGKIVDRNGDPVNLKLVDGKHQVVDKAGKPFDVASGTNYAAFSGKELSPS
WP_005756141.1        YKNPLGLQLKEGKIVDRNGDPVNLKLVDGKHQVVDKAGKPFDVASGTNYAAFSGKELSPS
AAQ14873.1            YKNPLGLQLKEGKIVDRNGDPVNLQLVDGKHQVVDKAGKPFDVTSGTNYAAFSGKQLGPS
WP_061405928.1        YKNPLGLQLKEGKIVDRNGDPVNLQLVDGKHQVVDKAGKPFDVTSGTNYAAFSGKQLGPS
                      **********:*:****:*:****:*::*:*:**** .* *.::.  * ***.**:*. *

WP_053521090.1        GFWFDCTVFDCDKPVRTYKYKYSSSNPAVENVELNKFMQVNGKRFATYEDKIQSSEKRYV
1121_HgbA_968aa       SFWLDCSIFDCSKPINTYKYRYTSSEPTLQQITLNKTMEINGKTFATYDG-----RGHYI
WP_005756141.1        SFWLDCSIFDCSKPINTYKYRYTSSEPTLQQITLNKTMEINGKTFATYDG-----RGHYI
AAQ14873.1            YFWLECTVFDCSKPVTTYKYRYSTETPVKEDIQLNKTMEVNGKTFATYDMG---RERRYI
WP_061405928.1        YFWLDCTVFDCSKPVTTYKYRYSTETPVKEDIQLNKTMEVNGKTFATYDMG---RERRYI
                       **::*::***.**: ****:*::. *. ::: *** *::*** ****:      . :*:
```

FIG. 15-2.

```
WP_053521090.1      ILPNSKGYLPLDYKERDLNTKTKQINLDLTKAFTLFEIENELSYGGVYAKTTKEMVNKAG
1121_HgbA_968aa     ILPNSKGYLPLDYKERDLNTKTKQINLDLTKAFTLFEIENELSYGGVYAKTTKEMVNKAG
WP_005756141.1      ILPNSKGYLPLDYKERDLNTKTKQINLDLTKAFTLFEIENELSYGGVYAKTTKEMVNKAG
AAQ14873.1          ILPNSQGYLPLDYKERDLNTKTKQINLDLTKAFTLFEIENELSYGGVYAKTTNGVVNKAG
WP_061405928.1      ILPNSQGYLPLDYKERDLNTKTKQINLDLTKAFTLFEIENELSYGGVYAKTTKEMVNKAG
                    *****:**********************************************: :*****

WP_053521090.1      YYGRNPTWWAERTLGQDLSGNQHNCNTNSSYNGMLCPRHEPLTSFLIPVEATTKSLYFSD
1121_HgbA_968aa     YYGRNPTWWAERTLGQSW-GKLRECKTSSSYNGMLCPRHEPLTSFLIPVEATTKSLYFAD
WP_005756141.1      YYGRNPTWWAERTLGQSW-GKLRECKTSSSYNGMLCPRHEPLTSFLIPVEATTKSLYFAD
AAQ14873.1          YYGRNPTWWAERTLGQSWNGTLRECKTSSSYNGMLCPRHEPLTSFLIPVEATTKSLYFAD
WP_061405928.1      YYGRNPTWWAERTLGQSWNGTLRECKTSSSYNGMLCPRHEPLTSFLIPVEATTKSLYFAD
                    ****************.  *. ::*:*.******************************:*

WP_053521090.1      NIKLHNMLSVDLGYRYDDIKYQPEYIPGVTPKIADDMVKGIFIPLPKGEKIKIGNYETTK
1121_HgbA_968aa     NIKLHNMLSVDLGYRYDDIKYQPEYIPGVTPKIADDMVKGLFIPLPEGEKVTVGTMVFTK
WP_005756141.1      NIKLHNMLSVDLGYRYDDIKYQPEYIPGVTPKIADDMVKGLFIPLPEGEKVTVGTMVFTK
AAQ14873.1          NIKLHNMLSVDLGYRYDDIKYQPEYIPGVTPKIADDMVKGLFIPLPEGEKVTVGTVVFTK
WP_061405928.1      NIKLHNMLSVDLGYRYDDIKYQPEYIPGVTPKIADDMVKGLFIPLPEGEKVTVGTVVFTK
                    ****************************************:*****:***:.:*.   **

WP_053521090.1      PLTPEQIRKNAEENIAYIAQEKRFKKHSYSLGATFDPLNFLRVQVKYSKGFRAPTSDELY
1121_HgbA_968aa     PLTQAQIRKNAEENIAYIAQEKRFKKHSYSLGATFDPLNFLRVQVKYSKGFRAPTSDELY
WP_005756141.1      PLTQAQIRKNAEENIAYIAQEKRFKKHSYSLGATFDPLNFLRVQVKYSKGFRAPTSDELY
AAQ14873.1          PLTPEQIRKNAEENIAYIAQGKRFKKHSYSLGTTFDPLNFLRVQVKYSKGFRAPTSDELY
WP_061405928.1      PLTPEQIRKNAEENIAYIAQEKRFKKHSYSLGATFDPLNFLRVQVKYSKGFRAPTSDELY
                    ***  *************** ***********:***************************

WP_053521090.1      FTFKHPDFTILPNPVLKPEEAKNQEIALTVHDNWGFVSTSVFQTKYRHFIDLAYLGSRNL
1121_HgbA_968aa     FTFKHPDFTILPNPVLKPEEAKNQEIALTVHDNWGFVSTSVFQTKYRHFIDLAYLGSRNL
WP_005756141.1      FTFKHPDFTILPNPVLKPEEAKNQEIALTVHDNWGFVSTSVFQTKYRHFIDLAYLGSRNL
AAQ14873.1          FTFKHPDFTILPNPVLKPEEAKNQEIALTVHDNWGFVSTSVFQTKYRHFIDLAYLGSRNL
WP_061405928.1      FTFKHPDFTILPNPVLKPEEAKNQEIALTVHDNWGFVSTSVFQTKYRHFIDLAYLGSRNL
                    ************************************************************

WP_053521090.1      SNSVGGQAQARDFQVYQNVNVDNAKVKGLEINARLNLGYFWHVLDGFNTSYKFTYQRGRL
1121_HgbA_968aa     SNSVGGQAQARDFQVYQNVNVDNAKVKGLEINARLNLGYFWHVLDGFNTSYKFTYQRGRL
WP_005756141.1      SNSVGGQAQARDFQVYQNVNVDNAKVKGLEINARLNLGYFWHVLDGFNTSYKFTYQRGRL
AAQ14873.1          SNSVGGQAQARDFQVYQNVNVDNAKVKGLEINARLNLGYFWHVLDGFNTSYKFTYQRGRL
WP_061405928.1      SNSVGGQAQARDFQVYQNVNVDNAKVKGLEINARLNLGYFWHVLDGFNTSYKFTYQRGRL
                    ************************************************************

WP_053521090.1      DGDRPMNAIQPKASVFGLGYDHKENKFGADLYITRVSEKKAKDTYNMFYKEEKKKDSAIH
1121_HgbA_968aa     DGDRPMNAIQPKASVFGLGYDHKENKFGADLYITRVSEKKAKDTYNMFYKEQGYKDSAVR
WP_005756141.1      DGDRPMNAIQPKASVFGLGYDHKENKFGADLYITRVSEKKAKDTYNMFYKEQGYKDSAVR
AAQ14873.1          DGDRPMNAIQPKASVFGLGYDHKENKFGADLYITRVSEKKAKDTYNMFYKEQGYKDSAIR
WP_061405928.1      DGDRPMNAIQPKASVFGLGYDHKENKFGADLYITRVSEKKAKDTYNMFYKEQGYKDSAVR
                    ***************************************************:  ****::

WP_053521090.1      WRSDDYTLVDFVTYIKPVKNVTLQFGIYNLTDRKYLTWESARSIKPFGTSNLINQQTGAG
1121_HgbA_968aa     WRSDDYTLVDAVGYIKPIKNLTLQFGVYNLTDRKYLTWESARSIKPFGTSNLINQKTGAG
WP_005756141.1      WRSDDYTLVDAVGYIKPIKNLTLQFGVYNLTDRKYLTWESARSIKPFGTSNLINQKTGAG
AAQ14873.1          WRSDDYTLVDAVGYIKPIKNLTLQFGVYNLTERKYLTWESARSIKPFGTSNLINQKTGAG
WP_061405928.1      WRSDDYTLVDAVGYIKPIKNLTLQFGVYNLTDRKYLTWESARSIKPFGTSNLINQKTGAG
                    ********** * ****:**:*****:****:***********************:****

WP_053521090.1      INRFYSPGRNYKLSAEITF-
1121_HgbA_968aa     INRFYSPGRNFKFSAEITF*
WP_005756141.1      INRFYSPGRNFKFSAEITF-
AAQ14873.1          INRFYSPGRNFKFSAEITF-
WP_061405928.1      INRFYSPGRNFKLSAEITF-
                    **********:*:******
```

FIG. 16-1.

```
ESQ71136.1          MEKIDMESAKNPLKKTTLALLCCSTAFSLSAKTDTNADKNHFLTEIVVYADQNKSMSSTQ
WP_014391205.1      -----MESAKNPLKKTTLALLCCSTAFSLSAKTDTDSDKNHFLTEIVVYADQNKSMSSTQ
WP_016534044.1      -----MEYAKNPLKKTTLALLCCSTAFSLSAKTDTNADKNHFLTEIVVYADQNKSMSSTQ
1121_FepA_790aa     -----MESAKNPLKKTTLALLCCSTAFSLSAKTDTNADKNHFLTEIVVYADQNKSMSSTQ
WP_005756883.1      -----MESAKNPLKKTTLALLCCSTAFSLSAKTDTNADKNHFLTEIVVYADQNKSMSSTQ
                         ** ****************************::**********************

ESQ71136.1          SVTQDDMKKSPVTNGNITDYLRSNPHVRYENSDQNGLQRGEIKPENISINGADYQQTTFF
WP_014391205.1      SVTQDDMKKSPVTNGNITDYLRSNPHVRYENSDQNGLQRGEIKPENISINGADYQQTTFF
WP_016534044.1      SVTQEDMKKSPVTNGNITDYLRSNPHVRYENSDQNGLQRGEIKPENISINGADYQQTTFF
1121_FepA_790aa     SVTQDDMKKSPVTNGNITDYLRSNPHVRYENSDQNGLQRGEIKPENISINGADYQQTTFF
WP_005756883.1      SVTQDDMKKSPVTNGNITDYLRSNPHVRYENSDQNGLQRGEIKPENISINGADYQQTTFF
                    ****:*******************************************************

ESQ71136.1          VDNVNINNDMGFGSDLFDGTMATVPFANHSQGYFFDANLLSSIVVHDSNVSASLGGFAGG
WP_014391205.1      VDNVNINNDMGFGSDLFDGTMATVPFANHSQGYFFDANLLSSIVVHDSNVSASLGGFAGG
WP_016534044.1      VDNVNINNDMGFGSDLFDGTMATVPFANHSQGYFFDANLLSSIVVHDSNVSASLGGFAGG
1121_FepA_790aa     VDNVNINNDMGFGSDLFDGTMATVPFANHSQGYFFDANLLSSIVVHDSNVSASLGGFAGG
WP_005756883.1      VDNVNINNDMGFGSDLFDGTMATVPFANHSQGYFFDANLLSSIVVHDSNVSASLGGFAGG
                    ************************************************************

ESQ71136.1          AVVAKTKQYDGKDQLKFSYRTTDASWAKFKVEDKDLERFKNAIPEGSVAEFQPKYSKHFF
WP_014391205.1      AVVAKTKQYDGKDRLKFSYRTTDASWAKFKVEDKDLERFKNAIPEGSVAEFQPKYSKHFF
WP_016534044.1      AVVAKTKQYDGKDRLKFSYRTTDASWAKFKVEDKDLERFKNAIPEGSVAEFQPKYSKRFF
1121_FepA_790aa     AVVAKTKQYDGKDRLKFSYRTTDASWAKFKVEDKDLERFKNAIPEGSVAEFQPKYSKHFF
WP_005756883.1      AVVAKTKQYDGKDRLKFSYRTTDASWAKFKVEDKDLERFKNAIPEGSVAEFQPKYSKHFF
                    *************:*******************************************:**

ESQ71136.1          NITAEKGLSENLGMVIGLSRRTSSIQQSRQINPQGDRDKQTHTRRSDNALLNFNLTPNDK
WP_014391205.1      NITAEKGLSENLGMVIGLSRRTSSIQQSRQINPQGDRDKQTHTRRSDNALLNFNLTPNDK
WP_016534044.1      NITAEKGLSENLGMVIGLSRRTSSIQQSRQINPQGDRDKQTHTRRSDNALLNFNLTPNDK
1121_FepA_790aa     NITAEKGLSENLGMVIGLSRRTSSIQQSRQINPQGDRDKQTHTRRSDNALLNFNLTPNDK
WP_005756883.1      NITAEKGLSENLGMVIGLSRRTSSIQQSRQINPQGDRDKQTHTRRSDNALLNFNLTPNDK
                    ************************************************************

ESQ71136.1          HRFELGFRYSNYRERKFFNTNIDSNVFDYHRAYGVTFSWINALQSGILTTTLAYDNFDDT
WP_014391205.1      HRFELGFRYSNYRERKFFNTNIDSNVFDYHRAYGVTFSWINALQSGILTTTLAYDNFDDT
WP_016534044.1      HRFELGFRYSNYRERKFFNTNIDSNVFDYHRAYGVTFSWINALQSGILTTTLAYDNFDDT
1121_FepA_790aa     HRFELGFRYSNYRERKFFNTNIDSNVFDYHRAYGVTFSWINALQSGILTTTLAYDNFDDT
WP_005756883.1      HRFELGFRYSNYRERKFFNTNIDSNVFDYHRAYGVTFSWINALQSGILTTTLAYDNFDDT
                    ************************************************************

ESQ71136.1          RKSASTSMKTII-EDENDYTLGGMGNSQLNQKNSHFSLEYAMNSFDLSHINHSISLGSVF
WP_014391205.1      RKSASTYMKTTLTDDGEEYTEGGMGNSQLNQKNLHTSLEYAMNPFNLGSIEHSVSLGGIY
WP_016534044.1      RKSASTYMKTTLTEEGEEYTEGGMGNSQLNQKNLHTSLEYAMNPFNLGSIEHSVSLGGIY
1121_FepA_790aa     RKSASTYMKTTLTEEGEEYTEGGMGNSQLNQKNLHTSLEYAMNPFNLGSIEHSVSLGGIY
WP_005756883.1      RKSASTYMKTTLTEEGEEYTEGGMGNSQLNQKNLHTSLEYAMNPFNLGSIEHSVSLGGIY
                    ****** *** : :: ::** ************ * ******* *:*. *:**:***.::

ESQ71136.1          QHTQYRFHRESDAEAEIINRIDLEN------EKIEIKSSNLAKKGTVKTRYQNIALYVED
WP_014391205.1      QATKYRFTRHSDAVGELYTPNWLDNNSNDIYDELTLAQRNIAKKGTVKTRYQNIALYVED
WP_016534044.1      QATKYRFTRHSDAVGELYTPDWLNGNT----DKLILTQRNIAKKGTVKTRYQNIALYVED
1121_FepA_790aa     QATKYRFTRHSDAVGELYTPDWLNGNT----DKLILTQRNIAKKGTVKTRYQNIALYVED
WP_005756883.1      QATKYRFTRHSDAVGELYTPDWLNGNT----DKLILTQRNIAKKGTVKTRYQNIALYVED
                    * *:*** *.*** .*: .   *:.      ::: :  . *:*******************

ESQ71136.1          LMTWKNLEFRAGLRLERDDYLKNTNLAPRTVFRYKPFEDTAFSVGWNRYYGRSFASMKLS
WP_014391205.1      LMTWKNLEFRAGLRLERDDYLKNTNLAPRTVFRYKPFEDTAFSVGWNRYYGRSFASMKLS
WP_016534044.1      LMTWKNLEFRAGLRLERDDYLKNTNLAPRTVFRYKPFEDTAFSVGWNRYYGRSFASMKLS
1121_FepA_790aa     LMTWKNLEFRAGLRLERDDYLKNTNLAPRTVFRYKPFEDTAFSVGWNRYYGRSFASMKLS
WP_005756883.1      LMTWKNLEFRAGLRLERDDYLKNTNLAPRTVFRYKPFEDTAFSVGWNRYYGRSFASMKLS
                    ************************************************************
```

FIG. 16-2.

```
ESQ71136.1          EGIFKLDGHDTFRYKDLSQFKTPYSDELSFGVEQYVANLAFHLKYILRDNKQRIVLQEED
WP_014391205.1      EGIFKLDGHDTFRYKDLSQFKTPYSDELSFGVEQYVANLAFHLKYILHDNKQRIVLQEED
WP_016534044.1      EGIFKLDGHDTFRYKDLSQFKTPYSDELSFGVEQYVANLAFHLKYILRDNKQRIVLQEED
1121_FepA_790aa     EGIFKLDGHDTFRYKDLSQFKTPYSDELSFGVEQYVANLAFHLKYILRDNKQRIVLQEEE
WP_005756883.1      EGIFKLDGHDTFRYKDLSQFKTPYSDELSFGVEQYVANLAFHLKYILRDNKQRIVLQEED
                    ***********************************************:***********:

ESQ71136.1          VMLNGEKKKLRYYQRGKDYKTNVLTFQINTQAPWELGPTRWTSAVAFDWLDSKAIDHGRG
WP_014391205.1      VMLNGEKKKLRYYQRGKDYKTNVLTFQISTQAPWEFGPTRWTSALAFDWLDSKAIDHGRG
WP_016534044.1      VMLNGERKKLRYYQRGKDYKTNVLTFQINTQAPWELGPTRWTSAVAFDWLDSKAIDHGRG
1121_FepA_790aa     VMLNGERKKLRYYQRGKDYKTNVLTFQINTQAPWELGPTRWTSAVAFDWLDSKAIDHGRG
WP_005756883.1      VMLNGEKKKLRYYQRGKDYKTNVLTFQINTQAPWELGPTRWTSAVAFDWLDSKAIDHGRG
                    ******:*********************.******:********:***************

ESQ71136.1          YNGSTPVILDGKLMTYEQMLKKVNAYKETWGLRLNLDMFVPRFDLSWANTIYVKPPTTLT
WP_014391205.1      YNGSTPVILDGKLMTYEQMLKKVNAYKETWGLRLNLDMFVPKFDLSWANTIYVKPPTTLT
WP_016534044.1      YNGSTPVILDGKLMTYEQMLKKVNAYKETWGLRLNLDMFVPRFDLSWANTIYVKPPTTLT
1121_FepA_790aa     YNGSTPVILDGKLMTYEQMLKKVNAYKETWGLRLNLDMFVPIFDLSWANTIYVKPPTTLT
WP_005756883.1      YNGSTPVILDGKLMTYEQMLKKVNAYKETWGLRLNLDMFVPRFDLSWANTIYVKPPTTLT
                    ***************************************** ******************

ESQ71136.1          ERVSSNTPEVYRSYDYGTYTQWDTSLRWQPTFAEKHRPYIKLDVLNVLNKTRKGAGPNGQ
WP_014391205.1      ERVSSNTPEVYRSYDYGTYTQWDTSLRWQPTFAEKHRPYIKLDVLNVLNKTRKGAGPNGQ
WP_016534044.1      ERVSSNTPEVYRSYDYGTYTQWDTSLRWQPTFAEKHRPYIKLDVLNVLNKTRKGAGPNGQ
1121_FepA_790aa     ERVSSNTPEVYRSYDYGTYTQWDTSLRWQPTFAEKHRPYIKLDVLNVLNKTRKGAGPNGQ
WP_005756883.1      EHVSSSTPEVYRSYDYGTYTQWDTSLRWQPTFAEKHRPYIKLDVLNVLNKTRKGAGPNGQ
                    *:***.******************************************************

ESQ71136.1          DLGIYTPGREFWLEVGYEF
WP_014391205.1      DLGIYTPGREFWLEVGYEF
WP_016534044.1      DLGIYTPGREFWLEVGYEF
1121_FepA_790aa     DLGIYTPGREFWLEVGYEF
WP_005756883.1      DLGIYTPGREFWLEVGYEF
                   *******************
```

FIG. 17-1.

```
WP_071522773.1      MSFKHKTLALFVAHACCTSVLAENAATTLEPIVVSDLSHTTLNLDQNKLEKESPKDLKAI
WP_016534444.1      MSFKHKTLALFVAHACCTSALAENAATTLEPIVVSELSHTTLNLDQNKLEKESPKDLKAI
WP_005755819.1      MSFKHKTLALFVAHACCTSALAENVATTLEPIVVSDLSHTTLNLDQNKLEKESPKDLKAI
1121_PfhR_727aa     MSFKHKTLALFVAHACCTSALAENVATTLEPIVVSDLSHTTLNLDQNKLEKESPKDLKAI
EGP05580.1          MSFKHKTLALFVAHACCTSALAENAATTLEPIVVSDLSHTTLNLDQNKLEKESPKDLKAI
                    *******************.****.**********:************************

WP_071522773.1      FATTPNINVIHTGHAQLGDIEIRGMGSSREIFATGANRVTMELDGMDISPSFYFGHSSRH
WP_016534444.1      FTTTPNINVIHTGHAQLGDIEIRGMGSSREIFATGANRVTMELDGMDISPSFYFGHSSRH
WP_005755819.1      FATTPNINVIHTGHAQLGDIEIRGMGSSREIFATGANRVTMELDGMDISPSFYFGHSSRH
1121_PfhR_727aa     FATTPNINVIHTGHAQLGDIEIRGMGSSREIFATGANRVTMELDGMDISPSFYFGHSSRH
EGP05580.1          FATTPNINVIHTGHAQLGDIEIRGMGSSREIFATGANRVTMELDGMDISPSFYFGHSSRH
                    *:**********************************************************

WP_071522773.1      GRQYFDPSDLKRVEVHKGPNSQGVAGHVRFQTKDPHDYLLPNQRTGAQLRAGYLGDSDAY
WP_016534444.1      GRQYFDPSDLKRVEIHKGPNSQGVAGHVRFQTKDPRDYLLPNQRTGAQLRAGYLGDSDAY
WP_005755819.1      GRQYFDPSDLKRVEIHKGPNSQGVAGHVRFQTKDPRDYLLPNQRTGAQLRAGYLGDSDAY
1121_PfhR_727aa     GRQYFDPSDLKRVEIHKGPNSQGVAGHVRFQTKDPRDYLLPNQRTGAQLRAGYLGDSDAY
EGP05580.1          GRQYFDPSDLKRVEIHKGPNSQGVAGHVRFQTKDPRDYLLPNQRTGAQLRAGYLGDSDAY
                    **************:********************:************************

WP_071522773.1      YVGITGAALLDEHSSALVSYTRRWFNEFNNKGGLDVTGSQRTKSNPSSGYSNAVNSKLRY
WP_016534444.1      YVGITGATLLDEHSSALVSYTRRWFNEFNNKGGLDVTGSQRTKSNPSSGYSNAVNSKLRY
WP_005755819.1      YVGITGATLLDEHSSALVSYTRRWFNEFNNKGGLDVTGSQRTKSNPSSGYSNAVNSKLRY
1121_PfhR_727aa     YVGITGATLLDEHSSALVSYTRRWFNEFNNKGGLDVTGSQRTKSNPSSGYSNAVNSKLRY
EGP05580.1          YVGITGATLLDEHSSALMSYTRRWFNEFNNKGGLDVTGSQRTKSNPSSGYSNAVNSKLRY
                    *******:**********:*****************************************

WP_071522773.1      SPNDRHKFTLNLQHYDLKRTAYLEDSLGTTTTRRGTKTVHHNTNIQKNQRHAIAFSHDMQ
WP_016534444.1      SPNDRHKFTLNLQHYDLKRTAYLEDSLGTTTTRRGTKTVHHNTNIQKNQRHAIAFSHDMQ
WP_005755819.1      SPNDRHKFTLNLQHYDLKRTAYLEDSLGTTTTRRGTKTVHHNTNIQKNQRHAIAFSHDMQ
1121_PfhR_727aa     SPNDRHKFTLNLQHYDLKRTAYLEDSLGTTTTRRGTKTVHHNTNIQKNQRHAIAFSHDMQ
EGP05580.1          SPNDRHKFTLNLQHYDLKRTAYLEDSLGTTTTRRGTKTVHHNTNIQKNQRHAIAFSHDMQ
                    ************************************************************

WP_071522773.1      QTNHSIFDHLHWQIALQQTKSTSRNTGAVTSTSGSPPPSTPKFSQERSLDGFKTKTISLK
WP_016534444.1      QTT-AFFDHLHWQIALQQTKSTSRNTGTVTSTSAPPPPSTPKFSQERSFDGFKTKTISLK
WP_005755819.1      QTT-AFFDHLHWQIALQQTKSTSRNTGAVTSTSASPPPSTPKFSQERSFDGFKTKTISLK
1121_PfhR_727aa     QTT-AFFDHLHWQIALQQTKSTSRNTGAVTNTSASPPPSTPKFSQERSLDGFKTKTISLK
EGP05580.1          QTT-AFFDHLHWQIALQQTKSTSRNTGAVTNTSASPPPSTPKFSQERSLDGFKTKTISLK
                    **. ::*********************:**.**. *************:***********

WP_071522773.1      TEFNKSLGQHVVHELHYGLKLQYSQMQALRQTQSLNEQGSNTRTSAFFPTQQQWQSKLHL
WP_016534444.1      TEFNKSLGQHVVHELHYGLKLQYSQMQALRQTQSLNEQGSNTRTSAFFPTQQQWQSKFHL
WP_005755819.1      TEFNKSLGQHVVHELHYGLKLQYSQMQALRQTQSLNEQGSNTRTSAFFPTQQQWQSKLHL
1121_PfhR_727aa     TEFNKSIGQHVVHELHYGLKLQYSQMQALRQTQSLNEQGSNTRTSAFFPTQQQWQSKLHL
EGP05580.1          TEFNKSIGQHVVHELHYGLKLQYSQMQALRQTQSLNEQGSNTRTSAFFPTQQQWQSKLHL
                    ******:**************************************************:**

WP_071522773.1      SDRISFGKSGLSLTPSIHLTQIRIKPKTENVSKKNREQLFTYKDTAIGYGLRVDYALNEA
WP_016534444.1      SDRISFGKSGLSLTPSIHLTQIRIKPKTENVSKKNREQLFTYKDTAIGYGLRVDYALNEA
WP_005755819.1      SDRISFGKSGLSLTPSIHLTQIRIKPKTENVSKKNREQLFTYKDTAIGYGLRVDYALNEA
1121_PfhR_727aa     SDRISFGKSGLSLTPSIHLTQIRIKPKTENVSKKNREQLFTYKDTAIGYGLRVDYALNEA
EGP05580.1          SDRISFGKSGLSLTPSIHLTQIRIKPKTENVSKKNREQLFTYKDTAIGYGLRVDYALNEA
                    ************************************************************
```

FIG. 17-2.

```
WP_071522773.1        NLLSLNYQHATRLPGYGENNAQSYGHWPAKPNPHLQPETSDGIELSWRSAGAIGQQTTTL
WP_016534444.1        NLLSLNYQHATRLPGYGENNAQSYGHWPAKPNPHLQPETSDGVELSWRSAGAIGQQTTTL
WP_005755819.1        NLLSLNYQHATRLPGYGENNAQSYGHWPAKPNPHLQPETSDGIELSWRSAGAIGQQTTTL
1121_PfhR_727aa       NLLSLNYQHATRLPGYGENNAQSYGHWPAKPNPHLQPETSDGIELSWRSAGAIGQQTTTL
EGP05580.1            NLLSLNYQHATRLPGYGENNAQSYGHWPAKPNPHLQPETSDGIELSWRSAGAIGQQTTTL
                      ******************************************:*****************

WP_071522773.1        FYNRYNDLIYLDTTACYADRTGQVQVPCDLANEKGRSYSYGIEFDGKLNLDTIGFAQGTY
WP_016534444.1        FYNRYNDLIYLDTTACYADRTGQ--VPCDLANEKGRSYSYGIEFDGKLNLDTIGFAQGTY
WP_005755819.1        FYNRYNDLIYLDTTACYADRTGQ--VPCDLANEKGRSYSYGIEFDGKLNLDTIGFAQGTY
1121_PfhR_727aa       FYNRYNDLIYLDTTACYADRTGQ--VPCDLANEKGRSYSYGIEFDGKLNLDTIGFAQGTY
EGP05580.1            FYNRYNDLIYLDTTACYADRTGQ--VPCDLANEKGRSYSYGIEFDGKLNLDTIGFAQGTY
                      ***********************  ***********************************

WP_071522773.1        LNAGFAYSKGKTANKQPQGRLDPLTGFVGLGYQQPMDVWGIEGKLKFAAKKKTKDLPANQ
WP_016534444.1        LNAGFAYSKGKTANKQPQGRLDPLTGFVGLGYQQPMDVWGIEGKLKFAAKKKTKDLPANQ
WP_005755819.1        LNAGFAYSKGKTANKQPQGRLEPLTGFVGLGYQQPMDVWGIEGKLKFAAKKKTKDLPANQ
1121_PfhR_727aa       LNAGFAYSKGKTANKQPQGRLDPLTGFVGLGYQQPMDVWGIEGKLKFAAKKKTKDLPANQ
EGP05580.1            LNAGFAYSKGKTANKQPQGRLDPLTGFVGLGYQQPMDVWGIEGKLKFAAKKKTKDLPANQ
                      *********************:**************************************

WP_071522773.1        GFEGLPGYAVVDLTAYYNVTKQLYLGIGIYNVLDKKYARWAMARGDIKHGNYDKHTEAGR
WP_016534444.1        GFEGLPGYAVVDLTAYYNVTKQLYLGIGIYNVLDKKYARWAMARGDIKHGNYDKHTEAGR
WP_005755819.1        GFEGLPGYAVVDLTAYYNVTKQLYLGIGIYNVLDKKYARWAMARGDIKHGNYDKHTEAGR
1121_PfhR_727aa       GFEGLPGYAVVDLTAYYNVTKQLYLGIGIYNVLDKKYARWAMARGDIKHGNYDKHTEAGR
EGP05580.1            GFEGLPGYAVVDLTAYYNVTKQLYLGIGIYNVLDKKYARWAMARGDIKHGNYDKHTEAGR
                      ************************************************************

WP_071522773.1        HFGANIRYHF
WP_016534444.1        HFGANIRYHF
WP_005755819.1        HFGANIRYHF
1121_PfhR_727aa       HFGANIRYHF
EGP05580.1            HFGANIRYHF
                      **********
```

FIG. 18-1.

```
1135_PM0300_964aa      MRTTTIKFSAITLALLSYCGVILADSHQEATELDTITVSSQQDEMNIKEKKVGETVKTAS
WP_005753642.1         MRTTTIKFSAITLALLSYCGVILADSHQEATELDTITVSSQQDEMNIKEKKVGETVKTAS
WP_016534557.1         MRTTTIKFSAITLALLSYCGAILADSHQEATELDTITVSSQQDEMNIKEKKVGETVKTAS
WP_010906573.1         MRTTTIKFSAITLALLSYCGAILADSHQEATELDTITVSSQQDEMNIKEKKVGETVKTAS
AAQ14873.1             MRTTTIKFSAITLALLSYCGVILADSHQEATELDTITVSSQQDEMNIKEKKVGETVKTAS
1121_HgbA_968aa        MRTTTIKFSAITLALLSYCGAILADSHQEATELDTITVSSQQDEMNIKEKKVGETVKTAS
                       ********************.***************************************

1135_PM0300_964aa      QLKRQQVQDSRDLVRYETGVTVVEAGRFGSSGYAIRGVDENRVAITVDGLHQAETLSSQG
WP_005753642.1         QLKRQQVQDSRDLVRYETGVTVVEAGRFGSSGYAIRGVDENRVAITVDGLHQAETLSSQG
WP_016534557.1         QLKRQQVQDSRDLVRYETGVTVVEAGRFGSSGYAIRGVDENRVAITVDGLHQAETLSSQG
WP_010906573.1         QLKRQQVQDSRDLVRYETGVTVVEAGRFGSSGYAIRGVDENRVAITVDGLHQAETLSSQG
AAQ14873.1             QLKRQQVQDSRDLVRYETGVTVVEAGRFGSSGYAIRGVDENRVAITVDGLHQAETLSSQG
1121_HgbA_968aa        QLKRQQVQDSRDLVRYETGVTVVEAGRFGSSGYAIRGVDENRVAITVDGLHQAETLSSQG
                       ************************************************************

1135_PM0300_964aa      FKELFEGYGNFNNTRNSVEIETLKVAKIAKGADSVKVGSGSLGGAVLFETKDARDFLTEK
WP_005753642.1         FKELFEGYGNFNNTRNSVEIETLKVAKIAKGADSVKVGSGSLGGAVLFETKDARDFLTEK
WP_016534557.1         FKELFEGYGNFNNTRNSVEIETLKVAKIAKGADSVKVGSGSLGGAVLFETKDARDFLTEK
WP_010906573.1         FKELFEGYGNFNNTRNSVEIETLKVAKIAKGADSVKVGSGSLGGAVLFETKDARDFLTEK
AAQ14873.1             FKELFEGYGNFNNTRNSVEIETLKVAKIAKGADSVKVGSGSLGGAVLFETKDARDFLTEK
1121_HgbA_968aa        FKELFEGYGNFNNTRNSVEIETLKVAKIAKGADSVKVGSGSLGGAVLFETKDARDFLTEK
                       ************************************************************

1135_PM0300_964aa      DWHIGYKAGYSTADNQGLNAVTLAGRYQMFDALIMHSKRHGHELENYDYKNGRDIQGKER
WP_005753642.1         DWHIGYKAGYSTADNQGLNAVTLAGRYQMFDALIMHSKRHGHELENYDYKNGRDIQGKER
WP_016534557.1         DWHIGYKAGYSTADNQGLNAVTLAGRYQMFDALIMHSKRHGHELENYDYKNGRDIQGKER
WP_010906573.1         DWHIGYKAGYSTADNQGLNAVTLAGRYQMFDALIMHSKRHGHELENYDYKNGRDIQGKER
AAQ14873.1             DWHIGYKAGYSTADNQGLNAVTLAGRYQMFDALIMHSKRHGHELEIYDYKNGRDIQGKER
1121_HgbA_968aa        DWHIGYKAGYSTADNQGLNAVTLAGRYQMFDALIMHSKRHGHELENYDYKNGRDIQGKER
                       ********************************************* **************

1135_PM0300_964aa      EKADPYTITKESTLVKFSFSPTENHRFTVASDTYIQRSRGHDRSYSLQPQSNYFTYDEKE
WP_005753642.1         EKADPYTITKESTLVKFSFSPTENHRFTVASDTYIQRSRGHDRSYSLQPQSNYFTYDEKE
WP_016534557.1         EKADPYTITKESTLVKFSFSPTENHRFTVASDTYIQRSRGHDRSYSLQPQSNYFTYDEKE
WP_010906573.1         EKADPYTITKESTLVKFSFSPTENHRFTVASDTYIQRSRGHDRSYSLQPQSNYFTYDEKE
AAQ14873.1             EKADPYTITKESTLVKFSFSPTENHRFTVASDTYLQHSRGHDLSYNLVA-TTYIQLDEKE
1121_HgbA_968aa        EKADPYTITKESTLVKFSFSPTENHRFTVASDTYLQHSRGHDLSYNLVA-TTHIQLDEKE
                       **********************************:*:***** **.*   :.::  ****

1135_PM0300_964aa      SRHANDLTKRKNVSFTYENYSVTPFWDTLKLSYSQQKIRTRARTEDYCDGNEKCDSYKNP
WP_005753642.1         SRHANDLTKRKNVSFTYENYSVTPFWDTLKLSYSQQKIRTRARTEDYCDGNEKCDSYKNP
WP_016534557.1         SRHANDLTKRKNVSFTYENYSVTPFWDTLKLSYSQQKIRTRARTEDYCDGNEKCDSYKNP
WP_010906573.1         SRHANDLTKRKNVSFTYENYSITPFWDTLKLSYSQQKIRTRARTEDYCDGNEKCDSYKNP
AAQ14873.1             SRHANDLTKRKNVSFTYENYTVTPFWDTLKLSYSQQRITTRARTEDYCDGNEKCDSYKNP
1121_HgbA_968aa        SRHANDLTKRKNVSFTYENYTVTPFWDTLKLSYSQQRITTRARTEDYCDGNEKCDSYKNP
                       ********************::**************:* *********************

1135_PM0300_964aa      LGLQLKDGKIVDPEGNQITLKGTGFNTEIVDKNGNPFPTTSGTNNAAFSNNIQLGPKEFW
WP_005753642.1         LGLQLKDGKIVDPEGNQITLKGTGFNTEIVDKNGNPFPTTSGTNNAAFSNNIQLGPKEFW
WP_016534557.1         LGLQLKDGKIVDPAGNQITLKGTGFNTEIVDKDGKPFPTTSGTNNAAFSNNLQLSPTGFW
WP_010906573.1         LGLQLKDGKIVDPAGNQITLKGTGFNTEIVDKDGKPFPTTSGTNNAAFSNNLQLSPTGFW
AAQ14873.1             LGLQLKEGKIVDRNGDPVNLQLVDGKHQVVDKAGKPFDVTSGTNYAAFSG-KQLGPSYFW
1121_HgbA_968aa        LGLQLKEGKIVDRNGDPVNLKLVDGKHQVVDKAGKPFDVASGTNYAAFSG-KELSPSSFW
                       ******:*****  *: :.*: .. : ::*** *:** .:**** ****.  :*.*. **
```

FIG. 18-2.

```
1135_PM0300_964aa     LDCSLFDCTQPFTVYNYQNGQYTPKQ--VELSEEITVNGKLYKTAKEERGVRNYLILPNS
WP_005753642.1        LDCSLFDCTQPFTVYNYQNGQYTPKQ--VELSEEITVNGKLYKTAKEERGVRNYLILPNS
WP_016534557.1        LDCTIFDCTKPFTVYNYKQNKYEPRE--VMLSEEITIDGKLYKTAKEESGVRNYLILPNS
WP_010906573.1        LDCTIFDCTKPFTVYNYKQNKYEPRE--VMLSEEITIDGKLYKTAKEESGVRNYLILPNS
AAQ14873.1            LECTVFDCSKPVTTYKYRYSTETPVKEDIQLNKTMEVNGKTFATYDM-GRERRYIILPNS
1121_HgbA_968aa       LDCSIFDCSKPINTYKYRYTSSEPTLQQITLNKTMEINGKTFATYDG---RGHYIILPNS
                      *:*::***::*...*:*:     *    : *.: : ::** : * .      .*:*****

1135_PM0300_964aa     KGYLPYDYKERDLDSNTKQINLDLTKTFSTFNIENELLYGAIYSRTEKKMVNKAGYDGRN
WP_005753642.1        KGYLPYDYKERDLDSNTKQINLDLTKTFSTFNIENELLYGAIYSRTEKKMVNKAGYDGRN
WP_016534557.1        KGYLPYDYKERDLDSNTKQINLDLTKTFSTFNIENELLYGAIYSRTEKKMVNKAGYDGRN
WP_010906573.1        KGYLPYDYKERDLDSNTKQINLDLTKTFSTFNIENELLYGAIYSRTEKKMVNKAGYDGRN
AAQ14873.1            QGYLPLDYKERDLNTKTKQINLDLTKAFTLFEIENELSYGGVYAKTTNGVVNKAGYYGRN
1121_HgbA_968aa       KGYLPLDYKERDLNTKTKQINLDLTKAFTLFEIENELSYGGVYAKTTKEMVNKAGYYGRN
                      :**** *******:::**********:*: *:***** **.:*::* : :****** ***

1135_PM0300_964aa     PTWWADRILGKST---------NCNYNGLKCPRHEPLTSFLIPVEATTKSLYFSDNIKLH
WP_005753642.1        PTWWADRILGKST---------NCNYNGLKCPRHEPLTSFLIPVEATTKSLYFSDNIKLH
WP_016534557.1        PTWWADRILGKST---------NCNYNGLKCPRHEPLTSFLIPVEATTKSLYFSDNIKLH
WP_010906573.1        PTWWADRILGKST---------NCNYNGLKCPRHEPLTSFLIPVEATTKSLYFSDNIKLH
AAQ14873.1            PTWWAERTLGQSWNGTLRECKTSSSYNGMLCPRHEPLTSFLIPVEATTKSLYFADNIKLH
1121_HgbA_968aa       PTWWAERTLGQSW-GKLRECKTSSSYNGMLCPRHEPLTSFLIPVEATTKSLYFADNIKLH
                      *****:* **:*          ...***: ***********************:******

1135_PM0300_964aa     NMLSVDLGYRYDDIKYQPEYIPGVTPKIADDMVKGIFIPLPKGEKVTTPWGAEYTKPLTQ
WP_005753642.1        NMLSVDLGYRYDDIKYQPEYIPGVTPKIADDMVKGIFIPLPKGEKVTTPWGAEYTKPLTQ
WP_016534557.1        NMLSVDLGYRYDDIKYQPEYIPGVTPKIADDMVKGIFIPLPKGEKIKIE-NYETTKPLTP
WP_010906573.1        NMLSVDLGYRYDDIKYQPEYIPGVTPKIADDMVKGIFIPLPKGEKIKIG-NYETTKPLTP
AAQ14873.1            NMLSVDLGYRYDDIKYQPEYIPGVTPKIADDMVKGLFIPLPEGEKVTVG-TVVFTKPLTP
1121_HgbA_968aa       NMLSVDLGYRYDDIKYQPEYIPGVTPKIADDMVKGLFIPLPEGEKVTVG-TMVFTKPLTQ
                      ***********************************:*****:***:.       *****

1135_PM0300_964aa     EQIRKNAEENIAYIAQEKRFKKHSYSLGATFDPLNFLRVQVKYSKGFRAPTSDELYFTFK
WP_005753642.1        EQIRKNAEENIAYIAQEKRFKKHSYSLGATFDPLNFLRVQVKYSKGFRAPTSDELYFTFK
WP_016534557.1        EQIRKNAEENIAYIAQEKRFKKHSYSLGATFDPLNFLRVQVKYSKGFRAPTSDELYFTFK
WP_010906573.1        EQIRKNAEENIAYIAQEKRFKKHSYSLGATFDPLNFLRVQVKYSKGFRAPTSDELYFTFK
AAQ14873.1            EQIRKNAEENIAYIAQGKRFKKHSYSLGTTFDPLNFLRVQVKYSKGFRAPTSDELYFTFK
1121_HgbA_968aa       AQIRKNAEENIAYIAQEKRFKKHSYSLGATFDPLNFLRVQVKYSKGFRAPTSDELYFTFK
                       *************** ***********:*******************************

1135_PM0300_964aa     HPDFTILPNPVLKPEEAKNQEIALTVHDNWGFVSTSVFQTKYRHFIDLAYLGSRNLSNSV
WP_005753642.1        HPDFTILPNPVLKPEEAKNQEIALTVHDNWGFVSTSVFQTKYRHFIDLAYLGSRNLSNSV
WP_016534557.1        HPDFTILPNPVLKPEEAKNQEIALTVHDNWGFVSTSVFQTKYRHFIDLAYLGSRNLSNSV
WP_010906573.1        HPDFTILPNPVLKPEEAKNQEIALTVHDNWGFVSTSVFQTKYRHFIDLAYLGSRNLSNSV
AAQ14873.1            HPDFTILPNPVLKPEEAKNQEIALTVHDNWGFVSTSVFQTKYRHFIDLAYLGSRNLSNSV
1121_HgbA_968aa       HPDFTILPNPVLKPEEAKNQEIALTVHDNWGFVSTSVFQTKYRHFIDLAYLGSRNLSNSV
                      ************************************************************

1135_PM0300_964aa     GGQAQARDFQVYQNVNVDNAKVKGLEINARLNLGYFWHVLDGFNTSYKFTYQCGRLDGDR
WP_005753642.1        GGQAQARDFQVYQNVNVDNAKVKGLEINARLNLGYFWHVLDGFNTSYKFTYQRGRLDGDR
WP_016534557.1        GGQAQARDFQVYQNVNVDNAKVKGLEINARLNLGYFWHVLDGFNTSYKFTYQRGRLDGDR
WP_010906573.1        GGKAQARDFQVYQNVNVDNAKVKGVEINARLNLGYFWHVLDGFNTSYKFTYQRGRLDGDR
AAQ14873.1            GGQAQARDFQVYQNVNVDNAKVKGLEINARLNLGYFWHVLDGFNTSYKFTYQRGRLDGDR
1121_HgbA_968aa       GGQAQARDFQVYQNVNVDNAKVKGLEINARLNLGYFWHVLDGFNTSYKFTYQRGRLDGDR
                      **:*********************:*************************** *******
```

FIG. 18-3.

```
1135_PM0300_964aa     PMNAIQPKASVFGLGYDHKENKFGADLYITRVSEKKAKDTYNMFYKEQGYKDSAIRWRSD
WP_005753642.1        PMNAIQPKASVFGLGYDHKENKFGADLYITRVSEKKAKDTYNMFYKEQGYKDSAIRWRSD
WP_016534557.1        PMNAIQPKASVFGLGYDHKENKFGADLYITRVSEKKAKDTYNMFYKEQGYKDSAIRWRSD
WP_010906573.1        PMNAIQPKASVFGLGYDHKENKFGADLYITRVSEKKAKDTYNMFYKEQGYKDSAIRWRSD
AAQ14873.1            PMNAIQPKASVFGLGYDHKENKFGADLYITRVSEKKAKDTYNMFYKEQGYKDSAIRWRSD
1121_HgbA_968aa       PMNAIQPKASVFGLGYDHKENKFGADLYITRVSEKKAKDTYNMFYKEQGYKDSAVRWRSD
                      ******************************************************:*****

1135_PM0300_964aa     DYTLVDAVGYIKPIKNLTLQFGVYNLTDRKYLTWESARSIKPFGTSNLINQKTGAGINRF
WP_005753642.1        DYTLVDAVGYIKPIKNLTLQFGVYNLTDRKYLTWESARSIKPFGTSNLINQKTGAGINRF
WP_016534557.1        DYTLVDAVGYIKPIKNLTLQFGVYNLTDRKYLTWESARSIKPFGTSNLINQKTGAGINRF
WP_010906573.1        DYTLIDAVGYIKPIKNLTLQFGVYNLTDRKYLTWESARSIKPFGTSNLINQKTGAGINRF
AAQ14873.1            DYTLVDAVGYIKPIKNLTLQFGVYNLTERKYLTWESARSIKPFGTSNLINQKTGAGINRF
1121_HgbA_968aa       DYTLVDAVGYIKPIKNLTLQFGVYNLTDRKYLTWESARSIKPFGTSNLINQKTGAGINRF
                      ****:**********************:********************************

1135_PM0300_964aa     YSPGRNFKFSAEITF
WP_005753642.1        YSPGRNFKFSAEITF
WP_016534557.1        YSPGRNFKFSAEITF
WP_010906573.1        YSPGRNFKLSAEITF
AAQ14873.1            YSPGRNFKFSAEITF
1121_HgbA_968aa       YSPGRNFKFSAEITF
                      ********:******
```

FIG. 19-1.

```
WP_017861186.1      MQKSQPYPIHLGIFLMLGLPTWAFSQANLEKSTINKLETILVNESEEKNKFDENLIKTYL
AAU29202.1          MQKQQPYPIHLGIFLMLGLPTWAFSQANLEKSTINKLETILVNESEEKNKFDENLIKTYL
EGP04511.1          MQKQQPYPIHLGIFLMLGLPTWAFSQANLEKSTINKLETILVNESEEKNKFDENLIKTYL
1135_HasR_848aa     MQKQQPYPIHLGIFLMLGLPTWAFSQANLEKSTINKLETILVNESEEKNKFDENLIKTYL
WP_005752163.1      MQKQQPYPIHLGIFLMLGLPTWAFSQANLEKSTINKLETILVNESEEKNKFDENLIKTYL
                    ***.********************************************************

WP_017861186.1      SSGSYSYLSQSDISTFRGSSVGDFLSGVPGVIVGNKRNSGALSVNIRGIANENRVPVWID
AAU29202.1          SSGSYSYLSQSDISTFRGSSVGDFLSGVPGVIVGNKRNSGALSVNIRGIANENRVPVWID
EGP04511.1          SSGSYSYLSQSDISTFRGSSVGDFLSGVPGVIVGNKRNSGALSVNIRGIANENRVPVWID
1135_HasR_848aa     SSGSYSYLSQSDISTFRGSSVGDFLSGVPGVIVGNKRNSGALSVNIRGIANENRVPVWID
WP_005752163.1      SSGSYSYLSQSDISTFRGSSVGDFLSGVPGVIAGNKRNSGALSVNIRGIANENRVPVWID
                    ********************************.***************************

WP_017861186.1      KGLQSVPSYQGYAGSSTRTYLDPDLISQVEIEKGPSLQMDATGATGGVVRVETLRWQDII
AAU29202.1          KGLQSVPSYQGYAGSSTRTYLDPDLISQVEIEKGPSLQMDATGATGGVVRVETLRWQDII
EGP04511.1          KGLQSVPSYQGYAGSSTRTYLDPDLISQVEIEKGPSLQMDATGATGGVVRVDTLRWQDII
1135_HasR_848aa     KGLQSVPSYQGYAGSSTRTYLDPDLISQVEIEKGPSLQMDATGATGGVVRVETLRWQDII
WP_005752163.1      KGLQSVPSYQGYAGSSTRTYLDPDLISQVEIEKGPSLQMDATGATGGVVRVETLRWQDII
                    ***************************************************:********

WP_017861186.1      PQGNKLGVRLKLGTMTNTVSPPPYYTRGGYQTKYISKCLSNHTGLCQTQTYAPNARYSSH
AAU29202.1          PQGKNWGVRLKLGTMANTVSPPPYYTRGGYQTKYISKCLSNHTGLCQTQTYAPNARYSSH
EGP04511.1          PQGKNWGVRLKLGTMTNTVSPPPYYTRGGYQTKYISKCLSNDTGLCQTQTYAPNARYSSH
1135_HasR_848aa     PQGKNWGVRLKLGTMTNTVSPPPYYTRGGYQTKYISKCLSNDTGLCQTQTYAPNARYSSH
WP_005752163.1      PQGKNWGVRLKLGTMTNTVSPPPYYTRGGYQTKYISKCLSNDTGLCQTQTYAPNARYSSH
                    ***:: *********:*************************.******************

WP_017861186.1      GFDLNAYNYSLAFANKWSNADLVLAYAKRKQGNYFVGRHGQTPVIESIEFEEDSVEVKEP
AAU29202.1          GFDLNAYNYSLAFANKWQNADLVLAYAKRKQGNYFVGRHGQTPVIESIEFEEDSVEVKEP
EGP04511.1          GFDLNAYNYSLAFANKWQNADLVLAYAKRKQGNYFVGRHGQTPVIESIKFEEDSVEVKEP
1135_HasR_848aa     GFDLNAYNYSLAFANKWQNADLVLAYAKRKQGNYFVGRHGQTPVIESIEFEEDSVEVKEP
WP_005752163.1      GFDLNAYNYSLAFANKWQNADLVLAYAKRKQGNYFVGRHGQTPVIESIEFEEDSVEVKEP
                    *****************.******************************:***********

WP_017861186.1      RVHEDVEIGSLTFKENRSTLYRPGEEALNTSQDNTSYLAKINVYNDVHRLGLAYRHYHSR
AAU29202.1          RVHEDVEIGSLTFKENRSTLYRPGEEALNTSQDNTSYLAKINVYNDVHRLGLAYRHYHSR
EGP04511.1          RVHEDVEIGSLTFKENRSTLYRPGEEALNTSQDNTSYLAKINVYNDVHRLGLAYRHYHSR
1135_HasR_848aa     RVHEEVEIGSLTFKENRSTLYRPGEEALNTSQDNTSYLAKINVYNDVHRLGLAYRHYHSR
WP_005752163.1      RVHEEVEIGSLTFKENRSTLYRPGEEALNTSQDNTSYLAKINVYNDVHRLGLAYRHYHSR
                    ****:*******************************************************

WP_017861186.1      FGEIMSSILNFRAYGALQGEGTEVKVDSYHANYSYNPTTPYVNLSVNAYFTDSDSSNFTP
AAU29202.1          FGEIMSSILNFRAYGALQGEGTEVKVDSYHANYSYNSTTPYVNLSVNAYFTDSDSSNFTP
EGP04511.1          FGEIMSSILNFRAYGALQGEGTEVKVDSYHANYSYNPTTPYVNLNVNAYFTDSDSSNFTP
1135_HasR_848aa     FGEIMSSILNFRAYGALQGEGTEVKVDSYHANYSYNPTTPYVNLNVNAYFTDSDSSNFTP
WP_005752163.1      FGEIMSSILNFRAYGALQGEGTEVKVDSYHANYSYNPTTPYVNLNVNAYFTDSDSSNFTP
                    ************************************ *******.***************

WP_017861186.1      FIEEYGYSLSSRHAHFLVSKQKGLSIENTSIFQLNDKPFTLKYGLAHSYERIYQPRNAQA
AAU29202.1          FIEEYGYSLSSRHAHFLVSKQKGLSIENTSIFQLNDKPFTLKYGLAHSYERIYQPRNAQA
EGP04511.1          FIEEYGYSLSSRHAHFLVSKQKGLSIENTSIFQLNDKPFTLKYGLAHSYERIYQPRNAQA
1135_HasR_848aa     FIEEYGYSLSSRHAHFLVSKQKGLSIENTSIFQLNDKPFSLKYGLAHSYERIYQPRNAQA
WP_005752163.1      FIEEYGYSLSSRHAHFLVSKQKGLSIENTSIFQLNDKPFTLKYGLAHSYERIYQPRNAQA
                    ***************************************:********************
```

FIG. 19-2.

```
WP_017861186.1       RVRAKGYPEDAIGPLYIRDGKRKEWSAFVAANYPITSWLKADIGLRYLQSTIYDYIVRTE
AAU29202.1           RVRAKGYPEDAIGPLYIRDGKRKEWSAFVAANYPITSWLKADIGLRYLQSTIYDYIVRTE
EGP04511.1           RVRAKGYPEDAIGPLYIRDGKRKEWSAFVAANYPINSWLKADIGLRYLQSTIYDYIVRTE
1135_HasR_848aa      RVRAKGYPEDAIGPLYIRDGKRKEWSAFVAANYPITSWLKADIGLRYLQSTIYDYIVRTE
WP_005752163.1       RVRAKGYPEDAIGPLYIRDGKRKEWSAFVAANYPITSWLKADIGLRYLQSTIYDYIVRTE
                     ***********************************.************************

WP_017861186.1       RVNIGGALVPNPNGSGNIWVEKYKDVVHKQAPVKNKGMSPIVMFTFEPINGVQIYTKYAE
AAU29202.1           RVNIGGALVPNPNGSGNIWVEKYKDVVHKQAPVKNKGMSPIVMFTFEPINGVQIYTKYAE
EGP04511.1           RVNIGGALVPNPNGPGNIWVEKYKDVVHKQAPVKNKGMSPIVMLTFEPINGVQIYTKYAE
1135_HasR_848aa      RVNIGGALVPNPNGSGNIWVEKYKDVVHKQAPVKNKGMSPIVMLTFEPINGVQIYTKYAE
WP_005752163.1       RVNIGGALVPNPNGSGNIWVEKYKDVVHKQAPVKNKGMSPIVMLTFEPINGVQIYTKYAE
                     ************** ****************************:****************

WP_017861186.1       ALRSPSLFQATKGWSMSATEDNLEQLRPERAKNWEAGINLFYENLGGKDNILGFKLAYFN
AAU29202.1           ALRSPSLFQATKGWSMSATADNLEQLRPERAKNWEAGINLFYENLGGKDNILGFKLAYFN
EGP04511.1           ALRSPSLFQATKGWSMSATADNLEQLRPERAKNWEAGINLFYENLGGKDNILGFKLAYFN
1135_HasR_848aa      ALRSPSLFQATKGWSMSATADNLEQLRPERAQNWEAGINLFYENLGGKDNILGFKLAYFN
WP_005752163.1       ALRSPSLFQATKGWSMSATADNLEQLRPERAKNWEAGINLFYENLGGKDNILGFKLAYFN
                     ******************* ***********:****************************

WP_017861186.1       NRIKDYLTRSYSPKDKVTQTINIQSAQFKGIELSAYYDMGKFYAKLAGTYYTKTKFCLTA
AAU29202.1           NRIKDYLTRSYSPKDKVTQTINIQSAQFKGIELSAYYDMGKFYAKLAGTYYTKTKFCLTA
EGP04511.1           NRIKDYLTRSYSPKDKVTQTINIQSAQFKGIELSAYYDMGKFYTKLAGTYYTKTKFCLTA
1135_HasR_848aa      NRIKDYLTRSYSPKDKVTQTINIQSAQFKGIELSAYYDMGKFYAKLAGTYYTKTKFCLTA
WP_005752163.1       NRIKDYLTRSYSPKDKVTQTINIQSAQFKGIELSAYYDMGKFYTKLAGTYYTKTKFCLTA
                     *******************************************:****************

WP_017861186.1       EQAGKGEQCNSGYVYRSNLNNAVPPRLNLHATLGTRLFEQKLDIGARYSYYSKRLVPVLS
AAU29202.1           EQAGKGEQCNSGYVYRSNLNNAVPPRLNLHATLGTRLFEQKLDIGARYSYYSKRLVPVLS
EGP04511.1           EQAGKGEQCNSGYVYRSNLNNAVPPRLNLHATLGTRLFEQKLDIGARYSYYSKRLVPVLS
1135_HasR_848aa      EQAGKGEQCNSGYVYRSNLNNAVPPRLNLHATLGTRLFEQKLDIGARYSYYSKRLVPVLS
WP_005752163.1       EQAGKGEQCNSGYVYRSNLNNAVPPRLNLHATLGTRLFEQKLDIGARYSYYSKRLVPVLS
                     ************************************************************

WP_017861186.1       AERFVNTSSIEWAPYSLVDLYANYNVSNNLKLTMTMDNVFNRYYLDINNMGLNTAPGRTL
AAU29202.1           AERFVNTSSIEWAPYSLVDLYANYNVSNNLKLTMTMDNVFNRYYLDINNTGLNTAPGRTL
EGP04511.1           AERFVNTSSIEWAPYSLVDLYANYNVSNNLKLTMTMDNVFNRYYLDINNMGLNTAPGRTL
1135_HasR_848aa      AERFVNTSSIEWAPYSLVDLYANYNVSNNLKLTMTMDNVFNRYYLDINNMGLNTAPGRTL
WP_005752163.1       AERFVNTSSIEWAPYSLVDLYANYNVSNNLKLTMTMDNVFNRYYLDINNMGLNTAPGRTL
                     ************************************************* **********

WP_017861186.1       HLGLEYRF
AAU29202.1           HLGLEYRF
EGP04511.1           HLGLEYRF
1135_HasR_848aa      HLGLEYRF
WP_005752163.1       HLGLEYRF
                     ********
```

FIG. 20-1.

```
WP_005751557.1          MKYPLSYKNIARSIPFLSFIAFPLYAQETTELEQITVQESATAEVNKTSPTVISKSATTI
1135_PM0741_784aa       MKYPLSYKNIARSIPFLSFIAFPLYAQETTELEQITVQESATAEVNKTSPTVISKSATTI
WP_016534554.1          MKYPLSYKNIARSIPFLSFIAFPLYAQETTELEQITVQESATAEVNKTSPTVISKSATTI
WP_064972816.1          MKYPLSYKNIARSIPFLSFIAFPLYAQETTELEQITVQESATAEVNKTSPTVISKSATTI
WP_074865020.1          MKYPLSYKNIARSIPFLSFIAFPLYAQETTELEQITVQESATAEVNKTSPTVISKSATTI
                        ************************************************************

WP_005751557.1          QNKMIRDTRDLVRYTTDVGISDNGRFLKGFAMRGVEDNRVGISIDGVSLPDSEENSLYAR
1135_PM0741_784aa       QNEMIRDTRDLVRYTTDVGISDNGRFLKGFAMRGVEDNRVGISIDGVSLPDSEENSLYAR
WP_016534554.1          QNEMIRDTRDLVRYTTDVGISDNGRFLKGFAMRGVEDNRVGISIDDVSLPDSEENSLYAR
WP_064972816.1          QNEMIRDTRDLVRYTTDVGISDNGRFLKGFAMRGVEDNRVGISIDGVSLPDSEENSLYAR
WP_074865020.1          QNEMIRDTRDLVRYTTDVGISDNGRFLKGFAMRGVEDNRVGISIDGVSLPDSEENSLYAR
                        **:******************************************.**************

WP_005751557.1          YGNFNNSRLSIDPELIQTIDIVRGSDSFNAGSGSLGGGVNYNTLDPQHIVKAGNSVGALL
1135_PM0741_784aa       YGNFNNSRLSIDPELIQTIDIVRGSDSFNAGSGSLGGGVNYNTLDPQHIVKTGNSVGALL
WP_016534554.1          YGNFNNSRLSIDPELIQTIDIVRGSDSFNAGSGSLGGGVNYNTLDPQHIVKAGNSVGALL
WP_064972816.1          YGNFNNSRLSIDPELIQTIDIVRGSDSFNAGSGSLGGGVNYNTLDPQHIVKAGNSVGALL
WP_074865020.1          YGNFNNSRLSIDPELIQTIDIVRGSDSFNAGSGSLGGGVNYNTLDPQHIVKAGNSVGALL
                        ***************************************************:********

WP_005751557.1          RGSYASKNREWVRTLGIGYVGEKFDALLMYSQRTGHEFKSRGSGPEFRYSSSQHPDPVTQ
1135_PM0741_784aa       RGSYASKNREWVRTLGIGYVGEKFDALLMYSQRTGHEFKSRGSGPEFRYSSSQHPDPVTQ
WP_016534554.1          RGSYASKNREWVRTLGIGYVGEKFDALLMYSQRTGHEFKSRGSGPEFRYSSSQHPDPVTQ
WP_064972816.1          RGSYASKNREWVRTLGIGYVGEKFDALLMYSQRTGHEFKSRGSGPEFRYSSSQHPDPVTQ
WP_074865020.1          RGSYASKNREWVRTLGIGYVGEKFDALLMYSQRTGHEFKSRGSGPEFRYSSSQHPDPVTQ
                        ************************************************************

WP_005751557.1          RFHNYLAKMNYQINDNQRIGLTLNGQTGGRYIDERSYTLMGSQWREADDQNERLNANLYY
1135_PM0741_784aa       RFHNYLAKMNYQINDKQRIGLTLNGQTGGRYIDERSYTLMGSQWREADDQNERLNANLYY
WP_016534554.1          RFHNYLAKMNYQINDNQRIGLTLNGQTGGRYIDERSYTLMGSQWREADDQNERLNANLYY
WP_064972816.1          RFHNYLAKMNYQINDKQRIGLTLNGQTGGRYIDERSYTLMGSQWREADDQNERLNANLYY
WP_074865020.1          RFHNYLAKMNYQINDNQRIGLTLNGQTGGRYIDERSYTLMGSQWREADDQNERLNANLYY
                        ***************:********************************************

WP_005751557.1          IYAPSTGWLAYSKFDLDYQKTDLAAVNYKGGRHFTTDAKELNEIYDRRMKTVFTRGSVEL
1135_PM0741_784aa       IYAPSTGWLAYSKFDLDYQKTDLAAVNYKGGRHFTTDAKELNEIYDRRMKTVFTRGSVEL
WP_016534554.1          IYAPSTGWLAYSKFDLDYQKTDLAAVNYKGGRHFTTDAKELNEIYDRRMKTVFTRGSVEL
WP_064972816.1          IYAPSTGWLAYSKFDLDYQKTDLAAVNYKGGRHFTTDAKELNEIYDRRMKTVFTRGSVEL
WP_074865020.1          IYAPSTGWLAYSKFDLDYQKTDLAAVNYKGGRHFTTDAKELNEIYDRRMKTVFTRGSVEL
                        ************************************************************

WP_005751557.1          NAQPVHFYGEHTLTIKGYVSQRDFKNINQDRIGIGTNYDTQYHYTIQYPIRTKQYGLSLK
1135_PM0741_784aa       NAQPVHFYGEHTLTIKGYVSQRDFKNINQDRIGIGTNYDTQYHYTIQYPIRTKQYGLSLK
WP_016534554.1          NAQPVHFYGEHTLTIKGYVSQRDFKNINQDRIGIGTNYDTQYHYTIQYPIRTKQYGLSLK
WP_064972816.1          NAQPVHFYGEHTLTIKGYVSQRDFKNINQDRIGIGTNYDTQYHYTIQYPIRTKQYGLSLK
WP_074865020.1          NAQPVHFYGEHTLTIKGYVSQRDFKNINQDRIGIGTNYDTQYHYTIQYPIRTKQYGLSLK
                        ************************************************************

WP_005751557.1          DHVRWNDTFSSHLGLRYDHTKLKPKELNAPCSKACLEEGKPKPTRFSTVSTFAGLEAQLS
1135_PM0741_784aa       DHVRWNDTFSSHLGLRYDHTKLKPKELNAPCSKACLEEGKPKPTRFSTVSTFAGFEAQLS
WP_016534554.1          DHVRWNDTFSSHLGLRYDHTKLKPKELNAPCSNACLEEGKPKPTRFSTVSTFAGLEAQLS
WP_064972816.1          DHVRWNDTFSSHLGLRYDHTKLKPKELNAPCSKACLEEGKPKPTRFSTVSTFAGFEAQLS
WP_074865020.1          DHVRWNDTFSSHLGLRYDHTKLKPKELNAPCSKACLEEGKPKPTRFSTVSTFAGLEAQLS
                        ********************************:*********************:*****

WP_005751557.1          PSWMLGYNISTGYRVPTASEMFFSFTNAYGTWKSNPSLKPEKSINHTLSLKGNSEKGLLD
1135_PM0741_784aa       PSWMLGYNISTGYRVPTASEMFFSFTNAYGTWKSNPSLKPEKSINHTLSLKGNSEKGLLD
WP_016534554.1          PSWMLGYNISTGYRVPTASEMFFSFTNAYGTWKSNPSLKPEKSINHTLSLKGNSEKGLLD
WP_064972816.1          PSWMLGYNISTGYRVPTASEMFFSFTNAYGTWKSNPSLKPEKSINHTLSLKGNSEKGLLD
WP_074865020.1          PSWMLGYNISTGYRVPTASEMFFSFTNAYGTWKSNPSLKPEKSINHTLSLKGNSEKGLLD
                        ************************************************************
```

FIG. 20-2.

```
WP_005751557.1          LTLYQTNYRHFLFEQESLIQRTEIRYGQPYTYQSQEQQMVNLDKAKIYGVELKTHVNLDQ
1135_PM0741_784aa       LTLYQTNYRHFLFEQESLIQRTEMRYGRPYTYQSQEQQMVNLDKAKIYGVELKTHVNLDQ
WP_016534554.1          LTLYQTNYRHFLFEQESLIQRTEMRYGRPYTYQSQEQQMVNLDKAKIYGVELKTHVNLDQ
WP_064972816.1          LTLYQTNYRHFLFEQESLIQRTEMRYGRPYTYQSQEQQMVNLDKAKIYGVELKTHVNLDQ
WP_074865020.1          LTLYQTNYRHFLFEQESLIQRTEMRYGRPYTYQSQEQQMVNLDKAKIYGVELKTHVNLDQ
                        ***********************:***:********************************

WP_005751557.1          MIAVIPQGFKFYAALGYSKGKLSNNASLLSIQPLKIILGLDYEATNGKWAIFNRLTYLGE
1135_PM0741_784aa       MIAVIPQGFKFYAALGYSKGKLSNNASLLSIQPLKIILGLDYEATNGKWAIFNRLTYLGE
WP_016534554.1          MIAVIPQGFKFYAALGYSKGKLSNNASLLSIQPLKIILGLDYEATNGKWAIFNRLTYLGE
WP_064972816.1          MIAVIPQGFKFYAALGYSKGKLSNNASLLSIQPLKIILGLDYEATNGKWAIFNRLTYLGE
WP_074865020.1          MIAVIPQGFKFYAALGYSKGKLSNNASLLSIQPLKIILGLDYEATNGKWAIFNRLTYLGE
                        ************************************************************

WP_005751557.1          KRASDAKVYEIKRRCTEFVTETDPWSGEQITHCKKRELYPDLSTYKYLNKSAFVFDTFGY
1135_PM0741_784aa       KRASDAKVYEIKRRCTEFVTETDPWTGQQITRCKKRELYPDLSTYKHLNKSAFVFDTFGY
WP_016534554.1          KRASDAKVYEIKRRCTEFVTETDPWSGEQITRCKKRELYPDLSTYKHLNKSAFVFDTFGY
WP_064972816.1          KRASDAKVYEIKRRCTEFVTETDPWSGEQITRCKKRELYPDLSTYKHLNKSAFVFDTFGY
WP_074865020.1          KRASDAKVYEIKRRCTEFVTETDPWSGEQITRCKKRELYPDLSTYKHLNKSAFVFDTFGY
                        *************************:*:***:**************:*************

WP_005751557.1          YKITDDITFRAGIYNLFNKKYHTWDALRGINANSTLNSVDREGKGLQRFYAPGRNYAASL
1135_PM0741_784aa       YKITDDITFRAGIYNLFNKKYHTWDALRGINANSTLNSVDREGKGLQRFYAPGRNYAASL
WP_016534554.1          YKITDDITFRAGIYNLFNKKYHTWDALRGINANSTLNSVDREGKGLQRFYAPGRNYAASL
WP_064972816.1          YKITDDITFRAGIYNLFNKKYHTWDALRGINANSTLNSVDREGKGLQRFYAPGRNYAASL
WP_074865020.1          YKITDDITFRAGIYNLFNKKYHTWDALRGINANSTLNSVDREGKGLQRFYAPGRNYAASL
                        ************************************************************

WP_005751557.1          EIRF
1135_PM0741_784aa       EIRF
WP_016534554.1          EIRF
WP_064972816.1          EIRF
WP_074865020.1          EIRF
                        ****
```

FIG. 21-1.

```
WP_050948957.1                -MNIIINKRIFLLVTFVGIQLNVTAKQNSSNSNREELLPIIVNTDEDSNKLPGRSVLKQK
WP_014391043.1                MDKNLMKGCVFLLIVGCGIQIGLA--SNPNPPDVDELLPIIVNADED-NKLPGRSVLKQK
WP_016533738.1                MDKNLMKGCVFLSIVGCGIQIGLA--SNPNPPDVDELLPIIVNADED-NKLPGRSVLKQK
1135_P1062_0207600_742aa      MDKNLMKGCVFLSIVGCGIQIGLA--SNPNPPDVDELLPIIVNADED-NKLPGRSVLKQK
WP_025248456.1                MDKNLMKGCVFLSIVGCGIQIGLA--SNPNPPDVDELLPIIVNADED-NKLPGRSVLKQK
                                : :::  :** :.  ***:.::  .* .  : :********:*** ************

WP_050948957.1                NIEQQQADNAANLINILPGVNMAGGFRPGGQTLNINGMGDAEDVRVQLDGATKSFEKYQQ
WP_014391043.1                NIDQQQADNAADLINILPGVNMAGGFRPGGQTLNINGMGDAEDVRVQLDGATKSFEKYQQ
WP_016533738.1                NIDQQQADNAADLINILPGVNMAGGFRPGGQTLNINGMGDAEDVRVQLDGATKSFEKYQQ
1135_P1062_0207600_742aa      NIDQQQADNAADLINILPGVNMAGGFRPSGQTLNINGMGDAEDVRVQLDGATKSFEKYQQ
WP_025248456.1                NIDQQQADNAADLINILPGVNMAGGFRPGGQTLNINGMGDAEDVRVQLDGATKSFEKYQQ
                              **:********:****************.*******************************

WP_050948957.1                GSIFIEPELLRKVTVDKGNYSPQYGNGGFAGTVKFETRDARDFLKENQKIGGLLKYGNNS
WP_014391043.1                GSIFIEPELLRKVTVDKGNYSPQYGNGSFAGTVKFETKDATDFLKENQKIGGLFKYGNNS
WP_016533738.1                GSIFIEPELLRKVTVDKGNYSPQYGNGGFAGTVKFETKDATDFLKENQKIGGLFKYGNNS
1135_P1062_0207600_742aa      GSIFIEPELLRKVTVDKGNYSPQYGNGGFAGTVKFETKDATDFLKENQKIGGLFKYGNNS
WP_025248456.1                GSIFIEPELLRKVTVDKGNYSPQYGNGGFAGTVKFETKDATDFLKENQKIGGLFKYGNNS
                              ***************************.*********:** ************:******

WP_050948957.1                NNNQKTYSTALVLQNEQKNIDLLLFGSVRNAGDYKRPDNSKILFSKNNQKTGLIKVNWQI
WP_014391043.1                NNNQKTYSTALVLQNEQKNIDLLLFGSVRNASNYTRPDKSKILFSKNNQKSGLIKVNWQI
WP_016533738.1                NNNQKTYSTALVLQNEQKNIDLLLFGSVRNASNYTRPDKSKILFSKNNQKSGLIKVNWQI
1135_P1062_0207600_742aa      NNNQKTYSTALVLQNEQKNIDLLLFGSVRNASNYTRPDKSKILFSKNNQKSGLIKVNWQI
WP_025248456.1                NNNQKTYSTALVLQNEQKNIDLLLFGSVRNASNYTRPDKSKILFSKNNQKSGLIKVNWQI
                              *******************************.:*.***:***********:*********

WP_050948957.1                TPEHLLTLSSVYGIHKGWEPWAAKRDVTSRPTETEIKRYGIDVAWKRKLVYRDQKDESYS
WP_014391043.1                TPEHLLTLSSVYGIHKGWEPWAAKRDVMSRPTEKEIKRYGIDVAWKRKLVYRDQKDESYS
WP_016533738.1                TPEHLLTLSSVYGIHKGWEPWAAKRDVMSRPTETEIKRYGIDVAWKRKLVYRDQKDESYS
1135_P1062_0207600_742aa      TPEHLLTLSSVYGIHKGWEPWAAKRDVMSRPTETEIKHYGIDVAWKRKLVYRDQKDESYS
WP_025248456.1                TPEHLLTLSSVYGIHKGWEPWAAKRDVMSRPTETEIKHYGIDVAWKRKLVYRDQKDESYS
                              *************************** *****.***:**********************

WP_050948957.1                LKYRYLPENNKWINLSVQLSYSKTEQNDTRHEKVTSSFLGTLGNKSWITYSDLTFDISNT
WP_014391043.1                LKYRYLPENNKWINLSVQLSYSKTEQNDTRHEKVTSSFLGTLGNKSWITYSDLTFDISNT
WP_016533738.1                LKYRYLPENNKWINLSVQLSYSKTEQNDTRHEKVTSSFLGTLGNKSWITYSDLTFDISNT
1135_P1062_0207600_742aa      LKYRYLPENNKWINLSVQLSYSKTEQNDTRHEKVTSSFLGTLGNKSWITYSDLTFDISNT
WP_025248456.1                LKYRYLPENNKWINLSVQLSYSKTEQNDTRHEKVTSSFLGTLGNKSWITYSDLTFDISNT
                              ************************************************************

WP_050948957.1                STLNIGRAEHELLFGLQWLKNTRNTLMYHKGKMNDKTYNYGYFQPYYMPSGRQYTQAFYL
WP_014391043.1                STLNIGRAEHELLFGLQWLKNKRNTLMYHKEGVKKADYNYGYFQPYYMPSGRQYTQAFYL
WP_016533738.1                STLNIGRAEHELLFGLQWLKNKRNTLMYHKEGVKKADYNYGYFQPYYMPSGRQYTHAFYL
1135_P1062_0207600_742aa      STLNIGRAEHELLFGLQWLKNKRNTLMYHKGGVKKADYNYGYFQPYYMPSGRQYTQAFYL
WP_025248456.1                STLNIGRAEHELLFGLQWLKNKRNTLMYHKGGVKKADYNYGYFQPYYMPSGRQYTQAFYL
                              *********************.********  ::.  ******************:****

WP_050948957.1                QDQIKWKNIIFSTGARYDHINNIGQKNLAPQYNDISAGHNYSQKNYNGWSYYLGLKYDVN
WP_014391043.1                QDQIKWQNFLFTGGIRYDHINNIGQKNLAPRYNDISAGHDYSQKNYNGWSYYLGLKYDVN
WP_016533738.1                QDQIKWQNFLFTGGIRYDHINNIGQKNLAPRYNDISAGHDYSQKNYNGWSYYLGLKYDVN
1135_P1062_0207600_742aa      QDQIKWQNFLFTGGIRYDHINNIGQKNLAPRYNDISAGHDYSQKNYNGWSYYLGLKYDVN
WP_025248456.1                QDQIKWQNFLFTGGIRYDHINNIGQKNLAPRYNDISAGHDYSQKNYNGWSYYLGLKYDVN
                              ******:*::*: * ***************:********:********************

WP_050948957.1                HYLSLFTNFSRTWRAPVIDEQYETQYSKASVPATSLNLEKEMISQTRGGGIVTLNNLFQE
WP_014391043.1                HYLSLFTNFSKTWRAPVIDEQYETQYSQASVSATSLNLEKEMINQTRVGGIITLNHLFQE
WP_016533738.1                HYLSLFTNFSKTWRAPVIDEQYETQYSQASVSATSLNLEKEMINQTRVGGIITLNHLFQE
1135_P1062_0207600_742aa      HYLSLFTNFSKTWRAPVIDEQYETQYSQASVSATSLNLEKEMINQTRVGGIITLNHLFQE
WP_025248456.1                HYLSLFTNFSKTWRAPVIDEQYETQYSRASVSATSLNLEKEMINQTRVGGIITLNHLFQE
                              **********:****************:*** ***********.*** ***:***:****
```

FIG. 21-2.

```
WP_050948957.1              DDTFQFRATYFYHRGKNEIFKTRGVNCVGNALDVDNKICPKIISNYRNLPGYVIQGAELE
WP_014391043.1              NDAFQFRTTYFYNRGKNEIFKTRGVNCVENALDVDNSVCPKIISNYRNLPGYVIQGAELE
WP_016533738.1              NDAFQFRTTYFYNRGKNEIFKTRGVNCVENALDVDNSVCPKIISNYRNLPGYVIQGAELE
1135_P1062_0207600_742aa    NDAFQFRTTYFYNRGKNEIFKTRGVNCVENALDVDNSVCPKIISNYRNLPGYVIQGAELE
WP_025248456.1              NDAFQFRTTYFYNRGKNEIFKTRGVNCVENALDVDNSVCPKIISNYRNLPGYVIQGAELE
                            :*:****:****:*************** *******.:**********************

WP_050948957.1              AYYQSTYLFGELTYSYVKGKRDTSPRNPWGKTSTWIAEIPPRKATATLGFNVPKYYLTVG
WP_014391043.1              AYYQSSYLFGGLTYSYVKGKRDTSPRNPWSKTSTWIAETPPRKATATLGFNIPEYYFTAG
WP_016533738.1              AYYQSSYLFGGLTYSYVKGKRDTSPRNPWSKTSTWIAETPPRKATATLGFNIPEYYFTAG
1135_P1062_0207600_742aa    AYYQSSYLFGGLTYSYVKGKRDTSPRNPWSKTSTWIAETSPRKAIATLGFNIPEYYFTAG
WP_025248456.1              AYYQSSYLFGGLTYSYVKGKRDTSPRNPWSKTSTWIAETPPRKATATLGFNIPEYYFTAG
                            *****:**** ******************.********  **** ******:*:**:*.*

WP_050948957.1              WRAEFVRRQDRSPSSRDPKASYYLSLPASRGYSLHNLFLSWTPEKIKGMNIKITVDNLFN
WP_014391043.1              WRAEFVRKQDRSPLSNDSKASYW-ALPSSKGYSLHSVFFSWSPTKIKGMNFKVTVDNLFN
WP_016533738.1              WRAEFVRKQDRSPLSNDSKASYW-ALPSSKGYSLHSVFFSWSPTKIKGMNFKVTVDNLFN
1135_P1062_0207600_742aa    WRAEFVRKQDRSPLSNDSKASYW-ALPSSKGYSLHSVFFSWSPTKIKGMNFKVTVDNLFN
WP_025248456.1              WRAEFVRKQDRSPLSNDSKASYW-ALPSSKGYSLHSVFFSWSPTKIKGMNFKVTVDNLFN
                            *******:***** *.* ****: :**:*:*****.:*:**:* ******:*:*******

WP_050948957.1              RAYNPYLGELASGTGRNIKFSLSQKF
WP_014391043.1              RPYYPYLGELASGTGRNVKFSLTQQF
WP_016533738.1              RPYYPYLGELASGTGRNVKFSLTQQF
1135_P1062_0207600_742aa    RPYYPYLGELASGTGRNVKFSLTQQF
WP_025248456.1              RPYYPYLGELASGTGRNVKFSLTQQF
                            * * *************:****:*:*
```

FIG. 22-1.

SEQ ID NO:43

ATGATTTCAAGAGGTTGTAAAGTAAATAAATTTTTTGCTGTTTTGATGATGTGTTGCATTCCGCA
AGTAGTTTGGGCAAATACAGAAAAGAAGCAAATTGTTTTTTTAGATGAAATTAGTGTGGAGTCGA
AAGGTGCTGCTTTTCGTAGCGATCCCCTTTCCGGCTTACCAAAACAAAATGACATTTTAGTCAGT
AAGCAAAAATTAAAAACAGGATCCAGTACATTAGGTAATGCGTTAGCGGGTGAACTCAGTGTACA
TAGTAATCAATTTGGTGGTGGATCCAGTGCACCTGTCGTTCGAGGACAGGAAGGCGTGCGTTTAA
AAATCTTACAAAATGGTTCTGATGTCATTGATATGTCTCAACTTTCTCCTGACCATGCGATTGGT
GTCGATACGTTATTGGCAGAGCAAGTCGAAATTGTACGTGGTGCCTCAACATTGTTATATGCCAA
TGCGTCACCTGCTGGTGTGATTAATGTAGTAGATAAACGCATTCCAACACAGCTTCCTCAAAAGG
GCTATGAAGTGGATTTCAACACGCGTTATAACACGAATAGTCATGAAAAATTGGTAACGGCTGCA
CTGACTTTCGGGTTAGGTAAGCACATTGCTTTACGGGTAGAAGAACTGTTACGTGGCTCAAATAA
TTACCATGTGCCAGCATTTAAGCTAGACAAAACATTAAATTATGTCCCCGATACTCAAAATAAAA
CGAAGTCAGGTAACTATGGTGTGGCTTTTATCGGTGAGCGAGGTTATGTCGGTTTTGCCTACAAT
CTTCGTCGTGAGAAATATGGGTTACCGGGACATAACCATAAGCTAGATAGTTGTGCTGCGCATAT
TTGGGGTGGCAATGTACGTAATGACTATTATTTAGGGCTTTATCCTCATTTAATGCATGATACGG
ATCTAGTAAATACGCATTTCCATTGTGGATCAAATCATGACATGGATGGAAAACACAGTCATGAT
CATCCGTACGGTCACGATCATGACCATTCTATTGCCGGTCCATTGATTGATTCTTATGCTAAACG
TTATGACATACGTGCTGAAGTCAAACAGCCGATGAAAGCGATTGAGAAAATCAAACTCAGTTATT
CGGAAACCCGTTATAAACACGATGAAAAAGATGGCAATATCGCCGTGAATTTATTTAAAAATAAC
GGATATAACCTGCGCGTAGAAATTTTCCATACGCCCATAGCGGGGTTGAGTGGCGTTATAGGGGC
GCAGTATCAAACACAAACCAGCAGTGCGAATATTCCGCGTATTGCACCATGCTCAAATAATGCAA
GCGATCCTTGTCATAAGAAAAAGCAACGCGATCCGTCCAAAATCACTAAGGGTGATCGTAAGTCA
TGGGCATTGATTGAAAATACTCAATCACAAATGAGTTTTTTTGCTATAGAACAATTGCGTTGGCA
AGATTTTTTATTTGAAATTGGTGTACGTACGGAAAAACAACGCATTGATATTGAATATGATCGCG
CTTGGCTGTTTAAAGTAAAGCGAAAGCTAGAAGGCTGTGATCCGAATTCGTTCTTTTATAGCCCA
TCAGGATGTCGTCAAGGCAGTTATCCAGCACCTGATTTTGCCTCTTATCATGATCGCGCGACCTC
TTATTCTGGTGCTATCAGTTGGAATATGACGCCTGACTACACCCTTTCTTTGACTTACTCACATA
ACGAACGTCACCCAACACCGATGGAATTGTATTACCACGGCAAACATTTAGCGACGGTGTCATTT
GAACATGGCAATCGTAATCTGAAAAAAGAAGTTTCTGATAACTGGGAAGTCGGTCTTGCGTATCT
TGGTGACAAGCTAAGTTATAAAGTGAATGTATATTACAATGATTTTAAAAATCGGATTTTTAATC

FIG. 22-2.

AAACATTGAACAAATCCGGTAATTTATCTTTGAATCGTTATAATCAATCCAAAGCGAAATATTAT
GGTGTGGAAGGGCGTATTGACTATGCGTTGACACCTGAACTGCACATGGGACTTTTTGGTGATTA
TGTGCGTGGAAAACTGTATGATTTACCGCCAACGTACCGTGTCGATCATGTGGCGAATAGCTTAG
AACCCGTTCCTCAACCTGATCAAGACGCACCACGTGTCCCGCCAATGCGTTTAGGCTTTCGTGTG
AATATGGAGATGACTGAGAGTTTAACAAGTTCACTCGAATACACTTACGTTTATCAACAAAAGAA
AGTAGCGCCGTTAGAAAATCAAACGGCTGCATATAGTTTATTAAATATCGGAGTGGATTATTCAC
GCCAAATAGCTGGGGTAAATTATCAATTATTTGTTCAAGCAAATAATGTGTTAAACCGTAAAGTT
TATTCTCATACTTCTTTTTTACCCTTTGTACCGCAGATGGGGCGTAATGTGACTTTAGGATTAAA
CATCCATTTCTAA

SEQ ID NO:44

MISRGCKVNKFFAVLMMCCIPQVVWANTEKKQIVFLDEISVESKGAAFRSDPLSGLPKQNDILVS
KQKLKTGSSTLGNALAGELSVHSNQFGGGSSAPVVRGQEGVRLKILQNGSDVIDMSQLSPDHAIG
VDTLLAEQVEIVRGASTLLYANASPAGVINVVDKRIPTQLPQKGYEVDFNTRYNTNSHEKLVTAA
LTFGLGKHIALRVEELLRGSNNYHVPAFKLDKTLNYVPDTQNKTKSGNYGVAFIGERGYVGFAYN
LRREKYGLPGHNHKLDSCAAHIWGGNVRNDYYLGLYPHLMHDTDLVNTHFHCGSNHDMDGKHSHD
HPYGHDHDHSIAGPLIDSYAKRYDIRAEVKQPMKAIEKIKLSYSETRYKHDEKDGNIAVNLFKNN
GYNLRVEIFHTPIAGLSGVIGAQYQTQTSSANIPRIAPCSNNASDPCHKKKQRDPSKITKGDRKS
WALIENTQSQMSFFAIEQLRWQDFLFEIGVRTEKQRIDIEYDRAWLFKVKRKLEGCDPNSFFYSP
SGCRQGSYPAPDFASYHDRATSYSGAISWNMTPDYTLSLTYSHNERHPTPMELYYHGKHLATVSF
EHGNRNLKKEVSDNWEVGLAYLGDKLSYKVNVYYNDFKNRIFNQTLNKSGNLSLNRYNQSKAKYY
GVEGRIDYALTPELHMGLFGDYVRGKLYDLPPTYRVDHVANSLEPVPQPDQDAPRVPPMRLGFRV
NMEMTESLTSSLEYTYVYQQKKVAPLENQTAAYSLLNIGVDYSRQIAGVNYQLFVQANNVLNRKV
YSHTSFLPFVPQMGRNVTLGLNIHF

FIG. 25.

```
ZAP                1   --------------SKRRDNYGLPGHNHKFDFCTGHIYGNK-RD---KYAYTYLYPHLIG   42
AHG81836.1         239 LSFVGEQGYIGASYSKRRDNYGLPGHNHKFDFCTGHIYGNK-RD---KYAYTYLYPHLIG  294
WP_005612269.1     231 LSFVGEQGYIGASYSKRRDNYGLPGHNHKFDFCIGHIYGNK-QG---KYAYTYLYPHLIG  286
WP_027074597.1     242 ISFIGERGYIGAAYSHRKDTYGLPGHNHKFDFCTGHIYGVD-RD---KHAHTYLYPHLLT  297
AHG73391.1         242 LSFVGERGYIGAAYNERTDTYGLPGHNHKFDECIGHIYNEV-RD---KYAYTYKYPHLLD  297
WP_021114857.1     252 LSFIGEKGYLGASYNQRKDRYGLPGHNHKFDTCIAHIYDMRLQG---KHSYTNLYPHLMS  308
WP_026212957.1     232 LSYIGNQGHIGLAYSERRDKYGLVGHNHKFDNCEGHAFNTSRGLWGPERRYLIPYPHLMS  291
WP_028858792.1     274 LSYVGERGHIGVAYSEREDKYGLVGHNHKLDGCYGHVVYPQKNY--KNKPYLAAYPHLMG  331
WP_016534590.1     246 VAFIGERGYVGFAYNLRREKYGLPGHNHKLDSCAAHIWGGNVRN---DY-YLELYPHLMH  301
KDN24548.1         246 VSYIGDKGHIGVSYSRRQDKYGIPGHNHAYDNCIAHVLTPEAS---ISRYYLKAYPHLIQ  302
WP_027021676.1     249 VSWVGQNGHLGVSYSHRKDRYGLPGHNHMLDNCSGHVFDVTTAS-AVKRNYLLPYPHLIG  307
                                      . * : **: ****  * * .*           .  :   ****:

ZAP                43  EENIGSNPHFHCGTNHAEDGTHSHDNPFGHAHDHTHKGPWVDLES---------------   87
AHG81836.1         295 EENIGSNPHFHCGTNHAEDGTHSHDNPFGHDHDHTHPGPWVDLESKRFDVKAELRQPFKG  354
WP_005612269.1     287 EENIGSNPHFHCGTDHAEDGTHSHDNPFGHDHDHTHPGPWVDLESKRFDVKAELRQPFKG  346
WP_027074597.1     298 NELISENPHFHCGSDHGLDHNHSHDNPYGHKHDHTHKGPWVDLRSKRLDLKMELKQPFSG  357
AHG73391.1         298 EDLISHGPHFHCGTDHEMDAGHSHDNPYGHTHDHTHKGPWVDLKSKRIDVKGELLKPFRG  357
WP_021114857.1     309 DEMVTENPHFHCGTDYDLDPSHSHDHPYGHDHDHTHIGPWVDLHSKRIDIKGEIKQPLPM  368
WP_026212957.1     292 DEDMITSLHFHCGTNYDLDPSHSHEHVYGHKHDHTQKGPWVDMTSKTFSLQGEINQPIPS  351
WP_028858792.1     332 DEDLAESFHFHCDSDHNEDEPHSHDNPYGHDHDHTQGGPWVDMNSKSYYLQGELLEPIPA  391
WP_016534590.1     302 DTDL-VNTHFHCGSNHDMDGKHSHDHPYGHDHDHSIAGPLIDSYAKRYDIRAEVKQPMKA  360
KDN24548.1         303 NMDFSSSAHFHCGTDHAHDPGQSHEHPLGYEHDHTHPGPWIDMESERIDVRAQWEKPFKG  362
WP_027021676.1     308 DEDVNLSQHFHCHTEHSSNAKHSHDNVYGHKHDHGEPGPWIDMRVRRYDVRGEWRTQLPF  367
                       :  .    **** :::  :  :**:.  *: ***   ** :*
```

PROTEINS AND IMMUNIZING COMPOSITIONS CONTAINING *PASTEURELLA* PROTEINS AND METHODS OF USE

CROSS-REFERENCE TO RELATED APPLICATIONS

This application is a continuation of U.S. application Ser. No. 16/484,332, filed Aug. 7, 2019 and which is a § 371 U.S. National Stage of International Application No. PCT/US2018/017682, filed 9 Feb. 2018, which claims the benefit of U.S. Provisional Application No. 62/457,599, filed Feb. 10, 2017, the disclosures of which are incorporated by reference herein in their entireties.

SEQUENCE LISTING

This application contains a Sequence Listing electronically submitted via EFS-Web to the United States Patent and Trademark Office as an ASCII text file entitled "29300560201_SequenceListing_ST25.txt" having a size of 348 kilobytes and created on Apr. 11, 2018. The information contained in the Sequence Listing is incorporated by reference herein.

BACKGROUND

*Pasteurella* spp. are gram negative, facultatively anaerobic and pleomorphically rod shaped bacteria able to cause disease in a variety of animals as well as humans. Species of *Pasteurella* in domestic and wild animals have evolved a particular niche for mucosal membranes of the upper respiratory, mucosa of the oral cavity and lower genital tract. In farm animals, diseases are based on clinical symptoms and on the particular *Pasteurella* specie associated with disease. Today *Pasteurella multocida* and *Mannheimia haemolytica* are the two most widely recognized species of the Pasteurellaceae family associated with clinical disease in animal husbandry with particular reference to poultry, cattle, pigs and rabbits. The family Pasteurellaceae currently comprises five genera; *Pasteurella, Mannheimia, Actinobacillus, Haemophilus*, and *Lonepinella* and have been the subject of extensive reclassification (Angen et al. Int. J. Syst. Bacteriol. 49: 67-86 (1999). Recently *Pasteurella haemolytica* has been taxonomically reclassified as *Mannheimia haemolytica* based on ribosomal sequencing and DNA-DNA hybridization (Oystein et al. Int. J. Syst. Bacteriol. 49:6-86 (1999).

*Pasteurella multocida* is the etiological agent of avian pasteurellosis, commonly referred to as fowl cholera, a widely distributed and economically important disease of poultry, having a high incidence in chickens, turkeys, geese and ducks (Rhoades et al. Fowl Cholera. In: Adlam, C. F. and Rutter, J. M. (Eds.), *Pasteurella* and Pasteurellosis. Academic Press, London, pp. 95-113. 1989). The organism is also responsible for inducing clinical disease in wild birds, commercially raised game birds and Psittacines (Rhoades and Rimler, 1989, Fowl cholera. In *Pasteurella* and Pasteurellosis, pp. 95-113. Edited by C. F. Adlam & J. M. Rutter. London: Academic Press). All species of birds are susceptible to varying degrees. Heavy breeds appear more susceptible than light breeds, and adult birds and those in late growing phase appear more susceptible than younger birds (Jordan et al. Poultry Diseases. Ballierre Tindall, London, pp 42-50. 1990.). Four capsular serogroups (A, B, D and F) are recognized among avian strains of *Pasteurella multocida* (Rhoades et al. Avian Dis. 31: 895-898 (1987). In domestic poultry, strains belonging to capsular type A are recognized as the primary agent of pasteurellosis (Rhoades and Rimler, 1987, Avian Dis 31, 895-898; Rhoades et al. Fowl Cholera. In: Adlam, C. F. and Rutter, J. M. (Eds.), *Pasteurella* and Pasteurellosis. Academic Press, London, pp. 95-113. 1989; Wilson et al. J. Clin. Microbiol. 31: 255-259 1993)). It has been shown that avian strains of *Pasteurella multocida* are genetically diverse as demonstrated by multilocus enzyme electrophoresis and DNA-DNA hybridization. Based on these findings *P. multocida* has now been subdivided into three subspecies, *multocida, septica* and *gallicida.*

The pathogenesis of *P. multocida* is poorly understood but is dependent on both host and pathogen specific factors. To date no single virulence factor has been associated with disease among strains. Virulence factors that have been studied to date include; capsule, endotoxin, outer membrane proteins, serum resistance, iron-acquisition systems, heat shock proteins, neuraminidase production, adhesion factors, antibody cleaving enzymes and the potential existence of cytopathic toxins.

Clinical manifestation of disease may range from peracute/acute to chronic infections, and may initially arise by the colonization of the upper respiratory tract, followed by invasion and septicaemia. During acute infections, few clinical signs are observed before death which is generally dominated by septicaemic lesions. In chronic forms of *P. multocida* infections, suppurative lesions may be widely distributed involving the mucous membranes of the respiratory tract, the pharynx, nasal passages, conjunctiva and adjacent tissues of the head.

Because of the ubiquitous nature of *P. multocida*, and the potential for great economic loss, commercial vaccines have been developed to protect against outbreaks of Fowl cholera in layer and breeder broiler operations throughout the US and abroad. Inactivated commercial Fowl cholera vaccines currently available rely on somatic serotypes to offer protection. Most inactivated vaccines contain, at a minimum, *Pasteurella multocida* strains of serotype 1 (also referred to as A:1), serotype 3 (also referred to as A:3), and serotype 4 (also referred to as A:4). Fowl cholera vaccines made with one serotype do not cross protect against other serotypes, e.g., a vaccine made using a serotype 1 strain does not protect against serotypes 3 or 4.

The ability of *Pasteurella multocida* to evade the natural defense mechanisms of the vertebrate host depends in part on its ability to obtain host iron, which in turn, directly influences the host-pathogen interaction. Because of iron's essential nature, vertebrate hosts have developed elaborate mechanisms to bind iron in body fluids (e.g., transferrin in blood and lymph fluids and lactoferrin in external secretions). These high affinity iron binding proteins create an iron restricted environment within the host, reducing the level of iron to approximately $10^{-18}$ molar, a concentration too low to support the growth of nearly all bacteria. These iron sequestering mechanisms of the host act as a natural defense mechanism to combat bacterial invasion. To circumvent these iron-restrictive conditions many bacterial species have evolved mechanisms for obtaining iron. The most common mechanisms include the diffusion of soluble iron through porins and specialized transport systems that mediate the uptake of iron by siderophores. This latter system is one of the most common and well-studied mechanisms for iron acquisition and involves the specific chelation of ferric iron by siderophores and the synthesis of their cognate transport systems, which permits the bacteria to continue to replicate and overcome the non-specific defense mechanisms of the host. Continued replication, and thus each step in the infectious process, is ultimately dependent on the ability of the organism to obtain iron from its host.

Divalent metal ions such as iron, cobalt, copper, magnesium, manganese, molybdenum, nickel, selenium, and zinc are trace elements often required for the survival of bacteria infecting both animal and human hosts. These trace metal elements are used by bacteria as cofactors for enzymes that catalyze biochemical reactions for various metabolic pathways required by the organism. The impact of iron on the pathogenesis of bacteria has been studied extensively. Iron is essential for nearly all life and is required for enzymatic and metabolic pathways of organisms at all phylogenic levels. It has been well-documented that during bacterial sepsis there is an alteration in the concentration of a number of metal ions in serum such as, iron, copper, and zinc. For instance, serum levels of zinc decrease from 10 percent to 60 percent with the onset of infection. Following the onset of infection, zinc is then redistributed from plasma to liver where it is bound to metallothionein. Decreases in serum iron of up to 50 percent have been described during infectious illness, whereas serum copper has been shown to increase in response to inflammatory stimuli. The alteration of these trace metal ions in serum may directly affect the severity or progression of any bacterial infection.

With so many basic functions relying on the availability of iron, bacteria have evolved a complex regulatory network for acquiring iron under varying physiological conditions. Under anaerobic conditions, iron is present in the soluble ferrous form (Fe II) and can freely diffuse through outer membrane porins into the periplasm. For instance, in *E. coli* the FeoAB transport system present in the cytoplasmic membrane will transport the ferrous iron molecules into the cell cytoplasm. Under aerobic conditions and neutral pH, iron is primarily present in the insoluble ferric form (Fe III) and cannot pass through the outer membrane porins by passive diffusion. Instead, molecules called siderophores are secreted by bacteria, which have a high affinity for ferric iron. The ferric-siderophore complexes are recognized by receptors in the outer membrane collectively referred to as the TonB-dependent receptors. These receptors, once bound to loaded siderophores, are believed to interact with TonB and its associated proteins localized in the periplasm and cytoplasmic membrane. These protein-protein interactions, though poorly understood, serve to provide the energy necessary to transport the ferric-siderophore complexes across the outer membrane and through the periplasmic space. ABC transport systems present in the cytoplasmic membrane serve to transport the iron-siderophore complexes across the cytoplasmic membrane. Reductase enzymes reduce the ferric iron to its ferrous form, which dissociates it from the siderophore and releases iron into the cell.

Several species of pathogenic bacteria use additional mechanisms to obtain iron from mammalian hosts, including the direct binding of transferrin, heme, and other heme-containing compounds. The receptor proteins that bind these iron-containing molecules most likely rely on the TonB complex for the energy required to transport heme across the outer membrane, similar to the iron-siderophore complexes. Specialized ABC transporters are then used to transport the heme across the cytoplasmic membrane. In addition, some bacteria secrete hemophores, small molecules that can bind heme and present it to receptors on the bacterial cell surface. Several pathogenic species also produce hemolysins, which are toxins that lyse red blood cells, releasing heme and hemoglobin for uptake by the bacteria.

The outer membrane proteins of gram-negative bacteria control the selective permeability of many essential nutrients critical to the survival of bacteria, including all pathogenic bacteria that cause disease in animals and man. This selective permeability of nutrients is controlled by a class of membrane proteins called porins. It now appears that the majority of the outer membrane proteins on the surface of gram-negative bacteria are porins, identified as the general porins (e.g., OmpF), monomeric porins (e.g., OmpA), the specific porins (e.g., the maltose-specific porin LamB) and the TonB-dependent, gated porins (e.g., the siderophore receptor FepA). The porin class of proteins generally share structural features, including the presence of beta-barrels that span the outer membrane.

Beyond the role of iron as an essential nutrient for microbial survival, there are now many other well-defined transitional metals that play critical roles in bacterial survival, homeostasis, and pathogenesis such as iron, manganese, copper, zinc, magnesium, cobalt, and nickel (Waldron and Robinson and 2009; Porcheron; 2013). Iron, zinc and copper are the three most abundant divalent metal ions in mammals in descending order of concentration. The ability of a bacterium to utilize these transitional metals by finely regulated uptake or acquisition systems significantly contributes to the virulence of pathogenic bacteria. It is well known that bacteria within the same genus/species do not have the same uptake systems for the acquisition of transitional metals owing to the difference in pathogenicity from one strain of bacteria to another. These differences in the ability of bacteria to use different transitional metals based on expressed uptake systems may specifically direct what organ or tissue an organism can invade.

Little is known regarding the iron-acquisition by *Pasteurella multocida*; it has not been studied nearly to the extent of *E. coli* iron transport systems. The iron regulated proteins of *Pasteurella* have been investigated as potential immunogens as target antigens for different vaccine strategies in multiple animal species. It has been shown that these proteins provide protective efficacy against homologous challenge yet a combination of these proteins to provide heterologous protection has eluded researchers.

Glisson et al. (Avian Diseases 37:1074-1079, 1993) attempted to induce cross-protection across serotypes by preparing bacterins from *P. multocida* strains X-73 (serotype 1) and P-1059 (serotype 3) under iron-restricted culture conditions. They found that bacterins produced in medium low in iron did not consistently induce significant protection against heterologous challenge.

SUMMARY OF THE APPLICATION

We observed results similar to Glisson when growing two heterologous strains, one of serotype 3×4 and one of serotype 1, in iron-restricted medium and attempting a vaccination and challenge model with one strain as vaccine strain and the other as challenge strain (see Examples 6-9), i.e., some protection was observed when the vaccine and the challenge were different serotypes. However, when we compared field strains of pathogenic *Pasteurella multocida*, and particularly when we compared the patterns of metal regulated proteins present in these strains, we found two major patterns of metal regulated proteins predominate in these pathogenic strains. One pattern contains 2 or 3 major metal regulated proteins, and the other pattern contains 4 distinct metal regulated proteins. When the metal regulated proteins of these two pattern types were obtained from two *P. multocida* strains, one of serotype 2,5 and one of serotype 3,4, and combined and used to vaccinate animals, we observed heterologous protection across serotypes of *P. multocida*, including protection against a *P. multocida* of another serotype not represented in the two strains used to make the vaccine. This result was unexpected and surprising. We are not aware of any reports of this type of heterologous protection being observed in vaccines that protect against *P. multocida* infection.

Provided herein are compositions. In one embodiment, a composition includes an isolated protein having at least 80% similarity to amino acids 25-968 of SEQ ID NO:2, an isolated protein having at least 80% similarity to amino acids 27-790 of SEQ ID NO:4, an isolated protein having at least 80% similarity to amino acids 23-727 of SEQ ID NO:6, an isolated protein having at least 80% similarity to amino acids 25-964 of SEQ ID NO:8, an isolated protein having at least 80% similarity to amino acids 26-848 of SEQ ID NO:10, an isolated protein having at least 80% similarity to amino acids 27-784 of SEQ ID NO:12, an isolated protein having at least 80% similarity to amino acids 25-742 SEQ ID NO:14, an isolated protein having at least 80% similarity to amino acids 26-805 of SEQ ID NO:44, or a combination thereof. The composition protects an animal, such as a chicken, against challenge with *Pasteurella multocida*.

In another embodiment, a composition includes isolated proteins having molecular weights of 99 kDa, 81 kDa, and 80 kDa where the proteins are isolatable from a *Pasteurella multocida* when incubated in media that includes an iron chelator and not isolatable when grown in the media without the iron chelator, isolated proteins having molecular weights of 109 kDa, 89 kDa, and 87 kDa wherein the proteins are isolatable from a *P. multocida* when incubated in media comprising an iron chelator, where the proteins are expressed by the *P. multocida* when incubated in media without the iron chelator and expressed at an enhanced level during growth in media that includes an iron chelator. The composition protects an animal, such as a chicken, against challenge with *P. multocida*.

In one embodiment, a includes an isolated protein having at least 80% similarity to amino acids 26-805 of SEQ ID NO:44, wherein the composition protects a chicken against challenge with *P. multocida*.

A composition described herein can optionally include additional proteins, such as at least one isolated protein having a molecular weight of 249 kDa, 60 kDa, 42 kDa, 38 kDa, 27 kDa, 26 kDa, or 22 kDa, wherein the proteins are isolatable from the *P. multocida*.

In one embodiment, a composition includes an isolated whole cell that includes at least one of the proteins of a composition described herein. The composition protects an animal, such as a chicken, against challenge with *Pasteurella multocida*. In one embodiment, the whole cell is a cell engineered to express one or more of the proteins. In one embodiment, the cell is *E. coli*. Further provided is a composition that includes isolated antibody that specifically binds to a protein of a composition described herein. In one embodiment, the antibody is polyclonal antibody.

A composition described herein can further include a pharmaceutically acceptable carrier, an adjuvant, or a combination thereof.

Also provided are methods. In one embodiment, a method includes administering to a subject an amount of a composition described herein effective to induce the subject to produce antibody that specifically binds to at least one protein of the composition. In one embodiment, a method is for treating an infection in a subject, and includes administering an effective amount of the composition described herein to a subject having or at risk of having an infection caused by a *P. multocida*. In one embodiment, a method is for treating a symptom in a subject, and includes administering an effective amount of a composition described herein to a subject having or at risk of having an infection caused by a *P. multocida*. In one embodiment, a method is for decreasing colonization in a subject, and includes administering an effective amount of a composition described herein to a subject colonized by a *P. multocida*. In one embodiment, a method is for treating an infection in a subject, and includes administering an effective amount of a composition to a subject having or at risk of having an infection caused by a *P. multocida* wherein the composition includes antibody that specifically binds to a protein of a composition described herein. In one embodiment, a method is for treating a symptom in a subject, and includes administering an effective amount of a composition to a subject having or at risk of having an infection caused by a *P. multocida*., wherein the composition that includes antibody that specifically binds to a protein of a composition described herein. In one embodiment, a method is for decreasing colonization in a subject, and includes administering an effective amount of a composition to a subject colonized by a *P. multocida*., wherein the composition that includes antibody that specifically binds to a protein a composition described herein.

In one embodiment, the subject can be a mammal, such as a bovine, or an avian, such as a chicken or a turkey. In one embodiment, at least 700 micrograms (μg) to no greater than 1,200 μg of protein is administered.

Also provided are kits. In one embodiment, a kit is for detecting antibody that specifically binds a protein, and includes in separate containers (i) an isolated protein of the composition of claim 1 or 2, and (ii) a reagent that detects an antibody that specifically binds the protein. In one embodiment, a kit is for detecting a protein, and includes in separate containers (i) an antibody that specifically binds an isolated protein of a composition described herein, and a second reagent that specifically binds the protein.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims. It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 3. Table of proteins known to be in the reference challenge strains for serotype A:1 and serotype A:3 compared to the vaccine strain. Note the 8 proteins present in at least one of the reference strain genomes, but absent from the vaccine strain.

FIG. 6. Comparison of 38 expressed iron regulated proteins of 13 different isolates representing pattern types of FIG. 5. (+) indicates the protein is expressed, and (−) indicates the protein is not expressed at detectable levels. The ellipse identifies two potential vaccine targets that cover the majority of proteins.

FIGS. 8-1, 8-2, 9-1, 9-2, 10-1, 10-2, 11-1, 11-2, 12-1, 12-2, 13-1, 13-2, 14-1 and 14-2. The amino acid sequences of SEQ ID NOs:2, 4, 6, 8, 10, 12, and 14, and an example of a nucleotide sequence (SEQ ID NOs:1, 3, 5, 7, 9, 11, and 13, respectively) encoding each amino acid sequence.

FIGS. 15-1 and 15-2. Sequence alignment of SEQ ID NO:2 and four other sequences. WP 053521090.1 (SEQ ID NO:15), 1121_HgbA_968aa (SEQ ID NO:2), WP_005756141.1 (SEQ ID NO:16), AAQ14873.1 (SEQ ID NO:17), WP_061405928.1 (SEQ ID NO:18). All sequences are *P. multocida*, except WP 053521090.1 which is *Haemophilus influenzae*.

FIGS. 16-1 and 16-2. Sequence alignment of SEQ ID NO:4 and four other sequences. ESQ71136.1 (SEQ ID NO:19), WP_014391205.1 (SEQ ID NO:20), WP_016534044.1 (SEQ ID NO:21), 1121_FepA_790aa (SEQ ID NO:4), WP_005756883.1 (SEQ ID NO:22). All sequences are *P. multocida*.

FIGS. 17-1 and 17-2. Sequence alignment of SEQ ID NO:6 and four other sequences. WP_071522773.1 (SEQ ID NO:23), WP_016534444.1 (SEQ ID NO:24), WP_005755819.1(SEQ ID NO:25), 1121_PfhR_727aa (SEQ ID NO:6), EGP05580.1 (SEQ ID NO:26). All sequences are *P. multocida*.

FIGS. 18-1, 18-2 and 18-3. Sequence alignment of SEQ ID NO:8 and five other sequences. 1135_PM0300_964aa (SEQ ID NO:8), WP_005753642.1 (SEQ ID NO:27), WP_016534557.1 (SEQ ID NO:28), WP_010906573.1 (SEQ ID NO:29), AAQ14873.1 (SEQ ID NO:30), 1121_HgbA_968aa (SEQ ID NO:2). All sequences are *P. multocida*.

FIGS. 19-1 and 19-2. Sequence alignment of SEQ ID NO:10 and four other sequences. WP_017861186.1 (SEQ ID NO:31), AAU29202.1 (SEQ ID NO:32), EGP04511.1 (SEQ ID NO:33), 1135_HasR_848aa (SEQ ID NO:10), WP_005752163.1 (SEQ ID NO:34). All sequences are *P. multocida*.

FIGS. 20-1 and 20-2. Sequence alignment of SEQ ID NO:12 and four other sequences. WP_005751557.1 (SEQ ID NO:35), 1135_PM0741_784aa (SEQ ID NO:12), WP_016534554.1 (SEQ ID NO:36), WP_064972816.1 (SEQ ID NO:37), WP_074865020.1 (SEQ ID NO:38). All sequences are *P. multocida*.

FIGS. 21-1 and 21-2. Sequence alignment of SEQ ID NO:14 and four other sequences. WP_050948957.1 (SEQ ID NO:39), WP_014391043.1 (SEQ ID NO:40), WP_016533738.1 (SEQ ID NO:41), 1135_P1062_0207600_742aa (SEQ ID NO:14), WP_025248456.1 (SEQ ID NO:42). All sequences are *P. multocida*, except WP_050948957.1 which is *Haemophilus influenzae*.

FIGS. 22-1 and 22-2. The amino acid sequences of SEQ ID NO:44 and an example of a nucleotide sequence (SEQ ID NO:43) encoding the amino acid sequence. The first 78 nucleotides of SEQ ID NO:43 are predicted to encode the signal sequence of SEQ ID NO:44 (amino acids 1-26).

FIG. 25. Sequence alignment of the zinc affinity region of zinc acquisition proteins from *Mannheimia haemolytica* (ZAP, SEQ ID NO:45) and 10 other respiratory pathogens. AHG81836.1 (SEQ ID NO:46), WP_005612269.1 (SEQ ID NO:47), WP_027074597.1 (SEQ ID NO:48), AHG73391.1 (SEQ ID NO:49), WP_021114857.1 (SEQ ID NO:50), WP_026212957.1 (SEQ ID NO:51), WP_028858792.1

Figure 1:
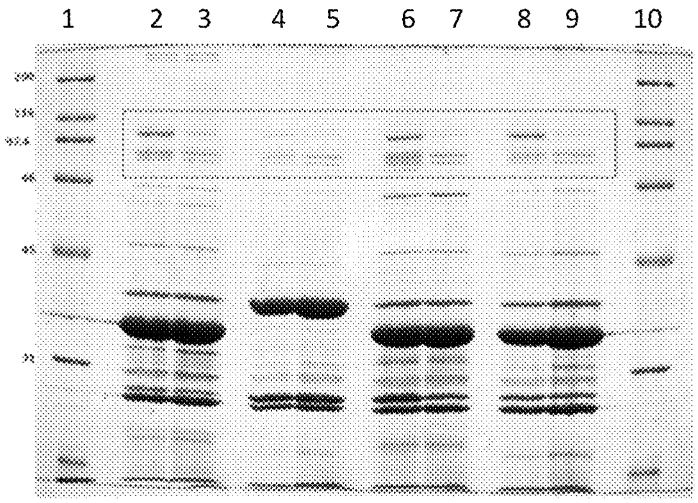
FIG. 1. SDS-PAGE gel of extract of bacteria grown under iron limiting and iron replete conditions. Lanes 1 and 10: Broad range molecular weight markers; Lane 2: Vaccine candidate MS061130 under iron restriction; Lane 3: Vaccine candidate strain under iron replete conditions. Lane 4: serotype 1 reference strain X-73 under iron limited conditions. Lane 5: X-73 under iron replete conditions. Lane 6: Serotype 3 reference strain P1059 under iron limiting conditions. Lane 7: P1059 under iron replete conditions. Lane 8: reference strain P-1662 under iron limiting conditions; lane 9: P-1662 under iron replete conditions. Note the similar molecular weights of the iron-regulated proteins as depicted within the rectangle.

(SEQ ID NO:52), WP_016534590.1 (SEQ ID NO:53), KDN24548.1 (SEQ ID NO:54), and WP_027021676.1 (SEQ ID NO:55).

DETAILED DESCRIPTION OF ILLUSTRATIVE EMBODIMENTS

In one aspect, this disclosure provides proteins and compositions including proteins. As used herein, "protein" refers to a polymer of amino acids linked by peptide bonds. Thus, for example, the terms peptide, oligopeptide, polypeptide, and enzyme are included within the definition of protein. This term also includes proteins that may include one or more post-expression modifications of the protein such as, for example, a glycosylation, an acetylation, a phosphorylation, and the like. The term protein does not connote a specific length of a polymer of amino acids. A protein may be isolatable directly from a natural source or can be prepared with the aid of recombinant, enzymatic, or chemical techniques. In the case of a protein that is naturally occurring, such a protein is typically isolated.

An "isolated" protein is one that has been removed from its natural environment. For instance, an isolated protein is a protein that has been removed from the cytoplasm or from the membrane of a cell, and many of the proteins, nucleic acids, and other cellular material of its natural environment are no longer present.

A protein characterized as "isolatable" from a particular source is a protein that, under appropriate conditions, is produced by the identified source, although the protein may be obtained from alternate sources using, for example, conventional recombinant, chemical, or enzymatic techniques. Thus, characterizing a protein as "isolatable" from a particular source does not imply any specific source from which the protein must be obtained or any particular conditions or processes under which the protein must be obtained.

A "purified" protein is one that is at least 60% free, preferably at least 75% free, and most preferably at least 90% free from other components with which they are naturally associated. Proteins that are produced outside the organism in which they naturally occur, e.g., through chemical or recombinant means, are considered to be isolated and purified by definition, since they were never present in a natural environment.

Generally, a protein may be characterized by molecular weight, amino acid sequence, mass fingerprint, nucleic acid that encodes the protein, immunological activity, or any combination of two or more such characteristics. The molecular weight of a protein, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence. Unless indicated otherwise, reference to molecular weight refers to molecular weight as determined by resolving a protein using an SDS polyacrylamide gel having a stacking gel of about 4% and a resolving gel of about 10% under reducing and denaturing conditions. In one embodiment, the molecular weight of a protein identified by SDS-PAGE includes molecular weights of 1, 2, 3, 4, or 5 kDa above and below the stated value.

The proteins described herein may be metal-regulated. As used herein, a "metal-regulated protein" is a protein that is expressed by a microbe at a greater level when the microbe is grown in low metal conditions compared to when the same microbe is grown in high metal conditions. Low metal and high metal conditions are described herein. For instance, certain metal-regulated proteins produced by *P. multocida* are not expressed at detectable levels during growth of the microbe in high metal conditions but are expressed at detectable levels during growth in low metal conditions. In one embodiment, a metal-regulated protein can be a siderophore receptor protein. Examples of metal-regulated proteins isolatable from a *P. multocida* after growth in low iron conditions include metal-regulated proteins having molecular weights of 104 kDa to 75 kDa. Specific examples of metal-regulated proteins isolatable from a *P. multocida* after growth in low iron conditions include proteins of 99 kDa, 81 kDa, and 80 kDa as determined by resolving a protein using an SDS polyacrylamide gel having a stacking gel of about 4% and a resolving gel of about 10% under reducing and denaturing conditions. In one embodiment, a low iron conditions is growth in the presence of 2,2'-dipyridyl. Examples of the iron regulated proteins having molecular weights of 99 kDa, 81 kDa, and 80 kDa, and nucleotide sequences encoding the proteins, are shown in FIGS. 10, 14-1 and 14-2, and 6, respectively. A specific example of metal-regulated proteins isolatable from a *P. multocida* after growth in low zinc conditions include a protein of 91 kDa as determined by resolving a protein using an SDS polyacrylamide gel having a stacking gel of about 4% and a resolving gel of about 10% under reducing and denaturing conditions. In one embodiment, a low zinc conditions is growth in the presence of N,N,N',N'-tetrakis(2-pyridylmethyl)ethylenediamine (TPEN) (Sigma-Aldrich, St. Louis Mo.). An example of the zinc regulated protein having a molecular weight of 91 kDa, and nucleotide sequences encoding the protein, is shown in FIG. 22.

The proteins described herein may be expressed at detectable levels during growth of the microbe in high metal conditions but expressed at higher levels during growth in low metal conditions. The expression of such proteins is referred to herein as "enhanced" during growth in low metal conditions. Typically, the increase in expression of a protein during growth in low metal conditions is between 50% and 500% compared to the expression of the protein during growth in high metal conditions.

Examples of metal-regulated proteins having enhanced expression and isolatable from *P. multocida* after growth in low iron conditions include metal-regulated proteins having molecular weights of and 114 kDa to 82 kDa. Specific examples of metal-regulated proteins isolatable from a *P. multocida* after growth in low iron conditions include proteins of 109 kDa, 89 kDa, and 87 kDa as determined by resolving a protein using an SDS polyacrylamide gel having a stacking gel of about 4% and a resolving gel of about 10% under reducing and denaturing conditions. Examples of the proteins having molecular weights of 109 kDa and nucleotide sequences encoding them are shown in FIGS. 8 and 11. Examples of the proteins having molecular weights of 89 kDa and 87 kDa, and nucleotide sequences encoding the proteins, are shown in FIGS. 13 and 9, respectively.

This disclosure also describes certain proteins that are not metal-regulated. Such proteins are expressed in the presence of a metal ion such as, for example, in the presence of ferric chloride, and also expressed when grown in low iron conditions. Examples of this type of protein isolatable from *P. multocida* have molecular weights of 254 kDa to 244 kDa, 65 kDa to 55 kDa, and 47 kDa to 17 kDa. Examples of molecular weights of this type of protein include 249 kDa, 60 kDa, 42 kDa, 38 kDa, 27 kDa, 26 kDa, and 22 kDa.

Additional examples of proteins include recombinantly-produced versions of proteins described herein. A recombinantly-produced protein may include the entire amino acid sequence translatable from an mRNA transcript. Alternatively, a recombinantly-produced protein can include a fragment of the entire translatable amino acid sequence. For example, a recombinantly-produced protein may lack a cleavable sequence at either terminus of the protein—e.g., a cleavable signal sequence at the amino terminus of the protein.

In one embodiment, a protein lacks one or more amino acids from the amino terminus of the protein encoded by a coding sequence obtained from a wild-type cell, e.g., the protein lacks a signal sequence. Thus, a fragment can lack at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, or at least 63 amino acids from the amino terminus of the protein. In one embodiment, a fragment of the protein depicted at SEQ ID NO:2 does not include amino acids 1-24. In one embodiment, a fragment of the protein depicted at SEQ ID NO:4 does not include amino acids 1-26. In one embodiment, a fragment of the protein depicted at SEQ ID NO:6 does not include amino acids 1-22. In one embodiment, a fragment of the protein depicted at SEQ ID NO:8 does not include amino acids 1-24. In one embodiment, a fragment of the protein depicted at SEQ ID NO:10 does not include amino acids 1-25. In one embodiment, a fragment of the protein depicted at SEQ ID NO:12 does not include amino acids 1-26. In one embodiment, a fragment of the protein depicted at SEQ ID NO:14 does not include amino acids 1-24. In one embodiment, a fragment of the protein depicted at SEQ ID NO:44 does not include amino acids 1-26.

Whether a protein is a metal-regulated protein, an enhanced protein, or a non-metal-regulated protein can be determined by methods useful for comparing the presence of proteins, including, for example, gel filtration, gel electrophoresis including sodium dodecyl sulfate-polyacrylamide gel electrophoresis (SDS-PAGE), capillary electrophoresis, mass spectrometry, isobaric tags for relative and absolute quantification (iTRAQ), and liquid chromatography including HPLC. Separate cultures of a microbe can be grown under high metal conditions and under low metal conditions, proteins may be isolated as described herein, and the proteins present in each culture can be resolved and compared. Typically, an equal amount of proteins from each culture is used. In one embodiment, the proteins can be resolved using an SDS polyacrylamide gel having a stacking gel of about 4% and a resolving gel of about 10% under reducing and denaturing conditions. For instance, 30 micrograms (μg) of total protein from each culture may be used and loaded into wells of a gel. After running the gel and staining the proteins with Coomassie Brilliant Blue, the two lanes can be compared. When determining whether a protein is or is not expressed at a detectable level, 30 μg of total protein from a culture is resolved on an SDS-PAGE gel and stained with Coomassie Brilliant Blue using methods known in the art. A protein that can be visualized by eye is considered to be expressed at a detectable level, while a protein that cannot be visualized by eye is considered to not be expressed at a detectable level.

Alternatively, whether a protein is a metal-regulated protein or a non-metal-regulated protein can be determined using microarray-based gene expression analysis. Separate cultures of a microbe can be grown under high metal conditions and under low metal conditions, RNA can be extracted from cells of each culture, and differences in RNA expression in cells grown in high metal conditions versus RNA expression in cells grown in low metal conditions can be detected and compared. For example, labeled cDNA can be prepared from 8-10 μg of bacterial RNA using established protocols. The labeled cDNA can be applied to a microarray of a microbe's genome. Such microarrays are commercially available and evaluating gene expression using such arrays is routine.

The proteins described herein can have immunological activity. "Immunological activity" refers to the ability of a protein to elicit an immunological response in an animal. An immunological response to a protein is the development in an animal of a cellular and/or antibody-mediated immune response to the protein. Usually, an immunological response includes but is not limited to one or more of the following effects: the production of antibodies, B cells, helper T cells, suppressor T cells, and/or cytotoxic T cells, directed to an epitope or epitopes of the protein. "Epitope" refers to the site on an antigen to which specific B cells and/or T cells respond so that antibody is produced. The immunological activity may be protective. "Protective immunological activity" refers to the ability of a protein to elicit an immunological response in an animal that inhibits or limits infection by *P. multocida*. Whether a protein has protective immunological activity can be determined by methods known in the art such as, for example, methods described in Examples 6-9 and 15-16. A protein may have seroactive activity. As used herein, "seroactive activity" refers to the ability of a candidate protein to react with antibody present in convalescent serum from an animal infected with a *P. multocida*.

A protein as described herein may have the characteristics of a reference protein. The characteristics can include, for example, molecular weight, mass fingerprint, amino acid sequence, or any combination thereof. In one embodiment, a protein can be obtained from a microbe. A microbe can express one, two, three, four, five, six, seven, eight, or nine of the proteins described herein. The reference protein can be isolatable from a gram negative microbe, preferably a member of the family Pasteurellaceae, including the genus *Pasteurella, Mannheimia*, or *Haemophilus*. A member of the genus *Pasteurella Mannheimia*, and *Haemophilus* is also referred to herein as *Pasteurella* spp., *Mannheimia* spp., and *Haemophilus* spp., respectively. In one embodiment, the reference protein is expressed by a *P. multocida*. In one embodiment, the *P. multocida* can be serotype 2,5 or serotype 3,4.

As used herein, a protein may be "structurally similar" to a reference protein if the amino acid sequence of the protein possesses a specified amount of sequence similarity and/or sequence identity compared to the reference protein. A protein also may be "structurally similar" to a reference protein if the protein exhibits a mass fingerprint possessing a specified amount of identity compared to a comparable mass fingerprint of the reference protein. Thus, a protein may be "structurally similar" to a reference protein if, compared to the reference protein, it possesses a sufficient level of amino acid sequence identity, amino acid sequence similarity, or a combination thereof. In one embodiment, a protein described herein can have an amino acid sequence that is structurally similar, as described below, to amino acids 25-968 of SEQ ID NO:2, amino acids 27-790 of SEQ ID NO:4, amino acids 23-727 of SEQ ID NO:6, amino acids 25-964 of SEQ ID NO:8, amino acids 26-848 of SEQ ID NO:10, amino acids 27-784 of SEQ ID NO:12, amino acids 25-742 of SEQ ID NO:14, or amino acids 26-805 of SEQ ID NO:44.

Protein Sequence Similarity and Protein Sequence Identity

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein or any known metal-regulated protein, as appropriate. Examples of reference proteins include, but are not limited to, amino acids 25-968 of SEQ ID NO:2, amino acids 27-790 of SEQ ID NO:4, amino acids 23-727 of SEQ ID NO:6, amino acids 25-964 of SEQ ID NO:8, amino acids 26-848 of SEQ ID NO:10, amino acids 27-784 of SEQ ID NO:12, amino acids 25-742 of SEQ ID NO:14, and amino acids 26-805 of SEQ ID NO:44. A candidate protein is the protein being compared to the reference protein. A candidate protein can be isolated, for example, from a microbe, or can be produced using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison Wis.). Alternatively, proteins may be compared using the Blastp program of the BLAST 2 search algorithm, as described by Tatiana et al. (*FEMS Microbiol Lett,* 174:247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a protein containing deletions or additions of one or more contiguous or noncontiguous amino acids that do not eliminate a functional activity-such as, for example, immunological activity—of the protein are also contemplated.

Thus, as used herein, a protein as described herein and/or the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, a protein as described herein and/or the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

FIGS. 15-21 show Clustal Omega alignments for proteins having the amino acid sequences shown in SEQ ID NOs:2, 4, 6, 8, 10, 12, and 14. The alignments indicate amino acids that are conserved in the variants of each protein across different *P. multocida* strains and, for FIGS. 15 and 21, *Haemophilus influenzae*. In FIGS. 15-21 an asterisk (*) indicates positions which have a single, fully conserved residue, a colon (:) indicates conservation between groups of strongly similar properties as roughly equivalent to scoring >0.5 in the Gonnet PAM 250 matrix, and a period (.) indicates conservation between groups of weakly similar properties as roughly equivalent to scoring=<0.5 and >0 in the Gonnet PAM 250 matrix. A person of ordinary skill in the art can deduce from such data regions of the protein in which substitutions, particularly conservative substitutions, may be permitted without unduly affecting activity (immunological activity, protective immunological activity, or seroactive activity of the modified protein.

Consequently, a protein as described herein can include certain variants including, for example, homologous proteins that originate—biologically and/or recombinantly—from microbial species or strains other than the microbial species or strain from which the protein was originally isolated and/or identified.

A protein described herein also can be designed to provide one or more additional sequences such as, for example, the addition of coding sequences for added C-terminal and/or N-terminal amino acids that may facilitate purification by trapping on columns or use of antibodies. Such tags include, for example, histidine-rich tags that allow purification of proteins on nickel columns. Such gene modification techniques and suitable additional sequences are well known in the molecular biology arts. A protein as described herein also may be designed so that certain amino acids at the C-terminus and/or N-terminus are deleted.

A protein described herein can include a "modification." A modification refers to a chemical or enzymatic derivatization at one or more constituent amino acids. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified proteins as described herein may retain the biological activity—such as, for example, immunological activity—of the unmodified protein or may exhibit a reduced or increased biological activity compared to the unmodified protein.

A protein as described herein (including a biologically active analog thereof and/or a modification thereof) can include a native (naturally occurring), a recombinant, a chemically synthesized, or an enzymatically synthesized protein. For example, a protein as described herein may be prepared by isolating the protein from a natural source or may be prepared recombinantly by conventional methods including, for example, preparation as fusion proteins in bacteria or other host cells.

Polynucleotide Sequence Similarity and Polynucleotide Sequence Identity

Proteins as described herein also can be identified in terms of the polynucleotide that encodes the protein. Thus, this disclosure provides polynucleotides that encode a protein as described herein or hybridize, under standard hybridization conditions, to a polynucleotide that encodes a protein as described herein, and the complements of such polynucleotide sequences.

As used herein, a polynucleotide as described herein and/or the nucleic acid sequence of one or more SEQ ID NOs:1, 3, 5, 7, 9, 11, 13, or 43, or a fragment thereof, can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides (for example, aligning the nucleotide sequence of the candidate sequence and a nucleotide sequence that includes, for example, a nucleotide sequence disclosed herein, such as SEQ ID NO:1, 3, 5, 7, 9, 11, 13, or 43, or a fragment thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes a nucleotide sequence described herein, for example, SEQ ID NO: 1, 3, 5, 7, 9, 11, or 13, or 43, or a fragment thereof. For example, two polynucleotide sequences can be compared using the Blastn program of the BLAST 2 search algorithm, as described by Tatusova et al., (*FEMS Microbiol Lett.,* 174:247-250 (1999)), and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x dropoff=50, expect=10, wordsize=11, and filter on.

Finally, a polynucleotide as described herein can include any polynucleotide that encodes a protein as described herein. Thus, the nucleotide sequence of the polynucleotide may be deduced from the amino acid sequence that is to be encoded by the polynucleotide.

This disclosure also provides whole cell preparations of microbes. In one embodiment, the preparation includes a microbe that has been engineered to express the proteins described herein. For instance, a microbe can be engineered to express proteins having structural similarity with SEQ ID NOs:2, 4, 6, 8, 10, 12, 14, or 44, or a fragment thereof, or any subcombination of those eight proteins. The microbe can be any microbial cell that is amenable to genetic manipulation, including a gram negative or a gram positive microbe. Examples of gram negative microbes include, but are not limited to, *E. coli, Salmonella* spp., and *Pasteurella* spp., such as *P. multocida.*

In one embodiment, the preparation includes two or more populations of microbes. Each of the populations do not express all of SEQ ID NOs:2, 4, 6, 8, 10, 12, and 14, or a fragment thereof. Rather, each of the populations express a subset of the seven proteins, and the two or more populations when considered as a whole express the seven proteins. For instance, in one embodiment one population of microbe expresses SEQ ID NOs: 2, 4, and 6, and a second population of microbe expresses SEQ ID NOs:8, 10, 12, and 14, or a fragment thereof. A population can be a wild-type microbe or an engineered microbe. A preparation can include one or more wild-type microbes, one or more engineered microbes, or a combination of wild-type and engineered microbes. Examples of wild-type cells include members of the genus *Pasteurella*, such as *P. multocida.* In one embodiment, the cell is an attenuated *P. multocida*. The inventors have determined that administering certain types of *Pasteurella* strains as whole cells is expected to result in immunological properties that are different than the result of administering the individual strains separately. The different immunological properties include the ability to protect against *P. multocida* strains having a different serotype than the *P. multocida* cells administered to the animal. In one embodiment, one whole cell is *P. multocida* serotype 2,5 and a second whole cell is *P. multodica* serotype 3,4, and one expresses three of the seven proteins and the other expresses four of the seven proteins. In one embodiment, one of more of the populations of microbes can express SEQ ID NO:44, or a fragment thereof.

The cells present in a whole cell preparation may be inactivated such that the cells cannot replicate but the immunological activity of the proteins as described herein expressed by the microbe is maintained. Typically, the cells may be killed by exposure to agents such as glutaraldehyde, formalin, or formaldehyde.

Compositions

A composition can include one protein isolated described herein, at least two isolated proteins described herein, or a number of proteins that is an integer greater than two (e.g., at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, and so on). In one embodiment, a composition including one protein described herein includes a protein identical to or having structural similarity with SEQ ID NO:44, or a fragment thereof. Unless a specific level of sequence similarity and/or identity is expressly indicated herein (e.g., at least 80% sequence similarity, at least 90% sequence identity, etc.), reference to the amino acid sequence of an identified SEQ ID NO includes variants having the levels of sequence similarity and/or the levels of sequence identity described herein in the section headed "Protein sequence similarity and protein sequence identity."

A recombinantly-produced protein may be expressed from a vector that permits expression of the protein when the vector is introduced into an appropriate host cell. A host cell may be constructed to produce one or more recombinantly-produced proteins as described herein and, therefore, can include one or more vectors that include at least one polynucleotide encoding a protein described herein. Thus, each vector can include one or more polynucleotides as described herein—i.e., a polynucleotide that encodes a protein as described herein. Methods for the genetic manipulation of microbes, such as *P. multocida*, are known and routine in the art.

Certain compositions such as, for example, those including recombinantly-produced proteins, can include a maximum number of proteins. In some embodiments, the maximum number of proteins can refer to the maximum total number of proteins. Certain compositions can include, for example, no more than 50 proteins such as, for example, no more than 40 proteins, no more than 30 proteins, no more than 25 proteins, no more than 20 proteins, no more than 17 proteins, no more than 16 proteins, no more than 15 proteins, no more than 14 proteins, no more than 13 proteins, no more than 12 proteins, no more than 11 proteins, no more than 10 proteins, no more than nine proteins, no more than eight proteins, no more than seven proteins, no more than six proteins, no more than five proteins, no more than four proteins, no more than three proteins, no more than two proteins, or no more than one protein. In other embodiments, a maximum number of recombinantly-produced proteins may be specified in a similar manner. In still other embodiments, a maximum number of non-recombinantly-produced proteins may be specified in a similar manner.

In one embodiment, a composition can include proteins isolatable from one microbe when the microbe is engineered to express one or more proteins identical to or having structural similarity with a protein described herein. In one embodiment, the microbe is engineered to express proteins identical to or having structural similarity with one of more of SEQ ID NOs:2, 4, 6, 8, 10, 12, 14, and 44, or a fragment thereof. In one embodiment, the microbe expresses a protein identical to or having structural similarity with SEQ ID NO:44, or a fragment thereof. In one embodiment, a composition can include proteins isolatable from two or more microbes. For instance, a composition can include proteins isolatable from two or more wild-type *P. multocida*.

In certain embodiments, a composition can include a preparation of whole cells. In one embodiment, the preparation is a whole cell that has been engineered to express one or more proteins identical to or having structural similarity with a protein described herein. In one embodiment, the microbe is engineered to express proteins identical to or have structural similarity with SEQ ID NOs:2, 4, 6, 8, 10, 12, and 14, or a fragment thereof. In one embodiment, the microbe is engineered to express proteins are identical to or have structural similarity with SEQ ID NOs:2, 4, 6, 8, 10, 12, 14, and 44, or a fragment thereof. In one embodiment, the microbe expresses a protein identical to or having structural similarity with SEQ ID NO: 44, or a fragment thereof. In one embodiment, the preparation is two or more populations of microbes where each of the populations express a subset of the proteins, e.g., the seven proteins (proteins identical to or having structural similarity with SEQ ID NOs:2, 4, 6, 8, 10, 12, and 14, or a fragment thereof), or the eight proteins (proteins identical to or having structural similarity with SEQ ID NOs:2, 4, 6, 8, 10, 12, 14, and 44, or a fragment thereof) and the two or more populations when considered as a whole express the seven proteins. In some of these embodiments, the whole cell can be a *P. multocida*, such as a wild-type *P. multocida*. In some embodiments, a composition can include whole cell preparations from two, three, four, five, or six strains.

Specific examples of compositions include, but are not limited to, the following. In one embodiment, a composition includes metal regulated proteins and enhanced proteins. The metal regulated proteins are isolatable from *P. multocida* after growth in low iron conditions and have molecular weights of 104 kDa to 75 kDa, such as 99 kDa, 81 kDa, and 80 kDa. The proteins can be, or have structural similarity with, a fragment of SEQ ID NOs:6, 10, or 14. The enhanced proteins are isolatable from *P. multocida* after growth in low iron conditions and have molecular weights of 156 kDa to 146 kDa, such as 151 kDa, and 114 kDa to 82 kDa, such as 109 kDa, 89 kDa, and 87 kDa. The proteins can be, or have structural similarity with, a fragment of SEQ ID NOs:2, 4, 8, or 12. Optionally, a composition can include non-metal regulated proteins that are isolatable from *P. multocida*. The non-metal regulated proteins can have molecular weights of 254 kDa to 244 kDa, such as 249 kDa, 65 kDa to 55 kDa, such as 60 kDa, and 47 kDa to 17 kDa, such as 42 kDa, 38 kDa, 27 kDa, 26 kDa, and 22 kDa. Another specific example of a composition is one that includes a protein that is, or has structural similarity with, a fragment of SEQ ID NO:44, or a fragment thereof.

Optionally, a protein described herein can be covalently bound to a carrier protein to improve the immunological properties of the protein. Useful carrier proteins are known in the art. The chemical coupling of a protein described herein can be carried out using known and routine methods. For instance, various homobifunctional and/or heterobifunctional cross-linker reagents such as bis(sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl) cycloheane-1-carboxylate, sulfosuccinimidyl 4-(p-maleimidophenyl) butyrate and (1-ethyl-3-(dimethyl-aminopropyl) carbodiimide can be used (Harlow and Lane, Antibodies, A Laboratory Manual, generally and Chapter 5, Cold Spring Harbor Laboratory, Cold Spring Harbor, N.Y., N.Y. (1988)).

A compositions described herein can include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (0-specific chain, the outer and inner core) and the lipid A region. The lipid A component of LPS is the most biologically active component of the LPS structure and together induces a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scaring or blemishes of the tissue at the injection site.

The concentration of LPS can be determined using routine methods known in the art. Such methods typically include measurement of dye binding by LPS (see, for instance, Keler and Nowotny, *Analyt. Biochem.,* 156, 189 (1986)) or the use of a *Limulus* amebocyte lysate(LAL) test (see, for instance, Endotoxins and Their Detection With the *Limulus* Amebocyte Lystate Test, Alan R. Liss, Inc., 150 Fifth Avenue, New York, N.Y. (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOXATE (Sigma Chemical Co., St. Louis, Mo.; see Sigma Technical Bulletin No. 210), and PYROTELL (Associates of Cape Cod, Inc., East Falmouth, Mass.). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for 1 hour undisturbed at 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, Md., Catalog No. 235503), and Associates of Cape Cod, Inc., (Catalog No. E0005). In general, when a composition of the present invention is prepared by isolating proteins from a microbe, such as *P. multocida*, by a method as described herein (e.g., a method that includes disrupting and solubilizing the cells, and collecting the insoluble proteins), the amount of LPS in a composition of the present invention is less than the amount of LPS present in a mixture of same amount of the microbe that has been disrupted under the same conditions but not solubilized. Typically, the level of LPS in a composition of the present invention is decreased by, in increasing order of preference, at least 50%, at least 60%, at least 70%, at least 80%, or at least 90% relative to the level of LPS in a composition prepared by disrupting, but not solubilizing, the same microbe.

A composition described herein optionally further includes a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. Exemplary pharmaceutically acceptable carriers include buffer solutions and generally exclude blood products such as, for example, whole blood and/or plasma. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous, intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition as described herein can also be administered via a sustained or delayed release implant. Implants suitable for use according to the invention are known and include, for example, those disclosed in International Publication No. WO 2001/037810 and/or International Publication No. WO 1996/001620. Implants can be produced at sizes small enough to be administered by aerosol or spray. Implants also can include nanospheres and microspheres.

A composition of the present invention is administered in an amount sufficient to provide an immunological response to proteins or whole cells described herein. The amount of protein present in a composition can vary. For instance, the dosage of protein can be between 0.01 micrograms (μg) and 3000 milligrams (mg), typically between 100 μg and 2000 ug. When the composition is a whole cell preparation, the cells can be present at a concentration of $10^6$ bacteria/ml, $10^7$ bacteria/ml, $10^8$ bacteria/ml, or $10^9$ bacteria/ml. When a mixture of whole cells is administered (e.g., one population of cells expressing a subset of proteins and a second population expressing another subset of proteins) the ratio of populations can be 1:1. For an injectable composition (e.g. subcutaneous, intramuscular, etc.) the protein is preferably present in the composition in an amount such that the total volume of the composition administered is 0.5 ml to 5.0 ml, typically 1.0-3.0 ml. When the composition is a whole cell preparation, the cells are preferably present in the composition in an amount that the total volume of the composition administered is 0.5 ml to 5.0 ml, typically 1.0-2.0 ml. The amount administered will vary depending on various factors including, but not limited to, the specific proteins or cells chosen, the weight, physical condition and age of the animal, and the route of administration. Thus, the absolute weight of the protein or number of cells included in a given unit dosage form can vary, and depends upon factors such as the species, age, weight and physical condition of the animal, as well as the method of administration. Such factors can be determined by one skilled in the art. Other examples of dosages suitable for the invention are disclosed in Emery et al. (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., a protein or whole cell described herein) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldiocradecylammonium bromide (DDA), avridine, aluminum hydroxide, oils, saponins, alpha-tocopherol, polysaccharides, emulsified paraffins (available from under the tradename EMULSIGEN from MVP Laboratories, Ralston, Nebr.), ISA-70, RIBI and other substances known in the art.

In another embodiment, a composition including a pharmaceutically acceptable carrier can include a biological response modifier, such as, for example, IL-2, IL-4 and/or IL-6, TNF, IFN-alpha, IFN-gamma, and other cytokines that effect immune cells. A composition can also include an antibiotic, preservative, anti-oxidant, chelating agent, etc. Such components are known in the art.

Methods of Making

This disclosure also provides methods for obtaining the proteins and whole cells described herein. Proteins and whole cell preparations described herein may be obtained by incubating a microbe, such as *P. multocida*, under conditions that promote expression of one or more of the proteins described herein. The proteins and whole cells as described herein may be isolatable from a microbe engineered to recombinantly express one or more of the proteins. In one embodiment, a *P. multocida* of serotype 2,5 or serotype 3,4 is used. In addition, such microbes are readily obtainable by techniques routine and known in the art. The microbes may be derived from an infected animal as a field isolate, and used to obtain the proteins and/or the whole cell preparations as described herein, or stored for future use, for example, in a frozen repository at from −20° C. to −95° C., or from −40° C. to −50° C., in bacteriological media containing 20% glycerol, and other like media.

The present invention also includes compositions prepared by the processes disclosed herein. Typically, such conditions are low metal conditions. As used herein, the phrase "low metal conditions" refers to an environment, typically a bacteriological medium that contains amounts of a free metal that cause a microbe to express a metal regulated protein at a detectable level. As used herein, the phrase "high metal conditions" refers to an environment that contains an amount of a free metal that causes a microbe to express a metal-regulated protein at a decreased level compared to expression of the metal-regulated protein under low metal conditions. In some cases, "high metal conditions" can refer to an environment that causes a cell to fail to express one or more of the metal-regulated proteins described herein at a detectable level. In some cases, "high metal conditions" can include a metal-rich natural environment and/or culture in a metal-rich medium without a metal chelator. In contrast, in some cases, "low metal conditions" can include culture in a medium that includes a metal chelator, as described in more detail below. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron, copper, or zinc.

Low metal conditions are generally the result of the addition of a metal chelating compound to a bacteriological medium, the use of a bacteriological medium that contains low amounts of a metal, or a combination thereof. High metal conditions are generally present when a chelator is not present in the medium, when a metal is added to the medium, or a combination thereof. Examples of metal chelators include natural and synthetic compounds. Examples of natural compounds include plant phenolic compounds, such as flavonoids. Examples of flavonoids include the iron chelator myricetin. Examples of synthetic iron chelators include 2,2'-dipyridyl (also referred to in the art as 2,2'-bipyridyl), 8-hydroxyquinoline, ethylenediamine-di hydroxyphenylacetic acid (EDDHA), desferrioxamine methanesulphonate (desferol), transferrin, lactoferrin, ovotransferrin, biological siderophores, such as the catecholates and hydroxamates, and citrate.

In one embodiment, 2,2'-dipyridyl is used for the chelation of iron. Typically, 2,2'-dipyridyl is added to the media at a concentration of at least 0.0025 micrograms/milliliter (μg/ml), at least 0.025 μg/ml, or at least 0.25 μg/ml. High levels of 2,2'-dipyridyl can be 10 μg/ml, 20 μg/ml, or 30 μg/ml.

Typically, TPEN is added to the media at a concentration of at least 25 micromolar (μM), at least 50 μM, or at least 70 μM. In one embodiment, TPEN can be 70 μM for expression of the polypeptide described herein, and higher levels may also be used.

It is expected that a *P. multocida* with a mutation in a fur gene will result in the constitutive expression of many, if not all, of the metal regulated proteins of the present invention. The production of a fur mutation in a *P. multocida* can be produced using routine methods including, for instance, electroporation and genetic constructs useful for gene knock-out in gram negative bacteria.

In one embodiment, the microbe, such as *P. multocida* used to make a composition described herein, e.g., a composition including isolated proteins or a composition including whole cells, may be produced using a *P. multocida* that has been engineered to recombinantly express one or more of the proteins described herein. In one embodiment, a *P. multocida* that expresses one or more of the proteins can be engineered to express the others. In one embodiment, such a *P. multocida* is incubated in the presence of low iron conditions, and the one or more recombinant proteins are expressed during the incubation in the low iron conditions. The result is a *P. multocida* that expresses iron-regulated proteins and the one or more recombinant proteins.

Many *Pasteurella* spp. are able to grow in low metal conditions in vitro in artificial media only after adaptation. For instance, a *Pasteurella* spp. can be adapted to low iron conditions in vitro by growth in the presence of low concentrations of an iron chelator and, after growth in a medium containing the chelator, gradually increasing the concentration of the chelator. For instance, a *Pasteurella* spp. can be adapted to growth in low iron conditions by adding 0.0025 μg/ml of 2,2'-dipyridyl to a medium, and gradually increasing the concentration of the chelator to a greater concentration, for instance 25 μg/ml.

The medium used to incubate the microbe is not critical, and conditions useful for the culture of *P. multocida* are known to the skilled person. The volume of medium used to incubate the microbe can vary. When a *P. multocida* microbe is being evaluated for the ability to produce the proteins described herein, the microbe can be grown in a suitable volume, for instance, 10 milliliters to 1 liter of medium. When a microbe is being grown to obtain proteins for use in, for instance, administration to animals, the microbe may be grown in a bioreactor to allow the isolation of larger amounts of proteins. Methods for growing microbes in a bioreactor are routine and known in the art. The conditions used for growing a microbe preferably include a metal chelator, more preferably an iron chelator, for instance 2,2'-dipyridyl, TPEN, or quercetin, a pH of between 6.5 and 7.5, preferably between 6.9 and 7.1, and a temperature of 37° C. When a fermentor is used, the culture may be purged with an appropriate gas to reduce dissolved oxygen content. Nitrogen is an example of such a gas. Dissolved oxygen may be regulated automatically or manually by agitation, the introduction of sterile air or pure oxygen to the culture.

In some aspects of the invention, a *P. multocida* may be harvested after growth. Harvesting includes concentrating the microbe into a smaller volume and suspending in a media different than the growth media. Methods for concentrating a microbe are routine and known in the art, and include, for example, filtration and/or centrifugation. Typically, the concentrated microbe is suspended in decreasing amounts of buffer. Preferably, the final buffer includes a metal chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted. In one embodiment, bacterial cells may be concentrated into a pellet by, for instance, centrifugation, and the concentrated cells suspended in osmotic shock buffer (OMS; 7.26 grams/liter Tris-base and 0.93 grams/liter EDTA adjusted to a pH of 8.5). The ratio of cells to OMS may be 50 grams cell pellet, 60 grams cell pellet, or 70 grams cell pellet to 1 liter of OMS. The suspension of cells in OMS can be incubated at 2-8° C. for at least 24 hours, at least 48 hours, or at least 60 hours to remove excess endotoxin from the cells. In one embodiment, the incubation is for no greater than 72 hours. After the incubation the suspension is centrifuged again and the supernatant discarded to remove free endotoxin and any extracellular material, e.g., secreted proteins.

When the *P. multocida* is to be used as a whole cell preparation, the harvested cells may be processed using routine and known methods to inactivate the cells. Alternatively, when a *P. multocida* is to be used to prepare proteins of the present invention, the *P. multocida* may be disrupted using chemical, physical, or mechanical methods routine and known in the art, including, for example, french press, sonication, or homogenization. Preferably, homogenization is used. As used herein, "disruption" refers to the breaking up of the cell. Disruption of a microbe can be measured by methods that are routine and known in the art, including, for instance, changes in optical density. Typically, a microbe is subjected to disruption until the percent transmittance is increased by 20% when a 1:100 dilution is measured. The temperature during disruption is typically kept at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., proteins, nucleic acids, carbohydrates) into the aqueous phase of the buffer in which the microbe was disrupted, and the formation of aggregates of insoluble cellular materials. The conditions for solubilization preferably result in the aggregation of proteins of the present invention into insoluble aggregates that are large enough to allow easy isolation by, for instance, centrifugation.

Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known in the art, including, for instance, changes in optical density. Typically, the solubilization is allowed to occur for at least 24 hours, more preferably, at least 48 hours, most preferably, at least 60 hours. The temperature during disruption is typically kept low, preferably at 4° C.

The insoluble aggregates that include the proteins described herein may be isolated by methods that are routine and known in the art, such as centrifugation, filtration, or a combination thereof. In one embodiment, the insoluble aggregates are isolated by filtration, such as tangential or crossflow filtration. Examples of a molecular weight cutoff to use with tangential filtration are 100 kDa or 300 kDa. In one embodiment, a tangential filtration system has a pore size of 0.2 microns. Tangential filtration may aid in removal of residual sarcosine from the protein suspension. Tangential filtration results in concentration of the protein suspension. Thus, the insoluble aggregates can be isolated at a significantly lower cost.

In one embodiment, the sarcosine is removed from the isolated proteins. Methods for removing sarcosine from the isolated proteins are known in the art, and include, for instance, diafiltration, precipitation, hydrophobic chromatography, ion-exchange chromatography, affinity chromatography, and ultra-filtration and washing the proteins in alcohol, such as isopropyl alcohol, by diafiltration. After isolation, the proteins suspended in buffer and stored at low temperature, for instance, −20° C. or below. In those aspects of the present invention where a whole cell preparation is to be made, after growth the microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

In other aspects, an isolated protein of the invention may be prepared recombinantly. When prepared recombinantly, a polynucleotide encoding the protein may be identified and cloned into an appropriate expression host. The recombinant expression host may be grown in an appropriate medium, disrupted, and the proteins isolated as described above.

Methods of Use

Also provided are methods of using the compositions described herein. The methods include administering to an animal an effective amount of a composition described herein. As used herein, an "effective amount" of a composition described herein is the amount able to elicit the desired response in the recipient. The composition can be administered at a time that maternal antibody may be present, for instance, as early as one day of age, or at a later time during the life of the animal. In one embodiment, the composition is administered before weaning, or at the time the animal is weaned (when the animal begins to be accustomed to food other than its mother's milk). The animal can be, for instance, fish, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, a dog or a cat), members of the family Cervidae (including, for instance, deer, elk, moose, caribou and reindeer), or a human. Examples of companion animals include dogs and cats. In one embodiment, an animal is a mouse. In one embodiment, an animal is a hooved animal.

The methods described herein refer to gram negative microbes. As used herein, a gram negative microbe includes, but is not limited to, members of the family Pasteurellaceae, such as *Pasteurella* spp. (including, for instance, *P. multocida* and *P. haemolytica*), *Photobacterium damsela* subsp., *piscicida* formerly known as *Pasteurella piscicida, Mannheimia* spp., and *Haemophilus* spp., members of the family Vibrionaceae (including, for instance, *Vibrio cholerae*), *Campylobacter* spp. (including, for instance, *C. jejuni*), members of the family Enterobacteriaceae (including, for instance, *Klebsiella* spp., *E. coli, Shigella* spp., *Salmonella* spp., *Proteus* spp., *Serratia* spp., and *Yersinia* spp.), and members of the family Pseudomonadaceae, preferably *Pseudomonas* spp., (including, for instance, *Pseudomonas aeruginosa*). Examples of *Klebsiella* spp. include *K. pneumoniae* and *K. oxytoca*. Examples of *Salmonella* spp. include *Salmonella enterica* serovars., Bredeney, Dublin, Agona, Blockley, *Enteriditis, Typhimurium*, Hadar, Heidelberg, Montevideo, Muenster, Newport senftenberg *Salmonella cholerasuis*, and *S. typhi*. Examples of strains of *P. multocida* include, for example, *P. multocida* serotypes 1 through 16 (serotype 1, 2, 3, 4, 5, 6, 7, 8, 9, 10, 11, 12, 13, 14, 15, or 16) or combinations thereof (for instance, 2,5, also referred to as 2×5 [both serotypes 2 and 5 are expressed by a *P. multocida*], or 3, 4 also referred to as 3×4 [both serotypes 3 and 4 are expressed by a *P. multocida*]). Examples of strains of *E. coli* include, for example, *E. coli* serotypes O1a, O2a, O78, and O157; different O:H serotypes including 0104, 0111, 026, 0113, 091; hemolytic strains of enterotoxigenic *E. coli* such as $K88^+$, $F4^+$, $F18ab^+$, and $F18ac^+$; enteropathogenic (EPEC), enterohemorrhagic (EHEC), enteroinvasive (EIEC) and enteroaggregative (EAEC) strains of *E. coli*; and *E. coli* able to cause extra-intestinal infections, such as uropathogenic strains. In one embodiment, the gram negative microbe is a pathogenic microbe. Respiratory pathogens such as *Bordetella* such species as *B. bronchiseptica, B. pertussis* and *B. parapertussis*, and *B. avium*.

In some embodiments, a method may further include additional administrations (e.g., one or more booster administrations) of the composition to the animal to enhance or stimulate a secondary immune response. A booster can be administered at a time after the first administration, for instance, one to eight weeks, preferably two to four weeks, after the first administration of the composition. Subsequent boosters can be administered one, two, three, four, or more times annually. Without intending to be limited by theory, it is expected that in some embodiments annual boosters will not be necessary, as an animal will be challenged in the field by exposure to microbes expressing proteins having epitopes that are structurally related to epitopes present on proteins of the composition administered to the animal.

In one embodiment, a method includes making antibody to a protein described herein, for instance by inducing the production of antibody in an animal, or by recombinant techniques. The antibody produced includes antibody that specifically binds at least one protein present in the composition. In this embodiment, an "effective amount" is an amount effective to result in the production of antibody in the animal. Methods for determining whether an animal has produced antibodies that specifically bind a protein present in a composition of described herein can be determined using routine methods. Also provided is antibody that specifically binds to a protein described herein, and compositions including such antibodies.

As used herein, an antibody that can "specifically bind" a protein is an antibody that interacts with the epitope of the antigen that induced the synthesis of the antibody, or interacts with a structurally related epitope. At least some of the epitopes present in the proteins described herein are epitopes that are conserved in the proteins of different species and different genera of microbes. Accordingly, antibody produced using a protein described herein is expected to bind to proteins expressed by more than one species of microbe, and provide broad spectrum protection against gram negative microbes.

In one embodiment, a method includes treating an infection in an animal, caused by a gram negative microbe. As used herein, the term "infection" refers to the presence of a gram negative microbe in an animal's body, which may or may not be clinically apparent. Treating an infection can be prophylactic or, alternatively, can be initiated after the animal is infected by the microbe. Treatment that is prophylactic—e.g., initiated before a subject is infected by a microbe or while any infection remains subclinical—is referred to herein as treatment of a subject that is "at risk" of infection. As used herein, the term "at risk" refers to an animal that may or may not actually possess the described risk. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered. The method includes administering an effective amount of a composition described herein to an animal having, or at risk of having, an infection caused by a gram negative microbe, and determining whether the number of microbes causing the infection has decreased. In this embodiment, an "effective amount" is an amount effective to reduce the number of the specified microbes in an animal or reduce the likelihood that the animal experiences a clinically-evident infection compared to an animal to which the composition is not administered. Methods for determining whether an infection is caused by a gram negative microbe are routine and known in the art, as are methods for determining whether the infection has decreased. The successful treatment of a gram negative microbial infection in an animal is disclosed in Examples 15-16, which demonstrates that a composition described herein made from two *P. multocida* strains, one serotype 2×5 and one serotype 3×4, protected chickens from challenge with a *P. multocida* of serotype 1.

In another embodiment, a method includes treating one or more symptoms or clinical signs of certain conditions in an animal that may be caused by infection by a gram negative microbe. The method includes administering an effective amount of a composition described herein to an animal having or at risk of having a condition, or exhibiting symptoms and/or clinical signs of a condition, and determining whether at least one symptom and/or clinical sign of the condition is changed, preferably, reduced. In one embodiment, the animal has a condition caused by a member of the family Pasteurellaceae, such as *Pasteurella* spp. (including, for instance, *P. multocida, P. haemolytica*, and *P. anatipestifer*), *Mannheimia* spp., or *Haemophilus* spp.

Examples of conditions include, but are not limited to, fowl cholera, new duck disease, Bovine Respiratory Disease Complex (also referred to as shipping fever pneumonia, or simply pneumonia), hemorrhagic septicemia in cattle, buffalo and bison in tropical and subtropical areas; pneumonia and atrophic rhinitis in swine; snuffles in rabbits; and mastitis and pneumonia in sheep. *Mannheimia haemolytica*, also known as *Pasteurella haemolytica*, can cause fibrinous pleuropneumonia involved in the shipping fever complex in cattle, septicemia in newborn and pneumonia and mastitis in adult sheep. *Haemophilus* spp. can cause Glasser's disease in swine, fowl coryza in chickens, contagious equine metritis. *P. multocida* can cause fowl cholera which, in the peracute form, is one of the most virulent and highly infectious diseases of poultry. *P. anatipestifer* can cause new duck disease (also known as duck septicaemia or infectious serositis).

Treatment of symptoms and/or clinical signs associated with conditions caused by infection by a gram negative microbe can be prophylactic or, alternatively, can be initiated after the development of a condition described herein. As used herein, the term "symptom" refers to subjective evidence of a disease or condition experienced by the patient and caused by infection by a microbe. As used herein, the term "clinical sign" or, simply, "sign" refers to objective evidence of disease or condition caused by infection by a microbe. Symptoms and/or clinical signs associated with conditions referred to herein and the evaluations of such symptoms are routine and known in the art. Treatment that is prophylactic, for instance, initiated before a subject manifests symptoms or signs of a condition caused by a microbe, is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administration of a composition can be performed before, during, or after the occurrence of the conditions described herein. Symptoms and/or clinical signs caused by a gram negative microbial infection are known to the person skilled in the art. Examples of symptoms and/or clinical signs include, but are not limited to, pneumonia, depression and toxemia, fever, serious to mucopurulent nasal discharge, moist cough, a rapid, shallow respiratory rate, abscesses and lesions in the lungs of cattle and swine; acute septicemia, joint infections and arthritis in poultry and wildfowl; turbinate atrophy in swine; superficial abscesses in cats; bite wound infections in humans, usually from dog or cat bites. Treatment initiated after the development of a condition may result in decreasing the severity of the symptoms or signs of one of the conditions, or completely removing the symptoms or signs. In this embodiment, an "effective amount" is an amount effective to prevent the manifestation of symptoms or signs of a disease, decrease the severity of the symptoms or signs of a disease, and/or completely remove the symptoms or signs.

Also provided is a method for decreasing colonization by a gram negative microbe, for instance blocking the attachment sites of a gram negative microbe, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioles, alveoli), digestive system (for instance, mouth, salivary glands, esophagus, liver, stomach, large and small intestine), excretory system (for instance, kidney, ureter, bladder, and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like.

Decreasing colonization in an animal may be performed prophylactically or, alternatively, can be initiated after the animal is colonized by the microbe. Treatment that is prophylactic—e.g., initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe and regardless of whether the animal may harbor a sub-colonization number of the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition described herein to an animal colonized by, or at risk of being colonized by, a gram negative microbe. In this embodiment, an "effective amount" is an amount sufficient to decrease colonization of the animal by the microbe, where decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art. For instance, colonization of an animal's respiratory tract by a microbe can be determined by measuring the presence of the microbe in the animal's specimens from the lower respiratory tract by tracheal swab, transtracheal wash, or bronchoalveolar lavage. It is expected that decreasing the colonization of an animal by a microbe will reduce transmission of the microbe to other animals of the same or different species.

Also provided is the use of such antibody to target a microbe expressing a protein having an epitope structurally related to an epitope present on a protein described herein. A composition described herein can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc.

for passive immunization therapies. Antibody compositions including monoclonal antibodies and/or anti-idiotypes can also be prepared using known methods. Chimeric antibodies include human-derived constant regions of both heavy and light chains and murine-derived variable regions that are antigen-specific (Morrison et al., Proc. Natl. Acad. Sci. USA, 1984, 81(21):6851-5; LoBuglio et al., Proc. Natl. Acad. Sci. USA, 1989, 86(11):4220-4; Boulianne et al., Nature, 1984, 312(5995):643-6.). Humanized antibodies substitute the murine constant and framework (FR) (of the variable region) with the human counterparts (Jones et al., Nature, 1986, 321(6069):522-5; Riechmann et al., Nature, 1988, 332(6162):323-7; Verhoeyen et al., Science, 1988, 239(4847):1534-6; Queen et al., Proc. Natl. Acad. Sci. USA, 1989, 86(24):10029-33; Daugherty et al., Nucleic Acids Res., 1991, 19(9):2471-6.). Alternatively, certain mouse strains can be used that have been genetically engineered to produce antibodies that are almost completely of human origin; following immunization the B cells of these mice are harvested and immortalized for the production of human monoclonal antibodies (Bruggeman and Taussig, Curr. Opin. Biotechnol., 1997, 8(4):455-8; Lonberg and Huszar, Int. Rev. Immunol., 1995; 13(1):65-93; Lonberg et al., Nature, 1994, 368:856-9; Taylor et al., Nucleic Acids Res., 1992, 20:6287-95.). Passive antibody compositions and fragments thereof, e.g., scFv, Fab, $F(ab')_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a protein having an epitope structurally related to an epitope present on a protein described herein.

Animal models are available for experimentally evaluating the compositions described herein. These models are commonly accepted models for the study of disease caused by gram negative microbes. In those cases where a gram negative microbe causes disease in an animal, for instance a cow or a chicken, the natural host can be used to experimentally evaluate the compositions described herein.

However, protection in an animal model is not the only way to assess whether a composition can confer protection to an animal against infection by a gram negative microbe. The adaptive immune response consists of two primary divisions: the humoral (antibody) response and the cellular (T cell) response. Following infection by a bacterial pathogen, dendritic cells at the infection site encounter microbial antigens and produce signaling molecules such as, for example, surface receptors and cytokines in response to conserved molecular patterns associated with the specific bacterium. These signals are shaped by the nature of the pathogen and ideally lead to the appropriate antibody and T cell responses that protect the host from disease. While some bacterial diseases are controlled primarily through antibody functions, others require T cell responses or both antibody and T cell responses for protection. The goal of vaccine biology is to identify the immune responses that provide protection and then design a vaccine to reproduce one or more of these responses in humans.

Antibodies can have many different functions in conferring protection against infection such as, for example, complement fixation, opsonization, neutralization, and/or agglutination. Moreover, some subclasses of antibodies are better than others at specific functions; for example, or complement fixation the following hierarchy exists for human IgG subclasses: IgG3>IgG1>IgG2>IgG4.

Antibody immunological functions can be studied in a variety of ways. For instance, Western blots are used to identify antigen-specific binding based on size of separated proteins, while the standard enzyme-linked immunosorbant assay (ELISA) is used to produce quantitative information about antibody titers within serum. Antibody surface binding studies are used to determine whether antibody in serum are able to recognize antigens on the surface of intact bacteria, an important indicator of whether the antibodies have the potential to work in vivo. Thus, one skilled in the art recognizes that antibody binding assays such as a Western blot, ELISA (e.g., using human antisera), and/or surface binding correlate positively with the specifically-bound antigens providing immunological activity against microbial infection. However, one skilled in the art further recognizes that a lack of antibody binding in an assay such as, for example, a Western blot, ELISA, or surface binding assay does not mean that the assayed antigen fails to provide immunological activity against microbial infection.

Antibodies can mediate bacterial death by blocking the acquisition of nutrients or initiating complement-mediated membrane perforation that leads to osmotic lysis. Bactericidal antibodies can be assayed by mixing serum with live cultures and measuring for the presence of viable bacteria under appropriate conditions known to those skilled in the art. Techniques such as opsonophagocytosis assays (OPA), in which antibody and complement-bound bacteria are combined with human or mouse phagocytes to determine levels of bacterial killing, are useful for studying antibody function. A similar oxidative burst assay can be used to assess the level of reactive oxygen species (ROS) by fresh human or mouse neutrophils following interaction with antibody and complement-bound bacteria.

In some cases, one can determine that a protein described herein possesses cell-mediated immunological activity against a gram negative microbe and, therefore, the protein may exhibit immunological activity in the absence of inducing the production of antibodies. Cytotoxic or CD8 T cells primarily kill infected cells directly through various effector mechanisms, while helper CD4 T cells function to provide important signaling in the way of cytokines. These T cell classes can be further subdivided based on the cytokines they produce, and different subclasses are effective against different bacterial pathogens. T cells are often studied by assessing their phenotypes with flow cytometry, where antibodies are used to visualize the levels of specific surface markers that enable classification of the T cells as, for example, a recently activated $CD4^+$ T cell, a memory $CD8^+$ T cell, etc. In addition, cytokines and other products of T cells can be studied by isolating the T cells from lymphoid tissue and restimulating them with cognate antigen. Following antigen stimulation the T cells produce cytokines that may be visualized by, for example, intracellular cytokine staining coupled with flow cytometry, or collecting the cell supernatants and using Luminex bead technology to measure 15-25 cytokines simultaneously.

Thus, in addition to animal models, those of ordinary skill in the art recognize that immunological activity commensurate with the methods described herein may correlate with any one or more of the following: Western blot data showing that serum from animals exposed to a microbial pathogen contains antibody that specifically binds to a protein described herein, Western blot data showing that serum from animals exposed to protein described herein contains antibody that specifically binds to a gram negative microbe, cell surface binding assays demonstrating that antibody that specifically binds to a protein described herein specifically binds to a gram negative microbe, opsonophagocytosis data, and cytokine induction.

Also provided is a method for detecting antibody that specifically binds proteins described herein. These methods are useful in, for instance, detecting whether an animal has antibody that specifically binds a protein described herein, and diagnosing whether an animal may have a condition caused by a microbe expressing proteins that share epitopes with the proteins described herein. Such diagnostic systems may be in kit form. The methods include contacting an antibody with a preparation that includes a protein described herein to result in a mixture. The antibody may be present in a biological sample, for instance, blood, milk, or colostrum. The method further includes incubating the mixture under conditions to allow the antibody to specifically bind the protein to form a protein:antibody complex. As used herein, the term "protein:antibody complex" refers to the complex that results when an antibody specifically binds to a protein. The preparation that includes the proteins described herein may also include reagents, for instance a buffer, that provide conditions appropriate for the formation of the protein: antibody complex. The protein:antibody complex is then detected. The detection of antibodies is known in the art and can include, for instance, immunofluorescence or peroxidase. The methods for detecting the presence of antibodies that specifically bind to proteins described herein can be used in various formats that have been used to detect antibody, including radioimmunoassay and enzyme-linked immunosorbent assay.

Kits

Also provided are kits. In one embodiment, a kit is for detecting antibody that specifically binds a protein described herein. The antibody detected may be obtained from an animal suspected of having an infection caused by a gram negative microbe. In another embodiment, a kit is for detecting a protein described herein. In yet another embodiment, a kit is for using a protein described herein, such as using a protein to produce antibody, treat a condition, or treat an infection.

The kit includes at least one of the proteins described herein (e.g., one, at least two, at least three, etc.), or an antibody described herein in a suitable packaging material in an amount sufficient for at least one assay or use. Optionally, other reagents such as buffers and solutions are also included. For instance, a kit may also include a reagent to permit detection of an antibody that specifically binds to a protein described herein, such as a detectably labeled secondary antibody designed to specifically bind to an antibody obtained from an animal. Instructions for use of the packaged antibody or protein are also typically included. As used herein, the phrase "packaging material" refers to one or more physical structures used to house the contents of the kit. The packaging material is constructed by routine methods, generally to provide a sterile, contaminant-free environment. The packaging material may have a label which indicates that the proteins can be used for detecting antibody that specifically binds a protein described herein, or using a protein described herein. In addition, the packaging material contains instructions indicating how the materials within the kit are employed to detect the antibody or administer a protein to an animal. As used herein, the term "package" refers to a container such as glass, plastic, paper, foil, and the like, capable of holding within fixed limits the proteins, and other reagents, for instance a secondary antibody. Thus, for example, a package can be a microtiter plate well to which microgram quantities of proteins have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

Example 1

Selection and Preparation of Type Strains

*Pasteurella multocida* strains X-73, P-1059 and P-1662 are reference strains for serotype A:1, A:3 and A:4, respectively. Serotypes A:1, A:3, and A:4 are also referred to as serotypes 1, 3, and 4, respectively. Each of these strains was obtained from the USDA National Veterinary Services Laboratory (NVSL) (Ames, Iowa) as a lyophilized culture. The cultures were resuspended in sterile saline, streaked for isolation using a sterile inoculating loop onto trypticase soy agar(TSA)+5% sheep blood (Becton Dickenson, Sparks Md.), and incubated overnight at 37° C. Several isolated colonies were picked from the plate with a sterile inoculating loop and transferred to a cryobank tube (Copan diagnostics, Murrietta Calif.) containing polystyrene beads for the purpose of cryopreservation. The cryobank tubes were then stored at <−60° C.

Example 2

Preparation of *Pasteurella multocida* Isolate

A *Pasteurella multocida*, serotype 3×4 was originally isolated from the liver and lungs of a 44 week old turkey breeder hen under natural field conditions showing clinical signs of Pasteurellosis. The isolate was plated on a tryptic soy agar (TSA) plus 5% sheep blood. After initial isolation, the organism was passed 5 times in non-animal-based Trypticase Soy Broth (naTSB) (EM Science, Darmstadt, Germany) (supplemented with 18 μg/ml 2,2' Dipyridyl (DP) (Sigma Aldrich, St. Louis, Mo.) and 6 g/l Yeast Extract (Becton Dickenson, Sparks, Md.). Briefly, colonies were picked and inoculated into 500 ml naTSB and the culture was incubated for 16 hours and 25 minutes at 37° C. on a table-top shaker set at 105 revolutions per minute (RPM). The following morning, 25 ml of the overnight culture was transferred to 500 ml fresh naTSB and incubated for 8 hours at the same temperature and agitation. Five ml of the culture was transferred to 500 ml fresh naTSB and incubated for 15 hours in the same conditions as above. Fifty ml of this culture was transferred to 500 ml fresh naTSB and incubated in the same manner for 4 hours. Four bottles containing 900 ml naTSB each were each inoculated with 100 ml of the previous media and incubated for 3 hours and 45 minutes. The four liters of culture was aseptically dispensed into sterile 500 ml Nalgene jars and centrifuged in a Beckman model J2-21 centrifuge (Beckman Coulter, Brea Calif.) at 3500 rpm or approximately 1350×g for 20 minutes to pellet the bacterial cells. The supernatant was aseptically removed by aspiration and the cell pellets were resuspended in a total of 500 ml of naTSB containing 20% glycerol as a cryo-preservative. The cell suspension was then dispensed into 243 vials at 2 ml per vial and frozen at <−60° C. This frozen Master Seed was designated MS061130.

A working seed was prepared from the above frozen Master Seed. Briefly, 1-25 μl of the frozen seed was inoculated into 100 ml modified tryptose phosphate broth (mTPB) containing 6 g/l yeast extract. The culture was incubated for 13 hours at 37° C. on a table-top shaker until the culture reached an optical density (O.D.) of 0.6 to 0.8 on a Spectronic 20D spectrophotometer (Thermo Fisher Scientific, Mississauga, Ontario, Canada) set at 540 or 630 nm. The culture was transferred, 10 ml into 90 ml mTPB with 18 μg/ml 2, 2' dipyridyl and incubated for 2-3 hours at 37° C. with agitation. The culture was transferred and grown in the same manner two additional times as above. When the culture reached on O.D. of 0.8, the cells were centrifuged at approx. 3500 rpm for 20 minutes, the supernatant was aseptically removed by aspiration, and the culture was resuspended in the original volume of fresh mTPB. Sterile glycerol was added to reach 20% final concentration. The culture was mixed well, dispensed into sterile cryogenic vials at 2 ml per vial, and stored frozen at <−60° C.

Example 3

Production of Metal Regulated Proteins

*Pasteurella multocida* Type strains (X-73, P-1059, and P-1662) and the vaccine candidate strain (MS061130) of example 2 were grown in iron limiting and iron replete conditions in order to show differential membrane protein expression.

Each of the frozen type strain cultures from example 1 and the working seed isolate from example 2 were inoculated into 10 ml of porcine brain heart infusion broth (BD-Difco, Sparks Md.)+6 g yeast extract (pBHI) and incubated overnight at 37° C. with agitation. Two of the cultures did not grow directly in broth and so were first inoculated onto TSA+ blood agar plates and incubated overnight at 37° C. prior to transferring colonies to pBHI. Five ml of each overnight culture was transferred to 100 ml fresh pBHI containing either 20 μg/ml $FeCl_3$ or DP for iron-replete or iron-deplete conditions, respectively. The cultures were incubated at 37° C. for 7 hours and 30 minutes with agitation on a table top shaker (Barnstead, Dubuque Iowa). Bottles displayed turbidity indicating strong growth after incubation, and the cultures were then transferred, 50 ml into 500 ml of fresh pBHI containing either $FeCl_3$ or DP and incubated for 15 hours at 37° C., with agitation.

The cultures were processed to isolate outer membrane proteins. Briefly, the cultures were centrifuged for 20 minutes at approximately 11,000×g in a Beckman floor model centrifuge equipped with a JA-10 rotor (Beckman Coulter, Brea Calif.). The supernatant was decanted and discarded. The cell pellet was resuspended in 35 ml of Osmotic Shock Buffer (OMS) containing 7.26 grams/liter Tris-base and 0.93 grams/liter EDTA adjusted to a pH of 8.5, and the cell suspension was frozen at −80° C. for 3 hours to help weaken the cell wall structure. The cell suspension was then thawed and sonicated (Branson sonifier, model 102c) (Branson Ultrasonics, Danbury, Conn.) for 90 seconds in an ice water bath to prevent excessive heating of the disrupted cell suspension. Cell debris was removed by centrifugation at approximately 37,000×g for 20 minutes. Sodium lauroyl sarcosyl was added to the retained supernatant to reach a concentration of 3% v/v and the protein suspension was allowed to solubilize for 18-24 hours at 4° C. with slight agitation. Insoluble membrane proteins were collected by centrifugation at 37,000×g for at least two hours. The pellet was resuspended in tris buffered water and the resulting antigen was measured for protein content via the bicinchoninic acid (BCA) assay (Pierce BCA protein assay, ThermoFisher Scientific, Waltham Mass.) according to the manufacturer instructions.

Example 4

Test for Metal Regulated Protein Pattern Coverage by SDS-Page and Analysis of Protein Banding Cell extracts, derived from each isolate grown under iron restriction, were size-fractionated on SDS-PAGE gels using a 4% stacking gel and 10% resolving gel. Samples for electrophoresis were prepared by combining 30 μg of sample with 30 μl of SDS reducing sample buffer (62.5 mM Tris-HCL pH 6.8, 20% glycerol, 2% SDS, 5% beta-mercaptoethanol) boiled for 4 minutes. A sample of each extract was resolved on a 10% SDS-PAGE gel per standard methods and visualized by Coomassie Blue staining (FIG. 1). The vaccine candidate strain (MS061130) was compared to the type strains on SDS-PAGE gels. Specific attention was given to the banding patterns in the regions between 66 and 116 kDa. The vaccine candidate strain demonstrated bands overlapping with type strains, as shown in FIG. 1, and was considered a strong candidate for further protection studies.

Example 5

Production of Metal Regulated Proteins

Two separate antigen compositions were prepared at production scale using a single Master Seed MS061130 strain of *Pasteurella multocida* designated as antigen A and antigen B. This was done to evaluate the consistency of the manufacturing process.

Fermentation

A cryogenic vial of the working seed of example 2 was thawed at 30-35° C. for 10-15 minutes and 0.1 ml of the thawed cell suspension was added to 250 ml of 37° C. mTPB. The culture was incubated for 6.5 hours at 37° C. on a tabletop shaker set at 70 rpm. After incubation, 25 ml of the culture was transferred to 300 ml of mTPB plus 18 μg/ml DP to restrict iron. This second culture was incubated for approximately 2 hours at 37° C. shaking at 70 rpm. The culture was transferred 250 ml into 3 liters of the above media, and the culture was incubated for approximately 3 hours at 37° C. shaking at 70 rpm until an OD of 1 was reached (as measured at 540 nm). The entire culture was used to inoculate a 130 liter fermentor (Bio-Service, Easton, Pa.) charged with 70 liters of mTPB+18 μg/ml DP and 0.5 ml/1 antifoam (MAZU DF 204 Chem/Serv, Minneapolis, Minn.). The parameters of the fermentation were as follows: Dissolved oxygen (DO) was maintained at 20% (target 15-30%) by automatic agitation control and airflow sparge set at 60 liters per minute (LPM) and 5 pounds per square inch (PSI) back pressure. The culture was incubated with agitation controlled automatically by controlling dissolved oxygen at 20%. The pH was controlled automatically between 6.9 and 7.1 by the automatic titration of 50% sodium hydroxide or 10% hydrochloric acid. The temperature was maintained at 37° C. The culture was allowed to grow in this manner for approximately 5 hours until an optical density of 4.21 at 540 nm was reached as measured by a Beckman DU600 spectrophotometer (Beckman Instruments, Fullerton, Calif.). The entire expansion culture was transferred to a 1200 liter fermentation vessel (New Brunswick Scientific, Edison, N.J.) charged with 9891 of mTPB plus DP and antifoam as listed above. The fermentation conditions were as follows: Airflow was set to 300 LPM and back pressure set at 5 PSI. Agitation was initially set to 100 RPM and then controlled by dissolved oxygen set point of 20% with a range of 15-30%. The culture was allowed to grow for another 5 hours until growth plateaued, as measured by optical density measurements being steady at approximately 2.5 at 540 nm at a 1:100 dilution for 1.5 hours. Growth was suspended by adjusting the culture pH to 8.7 and the temperature to 23° C. until harvest.

Harvest

The Bacterial Cells were Collected by Tangential Flow Filtration.

The bacterial fermentation was concentrated and washed using a Pall Filtron Tangential Flow Maxisette-25 (Pall Filtron Corporation, Northboro, Mass.) equipped with two 30 $ft^2$ Alpha 300-K open channel filters, catalog No. AS30005, (Pall Filtron) connected to a Waukesha Model U-60 feed pump (Waukesha Chemy-Burrell, Delevan, Wis.) set at about 44 Hz. The original culture volume of 1078 liters was reduced to approximately 100 liters into a process tank (Lee Industries, model 2000LBDT) using a filter inlet pressure of 30 psi and a retentate pressure of 12-14 psi. The retentate (100 liters) was adjusted to 200 liters using sterile Osmotic Shock Buffer (OMS) containing 7.26 grams/liter Tris-base and 0.93 grams/liter EDTA adjusted to a pH of 8.5. The EDTA in the OMS serves to remove LPS from the cell wall, while the elevated pH prevents much of the proteolytic degradation after freezing and disruption. Protease inhibitors may be used instead, or in addition to, an elevated pH. The retentate was concentrated back down to approximately 65 liters and the system was flushed with 20 liters of OMS. The retentate was mixed thoroughly while in the 200-liter tank using a bottom mount magnetically driven mixer.

The retentate was sterilely dispensed (3.5 liters) into sterile 4 liter NALGENE containers No. 2122 in a biosafety cabinet and placed into a −20° C. freezer for storage. Freezing the bacterial pellet serves to weaken the cell wall structure making downstream disruption more efficient. The pellet mass was calculated by centrifuging 30 ml samples of the fermented culture and final harvest. Briefly, preweighted 50 ml NALGENE conical tubes were centrifuged at 39,000×g for 90 minutes in a BECKMAN J2-21 centrifuge using a JA-21 rotor (Beckman Instruments, Palo Alto Calif.). At the end of the run, the supernatant was poured off and the tubes were weighed again. The pellet mass was calculated for each stage. The fermentation process yielded a wet pellet mass of 3.7 kilograms.

Alternative methods for bacterial harvest can be used. Bacterial harvest may be performed by the use of hollow fiber filter methods. Bacterial culture is harvested using filter cartridges ranging in size from 0.6 μM to 750 kDa; preferably with a 750 kDa cartridge. Culture is reduced in volume from 2-20× and subsequently washed 1-5× by diafiltration with buffer prior to storage at 4° C. or freezing at −20° C. In this manner, undesired media proteins, bacterial proteins and LPS are removed from the culture. In another alternative, bacterial harvest may be performed by the use of industrial scale centrifugation, for example, by use of a disc-stack centrifuge.

Disruption

Sixty five Liters of frozen bacterial cell slurry in OMS were thawed at 4° C. (3.7 kg of pellet mass). The liquid culture suspension from each container was aseptically aspirated into a steam in place 150 liter jacketed process tank (Lee, Model Style U). The cell suspension was disrupted by homogenization. Briefly, the 150 liter tank containing the bacterial suspension was connected to an Avestin model EF-0500B Homogenizer (Avestin, Inc. Ottawa, ON, Canada). A 250 liter jacketed process tank (empty) (Lee, Model 259LU) with a top mounted mixer (Eastern, Model TME-1/2, EMI Incorporated, Clinton, Conn.) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of the pass, fluid was circulated at 60 psi via a Waukesha model 10DO pump (Waukesha) through the homogenizer (500 gallons/hour) and back to the tank of origin, while the homogenizer pressure was adjusted to 15,000 psi. Prior to homogenization, two pre-homogenizing samples were withdrawn from the homogenizer to establish a baseline for determining the degree of disruption and monitoring of pH. The degree of disruption was monitored by transmittance (% T at 540 nm at 1:100 dilution) compared to the non-homogenized sample. The starting % T was 86.65 at a 1:100 dilution. The cell slurry was passed once through the homogenizer, and the resulting % T was 89.9 at a 1:100 dilution.

After homogenization, 1 liter Sodium Lauroyl Sarcosinate (Hamposyl L-30, Chem Serv, Minneapolis, Minn.) was aseptically passed to the 81 liters of homogenized slurry for solubilization. The jacketed vessel removed from the homogenizer and was kept on a chiller loop at 5° C. mixing at 30% mixer speed. After 29 hours, 121 ml of formaldehyde was added as a preservative, followed by a 2 liter wash of OMS. Solubilization continued for a total of 46 hours and 16 minutes. This time period was important for complete solubilization. It was discovered that increasing the solubilization time in OMS at an elevated pH (8.0-8.5) that metal regulated proteins aggregated together forming large insoluble aggregates that were easily removed by centrifugation.

Protein Harvest

The aggregated metal regulated proteins within the solubilized process fluid were collected by centrifugation using T-1 SHARPLES, (Alfa Laval Separations, Warminster, Pa.). Briefly, the tank of solubilized homogenate was fed into twelve Sharples with a feed rate of 170 ml/minute at 11 psi. The first pass protein collected on the bowls of the Sharples was discarded. This consists of large cell debris and cell wall material. The effluent was collected into a second 250 liter jacketed process tank through a closed sterile loop allowing for multiple passes through the centrifuges while maintaining a closed system. The temperature during centrifugation was kept at 4° C. The solubilized homogenate was passed an additional 7 times across the centrifuges, at a feed rate of 150 ml/minute and a pressure of 21 PSI. Protein was collected after each pass. The protein was collected, resuspended and dispensed in 7.46 liters Tris-buffer pH 8.5. Twenty five ml of formaldehyde (Sigma) was added, to reach 0.3% concentration, as a preservative.

Alternative methods for protein harvest can be used. For example, the desired proteins can be harvested by the use of hollow fiber filter methods. Proteins can be harvested using filter cartridges ranging in size from 5 kDa to 0.2 μM; preferably with a 50 kDa to 750 kDa cartridge. Culture is reduced in volume from 2-20× and subsequently washed 1-5× by diafiltration with buffer prior to storage at 4° C. or freezing at −20° C.

Diafiltration

The protein suspension was washed by diafiltration at 4° C. to remove any contaminating sarcosine that may have been bound to the protein. Briefly, the 8640 ml of protein was sterilely aspirated into a 200 liter process tank containing 50 liters sterile Tris-buffer, pH 8.5, equipped with a bottom mount Dayton mixer, Model 2Z846 (Dayton Electric, Chicago, Ill.) rotating at 125 rev/minute. The process tank was sterilely connected to a MILLIPORE PELLICON TANGENTIAL FLOW FILTER assembly (Millipore Corporation), equipped with a 25 ft2 screen-channel series Alpha 10K Centrasette filter (Pall Filtron) connected to a Waukesha Model U30 feed pump. The 59 liter protein solution was brought to 150 liters by adding TBW, concentrated down to 35 liters, brought up to a volume of 110 liters of TBW and then concentrated down to 10.4 L final antigen volume. The protein concentrate was aseptically dispensed (3.5 liters) into sterile 4 liter NALGENE containers and placed into a −20° C. freezer for storage.

This process produced a composition containing metal regulated proteins with a decrease in the amount of LPS and very little to no sarcosine residue. The protein was examined by SDS-PAGE for purity and banding profile, and also examined for bacterial contamination, residual sarcosine and LPS. The banding profile of the finished product showed consistent patterns as examined by electrophoresis. The composition was tested for sarcosine by the use of a modified agar gel diffusion test in which sheep red blood cells (5%) were incorporated into an agar base (1.5%). Wells were cut into the agar and samples of the finished product along with control samples of known concentrations of sarcosine at 0.05, 0.1, 0.2, 0.3, 0.4, 0.5 1.0 and 2.0% were placed into the wells. The gel was incubated at 25° C. for 24 hours and the degree of hemolysis was determined compared to the controls. The process removes the level of detectable sarcosine below 0.05%, which at this concentration showed minimal hemolysis in control samples. The concentration of LPS is examined by a *Limulus* amebocyte lysate (LAL) test available under the tradename PYROTELL (Associates of Cape Cod, Inc., East Falmouth, Mass.).

Example 6

Preparation of Immunizing Compositions Derived from *Pasteurella multocida*

Three vaccine serials consisting of the same antigen was prepared from the Master Seed MS061130 of Example 5. Please Note: two antigen preparation representing two separate fermentation processes were used to prepare two antigen lots designated as antigen A and antigen B. Thus, The first vaccine serial was prepared using a mixture of antigen A and antigen B, the second vaccine serial was prepared only using antigen A, and the third vaccine serial was prepared using only antigen B.

The vaccine compositions consisting of antigen A, B and A+B were prepared in the following constituents: 44.44% aqueous protein suspension in 0.1% formalized saline, (standardized to 150 μg protein per chicken dose) 50% Drakeol 6 mineral oil (VOPAK USA, Inc, Kirkland, Wash.), 3.0% Span 85 and 2.56% Tween 85 (Ruger Chemicals, Hillside, N.J.). Briefly the Mineral Oil and Span 85 were combined and dispensed into a vessel equipped with a high-speed emulsifier (IKA model Process pilot 2000/4 or equivalent). Antigen, Tween 85 and 0.1% formalized saline was dispensed into a second vessel. The emulsifier was set at 60 hz, and the aqueous solution was pumped into the oil, which was pre-cooled to 7° C. The vaccine was continuously stirred as it was pumped into sterile bottles.

Example 7

Vaccination of Chickens

Leghorn type Specific Pathogen Free (SPF) chickens (Hy-Vac, Adel, Iowa) were vaccinated with the compositions of example 6. Briefly, 74 specific pathogen free (SPF) leghorn chickens were obtained at 11 weeks of age (WOA) and were allowed to acclimate for one week prior to vaccination. Birds were divided into 3 groups designated as Antigen A+B (21 Birds), Antigen A (21 birds), Antigen B (21 Birds and a group of non-vaccinated controls (11 Birds). Birds were identified by colored leg bands. At 12 WOA, all birds in groups Antigen A+B, Antigen A and Antigen B were vaccinated with 0.25 ml of the appropriate vaccine intramuscularly in the breast. A group of 11 chickens received no vaccine and served as the control group. At 15 weeks of age or twenty one days post second vaccination all vaccinated birds received a second vaccination

Example 8

Preparation and Administration of Challenge Organism

One day prior to challenge, one cryogenic bead of *Pasteurella multocida*, strain X-73 of example 1, was aseptically removed from the frozen stock and spread onto two TSA II plates with 5% sheep blood (Becton Dickenson) which were then streaked for isolation of colonies. The plates were incubated for 16-19 hours at 37° C. On day 14 or 14 days post second vaccination several colonies from the sheep blood agar plate were scraped from the blood plate and suspended in a sterile 13×100 test tube. Colonies were added or the suspension diluted with tryptose broth to obtain a % T of 71-75% at 630 nm using a Spectronics 20D (ThermoFisher) spectrophotometer. The suspension was serially diluted in tryptose broth to 1:100,000 dilution. This dilution was dispensed into serum vials for challenge.

Twenty chickens of each vaccinated group and 10 chickens of the control group were inoculated intramuscularly in the breast with 0.5 ml of the above diluted challenge. The extra chickens from the vaccinated and the control group were removed at this time.

Example 9

Challenge Results

Figure 2:
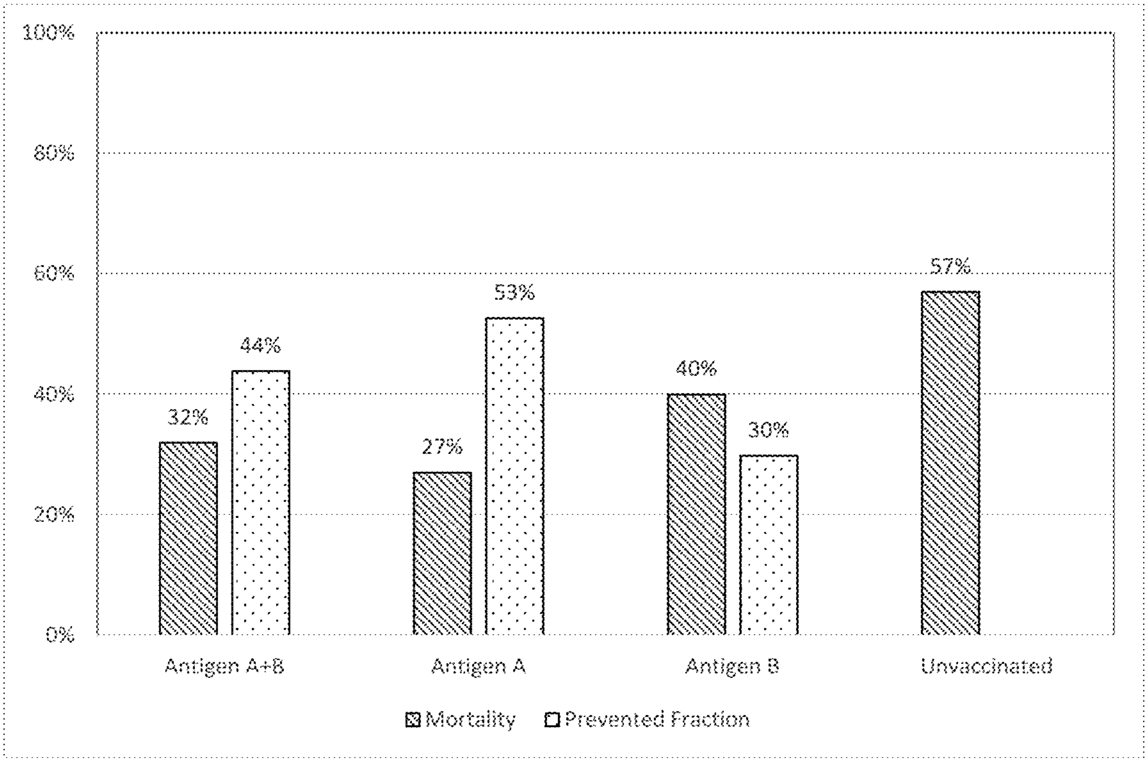
FIG. 2. Efficacy of three *Pasteurella multocida* vaccine serials produced from a single strain against challenge with heterologous *Pasteurella* serotype 1. Three vaccine serials consisting of the same antigen were prepared from the Master Seed MS061130. Note: two antigen preparation representing two separate fermentation processes were used to prepare two antigen lots designated as antigen A and antigen B. The first vaccine serial was prepared using a mixture of antigen A and antigen B, the second vaccine serial was prepared only using antigen A, and the third vaccine serial was prepared using only antigen B.

The results, shown in FIG. 2, are an average of three separate challenge studies conducted with the three serials. The term Prevented Fraction (PF) is the complement of the Risk Ratio (RR) and has long been used by epidemiologists as an expression of the preventative role of a protective factor, or the preventative success of an implemented program of intervention (Miettinen, 1974, Am J Epidemiol 99:

325-332) (Field Epidemiology, Oxford University Press, 2002, pp 147-'7). Prevented Fraction PF=1−p2/p1, where p2=affected fraction in the vaccinated group, and p1=affected fraction in the unvaccinated or placebo group. Veterinary fowl cholera vaccines are expected to routinely demonstrate a PF of 53% or greater, preferably 62.5% or greater Vaccines that demonstrate a PF of less than 53% demonstrate protection.

Table 1 presents mortality data from FIG. 2 and the calculations for Prevented Fraction for Antigen B of FIG. 2. Vaccine efficacy or prevented fraction was calculated to be 30%, indicating that vaccination prevented 30% of the cases that might have otherwise occurred among vaccinated birds had they not been vaccinated. These calculations were repeated for antigens A and A+B to obtain the prevented fraction for each vaccine.

TABLE 1

| | DEAD | NOT DEAD | TOTAL | RISK |
|---|---|---|---|---|
| Vaccinated Antigen B | 40% | 60% | 100% | 40% |
| Not Vaccinated | 57% | 43% | 100% | 57% |
| TOTAL | 97% | 103% | | |

Relative Risk = 40/57 = .70 or 70%
Vaccine Efficacy = (57 − 40)/57 = 0.3 or 30%

The difference between vaccinates and controls are significant ($p<0.05$) for two of the three vaccinate groups, but the prevented fraction was 53%, 30%, and 44% for antigen 1, antigen 2, and the combined antigen, respectively. While the vaccine met the 53% PF level in one case, it could not be demonstrated consistently, and therefore is inadequately effective for a commercial fowl cholera vaccine. Based upon the banding profiles observed in example 4, we expected very good protection. Unfortunately, the protection observed was less than expected. These unexpected results suggest that bands visually appearing to overlap on a SDS-PAGE gel as shown in FIG. 1 are not enough to confer the desired protection level.

Example 10

Known Genome Analysis

Current known genomes were surveyed for potential metal regulated proteins. Several strains of *Pasteurella multocida* have full or partial genome sequences available in the public domain. The Universal Protein Resource (Uniprot) is a comprehensive resource for protein sequence and annotation data. At the time of the search, the full or partial sequence data of serotype 1 reference strain X-73 and the serotype 3 reference strain P-1059 were present in this database. For each of these organisms, we searched the database for all proteins having molecular weights between 50 kilodaltons and 150 kilodaltons that had any annotation reference to iron uptake. The identified proteins were organized into a table (FIG. 3), where those of different strains having a similarity of greater than or equal to 95% were grouped together. Fourteen distinct proteins were identified among these strains.

The proteins were compared to expressed metal regulated proteins of the previous vaccine candidate (MS061130) as identified by MALDI-TOF analysis. There were eight proteins that appeared to be absent from the vaccine candidate, but were identified in additional genomes of other *Pasteurella multocida* strains derived from avian species. (See FIGS. 3 and 4).

Figure 4:
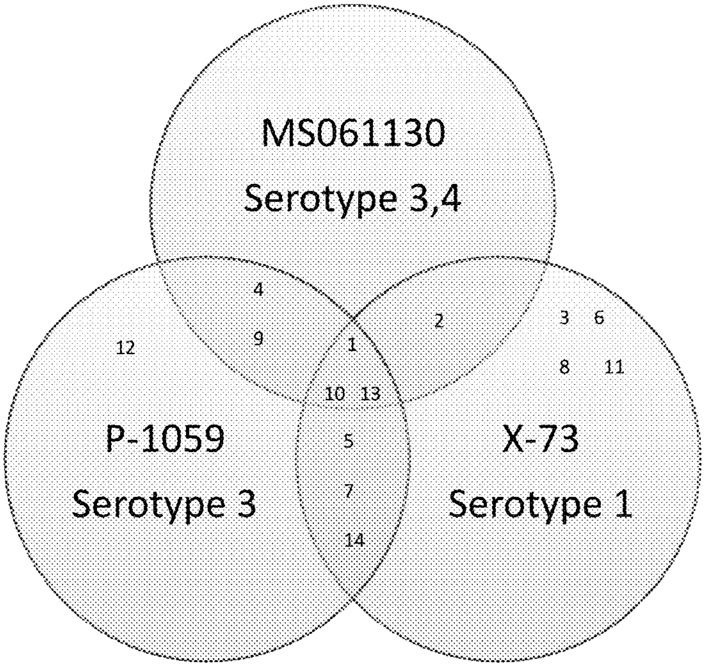
FIG. 4. Venn diagram illustrating outer membrane proteins missing from the vaccine strain (MS061130). Numbers correlate to the protein identification numbers of FIG. 3.

These results demonstrated that our vaccine candidate (MS061130) was potentially missing 7 desirable proteins that were identified by genomic analysis of additional strains of *Pasteurella*. This same observation was seen in the analysis of the genome of the challenge strain that was used in example 9 which also had the seven protein subset that was not present in the MS061130 vaccine candidate. Thus, the vaccine strain described in Examples 6-9 was missing 7 proteins that were present in the challenge strain (FIG. 3). The Venn diagram in FIG. 4 illustrates the number of proteins present in relevant challenge strains P1059 and X73 that are not present in the vaccine strain MS061130. These observations led us to hypothesize that a combination of two or more strains with comprehensive siderophore receptor coverage of the seven protein subset would provide a higher degree of protective efficacy as well show cross protection independent of serotype.

Example 11

Comparison of Iron-Restricted Protein Banding Patterns in Wild and Type Strains of *Pasteurella multocida*

Figure 5:
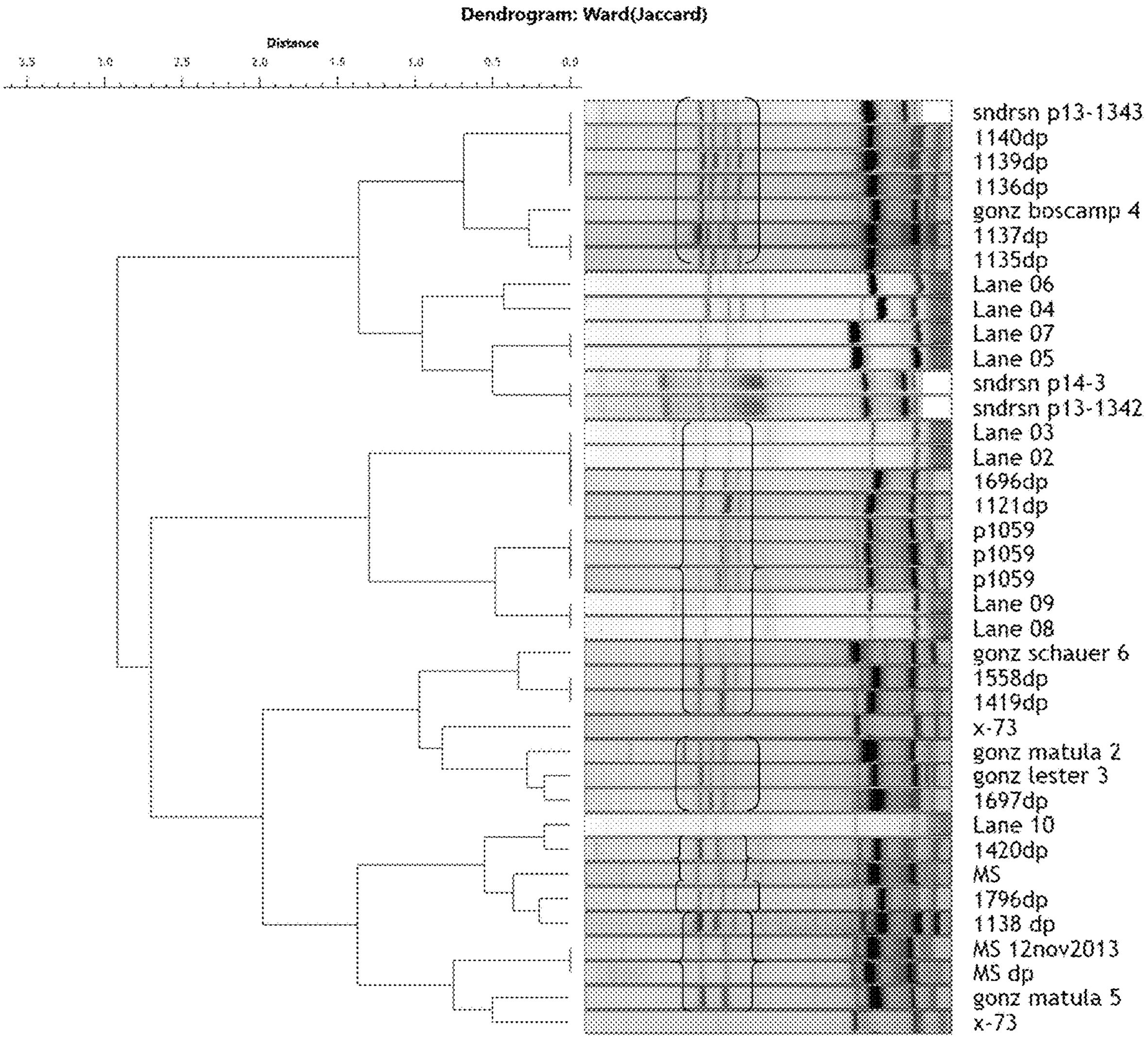
FIG. 5. Dendogram of metal regulated protein banding patterns of 30+ clinical field isolates and reference strains of *Pasteurella multocida*. Note the two major banding patterns as depicted as a four band pattern in brackets[ ], and a three band pattern in braces{ }. Most other strains appear to be variations on these two patterns.

In order to more fully understand metal regulated proteins in *Pasteurella*, thirty three type strains and clinical field strains of *Pasteurella multocida* were grown in iron-restricted medium and processed to purify membrane bound proteins in the manner of example 3. The resulting protein compositions were analyzed for metal regulated protein banding patterns on Sodium Dodecyl Sulfate-poly-acrylimide gel electrophoresis (SDS-PAGE) gels (Criterion TGX Stain-free gels, Bio-Rad laboratories, Hercules, Calif.). The individual lanes were compared and grouped using Phoretix 1D, a 1-dimensional gel analysis program (TotalLab, Newcastle upon Tyne, UK). A dendogram was created with Phoretix 1D software showing banding pattern similarities as illustrated in FIG. 5. The analysis of the type strains and clinical field isolates revealed two predominant patterns of expressed metal regulated proteins; a four-band pattern as marked by the brackets [ ], and a three-band pattern as shown by braces{ }. Other strains appear to have variations on these two patterns, missing one or two protein bands.

Example 12

Analysis of Proteins by MALDI-TOF

Thirteen isolates were chosen from example 11 as representative of the various band patterns observed in FIG. 5. Each protein band in the molecular weight range of 75,000 to 115,000 from these thirteen isolates of example 11 were excised from the SDS-PAGE gels for protein identification analysis via Matrix Assisted Laser Desorbtion Time of Flight mass spectrometry (MALDI-TOF MS) and peptide mass fingerprinting. The peptide masses were compared to a database (Uniprot, in this case) containing known protein sequences of the genome. This was achieved by using computer programs that translate the known genome of the organism into proteins, then theoretically cut the proteins into peptides, and calculate the absolute masses of the peptides from each protein. They then compare the masses of the peptides of the unknown protein to the theoretical peptide masses of each protein encoded in the genome. The results are statistically analyzed to find the best match. The identities of these proteins were grouped in a greater than 93 percent similarity and the results are shown in the table in FIG. 6. A total of 38 bands from the 13 isolates were analyzed and were identified to be one of seven proteins as indicated by their molecular weight in FIG. 6. Two of the isolates (1121 and 1135, indicated by the ellipse in FIG. 6), when combined, expressed all seven protein bands. These two strains were chosen for a new combination vaccine because together they expressed all the proteins of the remaining eleven isolates in FIG. 6, and also were representative of the two major banding patterns identified in FIG. 5.

Example 13

*Pasteurella* Culture Seed Preparation

Master seed stocks of *Pasteurella multocida* strains 1121 and 1135 from example 12 and FIG. 6 were prepared. Strain 1121 was identified to be serotype 3×4 and strain 1135 was identified to be serotype 2×5. These isolates were isolated from turkeys that had died from avian Pasteurellosis. Typically, the liver or lung was swabbed and the resulting swab was streaked to 5% sheep blood agar plate and incubated at 37° C. for 24 hours. A Master Seed was prepared by inoculating the isolate into pBHI containing 6 g/l yeast extract and 12 ug/ml DP. The culture was then successively transferred into the above media with 18 μg/ml DP for five more passes to adapt the organisms to an iron-restricted environment and to maximize growth and expression of desired proteins. The cultures were concentrated by centrifugation for 30 minutes at 7,000 rpm (Beckman Coultier, Brea, Calif.) and resuspended in fresh pBHI containing 20% glycerol (as a cryoprotectant) but no DP. The resulting Master Seeds were aliquoted in 2.2 ml volumes into 3 ml cryovials and stored at or below −60° Celsius. The isolates were given the identification numbers PM1121 20140911 and PM1135 20140925 and established as Master Seeds MS1121 and MS1135, respectively. The Master Seeds were then expanded into working seeds that were used for the production of metal regulated proteins.

Example 14

Production of Metal Regulated Proteins

*Pasteurella multocida* can be grown under controlled fermentation conditions so as to express proteins, including proteins associated with the outer membrane. The bacteria can then be harvested and the proteins isolated, purified, and used as immunogens in a composition.

Fermentation:

A cryogenic vial of the working seed of strain 1135 (1 ml at $10^9$ CFU/ml) of example 13 was used to inoculate 300 ml of 37° C. modified porcine brain heart infusion media (pBHI) (BD Difco) containing 6 g/l yeast extract (BD). The culture was incubated at 35-38° C. while shaking at 30-400 rpm for 5 hours, at which point was transferred to 1500 ml of modified pBHI containing 22 ug/ml DP to restrict available iron. The culture was incubated at 37° C. for 2 hours and 38 minutes until it reached an optical density greater than or equal to 0.6. The entire culture was transferred to 15 liters of modified pBHI plus 22 ug/ml DP in an 18 liter flask. This culture was incubated for approximately 2 hours and 30 minutes and reached an optical density of 0.75 at 540 nm. The culture was then transferred to a 300 liter fermentor containing 270 liters of modified pBHI with 22 μg DP to maintain iron restriction, and 40 ml per liter of a 50% glucose solution as a carbon source. The culture was incubated at 35-38° C. with agitation controlled by dissolved oxygen content which was maintained at or above 30%. The culture grew to an optical density, as measured by a Beckman series 600 spectrophotometer, of approximately 5.4. At the end of fermentation, the culture pH was adjusted above 8.5 and the temperature adjusted at or below 15° C.

Harvest of Whole Cells:

The whole cell bacterial suspension was concentrated to approximately 1/10 volume by tangential flow filtration with a Pall Filtron Tangential Flow Maxisette-25 (Pall Filtron) equipped with two 30 $ft^2$ Alpha 300-K open channel filters, catalog No. AS30005, (Pall Filtron) connected to a Waukesha Model U-60 feed pump (Waukesha Chemy-Burrell, Delevan, Wis.) set at about 44 Hz. The culture was further washed with Tris-buffered saline, and then concentrated to ~45 liters of whole cell suspension. A subsample of the cell suspension was dried and weighed to yield a final dried pellet weight. The final whole cell suspension was then frozen at −20°.

Whole Cell Disruption.

The whole cell suspension was thawed at 5-7° C. for 3 days. Individual containers of whole cell were pooled and mixed in a sterile tank equipped with a mixer set at 40%. The liquid cell suspension was disrupted by homogenization. Briefly, the suspended whole cell was passed twice through an Avestin homogenizer, model Emulsiflix C500B, (Avestin, Inc., Ottawa, Canada) at a pressure of 15,000-18,000 pounds per square inch (PSI) until a 1:100 dilution of homogenate reached 80 percent transparency (% T at 540 nm) on a Beckman series 600 Spectrophotometer (Beckman instruments, Brea, Calif.). A second process tank was connected to the homogenizer such that the fluid could be passed back and forth through the homogenizer for multiple passes while maintaining a closed system. Sodium lauroyl sarcosinate (Hamposyl L-30, Chattem Chemicals, Chattanooga, Tenn.) was added at 3% volume/volume to the disrupted cell homogenate to solubilize the cell membrane and non-membrane proteins. Solubilization continued for approximately 72 hours at 2-7° C. Cell debris was removed by centrifugation utilizing a Sharples Ti continuous centrifuge set at 11 PSI.

Protein Harvest:

The protein suspension was washed with 800 liters of Tris-buffered water (TBW) (pH 7.4) containing 0.2% formalin by continuous wash tangential flow filtration (Maxisette 300 kDa filter, Pall corp, NY, N.Y.). The protein was further washed with 100 liter of TBW containing formalin and 10% ethanol. Following the ethanol wash, the protein suspension was further washed with 200 liters of TBW plus formalin (0.2%) to remove the ethanol. When the remaining TBW was washed from the system, the volume was reduced by continued filtration until the final antigen volume was approximately 20 liters. The final antigen lot 1135-A0001 was then inactivated with the 0.2% formalin with continuous mixing at 33° C. for 93 hours.

The working seed of strain 1121 was used to prepare antigen lot 1121-A0001 in the same manner as strain 1135.

Example 15

Preparation of Vaccine

The antigens prepared in Example 14 were used to prepare two 20 liter water in oil vaccines with 50% mineral oil as adjuvant and tween/span emulsifier as described in example 6. Briefly, 10,145 ml of Drakeol 6 mineral oil and 609 ml Span 85, as an emulsifier, were added to a sterile vessel equipped with a Silverson model 150UHSLS mixer (Silverson Machines, East Longmeadow, Mass.). The mixer was set to 52 hz and the adjuvant phase recirculation was set at 2.5 liters per minute. The aqueous phase ingredients were added to a second vessel: Tween 85 (517 ml), 540 ml of antigen lot 1121-A0001, 1420 ml of antigen lot 1135-A0001 and 7010 ml of phosphate buffered saline, pH 7.4,—was slowly added over the course of 20 minutes. The vaccines were formulated to contain 100 μg total antigen (50 ug from each strain) per 0.25 ml dose, and 200 μg total antigen (100 μg of each strain), respectively. These two antigens, combined, represent the 7 proteins, of example 12 and FIG. 6, required for increased heterologous serotype protection.

Example 16

Vaccination and Challenge Model

Figure 7:
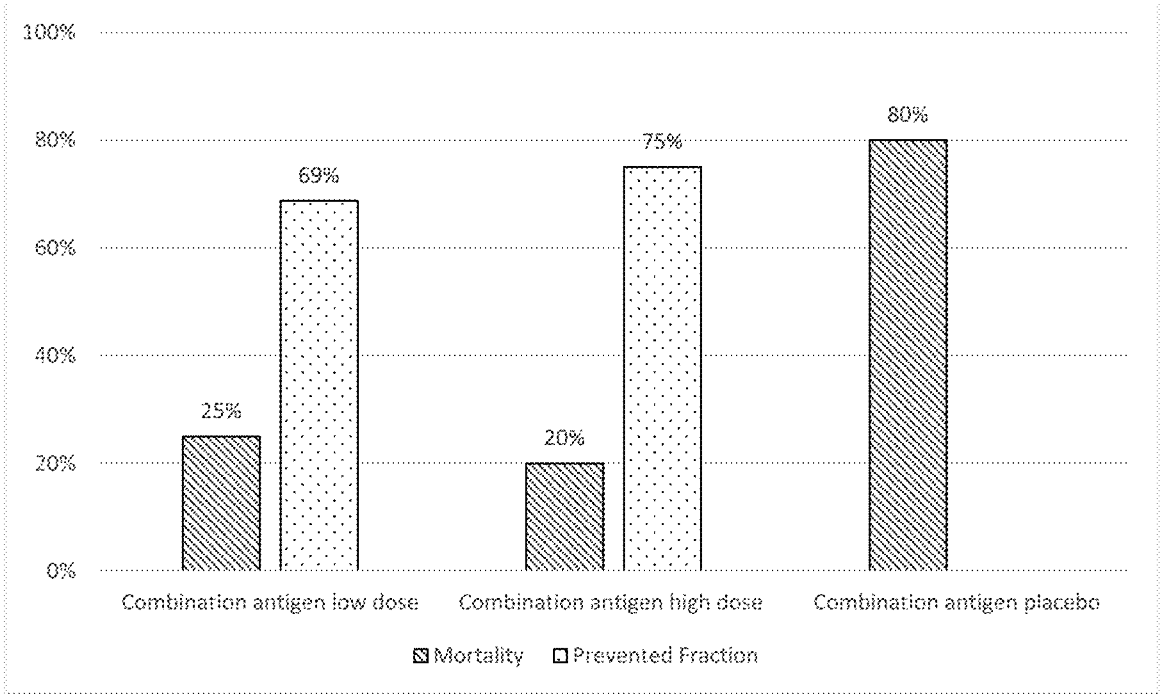
FIG. 7. Vaccine efficacy using a vaccine composed of two Master seed strains challenged with *Pasteurella* serotype 1 in chickens showing heterologous protection.

The vaccines prepared in example 15 was used in a vaccination challenge model against type 1 challenge in SPF chickens. Briefly, 60 SPF leghorn chickens, both males and females, were obtained from Valo BioMedia (Adel, Iowa). The chickens were sorted by sex, and divided into three groups of 20 birds of mixed hens and roosters, each group with equal numbers of males and females. The birds were identified by numbered wing bands; each bird received identical numbers on the left and right wing to preserve identity. One group was vaccinated with 0.25 ml of the 200 μg vaccine of example 14. A second group was vaccinated with 0.25 ml of the 100 μg vaccine of example 14. A third group was vaccinated with a placebo containing the oil adjuvant in phosphate buffered saline (PBS) in place of the antigen. All birds were vaccinated subcutaneously in the back of the neck at 12 and 15 weeks of age, and all birds were challenged intramuscular in the breast at 17 weeks of age with approximately 6,000 cfu of the serotype 1 challenge strain X-73 prepared in the manner of example 8. The results of the study are shown in FIG. 7. It is clear that the level of protection is vastly improved with a preventive fraction of 69 and 75 percent and a p-value of 0.001 and <0.0004 for the 100 μg and 200 μg vaccinated groups, respectively. These results clearly show that the combination of two antigens, expressing all seven proteins of FIG. 6, confer increased prevented fraction against heterologous challenge in a chicken vaccination and challenge model.

Example 17

Zinc and Respiratory Pathogens

In our previous research (data not shown) we have shown that many gram-negative pathogens express a novel protein under zinc restriction. An abundance of these bacteria are respiratory pathogens. Some of these pathogens include *Moraxella catarrhalis, Haemophilus* parasuis, *Mannheimia haemolytica, Acinetobacter baumannii, Pasteurella multocida, Bordetella pertussis*, and *Actinobacillus* pleuropneumonia (Stork et al. PLoS Pathogens, 6(7), e1000969 2010). It has been reported that this Zinc acquisition protein is a transmembrane beta-barrel protein now identified as ZnuD located in the outer cell wall that utilizes a single surface exposed loop containing two cysteines that when brought together by a disulfide linkage forms a cluster of histidines that can interact with a zinc ion (Stork et al., PLoS Pathogens, 6(7), e1000969. 2010). ZnuD thereby acts as a scavenger protein used for the acquisition of zinc sequestered by the host organism.

All these ZnuD homologs contain His- and Asp-rich regions that have been identified in the binding of zinc. This suggests that zinc acquisition mechanisms are important for bacteria residing in the respiratory tract. The current explanation is that unbound zinc concentration within the mucosal tract is too low to allow for simple diffusion across the bacterial membrane via porin proteins (Stork et al., PLoS Pathogens, 6(7), e1000969 2010). Thereby, proteins such as ZnuD are required to scavenge for zinc. This scavenging not only includes unbound zinc, but also the stripping of sequestered zinc from proteins such as calprotectin (Liu et al., Cell host & microbe, 11(3), pp 227-239. 2012). This theory has been supported by the detection of convalescent antibodies towards ZnuD from healthy carriers, which allows the assumption that ZnuD is expressed by bacteria that reside in the respiratory tract (Stork et al., PLoS Pathogens, 6(7), e1000969. 2010). The goal of this experiment was to identify, clone and evaluate the efficacy of a zinc acquisition protein of *Pasteurella multocida*. If a ZnuD homolog is expressed in *Pasteurella multocida*, it offers another possible target for vaccine development currently unexplored for controlling this respiratory pathogen.

Example 18

Genomic Sequencing of *Pasteurella multocida* P-1059

The isolate of *Pasteurella multocida* used for this study was reference strain P-1059 of example 1. The genomic DNA was isolated from the *Pasteurella multocida* isolate using the Invitrogen by Life Technologies ChargeSwitch gDNA Mini Bacteria Kit (Life Technologies, Carlsbad, Calif., product number: CS11301). Prior to extraction of genomic DNA, a fresh culture of the isolate was grown on Trypticase Soy Agar II with 5% Sheep Blood (Becton, Dickinson and Company, Franklin Lakes, N.J., product code: 221261) overnight at 37° C. The procedure followed the manufacturer protocol. The final yield was 33.7 μg of genomic DNA, which was stored at −20° C. until sequencing. The genomic DNA was submitted to ACGT, Inc. for sequencing (Wheeling, Ill.). Genbank reference sequences CP004752 and CP004753 were used in the assembly of the complete genomic sequence of the isolate.

Example 19

Possible Target Genes

After receiving the complete genomic sequence of the isolate, tblastn alignments were performed with the National Center for Biotechnology Information (NCBI) database to identify the possible genes of interest based on homology towards ZnuD (GenBank AAF62323.1). A blastx search was used to identify the proteins translated by the homologous genes found with the tblastn alignment. Pairwise sequence alignments of the identified ZnuD homologues and ZnuD zinc affinity region were performed using EMBOSS Matcher (Rice et al., Trends in genetics, 16(6), pp 276-277. 2000).).

Example 20

Expression of a Zinc Acquisition Protein

To identify the zinc acquisition protein of *Pasteurella multocida* we used the sequence of the zinc acquisition protein of *Mannheimia haemolytica* previously identified in our laboratory. Briefly, the expression of the target protein was evaluated by supplementing Bacto Brain Heart Infusion, Porcine culture medium (BHI) (Becton, Dickinson and Company, Franklin Lakes, N.J., product code: 256110) used for bacterial cell growth with TPEN (Tokyo Chemical Industry Co., Ltd., Portland, Oreg., product code: T1487). A titration of TPEN over a range of 0-100 μM during bacterial growth was used. The BHI media containing the various concentrations of TPEN were inoculated with a starter culture of the isolate in BHI containing no TPEN. The inoculum volume was 1 percent of the total volume of the final culture. The cultures were allowed to grow with vigorous agitation at 37° C. to an $OD_{540}$ of 1.0, unless bacteria were unable to grow at certain concentrations.

Once an OD of 1.0 was obtained, the bacteria were pelleted by centrifugation at 7,000×g for 10 minutes. An outer membrane preparation was performed on the pelleted bacteria to isolate the integral membrane proteins within the outer membrane following a procedure described by (Molloy et al., European Journal of Biochemistry, 267(10), pp 2871-2881. 2000) with modifications. The bacteria pellet was re-suspended in 30 ml of 60 mM Tris-HCl (Sigma-Aldrich, St. Louis, Mo., product code: T3253) and 2.5 mM EDTA (EMD, Billerica, Mass., product code: EX0539-3), pH 8.5. The bacteria were then lysed by sonication using a Sonifier S-450A analog ultrasonic processor with a ½" diameter Tipped Bio-Horn attached to a102-C converter (Branson Ultrasonics Corporation, Danbury, Conn., product code: 101-063-198, 101-47-037, and 101-135-066 respectively) for 1 minute and 30 seconds on ice at a power setting of 9 and a duty cycle of 90. The sample was clarified by centrifugation at 39,000×g and 4° C. for 20 minutes to remove large cell debris. To remove the inner membrane, peptidoglycan, and proteins not found within the outer membrane, Hamposyl L-30 (Chattem Chemicals, Inc., Chattanooga, Tenn., product code: BD2099) was added to the supernatant at a final concentration of 1% and incubated for 16 hours at 4° C. while rocking end-over-end. The outer membrane was pelleted by centrifugation at 39,000×g and 4° C. for 2 hours. The outer membrane pellet was washed and re-suspended in 25 mM Tris-HCl buffered water, pH 7.2.

The integral membrane proteins were visualized by SDS-PAGE. Prior to the electrophoresis, a BCA (Thermo Fisher Scientific Inc., Rockford, Ill., product code: 23225) was performed to quantify the protein within each sample as to allow for equivalent protein loads of 30 μg. Samples were brought up to equal volume prior to the addition of 3× loading buffer (New England BioLabs Inc., Ipswich, Mass., product number: B7703S). The samples were compared on the gel to look for expression of the target protein.

Example 21

Protein Identification

The banding profile from the outer membrane preparation was analyzed by Matrix-assisted Laser Desorption/Ionization Mass Spectrometry (MALDI) to determine if any of the bands of interest match the genes identified by BLAST homology. The bands were cut out of the gel with a scalpel and sent to the Mayo Clinic Proteomics Core facility to be analyzed.

Example 22

Structure Modeling

Swiss Model was used to create a 3-D structural model of zinc acquisition protein of *Mannheimia haemolytica* based on homology sequencing (Arnold et al., Bioinformatics, (22), pp 195-201. 2006).). The PDB template used to create the protein model was 4epaA. The extracellular loop (ECL) sequence positions were identified using the 3-D structural model obtained from Swiss Model (Arnold et al., Bioinformatics, (22), pp 195-201. 2006).), Prediction of TransMembrane Beta-Barrel Proteins (Bagos et al., BMC Bioinformatics, 5(29). 2004).), Orientations of Proteins in Membranes (OMP) database and Positioning of Proteins in Membranes (PPM) server (Lomize et al., Nucleic Acids Res, 40(Database issue):D370-6. 2012).

Example 23

Target Gene Identification

Once the proteins within the banding profile were identified, they were compared to the proteins of interest identified by BLAST homology. One protein within the banding profile matched a protein identified by the BLAST homology. The protein was identified as OMR family outer membrane iron receptor (GenBank: EDN73812.1) also referred to as the zinc acquisition protein in this paper. The target gene was located at nucleotides 1,160,319 . . . 1,162,691 within the genome. The signal peptide was identified using SignalP 4.1 (Petersen et al., Nature methods, 8(10), pp 785-786. 2011)). The nucleotide and amino acid sequences of the zinc acquisition protein identified in *Pasteurella multocida* is shown in FIG. 22.

Example 24

The Homology of the Zinc Acquisition Protein Across Respiratory Pathogens

Using the sequence of the acquisition protein of *Mannheimia haemolytica* (data not shown) the homology of zinc acquisition protein across respiratory pathogens, particularly the zinc affinity region, was determined with the protein blast search tool established by NCBI. Ten different species of bacteria were found to contain a zinc acquisition protein homologue with greater than 49% identity. All species identified are respiratory pathogens. Aligning the homologous proteins to the zinc affinity region of ZAP using Clustal Omega highlights strikingly similar amino acid motifs. All the homologues contain two cysteines and multiple histidines and aspartic acids. The amino acid motifs are emphasized in FIG. 25 using GLAM2. The spatial arrangement of the cysteines, histidines, and aspartic acids remain constant across the homologues.

TABLE 2

| Strain | Accession Number | % Identity | % Similarity |
|---|---|---|---|
| *Bibersteinia trehalosi* | AHG81836.1 | 98 | 97 |
| *Actinobacillus pleuropneumoniae* | WP_005612269.1 | 93 | 95 |
| *Mannheimia granulomatis* | WP_027074597.1 | 75 | 82 |
| *Mannheimia varigena* | AHG73391.1 | 72 | 79 |
| *Haemophilus parasuis* | WP_021114857.1 | 62 | 78 |
| *Moraxella boevrei* | WP_026212957.1 | 53 | 69 |
| *Psychrobacter phenylpyruvicus* | WP_028858792.1 | 54 | 69 |

TABLE 2-continued

| Strain | Accession Number | % Identity | % Similarity |
|---|---|---|---|
| *Pasteurella multocida* | WP_016534590.1 | 58 | 72 |
| *Moraxella bovoculi* | KDN24548.1 | 52 | 67 |
| *Conchiformibius steedae* | WP_027021676.1 | 49 | 64 |

The results show that multiple respiratory pathogens indeed show a degree of homology to the zinc acquisition protein of *Mannheimia Haemolytica* ranging from 49 to 98 percent identity.

Example 25

Expression and Identification of a Zinc Acquisition Protein

Cloning

The *Pasteurella multocida* zinc gene was PCR amplified from genomic DNA of strain P-1059 and inserted into plasmid vector pQE-T7-2 (Qiagen; Hilden, Germany) using Gibson assembly methods. The assembled plasmid was then transformed in to NEB T7 Express Competent *E. coli* (New England Biolabs; Ipswitch, Mass.; catalog #C2566H) for clonal selection and expression.

Expression

A starter culture of LB broth containing 50 μg/mL kanamycin was inoculated with a clone containing the recombinant plasmid. Culture was grown to an OD540 of 0.6 and then transferred to fresh LB broth. The new culture was allowed to grow again to an OD540 of 0.6. Expression was then induced with 1 mM IPTG and incubated an additional 16 hours. The cells were collected by centrifugation and stored at −80° C. until processing.

Inclusion Body Purification

Figure 24:
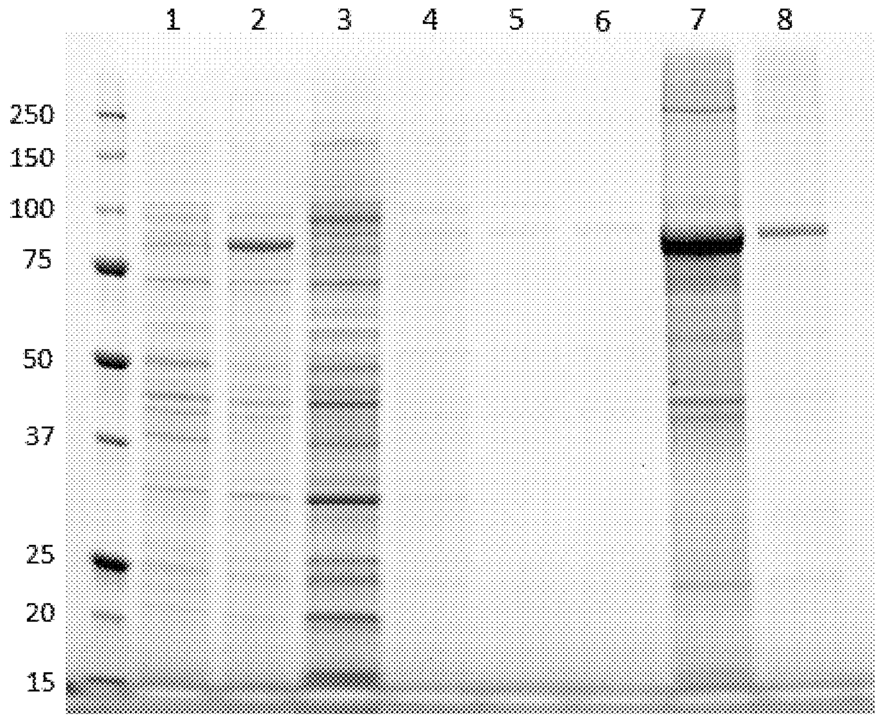
FIG. 24. Gel image showing the inclusion body preparation of *Pasteurella multocida* recombinant zinc acquisition protein. Lane 1: Un-Induced Whole Cell, lane 2: Induced Whole Cell, Lane 3: Lysed Cell Supernatant, Lane 4: 1× Bugbuster Wash, L:ane 5: 1/10× Bugbuster Wash, Lane 6: TBW Wash, Lane 7: Solubilized Inclusion Bodies and Lane 8: Pellet Post Solubilization showing the recombinant protein with a molecular weight of 90.85 kDa.

Cells were thawed and resuspended in BugBuster Protein Extraction Reagent (Merck Millipore; Billerica, Mass.; catalog #70584-4). 10 μL of Lysonase Bioprocessing Reagent (Merck Millipore; Billerica, Mass.; catalog #71230) was added and the suspension was incubated for 1 hour at ambient temperature. The suspension was then sonicated (Branson Sonifier, model 102c; Branson Ultrasonics, Danbury, Conn.) for 30 seconds using a micro tip, output 6, at a 90% duty cycle. The lysate was centrifuged at 16000×g for 20 minutes to collect the insoluble material. The pellet was washed three times: first with BugBuster, second with 1/10× BugBuster, and third with tris-buffered water. The inclusion body prep was solubilized in tris-buffered saline containing 8 M urea and 1 mM dithiothreitol at pH 8.0, yielding 10 mg recombinant protein. FIG. 24 shows the different stages of expression of the zinc acquisition protein run on a 10% Criterion stain free-free TGX Gel run at 300V (Bio-Rad, Hercules, Calif.) to include: the un-induced whole cell preparation, the induced whole cell preparation, the lysed cell supernatant, 1× bugbuster wash, 1/10× bugbuster wash, the solubilized inclusion bodies and the pellet post solubilization.

Example 26

Vaccine-Mediated Protection of a Novel Recombinant Zinc Protein of *Pasteurella multocida* in a Chicken Sepsis Model The purpose of the following experimental study was to evaluate the protective efficacy of a recombinant zinc protein (rZinc) against a virulent challenge of *Pasteurella multocida* in a chicken sepsis model. The efficacy of the rZinc protein of example 25 was compared to the efficacy of the *Pasteurella multocida* SRP extract composition of example 14 compared to non-vaccinated controls. Briefly, 30 SPF leghorn chickens, (males), were obtained from Valo BioMedia (Adel, Iowa). The chickens divided into three groups of 10 birds each. The birds were identified by colored leg bands. Treatment groups were designated as Group-A (Placebo), Group-B (rZinc protein) and Group C (*Pasteurella multocida* protein extract). The outcome parameter used to evaluate vaccine efficacy in this experiment was total mortality between vaccinates compared to the non-vaccinated Placebo group. Food and water was supplied ad libitum to all chickens.

Example 27

Preparation of the Immunizing Compositions

The vaccines (SRP extract and rZinc) were prepared from the protein compositions of examples 14 and 25 by diluting the antigen into phosphate buffered saline (PBS) containing 8.0 g/l NaCl, 0.2 g/l KCl, 1.44 g/l $Na_2HPO_4$ and 0.24 g/l $KH_2PO_4$ pH 7.4. Each vaccine was prepared by emulsifying the following ingredients: 44.44% aqueous protein suspension in 0.1% formalized saline, 50% Drakeol 6 mineral oil (VOPAK USA, Inc, Kirkland, Wash.), 3.0% Span 85 and 2.56% Tween 85 (Ruger Chemicals, Hillside, N.J.). The final bird dose for each vaccine composition (rZinc and SRP extract) was 250 μg and 400 μg administered in a volume of 0.5 ml and 0.25 ml respectively. The placebo was prepared by replacing the antigen with physiological saline and emulsifying the suspension using the above formulation in a dose volume of 0.5 ml. All birds were vaccinated subcutaneously at 14 and 17 weeks of age (21-day interval).

Example 28

Challenge and Results

Figure 23:
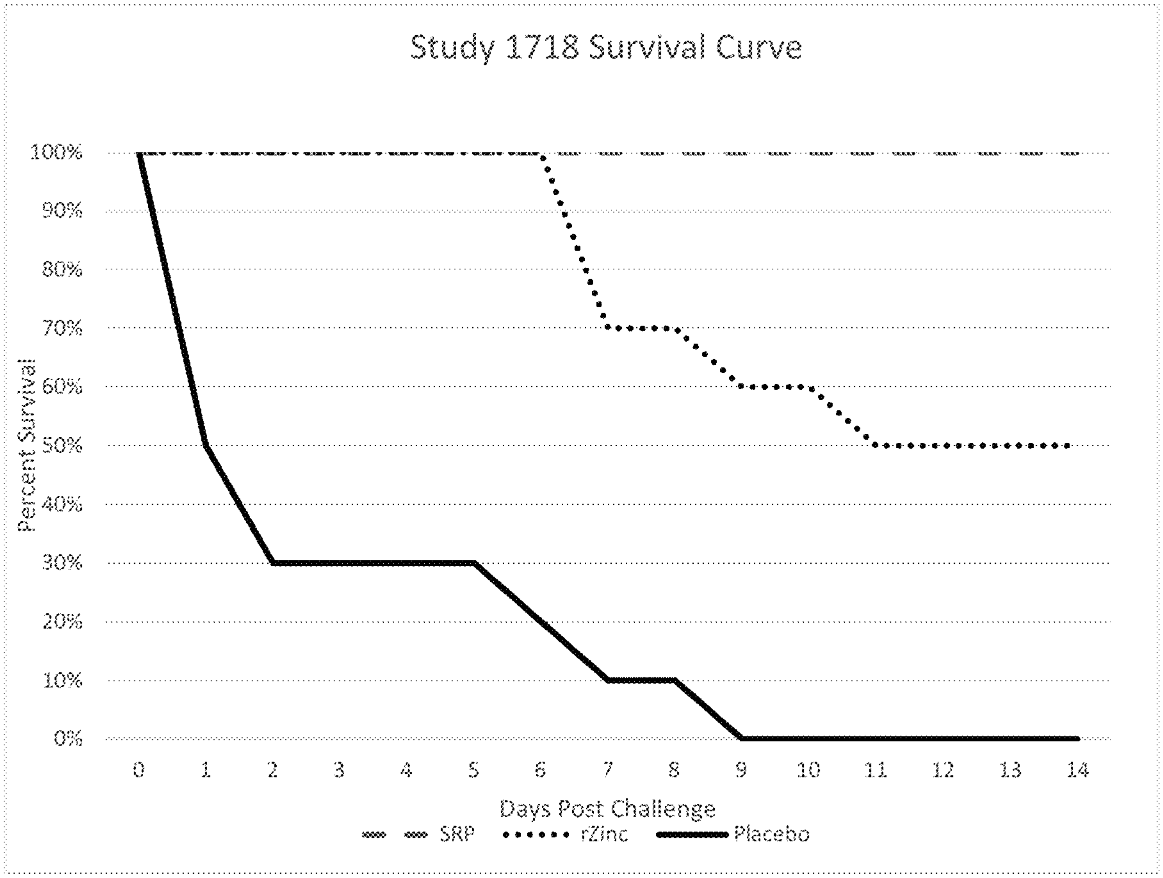
FIG. 23. The percent survival of chickens challenged with *Pasteurella multocida* comparing a recombinant zinc (rZinc) protein to SRP extract. The results clearly show the efficacy of both the *Pasteurella multocida* SRP extract and the rZinc protein compared to non-vaccinated Placebo controls.

At 19 weeks of age all birds were challenged intramuscularly in the breast with 5450 Colony Forming Units (CFU) of *Pasteurella multocida* (serotype 1) strain X-73 prepared as described example 8. Birds were observed for mortality for 14 days following challenge. The results clearly demonstrate the efficacy of both the *Pasteurella multocida* SRP Extract and the rZinc vaccines having a percent survival of 100% and 50% respectively, in contrast to the non-vaccinated controls having no survivors (FIG. 23). The recombinant zinc protein in this study was evaluated at a single concentration of 250 μg, showing a 50% survival rate (p=0.0325) against a virulent challenge.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising:

(i) an isolated protein having at least 90% similarity to amino acids 25-968 of SEQ ID NO:2, an isolated protein having at least 90% similarity to amino acids 27-790 of SEQ ID NO:4, and an isolated protein having at least 90% similarity to amino acids 23-727 of SEQ ID NO:6 or (ii) an isolated protein having at least 90% similarity to amino acids 25-964 of SEQ ID NO:8, an isolated protein having at least 90% similarity to amino acids 26-848 of SEQ ID NO:10, an isolated protein having at least 90% similarity to amino acids 27-784 of SEQ ID NO:12, and an isolated protein having at least 90% similarity to amino acids 25-742 of SEQ ID NO:14;

a pharmaceutically acceptable carrier; and an adjuvant.

2. A composition comprising an isolated protein having at least 90% similarity to amino acids 26-805 of SEQ ID NO:44.

3. The composition of claim 1 further comprising:

at least one isolated protein having a molecular weight of 249 kDa, 60 kDa, 42 kDa, 38 kDa, 27 kDa, 26 kDa, or 22 kDa, wherein the proteins are isolatable from the *P. multocida*.

4. A composition comprising:

(i) an isolated whole cell that is engineered to express at least seven proteins, wherein the seven proteins comprise a protein having at least 90% amino acid sequence identity to amino acids 25-968 of SEQ ID NO:2, a protein having at least 90% amino acid sequence identity to amino acids 27-790 of SEQ ID NO:4, a protein having at least 90% amino acid sequence identity to amino acids 23-727 of SEQ ID NO:6, a protein having at least 90% amino acid sequence identity to amino acids 25-964 of SEQ ID NO:8, a protein having at least 90% amino acid sequence identity to amino acids 26-848 of SEQ ID NO:10, a protein having at least 90% amino acid sequence identity to amino acids 27-784 of SEQ ID NO:12, and a protein having at least 90% amino acid sequence identity to amino acids 25-742 of SEQ ID NO:14, or (ii) two or more populations of microbes wherein each of the population expresses a subset of the seven proteins listed in (i), and the two or more populations when considered as a whole express the seven proteins.

5. The composition of claim 4 wherein the cell is *E. coli.*

6. The composition of claim 4 further comprising a pharmaceutically acceptable carrier.

7. The composition of claim 6 further comprising an adjuvant.

8. The composition of claim 4 wherein the two or more populations of microbes comprise a first population and a second population, wherein the first population comprises an isolated whole cell that is engineered to express a protein having at least 90% amino acid sequence identity to amino acids 25-968 of SEQ ID NO:2, a protein having at least 90% amino acid sequence identity to amino acids 27-790 of SEQ ID NO:4, and a protein having at least 90% amino acid sequence identity to amino acids 23-727 of SEQ ID NO:6; and wherein the second population comprises an isolated whole cell that is engineered to express a protein having at least 90% amino acid sequence identity to amino acids 25-964 of SEQ ID NO:8, a protein having at least 90% amino acid sequence identity to amino acids 26-848 of SEQ ID NO:10, a protein having at least 90% amino acid sequence identity to amino acids 27-784 of SEQ ID NO:12, and a protein having at least 90% amino acid sequence identity to amino acids 25-742 of SEQ ID NO:14.

9. The composition of claim 4, wherein the isolated cell or the two populations of microbes are engineered to further express 80% amino acid sequence identity to amino acids 26-805 of SEQ ID NO:44.

10. The composition of claim 1 further comprising an isolated protein having at least 90% similarity to amino acids 26-805 of SEQ ID NO:44.

11. The composition of claim 1 comprising:

(i) an isolated protein having at least 90% similarity to amino acids 25-968 of SEQ ID NO:2, an isolated protein having at least 90% similarity to amino acids 27-790 of SEQ ID NO:4, and an isolated protein having at least 90% similarity to amino acids 23-727 of SEQ ID NO:6, and (ii) an isolated protein having at least 90% similarity to amino acids 25-964 of SEQ ID NO:8, an isolated protein having at least 90% similarity to amino acids 26-848 of SEQ ID NO:10, an isolated protein having at least 90% similarity to amino acids 27-784 of SEQ ID NO:12, and an isolated protein having at least 90% similarity to amino acids 25-742 of SEQ ID NO:14;

a pharmaceutically acceptable carrier; and an adjuvant.

* * * * *

SEQUENCE LISTING

```
<160> NUMBER OF SEQ ID NOS: 55

<210> SEQ ID NO 1
<211> LENGTH: 2906
<212> TYPE: DNA
<213> ORGANISM: Pasteurella multocida

<400> SEQUENCE: 1

atgcgtacaa caacaataaa attttctgca attacattgg cattattgag ttattgtggg     60
gctattttgg cggatagtca tcaagaggcg actgaacttg atacgattac cgtttcttct    120
caacaagatg agatgaatat taaagagaaa aaagtcggtg aaactgtgaa aacggcgagt    180
caattgaaac gccagcaagt acaggatagt cgtgatcttg tgcgctatga aaccggtgtg    240
actgtggtag aagctggacg ttttgggtcg agcggttatg ccattcgtgg tgtggatgag    300
aaccgagtgg caattacagt agatggctta catcaagcag aaaccctttc ttctcaaggt    360
tttaaagaat tatttgaagg ttacggcaat tttaacaata cccgaaatag tgtggaaatt    420
gagacgttga aagtcgctaa aatcgcgaaa ggtgctgatt ctgtaaaagt gggtagtggt    480
tctttgggag gcgctgtact ttttgaaaca aaagatgcca gagatttcct gactgaaaaa    540
gattggcata tcggctataa agcgggctac tcaacggcag ataatcaggg attaaatgca    600
gtgactcttg caggtcgcta tcaaatgttt gatgcattga ttatgcattc taagcgacat    660
ggacatgaat tagaaaatta tgactataaa aatggcagag atattcaagg gaaagaaaga    720
gagaaagcgg atccttatac gattacgaaa gaaagtacat tagtgaaatt ctctttttcg    780
ccaacagaaa atcatcgttt tacagtcgct tctgatactt atcttcagca ttcccgcgga    840
catgatcttt catacaatct tgttgcaaca acacatattc agttagatga gaaagaatct    900
cgtcatgcaa atgatctgac aaaacgtaaa aatgtttcct ttacttatga aaattatact    960
gttacgccat tttgggatac gctcaagtta agctattcac aacaaagaat tacaacaaga   1020
gcaagaacag aagattactg tgatggtaat gaaaaatgtg actcttataa gaatccttta   1080
gggcttcaat taaaagaggg aaaaatcgtt gatcgtaatg gcgatcctgt taatttgaag   1140
cttgttgatg gtaaacatca agttgtagat aaagctggta agccttttga tgtagcctct   1200
ggaactaatt atgcggcttt ctcaggtaaa gaattaagtc cttcttcttt ttggttagat   1260
tgctctattt ttgattgttc taagcctatc aatacttata aatatcgcta tacctcttcg   1320
gagccaactt tgcagcaaat tactttaaat aaaaccatgg aaattaatgg aaagacattt   1380
gctacttatg atgggcgtgg acactatatt attttaccaa attctaaagg ttacttgcct   1440
ttggattata aagagcgtga tttaaataca aagacgaaac aaattaattt agatttaaca   1500
aaagcattta ctctctttga gattgaaaat gaactttcct atggtggtgt ttacgcgaaa   1560
```

```
acgaccaagg aaatggtgaa taaagcagga tattatgggc gtaatcctac ttggtgggcg   1620

gagagaacgt tagggcaatc atggggaaaa ttgagagagt gtaagacaag ttcttcatat   1680

aatgggatgc tatgtcctcg tcatgaacca ttaacctcct tcttaattcc ggtagaagca   1740

acaactaagt ctttatattt tgcagacaat atcaagttgc acaatatgtt aagtgtagat   1800

ttaggttatc gttatgatga tattaaatat cagccagaat atattcctgg tgtgacacct   1860

aaaattgcag atgatatggt aaaagggtta tttattccat tacctgaagg tgaaaaagta   1920

actgtaggga caatggtatt cacaaaacca ctcactcagg cgcaaattcg taagaatgcg   1980

gaggaaaata ttgcttatat tgcacaagaa aaacgcttta agaaacattc ttattctctt   2040

ggtgcaacgt tcgatcctct gaatttttta cgagtacaag taaaatattc aaaagggttt   2100

agggccccga cttcggatga actttatttt acctttaagc atccagattt tacgatttta   2160

ccgaaccccg tgttgaaacc agaggaagca aaaaatcaag agattgcatt aacagtgcac   2220

gataattggg gatttgttag cacaagtgtt ttccaaacaa agtatcgtca ttttattgat   2280

ttagcgtatt taggttcaag aaatttatcg aattccgtgg gagggcaggc acaagcaaga   2340

gatttccaag tttatcaaaa tgtcaatgtc gataatgcca aggttaaagg acttgaaatt   2400

aatgcacgtt tgaatttggg atatttctgg catgtgttgg atggatttaa tacgagctat   2460

aaattcactt accaacgtgg tcgtttggat ggcgatcgtc caatgaatgc gattcagcct   2520

aaagcttctg tttttggttt aggctatgat cataaagaaa ataaatttgg cgctgattta   2580

tatatcacac gtgtgagtga aaaaaagcga aagacactta taatatgttc tataaagaac   2640

agggatataa agatagtgct gttcgttgga gaagtgatga ctatacgcta gttgatgcgg   2700

ttggttatat taaaccgatt aagaatttaa cgttacagtt tggcgtttat aatttgacag   2760

accgtaaata cttgacatgg gaatctgctc gttcgattaa accatttggt acaagtaatt   2820

taattaatca gaaaacaggc gcaggaatta atcgttttta ctcaccaggt cgtaatttta   2880

aatttagtgc cgaaattacc ttctaa                                        2906
```

```
<210> SEQ ID NO 2
<211> LENGTH: 968
<212> TYPE: PRT
<213> ORGANISM: Pasteurella multocida

<400> SEQUENCE: 2

Met Arg Thr Thr Thr Ile Lys Phe Ser Ala Ile Thr Leu Ala Leu Leu
1               5                   10                  15

Ser Tyr Cys Gly Ala Ile Leu Ala Asp Ser His Gln Glu Ala Thr Glu
            20                  25                  30

Leu Asp Thr Ile Thr Val Ser Ser Gln Gln Asp Glu Met Asn Ile Lys
        35                  40                  45

Glu Lys Lys Val Gly Glu Thr Val Lys Thr Ala Ser Gln Leu Lys Arg
    50                  55                  60

Gln Gln Val Gln Asp Ser Arg Asp Leu Val Arg Tyr Glu Thr Gly Val
65                  70                  75                  80

Thr Val Val Glu Ala Gly Arg Phe Gly Ser Ser Gly Tyr Ala Ile Arg
                85                  90                  95

Gly Val Asp Glu Asn Arg Val Ala Ile Thr Val Asp Gly Leu His Gln
            100                 105                 110

Ala Glu Thr Leu Ser Ser Gln Gly Phe Lys Glu Leu Phe Glu Gly Tyr
        115                 120                 125

Gly Asn Phe Asn Asn Thr Arg Asn Ser Val Glu Ile Glu Thr Leu Lys
```

-continued

```
    130                 135                 140

Val Ala Lys Ile Ala Lys Gly Ala Asp Ser Val Lys Val Gly Ser Gly
145                 150                 155                 160

Ser Leu Gly Gly Ala Val Leu Phe Glu Thr Lys Asp Ala Arg Asp Phe
                165                 170                 175

Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Asn Tyr Asp Tyr Lys Asn Gly Arg Asp Ile Gln Gly Lys Glu Arg
225                 230                 235                 240

Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Leu Gln His Ser Arg Gly His Asp Leu Ser Tyr Asn Leu Val
        275                 280                 285

Ala Thr Thr His Ile Gln Leu Asp Glu Lys Glu Ser Arg His Ala Asn
    290                 295                 300

Asp Leu Thr Lys Arg Lys Asn Val Ser Phe Thr Tyr Glu Asn Tyr Thr
305                 310                 315                 320

Val Thr Pro Phe Trp Asp Thr Leu Lys Leu Ser Tyr Ser Gln Gln Arg
                325                 330                 335

Ile Thr Thr Arg Ala Arg Thr Glu Asp Tyr Cys Asp Gly Asn Glu Lys
            340                 345                 350

Cys Asp Ser Tyr Lys Asn Pro Leu Gly Leu Gln Leu Lys Glu Gly Lys
        355                 360                 365

Ile Val Asp Arg Asn Gly Asp Pro Val Asn Leu Lys Leu Val Asp Gly
    370                 375                 380

Lys His Gln Val Val Asp Lys Ala Gly Lys Pro Phe Asp Val Ala Ser
385                 390                 395                 400

Gly Thr Asn Tyr Ala Ala Phe Ser Gly Lys Glu Leu Ser Pro Ser Ser
                405                 410                 415

Phe Trp Leu Asp Cys Ser Ile Phe Asp Cys Ser Lys Pro Ile Asn Thr
            420                 425                 430

Tyr Lys Tyr Arg Tyr Thr Ser Ser Glu Pro Thr Leu Gln Gln Ile Thr
        435                 440                 445

Leu Asn Lys Thr Met Glu Ile Asn Gly Lys Thr Phe Ala Thr Tyr Asp
    450                 455                 460

Gly Arg Gly His Tyr Ile Ile Leu Pro Asn Ser Lys Gly Tyr Leu Pro
465                 470                 475                 480

Leu Asp Tyr Lys Glu Arg Asp Leu Asn Thr Lys Thr Lys Gln Ile Asn
                485                 490                 495

Leu Asp Leu Thr Lys Ala Phe Thr Leu Phe Glu Ile Glu Asn Glu Leu
            500                 505                 510

Ser Tyr Gly Gly Val Tyr Ala Lys Thr Thr Lys Glu Met Val Asn Lys
        515                 520                 525

Ala Gly Tyr Tyr Gly Arg Asn Pro Thr Trp Trp Ala Glu Arg Thr Leu
    530                 535                 540

Gly Gln Ser Trp Gly Lys Leu Arg Glu Cys Lys Thr Ser Ser Ser Tyr
545                 550                 555                 560
```

-continued

```
Asn Gly Met Leu Cys Pro Arg His Glu Pro Leu Thr Ser Phe Leu Ile
                565                 570                 575

Pro Val Glu Ala Thr Thr Lys Ser Leu Tyr Phe Ala Asp Asn Ile Lys
            580                 585                 590

Leu His Asn Met Leu Ser Val Asp Leu Gly Tyr Arg Tyr Asp Asp Ile
        595                 600                 605

Lys Tyr Gln Pro Glu Tyr Ile Pro Gly Val Thr Pro Lys Ile Ala Asp
    610                 615                 620

Asp Met Val Lys Gly Leu Phe Ile Pro Leu Pro Glu Gly Glu Lys Val
625                 630                 635                 640

Thr Val Gly Thr Met Val Phe Thr Lys Pro Leu Thr Gln Ala Gln Ile
                645                 650                 655

Arg Lys Asn Ala Glu Glu Asn Ile Ala Tyr Ile Ala Gln Glu Lys Arg
            660                 665                 670

Phe Lys Lys His Ser Tyr Ser Leu Gly Ala Thr Phe Asp Pro Leu Asn
        675                 680                 685

Phe Leu Arg Val Gln Val Lys Tyr Ser Lys Gly Phe Arg Ala Pro Thr
    690                 695                 700

Ser Asp Glu Leu Tyr Phe Thr Phe Lys His Pro Asp Phe Thr Ile Leu
705                 710                 715                 720

Pro Asn Pro Val Leu Lys Pro Glu Glu Ala Lys Asn Gln Glu Ile Ala
                725                 730                 735

Leu Thr Val His Asp Asn Trp Gly Phe Val Ser Thr Ser Val Phe Gln
            740                 745                 750

Thr Lys Tyr Arg His Phe Ile Asp Leu Ala Tyr Leu Gly Ser Arg Asn
        755                 760                 765

Leu Ser Asn Ser Val Gly Gly Gln Ala Gln Ala Arg Asp Phe Gln Val
    770                 775                 780

Tyr Gln Asn Val Asn Val Asp Asn Ala Lys Val Lys Gly Leu Glu Ile
785                 790                 795                 800

Asn Ala Arg Leu Asn Leu Gly Tyr Phe Trp His Val Leu Asp Gly Phe
                805                 810                 815

Asn Thr Ser Tyr Lys Phe Thr Tyr Gln Arg Gly Arg Leu Asp Gly Asp
            820                 825                 830

Arg Pro Met Asn Ala Ile Gln Pro Lys Ala Ser Val Phe Gly Leu Gly
        835                 840                 845

Tyr Asp His Lys Glu Asn Lys Phe Gly Ala Asp Leu Tyr Ile Thr Arg
    850                 855                 860

Val Ser Glu Lys Lys Ala Lys Asp Thr Tyr Asn Met Phe Tyr Lys Glu
865                 870                 875                 880

Gln Gly Tyr Lys Asp Ser Ala Val Arg Trp Arg Ser Asp Asp Tyr Thr
                885                 890                 895

Leu Val Asp Ala Val Gly Tyr Ile Lys Pro Ile Lys Asn Leu Thr Leu
            900                 905                 910

Gln Phe Gly Val Tyr Asn Leu Thr Asp Arg Lys Tyr Leu Thr Trp Glu
        915                 920                 925

Ser Ala Arg Ser Ile Lys Pro Phe Gly Thr Ser Asn Leu Ile Asn Gln
    930                 935                 940

Lys Thr Gly Ala Gly Ile Asn Arg Phe Tyr Ser Pro Gly Arg Asn Phe
945                 950                 955                 960

Lys Phe Ser Ala Glu Ile Thr Phe
                965
```

-continued

<210> SEQ ID NO 3
<211> LENGTH: 2373
<212> TYPE: DNA
<213> ORGANISM: Pasteurella multocida

<400> SEQUENCE: 3

```
atggaatccg caaaaaatcc actcaaaaag acgacacttg cactcctctg ttgttctacc     60
gccttctcgc tttccgcaaa aaccgatacg aacgccgata aaaatcactt tctgacggaa    120
attgtcgtgt atgcggatca aaataaatca atgagttcaa cacagagtgt cactcaagat    180
gacatgaaaa aaagccctgt cacaaatggt aatattactg actatttacg ttcaaatccg    240
catgtgcgtt atgagaatag cgatcaaaat ggattgcaac gaggtgaaat taaacccgaa    300
aacatttcaa ttaatggtgc agattatcag cagaccactt tttttgtcga taatgtaaat    360
atcaataatg atatgggatt tggtagtgat ctttttgacg gcaccatggc aacagtcccc    420
tttgccaatc attctcaagg ctactttttt gatgccaatc tgctctcttc aattgtagtg    480
catgacagta atgtttctgc cagcttagga ggatttgcgg ggggagccgt cgtggcgaaa    540
accaaacaat atgatgggaa agatcggtta aaatttagtt atcgtacaac tgatgcctca    600
tgggcaaaat ttaaagtaga agacaaagat cttgaacgtt ttaaaaatgc gattcctgaa    660
ggatcggtcg ccgaatttca acctaagtat tctaaacact tttcaatat cacggcagaa    720
aaagggttaa gtgaaaattt aggtatggtg atcggattaa gtcgtagaac atcaagtatc    780
caacaatcac gtcaaattaa tccacaaggt gatcgtgata aacaaacaca tacaagacgt    840
tcagacaatg cgttactgaa ttttaatctg acaccaaacg acaaacaccg tttcgaactc    900
ggtttcagat actcaaatta tcgtgagcgt aaattcttta atactaatat agacagtaat    960
gtttttgact atcaccgtgc ttatggtgtg actttctctt ggataaacgc ccttcagtct   1020
ggcattctca cgacgacact cgcctatgat aactttgatg acacgagaaa atcagcgtca   1080
acttatatga aaacgacgct cactgaagag ggtgaggaat ataccgaagg tggaatgggt   1140
aacagtcaat tgaaccaaaa aaatttacat acgtcacttg aatatgcgat gaatcctttt   1200
aatttaggtt caatagaaca ctctgtatca ttaggcggta tttatcaagc aacgaaatat   1260
cgctttacgc gacattcaga tgcagtcggt gaattgtata ctcctgattg gttaaatggt   1320
aatacagata aacttatatt gacgcaacgt aacatagcca aaaaagggac cgtaaaaaca   1380
cgttatcaaa atatcgcact ttacgtggaa gatttaatga cgtggaaaaa tctcgaattt   1440
cgggcgggac ttcgtcttga acgtgatgat tatttaaaaa acacgaattt ggcgccaaga   1500
accgtttttc gttataaacc atttgaagac accgcattca gtgtgggttg gaaccgttac   1560
tacggacgtt cctttgcctc aatgaaatta tctgaaggta tcttcaaatt agatggtcat   1620
gataccttcc gttacaaaga ccttagccaa tttaaaaccc cttattcaga cgaactgagc   1680
tttggtgtag aacaatatgt tgctaatctc gcctttcact tgaaatacat tttacgtgat   1740
aacaaacaac gtattgtttt acaagaagaa gaggtcatgt taaatggaga aaggaaaaaa   1800
ctccgctatt accaacgagg aaaagactac aaaacgaatg tgttaacctt ccaaattaac   1860
acacaagcgc cttgggagct tggtccaaca cgctggacaa gtgcagtggc atttgattgg   1920
ttagatagca aagctatcga tcatggcagg ggctataacg gttcgacacc tgtgatttta   1980
gacgggaaat taatgactta tgagcaaatg ttgaaaaaag tcaatgctta caaagaaaca   2040
tggggtctac gtttaaatct tgacatgttt gttccaatat ttgatctttc ttgggctaat   2100
acaatctatg tcaaaccacc aacaacctta accgaacgcg ttagcagtaa tacacctgag   2160
```

-continued

```
gtatatcgta gctatgatta tggtacttat acacaatggg ataccagtct tcgctggcag   2220

ccaactttcg cagaaaaaca ccgtccttat attaaattag atgtacttaa tgtgttaaat   2280

aaaacacgta aaggcgcggg tccaaatgga caagatctcg gcatctacac ccccggtcgt   2340

gagttctggc ttgaagttgg ttacgaattc taa                                2373


<210> SEQ ID NO 4
<211> LENGTH: 790
<212> TYPE: PRT
<213> ORGANISM: Pasteurella multocida

<400> SEQUENCE: 4

Met Glu Ser Ala Lys Asn Pro Leu Lys Lys Thr Thr Leu Ala Leu Leu
1               5                   10                  15

Cys Cys Ser Thr Ala Phe Ser Leu Ser Ala Lys Thr Asp Thr Asn Ala
            20                  25                  30

Asp Lys Asn His Phe Leu Thr Glu Ile Val Val Tyr Ala Asp Gln Asn
        35                  40                  45

Lys Ser Met Ser Ser Thr Gln Ser Val Thr Gln Asp Asp Met Lys Lys
    50                  55                  60

Ser Pro Val Thr Asn Gly Asn Ile Thr Asp Tyr Leu Arg Ser Asn Pro
65                  70                  75                  80

His Val Arg Tyr Glu Asn Ser Asp Gln Asn Gly Leu Gln Arg Gly Glu
                85                  90                  95

Ile Lys Pro Glu Asn Ile Ser Ile Asn Gly Ala Asp Tyr Gln Gln Thr
            100                 105                 110

Thr Phe Phe Val Asp Asn Val Asn Ile Asn Asn Asp Met Gly Phe Gly
        115                 120                 125

Ser Asp Leu Phe Asp Gly Thr Met Ala Thr Val Pro Phe Ala Asn His
    130                 135                 140

Ser Gln Gly Tyr Phe Phe Asp Ala Asn Leu Leu Ser Ser Ile Val Val
145                 150                 155                 160

His Asp Ser Asn Val Ser Ala Ser Leu Gly Gly Phe Ala Gly Gly Ala
                165                 170                 175

Val Val Ala Lys Thr Lys Gln Tyr Asp Gly Lys Asp Arg Leu Lys Phe
            180                 185                 190

Ser Tyr Arg Thr Thr Asp Ala Ser Trp Ala Lys Phe Lys Val Glu Asp
        195                 200                 205

Lys Asp Leu Glu Arg Phe Lys Asn Ala Ile Pro Glu Gly Ser Val Ala
    210                 215                 220

Glu Phe Gln Pro Lys Tyr Ser Lys His Phe Phe Asn Ile Thr Ala Glu
225                 230                 235                 240

Lys Gly Leu Ser Glu Asn Leu Gly Met Val Ile Gly Leu Ser Arg Arg
                245                 250                 255

Thr Ser Ser Ile Gln Gln Ser Arg Gln Ile Asn Pro Gln Gly Asp Arg
            260                 265                 270

Asp Lys Gln Thr His Thr Arg Arg Ser Asp Asn Ala Leu Leu Asn Phe
        275                 280                 285

Asn Leu Thr Pro Asn Asp Lys His Arg Phe Glu Leu Gly Phe Arg Tyr
    290                 295                 300

Ser Asn Tyr Arg Glu Arg Lys Phe Phe Asn Thr Asn Ile Asp Ser Asn
305                 310                 315                 320

Val Phe Asp Tyr His Arg Ala Tyr Gly Val Thr Phe Ser Trp Ile Asn
                325                 330                 335
```

-continued

```
Ala Leu Gln Ser Gly Ile Leu Thr Thr Thr Leu Ala Tyr Asp Asn Phe
            340                 345                 350

Asp Asp Thr Arg Lys Ser Ala Ser Thr Tyr Met Lys Thr Thr Leu Thr
        355                 360                 365

Glu Glu Gly Glu Glu Tyr Thr Glu Gly Gly Met Gly Asn Ser Gln Leu
    370                 375                 380

Asn Gln Lys Asn Leu His Thr Ser Leu Glu Tyr Ala Met Asn Pro Phe
385                 390                 395                 400

Asn Leu Gly Ser Ile Glu His Ser Val Ser Leu Gly Gly Ile Tyr Gln
                405                 410                 415

Ala Thr Lys Tyr Arg Phe Thr Arg His Ser Asp Ala Val Gly Glu Leu
            420                 425                 430

Tyr Thr Pro Asp Trp Leu Asn Gly Asn Thr Asp Lys Leu Ile Leu Thr
        435                 440                 445

Gln Arg Asn Ile Ala Lys Lys Gly Thr Val Lys Thr Arg Tyr Gln Asn
    450                 455                 460

Ile Ala Leu Tyr Val Glu Asp Leu Met Thr Trp Lys Asn Leu Glu Phe
465                 470                 475                 480

Arg Ala Gly Leu Arg Leu Glu Arg Asp Asp Tyr Leu Lys Asn Thr Asn
                485                 490                 495

Leu Ala Pro Arg Thr Val Phe Arg Tyr Lys Pro Phe Glu Asp Thr Ala
            500                 505                 510

Phe Ser Val Gly Trp Asn Arg Tyr Tyr Gly Arg Ser Phe Ala Ser Met
        515                 520                 525

Lys Leu Ser Glu Gly Ile Phe Lys Leu Asp Gly His Asp Thr Phe Arg
    530                 535                 540

Tyr Lys Asp Leu Ser Gln Phe Lys Thr Pro Tyr Ser Asp Glu Leu Ser
545                 550                 555                 560

Phe Gly Val Glu Gln Tyr Val Ala Asn Leu Ala Phe His Leu Lys Tyr
                565                 570                 575

Ile Leu Arg Asp Asn Lys Gln Arg Ile Val Leu Gln Glu Glu Glu Val
            580                 585                 590

Met Leu Asn Gly Glu Arg Lys Lys Leu Arg Tyr Tyr Gln Arg Gly Lys
        595                 600                 605

Asp Tyr Lys Thr Asn Val Leu Thr Phe Gln Ile Asn Thr Gln Ala Pro
    610                 615                 620

Trp Glu Leu Gly Pro Thr Arg Trp Thr Ser Ala Val Ala Phe Asp Trp
625                 630                 635                 640

Leu Asp Ser Lys Ala Ile Asp His Gly Arg Gly Tyr Asn Gly Ser Thr
                645                 650                 655

Pro Val Ile Leu Asp Gly Lys Leu Met Thr Tyr Glu Gln Met Leu Lys
            660                 665                 670

Lys Val Asn Ala Tyr Lys Glu Thr Trp Gly Leu Arg Leu Asn Leu Asp
        675                 680                 685

Met Phe Val Pro Ile Phe Asp Leu Ser Trp Ala Asn Thr Ile Tyr Val
    690                 695                 700

Lys Pro Pro Thr Thr Leu Thr Glu Arg Val Ser Ser Asn Thr Pro Glu
705                 710                 715                 720

Val Tyr Arg Ser Tyr Asp Tyr Gly Thr Tyr Thr Gln Trp Asp Thr Ser
                725                 730                 735

Leu Arg Trp Gln Pro Thr Phe Ala Glu Lys His Arg Pro Tyr Ile Lys
            740                 745                 750
```

-continued

```
Leu Asp Val Leu Asn Val Leu Asn Lys Thr Arg Lys Gly Ala Gly Pro
        755                 760                 765

Asn Gly Gln Asp Leu Gly Ile Tyr Thr Pro Gly Arg Glu Phe Trp Leu
    770                 775                 780

Glu Val Gly Tyr Glu Phe
785                 790
```

<210> SEQ ID NO 5
<211> LENGTH: 2184
<212> TYPE: DNA
<213> ORGANISM: Pasteurella multocida

<400> SEQUENCE: 5

```
atgtcattca aacataaaac actggcgctt tttgtcgcac atgcttgctg cacttctgcc     60

ttagcagaaa acgtggctac cacgttagaa cccatcgtgg tttctgatct cagtcatacc    120

acgctgaacc ttgatcaaaa taagcttgaa aaagaaagtc caaaagattt aaaagctatt    180

tttgccacaa cgccaaatat taatgttatc catacgggac atgcacaatt aggcgatatt    240

gaaattcgcg gtatgggaag cagccgagaa atctttgcta ccggcgcaaa ccgcgtcaca    300

atggaattag acggtatgga cattagcccg agtttttatt ttggacacag ctcacgccat    360

ggtcggcaat attttgatcc cagtgatcta aaacgtgttg agattcataa aggtccaaac    420

agtcaaggcg tggcagggca tgttcgtttc caaacgaaag atcctcgtga ttatctcttg    480

cctaaccaac gtacaggtgc acaacttcgt gctggctatt taggcgatag tgatgcttat    540

tatgttggga taactggtgc cactttattg gatgaacaca gtagtgcttt agtgagctat    600

acacgacgct ggtttaatga atttaataat aagggaggct tggatgtcac aggtagtcaa    660

cgtactaaaa gcaatccttc cagtggttat agtaatgcag tgaacagtaa attacgctat    720

tcaccaaatg accgccataa atttacgctg aatttgcaac attatgattt aaaacgcacc    780

gcctatttag aagatagctt aggaacaacg acaacacgac gtggcacaaa aacagttcat    840

cataatacca acattcagaa aaatcagcgt catgctattg ctttcagtca tgacatgcaa    900

caaaccacgg catttttttga tcacctgcac tggcaaattg cgttacaaca aacgaaaagc    960

acgagccgta atacaggggc agtcacgaat acatcagcat ctcctccccc aagtacgcca   1020

aaatttagcc aagagcgttc acttgatggc tttaaaacca aaaccatcag cttaaaaacg   1080

gaattcaata aaagcattgg gcaacatgtc gtacatgaac ttcactatgg actaaaatta   1140

caatatagcc aaatgcaagc tttacgccaa acacaatccc taaacgaaca agggagtaac   1200

actcgaacca gcgccttttt cccgacacag caacaatggc aaagtaaact ccatctttcc   1260

gatcggatca gttttggtaa atctggttta agcttgacac catccataca tctcacacag   1320

attagaatca aaccgaaaac agaaaatgta tcgaagaaaa accgtgaaca attatttact   1380

tacaaggata ccgccattgg ttacggtctg cgtgttgatt atgcactcaa tgaagcgaat   1440

ttactgagtc tgaactatca gcacgccact cgcttacccg gctatggtga aaacaatgcg   1500

caaagctatg gacactggcc agcaaaaccg aaccctcatc tacagccaga aacctcagat   1560

ggtattgaat taagttggcg tagtgcgggg gcgattggtc aacaaaccac gaccttgttc   1620

tataaccgtt acaatgactt aatttatctc gataccacgg catgttatgc tgaccgaaca   1680

ggtcaagtgc cttgtgattt agcaaatgaa aaaggacgta gttatagcta tggaatagaa   1740

ttcgacggta aactcaatct tgatacgatc ggcttcgctc aaggaacata tttaaatgct   1800

ggcttcgctt acagcaaagg gaagaccgcg aacaagcaac cacaaggacg tcttgatccc   1860
```

```
ctaacaggct ttgtcggtct tggctaccaa cagccaatgg atgtttgggg cattgaaggt   1920

aaactgaaat ttgccgcgaa gaaaaaaact aaagacttac ccgccaatca aggttttgaa   1980

ggcttaccgg gctatgctgt agttgatctt accgcctatt ataatgtgac gaaacagctt   2040

tatcttggca tcggcatcta taatgtgcta gataaaaaat atgctcgctg ggcaatggca   2100

agaggcgaca ttaaacatgg taactatgac aagcacactg aagcaggtcg tcattttggt   2160

gccaatattc gttaccactt ttaa                                          2184


<210> SEQ ID NO 6
<211> LENGTH: 727
<212> TYPE: PRT
<213> ORGANISM: Pasteurella multocida

<400> SEQUENCE: 6

Met Ser Phe Lys His Lys Thr Leu Ala Leu Phe Val Ala His Ala Cys
1               5                   10                  15

Cys Thr Ser Ala Leu Ala Glu Asn Val Ala Thr Thr Leu Glu Pro Ile
            20                  25                  30

Val Val Ser Asp Leu Ser His Thr Thr Leu Asn Leu Asp Gln Asn Lys
        35                  40                  45

Leu Glu Lys Glu Ser Pro Lys Asp Leu Lys Ala Ile Phe Ala Thr Thr
    50                  55                  60

Pro Asn Ile Asn Val Ile His Thr Gly His Ala Gln Leu Gly Asp Ile
65                  70                  75                  80

Glu Ile Arg Gly Met Gly Ser Ser Arg Glu Ile Phe Ala Thr Gly Ala
                85                  90                  95

Asn Arg Val Thr Met Glu Leu Asp Gly Met Asp Ile Ser Pro Ser Phe
            100                 105                 110

Tyr Phe Gly His Ser Ser Arg His Gly Arg Gln Tyr Phe Asp Pro Ser
        115                 120                 125

Asp Leu Lys Arg Val Glu Ile His Lys Gly Pro Asn Ser Gln Gly Val
    130                 135                 140

Ala Gly His Val Arg Phe Gln Thr Lys Asp Pro Arg Asp Tyr Leu Leu
145                 150                 155                 160

Pro Asn Gln Arg Thr Gly Ala Gln Leu Arg Ala Gly Tyr Leu Gly Asp
                165                 170                 175

Ser Asp Ala Tyr Tyr Val Gly Ile Thr Gly Ala Thr Leu Leu Asp Glu
            180                 185                 190

His Ser Ser Ala Leu Val Ser Tyr Thr Arg Arg Trp Phe Asn Glu Phe
        195                 200                 205

Asn Asn Lys Gly Gly Leu Asp Val Thr Gly Ser Gln Arg Thr Lys Ser
    210                 215                 220

Asn Pro Ser Ser Gly Tyr Ser Asn Ala Val Asn Ser Lys Leu Arg Tyr
225                 230                 235                 240

Ser Pro Asn Asp Arg His Lys Phe Thr Leu Asn Leu Gln His Tyr Asp
                245                 250                 255

Leu Lys Arg Thr Ala Tyr Leu Glu Asp Ser Leu Gly Thr Thr Thr Thr
            260                 265                 270

Arg Arg Gly Thr Lys Thr Val His His Asn Thr Asn Ile Gln Lys Asn
        275                 280                 285

Gln Arg His Ala Ile Ala Phe Ser His Asp Met Gln Gln Thr Thr Ala
    290                 295                 300

Phe Phe Asp His Leu His Trp Gln Ile Ala Leu Gln Gln Thr Lys Ser
305                 310                 315                 320
```

-continued

```
Thr Ser Arg Asn Thr Gly Ala Val Thr Asn Thr Ser Ala Ser Pro Pro
                325                 330                 335

Pro Ser Thr Pro Lys Phe Ser Gln Glu Arg Ser Leu Asp Gly Phe Lys
            340                 345                 350

Thr Lys Thr Ile Ser Leu Lys Thr Glu Phe Asn Lys Ser Ile Gly Gln
        355                 360                 365

His Val Val His Glu Leu His Tyr Gly Leu Lys Leu Gln Tyr Ser Gln
    370                 375                 380

Met Gln Ala Leu Arg Gln Thr Gln Ser Leu Asn Glu Gln Gly Ser Asn
385                 390                 395                 400

Thr Arg Thr Ser Ala Phe Phe Pro Thr Gln Gln Gln Trp Gln Ser Lys
                405                 410                 415

Leu His Leu Ser Asp Arg Ile Ser Phe Gly Lys Ser Gly Leu Ser Leu
            420                 425                 430

Thr Pro Ser Ile His Leu Thr Gln Ile Arg Ile Lys Pro Lys Thr Glu
        435                 440                 445

Asn Val Ser Lys Lys Asn Arg Glu Gln Leu Phe Thr Tyr Lys Asp Thr
    450                 455                 460

Ala Ile Gly Tyr Gly Leu Arg Val Asp Tyr Ala Leu Asn Glu Ala Asn
465                 470                 475                 480

Leu Leu Ser Leu Asn Tyr Gln His Ala Thr Arg Leu Pro Gly Tyr Gly
                485                 490                 495

Glu Asn Asn Ala Gln Ser Tyr Gly His Trp Pro Ala Lys Pro Asn Pro
            500                 505                 510

His Leu Gln Pro Glu Thr Ser Asp Gly Ile Glu Leu Ser Trp Arg Ser
        515                 520                 525

Ala Gly Ala Ile Gly Gln Gln Thr Thr Thr Leu Phe Tyr Asn Arg Tyr
    530                 535                 540

Asn Asp Leu Ile Tyr Leu Asp Thr Thr Ala Cys Tyr Ala Asp Arg Thr
545                 550                 555                 560

Gly Gln Val Pro Cys Asp Leu Ala Asn Glu Lys Gly Arg Ser Tyr Ser
                565                 570                 575

Tyr Gly Ile Glu Phe Asp Gly Lys Leu Asn Leu Asp Thr Ile Gly Phe
            580                 585                 590

Ala Gln Gly Thr Tyr Leu Asn Ala Gly Phe Ala Tyr Ser Lys Gly Lys
        595                 600                 605

Thr Ala Asn Lys Gln Pro Gln Gly Arg Leu Asp Pro Leu Thr Gly Phe
    610                 615                 620

Val Gly Leu Gly Tyr Gln Gln Pro Met Asp Val Trp Gly Ile Glu Gly
625                 630                 635                 640

Lys Leu Lys Phe Ala Ala Lys Lys Lys Thr Lys Asp Leu Pro Ala Asn
                645                 650                 655

Gln Gly Phe Glu Gly Leu Pro Gly Tyr Ala Val Val Asp Leu Thr Ala
            660                 665                 670

Tyr Tyr Asn Val Thr Lys Gln Leu Tyr Leu Gly Ile Gly Ile Tyr Asn
        675                 680                 685

Val Leu Asp Lys Lys Tyr Ala Arg Trp Ala Met Ala Arg Gly Asp Ile
    690                 695                 700

Lys His Gly Asn Tyr Asp Lys His Thr Glu Ala Gly Arg His Phe Gly
705                 710                 715                 720

Ala Asn Ile Arg Tyr His Phe
                725
```

-continued

<210> SEQ ID NO 7
<211> LENGTH: 2895
<212> TYPE: DNA
<213> ORGANISM: Pasteurella multocida

<400> SEQUENCE: 7
atgcgtacaa caacaataaa attttctgca attacattgg cattattgag ttattgtggg 60
gtcattttgg cggatagtca tcaagaggcg actgaacttg atacgattac cgtttcttct 120
caacaagatg agatgaatat taaagagaaa aaagtcggtg aaactgtgaa aacggcgagt 180
caattgaaac gccagcaagt acaggatagt cgtgatcttg tgcgctatga aaccggtgtg 240
actgtggtag aagctggacg ttttgggtcg agcggttatg ccattcgtgg tgtggatgag 300
aaccgagtgg caattacagt agatggctta catcaagcag aaaccctttc ttctcaaggt 360
tttaaagaat tattcgaagg ttacggcaat tttaacaata cccgaaatag tgtggaaatt 420
gagacgttga aagtcgctaa aatcgcgaaa ggtgctgatt ctgtaaaagt gggtagtggt 480
tctttgggag gcgctgtact tttgaaaca aaagatgcca gagatttcct gactgaaaaa 540
gattggcata tcggctataa agcgggctac tcaacggcag ataatcaggg attaaatgca 600
gtgactcttg caggtcgcta tcaaatgttt gatgcattga ttatgcattc taagcgacat 660
ggacatgaat tagaaaatta tgactataaa aatggcagag atattcaagg gaaagaaaga 720
gagaaagcgg atccttatac gattacgaaa gaaagtacat tagtgaaatt ctctttttcg 780
ccaacagaaa atcatcgttt tacagtcgct tctgatactt atatacaacg ttctcgtggc 840
catgatcgct cttattcttt acagcctcaa tctaattatt tcacatatga cgagaaagaa 900
tcgcgtcatg caaatgattt gacaaaacgt aaaaatgttt cttttactta tgaaaactat 960
agcgtaactc cattttggga tacgctaaaa ttgagttatt cacaacaaaa gatcagaaca 1020
agagcaagaa cagaagatta ttgtgatggt aatgaaaaat gtgattctta taaaaatcca 1080
ttagggcttc agttgaaaga tggcaaaatt gttgatccag agggaaatca gattacttta 1140
aaaggaacag gatttaatac agaaatagtt gataaaaatg gtaacccatt tcctacgaca 1200
tctggtacta ataatgcagc atttagtaat aatattcagt taggacctaa agaattttgg 1260
ttagattgtt ctctttttga ttgtactcag ccatttactg tttataacta tcaaaatggt 1320
caatatacgc caaaacaagt tgagttatct gaagaaatca ctgtcaatgg taaattatat 1380
aaaacagcta aagaagaaag aggtgttagg aactatttaa ttttacctaa ttcaaaaggt 1440
tatttaccat atgattacaa agaaagagat cttgattcaa atacaaaaca aatcaatttg 1500
gatttaacaa aaacattttc gacttttaat atagaaaatg aattattata cggtgccatt 1560
tattcacgta cagagaagaa aatggttaat aaagcaggtt acgatgggag aaatcctaca 1620
tggtgggctg atagaatttt agggaagagt acgaattgta actataatgg actgaaatgt 1680
cctcgtcatg aacctttaac ttctttctta attccagtag aagcgacaac caagtctcta 1740
tatttttcag ataatatcaa attacacaac atgttgagtg tagatttagg ttatcgttat 1800
gacgatatta aatatcaacc agaatatatt cctggtgtaa cacctaaaat tgcagatgat 1860
atggtgaaag gtatttttat tccattacct aagggagaaa aagtaacaac accttggggg 1920
gccgaatata caaaaccact cacacaggaa caaattcgta agaatgcgga ggaaaatatt 1980
gcttatattg cacaagaaaa acgctttaaa aaacattctt attctcttgg tgcaacgttc 2040
gatcctctga attttttacg agtacaagta aaatattcaa aagggtttag agccccgact 2100
tcggatgaac tttattttac ctttaagcat ccagatttta cgattttacc gaaccccgtg 2160

```
ttgaaaccag aggaagcaaa aaatcaagag attgcattaa cagtgcacga taattgggga   2220

tttgttagca caagtgtttt ccaaacaaag tatcgtcatt ttattgattt agcgtattta   2280

ggttcaagaa atttatcgaa ttccgtggga gggcaggcac aagcaagaga tttccaagtt   2340

tatcaaaatg tcaatgtcga taatgccaag gttaaaggac ttgaaattaa tgcacgtttg   2400

aatttgggat atttctggca tgtgttggat ggatttaata cgagctataa attcacttac   2460

caatgtggtc gtttggatgg cgatcgtcca atgaatgcga ttcagcctaa agcttctgtt   2520

tttggtttag gctatgatca taaagaaaat aaatttggcg ctgatttata tatcacacgt   2580

gtgagtgaga aaaaagcgaa agacacctat aatatgttct ataaagaaca ggggtataaa   2640

gatagtgcta ttcgttggag aagtgatgac tatacgctag ttgatgcggt tggttatatt   2700

aaaccgatta agaatttaac gttacagttt ggcgtttata atttgacaga ccgtaaatac   2760

ttgacatggg aatctgctcg ttcgattaaa ccatttggta caagtaattt aattaatcag   2820

aaaacaggcg caggaattaa tcgtttttac tcaccaggtc gtaattttaa atttagtgcc   2880

gaaattacct tctaa                                                    2895
```

```
<210> SEQ ID NO 8
<211> LENGTH: 964
<212> TYPE: PRT
<213> ORGANISM: Pasteurella multocida

<400> SEQUENCE: 8

Met Arg Thr Thr Thr Ile Lys Phe Ser Ala Ile Thr Leu Ala Leu Leu
1               5                   10                  15

Ser Tyr Cys Gly Val Ile Leu Ala Asp Ser His Gln Glu Ala Thr Glu
            20                  25                  30

Leu Asp Thr Ile Thr Val Ser Ser Gln Gln Asp Glu Met Asn Ile Lys
        35                  40                  45

Glu Lys Lys Val Gly Glu Thr Val Lys Thr Ala Ser Gln Leu Lys Arg
    50                  55                  60

Gln Gln Val Gln Asp Ser Arg Asp Leu Val Arg Tyr Glu Thr Gly Val
65                  70                  75                  80

Thr Val Val Glu Ala Gly Arg Phe Gly Ser Ser Gly Tyr Ala Ile Arg
                85                  90                  95

Gly Val Asp Glu Asn Arg Val Ala Ile Thr Val Asp Gly Leu His Gln
            100                 105                 110

Ala Glu Thr Leu Ser Ser Gln Gly Phe Lys Glu Leu Phe Glu Gly Tyr
        115                 120                 125

Gly Asn Phe Asn Asn Thr Arg Asn Ser Val Glu Ile Glu Thr Leu Lys
    130                 135                 140

Val Ala Lys Ile Ala Lys Gly Ala Asp Ser Val Lys Val Gly Ser Gly
145                 150                 155                 160

Ser Leu Gly Gly Ala Val Leu Phe Glu Thr Lys Asp Ala Arg Asp Phe
                165                 170                 175

Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Asn Tyr Asp Tyr Lys Asn Gly Arg Asp Ile Gln Gly Lys Glu Arg
225                 230                 235                 240
```

-continued

```
Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Ile Gln Arg Ser Arg Gly His Asp Arg Ser Tyr Ser Leu Gln
        275                 280                 285

Pro Gln Ser Asn Tyr Phe Thr Tyr Asp Glu Lys Glu Ser Arg His Ala
    290                 295                 300

Asn Asp Leu Thr Lys Arg Lys Asn Val Ser Phe Thr Tyr Glu Asn Tyr
305                 310                 315                 320

Ser Val Thr Pro Phe Trp Asp Thr Leu Lys Leu Ser Tyr Ser Gln Gln
                325                 330                 335

Lys Ile Arg Thr Arg Ala Arg Thr Glu Asp Tyr Cys Asp Gly Asn Glu
            340                 345                 350

Lys Cys Asp Ser Tyr Lys Asn Pro Leu Gly Leu Gln Leu Lys Asp Gly
        355                 360                 365

Lys Ile Val Asp Pro Glu Gly Asn Gln Ile Thr Leu Lys Gly Thr Gly
    370                 375                 380

Phe Asn Thr Glu Ile Val Asp Lys Asn Gly Asn Pro Phe Pro Thr Thr
385                 390                 395                 400

Ser Gly Thr Asn Asn Ala Ala Phe Ser Asn Asn Ile Gln Leu Gly Pro
                405                 410                 415

Lys Glu Phe Trp Leu Asp Cys Ser Leu Phe Asp Cys Thr Gln Pro Phe
            420                 425                 430

Thr Val Tyr Asn Tyr Gln Asn Gly Gln Tyr Thr Pro Lys Gln Val Glu
        435                 440                 445

Leu Ser Glu Glu Ile Thr Val Asn Gly Lys Leu Tyr Lys Thr Ala Lys
    450                 455                 460

Glu Glu Arg Gly Val Arg Asn Tyr Leu Ile Leu Pro Asn Ser Lys Gly
465                 470                 475                 480

Tyr Leu Pro Tyr Asp Tyr Lys Glu Arg Asp Leu Asp Ser Asn Thr Lys
                485                 490                 495

Gln Ile Asn Leu Asp Leu Thr Lys Thr Phe Ser Thr Phe Asn Ile Glu
            500                 505                 510

Asn Glu Leu Leu Tyr Gly Ala Ile Tyr Ser Arg Thr Glu Lys Lys Met
        515                 520                 525

Val Asn Lys Ala Gly Tyr Asp Gly Arg Asn Pro Thr Trp Trp Ala Asp
    530                 535                 540

Arg Ile Leu Gly Lys Ser Thr Asn Cys Asn Tyr Asn Gly Leu Lys Cys
545                 550                 555                 560

Pro Arg His Glu Pro Leu Thr Ser Phe Leu Ile Pro Val Glu Ala Thr
                565                 570                 575

Thr Lys Ser Leu Tyr Phe Ser Asp Asn Ile Lys Leu His Asn Met Leu
            580                 585                 590

Ser Val Asp Leu Gly Tyr Arg Tyr Asp Asp Ile Lys Tyr Gln Pro Glu
        595                 600                 605

Tyr Ile Pro Gly Val Thr Pro Lys Ile Ala Asp Asp Met Val Lys Gly
    610                 615                 620

Ile Phe Ile Pro Leu Pro Lys Gly Glu Lys Val Thr Thr Pro Trp Gly
625                 630                 635                 640

Ala Glu Tyr Thr Lys Pro Leu Thr Gln Glu Gln Ile Arg Lys Asn Ala
                645                 650                 655
```

```
Glu Glu Asn Ile Ala Tyr Ile Ala Gln Glu Lys Arg Phe Lys Lys His
            660                 665                 670

Ser Tyr Ser Leu Gly Ala Thr Phe Asp Pro Leu Asn Phe Leu Arg Val
        675                 680                 685

Gln Val Lys Tyr Ser Lys Gly Phe Arg Ala Pro Thr Ser Asp Glu Leu
    690                 695                 700

Tyr Phe Thr Phe Lys His Pro Asp Phe Thr Ile Leu Pro Asn Pro Val
705                 710                 715                 720

Leu Lys Pro Glu Glu Ala Lys Asn Gln Glu Ile Ala Leu Thr Val His
                725                 730                 735

Asp Asn Trp Gly Phe Val Ser Thr Ser Val Phe Gln Thr Lys Tyr Arg
            740                 745                 750

His Phe Ile Asp Leu Ala Tyr Leu Gly Ser Arg Asn Leu Ser Asn Ser
        755                 760                 765

Val Gly Gly Gln Ala Gln Ala Arg Asp Phe Gln Val Tyr Gln Asn Val
    770                 775                 780

Asn Val Asp Asn Ala Lys Val Lys Gly Leu Glu Ile Asn Ala Arg Leu
785                 790                 795                 800

Asn Leu Gly Tyr Phe Trp His Val Leu Asp Gly Phe Asn Thr Ser Tyr
                805                 810                 815

Lys Phe Thr Tyr Gln Cys Gly Arg Leu Asp Gly Asp Arg Pro Met Asn
            820                 825                 830

Ala Ile Gln Pro Lys Ala Ser Val Phe Gly Leu Gly Tyr Asp His Lys
        835                 840                 845

Glu Asn Lys Phe Gly Ala Asp Leu Tyr Ile Thr Arg Val Ser Glu Lys
    850                 855                 860

Lys Ala Lys Asp Thr Tyr Asn Met Phe Tyr Lys Glu Gln Gly Tyr Lys
865                 870                 875                 880

Asp Ser Ala Ile Arg Trp Arg Ser Asp Asp Tyr Thr Leu Val Asp Ala
                885                 890                 895

Val Gly Tyr Ile Lys Pro Ile Lys Asn Leu Thr Leu Gln Phe Gly Val
            900                 905                 910

Tyr Asn Leu Thr Asp Arg Lys Tyr Leu Thr Trp Glu Ser Ala Arg Ser
        915                 920                 925

Ile Lys Pro Phe Gly Thr Ser Asn Leu Ile Asn Gln Lys Thr Gly Ala
    930                 935                 940

Gly Ile Asn Arg Phe Tyr Ser Pro Gly Arg Asn Phe Lys Phe Ser Ala
945                 950                 955                 960

Glu Ile Thr Phe
```

```
<210> SEQ ID NO 9
<211> LENGTH: 2547
<212> TYPE: DNA
<213> ORGANISM: Pasteurella multocida

<400> SEQUENCE: 9

atgcaaaaac agcaacctta tcccattcac cttgggattt ttttgatgtt gggtttacca      60

acatgggcgt tcagtcaagc taatttagag aaatcaacaa tcaataaatt ggaaacgatt     120

ttggtcaatg agagtgaaga gaaaaataaa ttcgatgaga atttgatcaa aacttatctg     180

tcttcgggtt cttattctta tttatcgcaa tcggatatca gtacgttcag aggtagctcg     240

gtaggggatt tcctctctgg tgtaccagga gttattgtgg gaaataagcg taatagcggc     300

gctttatccg ttaatattcg aggaattgcg aatgaaaatc gtgtgcctgt ttggatagat     360
```

-continued

```
aaaggtctac aatcggtacc ctcttaccaa ggttatgcag gttcttcaac tcgaacctat    420
ttagatcccg atttgatcag ccaagtcgag attgaaaaag gtccctcttt gcaaatggac    480
gcaacaggcg cgacgggagg ggtagtgaga gtagagactt tacgttggca agatattatt    540
cctcaaggga aaaattgggg cgtgcgtttg aaactaggga cgatgactaa caccgtatca    600
cctccccctt attatacaag aggaggatat caaactaagt atattagtaa atgtctttct    660
aatgatactg gtttatgtca aacacaaaca tatgcaccaa atgcacgcta ttcttctcat    720
ggctttgatt tgaatgcata caattatagc ctggcttttg ctaataaatg gcaaaatgct    780
gatcttgtac ttgcgtatgc aaaacgtaaa cagggcaact attttgttgg gcgtcatgga    840
caaaccccag tgattgaatc cattgaattt gaggaagatt cagtagaagt caaagagcct    900
cgcgttcatg aagaggttga aattggttca ttaacattta aagaaaatcg cagcacctta    960
tatcgaccgg gtgaagaagc cctgaatacc tcacaagata atacctctta tctcgctaaa   1020
ataaatgtct acaatgatgt tcatcgttta gggttagcgt atcgccatta tcatagccgt   1080
tttggtgaga ttatgagctc aattttgaat ttcagagcgt atggcgcatt gcaaggtgaa   1140
gggacagaag tcaaagtcga tagctatcat gcaaattata gctataaccc aacgacacct   1200
tatgtgaatt tgaatgttaa tgcatatttt actgacagtg attcgtctaa ttttacccca   1260
tttattgaag aatatggtta ctctttatcc agtcgtcatg cccattttct ggtttctaag   1320
cagaaagggt taagtattga aaatactagc attttccagc ttaacgacaa accgtttagt   1380
ttaaaatatg gtcttgcgca tagttatgaa cggatttatc aaccacgtaa tgctcaagca   1440
cgtgtgagag ctaaagggta tccagaagat gcgattggtc cactttatat tcgagatggt   1500
aagcgtaaag aatggagcgc ttttgttgct gcgaactatc caatcacttc gtggttaaaa   1560
gccgacatcg ggctacgtta tcttcaatct actatttatg attatattgt gagaacggaa   1620
agagtgaata ttggaggggc acttgtgcct aatccaaatg gatccggtaa tatttgggtg   1680
gaaaaatata aagatgttgt gcataaacag gcgccagtga aaaataaagg catgtcgcca   1740
attgtgatgc tcacatttga acctattaac ggagtacaaa tttatacgaa atatgcagaa   1800
gcattgcgtt cgccaagttt attccaagca actaaaggct ggtccatgag tgcgacggca   1860
gataatctag aacaattgag acctgaacga gcccaaaatt gggaggcggg tattaacttg   1920
ttttatgaaa atctaggtgg taaggacaat attcttggtt ttaaattggc gtattttaat   1980
aataggataa aagattattt gacgcggagt tattcgccta aagataaggt gacgcagaca   2040
attaatatac aaagtgcaca atttaaagga attgagttat cagcgtatta tgatatgggg   2100
aaattttacg caaaattagc tggtacatat tacacaaaaa cgaaattttg tttaacagca   2160
gaacaagcag gcaaaggaga gcaatgtaat tcaggttatg tatatcgtag taatttaaat   2220
aatgccgttc ctccgcgttt aaatttacat gcgactttag gaacccgttt gtttgaacaa   2280
aaactcgata ttggtgcgcg ctatagttac tacagtaagc gattagtacc agtgctttct   2340
gcagaacgtt ttgttaacac atcaagtatt gagtgggcgc cttattcctt agtagattta   2400
tatgccaatt acaatgtgtc taataaccta aaacttacga tgaccatgga taatgtgttt   2460
aatcgctatt atttagatat caataatatg ggattaaata ccgcaccggg tagaacattg   2520
catttaggat tagaatatcg gttttag                                        2547
```

<210> SEQ ID NO 10
<211> LENGTH: 848
<212> TYPE: PRT
<213> ORGANISM: Pasteurella multocida

<400> SEQUENCE: 10

Met Gln Lys Gln Gln Pro Tyr Pro Ile His Leu Gly Ile Phe Leu Met
1 5 10 15

Leu Gly Leu Pro Thr Trp Ala Phe Ser Gln Ala Asn Leu Glu Lys Ser
20 25 30

Thr Ile Asn Lys Leu Glu Thr Ile Leu Val Asn Glu Ser Glu Glu Lys
35 40 45

Asn Lys Phe Asp Glu Asn Leu Ile Lys Thr Tyr Leu Ser Ser Gly Ser
50 55 60

Tyr Ser Tyr Leu Ser Gln Ser Asp Ile Ser Thr Phe Arg Gly Ser Ser
65 70 75 80

Val Gly Asp Phe Leu Ser Gly Val Pro Gly Val Ile Val Gly Asn Lys
85 90 95

Arg Asn Ser Gly Ala Leu Ser Val Asn Ile Arg Gly Ile Ala Asn Glu
100 105 110

Asn Arg Val Pro Val Trp Ile Asp Lys Gly Leu Gln Ser Val Pro Ser
115 120 125

Tyr Gln Gly Tyr Ala Gly Ser Ser Thr Arg Thr Tyr Leu Asp Pro Asp
130 135 140

Leu Ile Ser Gln Val Glu Ile Glu Lys Gly Pro Ser Leu Gln Met Asp
145 150 155 160

Ala Thr Gly Ala Thr Gly Gly Val Val Arg Val Glu Thr Leu Arg Trp
165 170 175

Gln Asp Ile Ile Pro Gln Gly Lys Asn Trp Gly Val Arg Leu Lys Leu
180 185 190

Gly Thr Met Thr Asn Thr Val Ser Pro Pro Pro Tyr Tyr Thr Arg Gly
195 200 205

Gly Tyr Gln Thr Lys Tyr Ile Ser Lys Cys Leu Ser Asn Asp Thr Gly
210 215 220

Leu Cys Gln Thr Gln Thr Tyr Ala Pro Asn Ala Arg Tyr Ser Ser His
225 230 235 240

Gly Phe Asp Leu Asn Ala Tyr Asn Tyr Ser Leu Ala Phe Ala Asn Lys
245 250 255

Trp Gln Asn Ala Asp Leu Val Leu Ala Tyr Ala Lys Arg Lys Gln Gly
260 265 270

Asn Tyr Phe Val Gly Arg His Gly Gln Thr Pro Val Ile Glu Ser Ile
275 280 285

Glu Phe Glu Glu Asp Ser Val Glu Val Lys Glu Pro Arg Val His Glu
290 295 300

Glu Val Glu Ile Gly Ser Leu Thr Phe Lys Glu Asn Arg Ser Thr Leu
305 310 315 320

Tyr Arg Pro Gly Glu Glu Ala Leu Asn Thr Ser Gln Asp Asn Thr Ser
325 330 335

Tyr Leu Ala Lys Ile Asn Val Tyr Asn Asp Val His Arg Leu Gly Leu
340 345 350

Ala Tyr Arg His Tyr His Ser Arg Phe Gly Glu Ile Met Ser Ser Ile
355 360 365

Leu Asn Phe Arg Ala Tyr Gly Ala Leu Gln Gly Glu Gly Thr Glu Val
370 375 380

Lys Val Asp Ser Tyr His Ala Asn Tyr Ser Tyr Asn Pro Thr Thr Pro
385 390 395 400

Tyr Val Asn Leu Asn Val Asn Ala Tyr Phe Thr Asp Ser Asp Ser Ser

-continued

```
                405                 410                 415

Asn Phe Thr Pro Phe Ile Glu Glu Tyr Gly Tyr Ser Leu Ser Ser Arg
            420                 425                 430

His Ala His Phe Leu Val Ser Lys Gln Lys Gly Leu Ser Ile Glu Asn
        435                 440                 445

Thr Ser Ile Phe Gln Leu Asn Asp Lys Pro Phe Ser Leu Lys Tyr Gly
    450                 455                 460

Leu Ala His Ser Tyr Glu Arg Ile Tyr Gln Pro Arg Asn Ala Gln Ala
465                 470                 475                 480

Arg Val Arg Ala Lys Gly Tyr Pro Glu Asp Ala Ile Gly Pro Leu Tyr
                485                 490                 495

Ile Arg Asp Gly Lys Arg Lys Glu Trp Ser Ala Phe Val Ala Ala Asn
            500                 505                 510

Tyr Pro Ile Thr Ser Trp Leu Lys Ala Asp Ile Gly Leu Arg Tyr Leu
        515                 520                 525

Gln Ser Thr Ile Tyr Asp Tyr Ile Val Arg Thr Glu Arg Val Asn Ile
    530                 535                 540

Gly Gly Ala Leu Val Pro Asn Pro Asn Gly Ser Gly Asn Ile Trp Val
545                 550                 555                 560

Glu Lys Tyr Lys Asp Val Val His Lys Gln Ala Pro Val Lys Asn Lys
                565                 570                 575

Gly Met Ser Pro Ile Val Met Leu Thr Phe Glu Pro Ile Asn Gly Val
            580                 585                 590

Gln Ile Tyr Thr Lys Tyr Ala Glu Ala Leu Arg Ser Pro Ser Leu Phe
        595                 600                 605

Gln Ala Thr Lys Gly Trp Ser Met Ser Ala Thr Ala Asp Asn Leu Glu
    610                 615                 620

Gln Leu Arg Pro Glu Arg Ala Gln Asn Trp Glu Ala Gly Ile Asn Leu
625                 630                 635                 640

Phe Tyr Glu Asn Leu Gly Gly Lys Asp Asn Ile Leu Gly Phe Lys Leu
                645                 650                 655

Ala Tyr Phe Asn Asn Arg Ile Lys Asp Tyr Leu Thr Arg Ser Tyr Ser
            660                 665                 670

Pro Lys Asp Lys Val Thr Gln Thr Ile Asn Ile Gln Ser Ala Gln Phe
        675                 680                 685

Lys Gly Ile Glu Leu Ser Ala Tyr Tyr Asp Met Gly Lys Phe Tyr Ala
    690                 695                 700

Lys Leu Ala Gly Thr Tyr Tyr Thr Lys Thr Lys Phe Cys Leu Thr Ala
705                 710                 715                 720

Glu Gln Ala Gly Lys Gly Glu Gln Cys Asn Ser Gly Tyr Val Tyr Arg
                725                 730                 735

Ser Asn Leu Asn Asn Ala Val Pro Pro Arg Leu Asn Leu His Ala Thr
            740                 745                 750

Leu Gly Thr Arg Leu Phe Glu Gln Lys Leu Asp Ile Gly Ala Arg Tyr
        755                 760                 765

Ser Tyr Tyr Ser Lys Arg Leu Val Pro Val Leu Ser Ala Glu Arg Phe
    770                 775                 780

Val Asn Thr Ser Ser Ile Glu Trp Ala Pro Tyr Ser Leu Val Asp Leu
785                 790                 795                 800

Tyr Ala Asn Tyr Asn Val Ser Asn Asn Leu Lys Leu Thr Met Thr Met
                805                 810                 815

Asp Asn Val Phe Asn Arg Tyr Tyr Leu Asp Ile Asn Asn Met Gly Leu
            820                 825                 830
```

```
Asn Thr Ala Pro Gly Arg Thr Leu His Leu Gly Leu Glu Tyr Arg Phe
        835                 840                 845


<210> SEQ ID NO 11
<211> LENGTH: 2355
<212> TYPE: DNA
<213> ORGANISM: Pasteurella multocida

<400> SEQUENCE: 11

atgaaatatc ccttaagcta taaaaatata gcaaggtcca ttccttttct ctcattcatt     60

gcgtttcctc tgtatgcgca agaaacgact gaattagaac aaattacagt acaagaaagc    120

gcaaccgctg aagtgaacaa aacctcacca acagtgatca gcaaaagcgc cacgaccatt    180

caaaacgaaa tgattcgaga caccagagat ttagtccgct acacaacgga tgtagggatt    240

agcgataatg ggcgtttttt gaaaggcttt gcgatgcgag gcgttgaaga taaccgcgtt    300

ggtatcagta ttgatggtgt ttctttgcct gattcagaag aaaactcact gtatgcgcgt    360

tatggtaact ttaataattc ccgcctaagc attgatcctg aattaattca aaccattgat    420

attgtacgcg gctcagattc ctttaatgca ggcagcggtt cattaggtgg cggtgtgaat    480

tataacactt tagatccaca acatattgtt aaaacaggta attccgttgg tgctttacta    540

cgaggcagtt atgccagtaa aaatcgtgaa tgggttcgta ctttagggat aggctatgtt    600

ggcgaaaaat ttgatgcctt attgatgtat tcacaacgca cagggcacga gtttaaaagt    660

cgtggttcag gtcctgaatt tcggtattcc agtagccagc atcccgatcc tgtgacacaa    720

cgcttccaca attatctcgc taaaatgaat tatcaaatta atgacaaaca acgtattggt    780

ttaacgctga atgggcaaac agggggggcgt tacattgatg agcgttctta tacgttaatg    840

ggctcacaat ggcgtgaagc cgatgatcaa aacgaacggt tgaatgcaaa cttatattat    900

atttatgcac caagcacggg atggttagcc tacagtaaat ttgatttaga ttatcaaaag    960

accgatctag cagcagttaa ctataaaggc ggacgccatt tcacgacaga tgctaaagag   1020

ctgaacgaaa tttatgatcg ccgtatgaaa accgtgttta cgcgcggcag tgtagaactc   1080

aatgcacaac ctgtacattt ctatggtgaa catactttaa ccatcaaagg ctatgttagt   1140

cagcgtgatt tcaaaaatat caatcaagat cgtatcggta ttggcacaaa ctacgacaca   1200

caataccact atacgattca atatcctatt agaaccaagc agtacgggct ttctttgaaa   1260

gatcatgtgc gctggaatga taccttctca agccatttag gtttacgtta tgaccataca   1320

aaactaaaac caaaggaact caatgcacct tgtagcaaag cctgtttaga agaaggaaaa   1380

cctaaaccga cccgtttctc taccgttagc acatttgcgg gatttgaggc acaactcagc   1440

ccctcatgga tgttaggcta caatattagc accggttatc gtgtaccaac ggcttcagaa   1500

atgttcttca gctttaccaa tgcgtatggc acgtggaaat ctaacccgag cttgaaaccc   1560

gaaaaaagta ttaaccatac actctctttg aaaggcaata gtgaaaaagg cttgcttgat   1620

ctcaccctct atcaaacaaa ctatcgtcat ttcttatttg aacaagaaag tttaattcaa   1680

cgtaccgaaa tgcgctatgg acgcccttat acttaccaaa gccaagaaca acaaatggtg   1740

aacttagata aagcaaaaat ttatggtgtg gaattgaaaa cccatgtcaa tttagatcag   1800

atgatcgctg tgataccaca aggctttaag ttctacgccg cgctcggtta tagcaaaggt   1860

aaactctcga ataacgccag cctactttcc attcaaccgc ttaaaattat tctggggttg   1920

gattatgaag caacaaacgg caaatgggct attttcaacc gcctaaccta tttgggtgaa   1980

aaaagagcta gtgatgcgaa agtgtatgaa attaaacgtc gctgtactga atttgtgaca   2040
```

```
gaaacagatc cttggactgg tcaacaaatt actcgctgta aaaaacggga attgtatcca   2100

gatttatcta cttataaaca cttaaataaa tctgcttttg tgtttgatac ttttggttat   2160

tacaagatca cggacgatat cacgttccga gctggcattt ataatctgtt taataaaaaa   2220

taccacactt gggatgcctt acgtggtatt aatgccaata gtacgttaaa ttcagttgac   2280

cgtgaaggga aagggttaca acgcttctat gcgcccggac gtaactatgc ggcttccctt   2340

gaaatccgtt tctaa                                                    2355


<210> SEQ ID NO 12
<211> LENGTH: 784
<212> TYPE: PRT
<213> ORGANISM: Pasteurella multocida

<400> SEQUENCE: 12

Met Lys Tyr Pro Leu Ser Tyr Lys Asn Ile Ala Arg Ser Ile Pro Phe
1               5                   10                  15

Leu Ser Phe Ile Ala Phe Pro Leu Tyr Ala Gln Glu Thr Thr Glu Leu
            20                  25                  30

Glu Gln Ile Thr Val Gln Glu Ser Ala Thr Ala Glu Val Asn Lys Thr
        35                  40                  45

Ser Pro Thr Val Ile Ser Lys Ser Ala Thr Thr Ile Gln Asn Glu Met
    50                  55                  60

Ile Arg Asp Thr Arg Asp Leu Val Arg Tyr Thr Thr Asp Val Gly Ile
65                  70                  75                  80

Ser Asp Asn Gly Arg Phe Leu Lys Gly Phe Ala Met Arg Gly Val Glu
                85                  90                  95

Asp Asn Arg Val Gly Ile Ser Ile Asp Gly Val Ser Leu Pro Asp Ser
            100                 105                 110

Glu Glu Asn Ser Leu Tyr Ala Arg Tyr Gly Asn Phe Asn Asn Ser Arg
        115                 120                 125

Leu Ser Ile Asp Pro Glu Leu Ile Gln Thr Ile Asp Ile Val Arg Gly
    130                 135                 140

Ser Asp Ser Phe Asn Ala Gly Ser Gly Ser Leu Gly Gly Gly Val Asn
145                 150                 155                 160

Tyr Asn Thr Leu Asp Pro Gln His Ile Val Lys Thr Gly Asn Ser Val
                165                 170                 175

Gly Ala Leu Leu Arg Gly Ser Tyr Ala Ser Lys Asn Arg Glu Trp Val
            180                 185                 190

Arg Thr Leu Gly Ile Gly Tyr Val Gly Glu Lys Phe Asp Ala Leu Leu
        195                 200                 205

Met Tyr Ser Gln Arg Thr Gly His Glu Phe Lys Ser Arg Gly Ser Gly
    210                 215                 220

Pro Glu Phe Arg Tyr Ser Ser Ser Gln His Pro Asp Pro Val Thr Gln
225                 230                 235                 240

Arg Phe His Asn Tyr Leu Ala Lys Met Asn Tyr Gln Ile Asn Asp Lys
                245                 250                 255

Gln Arg Ile Gly Leu Thr Leu Asn Gly Gln Thr Gly Gly Arg Tyr Ile
            260                 265                 270

Asp Glu Arg Ser Tyr Thr Leu Met Gly Ser Gln Trp Arg Glu Ala Asp
        275                 280                 285

Asp Gln Asn Glu Arg Leu Asn Ala Asn Leu Tyr Tyr Ile Tyr Ala Pro
    290                 295                 300

Ser Thr Gly Trp Leu Ala Tyr Ser Lys Phe Asp Leu Asp Tyr Gln Lys
```

-continued

```
305                 310                 315                 320

Thr Asp Leu Ala Ala Val Asn Tyr Lys Gly Gly Arg His Phe Thr Thr
                325                 330                 335

Asp Ala Lys Glu Leu Asn Glu Ile Tyr Asp Arg Arg Met Lys Thr Val
            340                 345                 350

Phe Thr Arg Gly Ser Val Glu Leu Asn Ala Gln Pro Val His Phe Tyr
        355                 360                 365

Gly Glu His Thr Leu Thr Ile Lys Gly Tyr Val Ser Gln Arg Asp Phe
    370                 375                 380

Lys Asn Ile Asn Gln Asp Arg Ile Gly Ile Gly Thr Asn Tyr Asp Thr
385                 390                 395                 400

Gln Tyr His Tyr Thr Ile Gln Tyr Pro Ile Arg Thr Lys Gln Tyr Gly
                405                 410                 415

Leu Ser Leu Lys Asp His Val Arg Trp Asn Asp Thr Phe Ser Ser His
            420                 425                 430

Leu Gly Leu Arg Tyr Asp His Thr Lys Leu Lys Pro Lys Glu Leu Asn
        435                 440                 445

Ala Pro Cys Ser Lys Ala Cys Leu Glu Glu Gly Lys Pro Lys Pro Thr
    450                 455                 460

Arg Phe Ser Thr Val Ser Thr Phe Ala Gly Phe Glu Ala Gln Leu Ser
465                 470                 475                 480

Pro Ser Trp Met Leu Gly Tyr Asn Ile Ser Thr Gly Tyr Arg Val Pro
                485                 490                 495

Thr Ala Ser Glu Met Phe Phe Ser Phe Thr Asn Ala Tyr Gly Thr Trp
            500                 505                 510

Lys Ser Asn Pro Ser Leu Lys Pro Glu Lys Ser Ile Asn His Thr Leu
        515                 520                 525

Ser Leu Lys Gly Asn Ser Glu Lys Gly Leu Leu Asp Leu Thr Leu Tyr
    530                 535                 540

Gln Thr Asn Tyr Arg His Phe Leu Phe Glu Gln Glu Ser Leu Ile Gln
545                 550                 555                 560

Arg Thr Glu Met Arg Tyr Gly Arg Pro Tyr Thr Tyr Gln Ser Gln Glu
                565                 570                 575

Gln Gln Met Val Asn Leu Asp Lys Ala Lys Ile Tyr Gly Val Glu Leu
            580                 585                 590

Lys Thr His Val Asn Leu Asp Gln Met Ile Ala Val Ile Pro Gln Gly
        595                 600                 605

Phe Lys Phe Tyr Ala Ala Leu Gly Tyr Ser Lys Gly Lys Leu Ser Asn
    610                 615                 620

Asn Ala Ser Leu Leu Ser Ile Gln Pro Leu Lys Ile Ile Leu Gly Leu
625                 630                 635                 640

Asp Tyr Glu Ala Thr Asn Gly Lys Trp Ala Ile Phe Asn Arg Leu Thr
                645                 650                 655

Tyr Leu Gly Glu Lys Arg Ala Ser Asp Ala Lys Val Tyr Glu Ile Lys
            660                 665                 670

Arg Arg Cys Thr Glu Phe Val Thr Glu Thr Asp Pro Trp Thr Gly Gln
        675                 680                 685

Gln Ile Thr Arg Cys Lys Lys Arg Glu Leu Tyr Pro Asp Leu Ser Thr
    690                 695                 700

Tyr Lys His Leu Asn Lys Ser Ala Phe Val Phe Asp Thr Phe Gly Tyr
705                 710                 715                 720

Tyr Lys Ile Thr Asp Asp Ile Thr Phe Arg Ala Gly Ile Tyr Asn Leu
                725                 730                 735
```

```
Phe Asn Lys Lys Tyr His Thr Trp Asp Ala Leu Arg Gly Ile Asn Ala
            740                 745                 750

Asn Ser Thr Leu Asn Ser Val Asp Arg Glu Gly Lys Gly Leu Gln Arg
        755                 760                 765

Phe Tyr Ala Pro Gly Arg Asn Tyr Ala Ala Ser Leu Glu Ile Arg Phe
    770                 775                 780

<210> SEQ ID NO 13
<211> LENGTH: 2229
<212> TYPE: DNA
<213> ORGANISM: Pasteurella multocida
<400> SEQUENCE: 13
atggataaaa atttaatgaa gggatgtgta ttcttatcaa tagtcggttg cggtatccaa      60
atagggctag catcaaatcc aaatcctcca gatgtggatg agttattacc tattattgtg     120
aatgctgatg aagataataa attaccaggt cgttctgtat taaaacagaa aaatatcgat     180
caacaacaag cagataatgc tgctgactta ataaatattt tgcctggtgt aaatatggcg     240
ggaggatttc gccctagtgg tcaaacatta aatattaatg gaatgggtga tgctgaagat     300
gttagagttc aactagacgg cgcaacaaaa agtttcgaaa aatatcaaca aggctctatt     360
tttattgaac ctgagttatt aagaaaggtg acagtagaca aaggaaatta ttctcctcaa     420
tatggcaatg gtggctttgc tggtactgta aaatttgaaa caaaagatgc aactgatttt     480
ttgaaagaaa atcagaaaat aggtggatta tttaaatatg gaaataatag caataataac     540
caaaaaactt atagtacagc cctagtttta cagaatgaac aaaaaaatat tgatttgtta     600
ttatttggtt ctgtaagaaa tgcaagcaat tatacaagac ctgataaaag taaaattctt     660
ttttcaaaaa acaatcaaaa aagtggatta ataaaagtaa attggcaaat tactcctgaa     720
catttattaa ctttatccag tgtttatggc attcataaag ggtgggaacc ttgggcagca     780
aaaagagatg tgatgtcgag accaacagaa acagaaataa aacactatgg gattgatgtt     840
gcgtggaaac gtaaacttgt ttatcgagat caaaaagatg aaagttattc attgaaatat     900
cgctatttac ctgaaaataa taagtggatt aatttatctg ttcagctgag ttatagtaaa     960
acagaacaga atgatactcg ccatgagaaa gtcacttctt cattcctagg tacattagga    1020
aataaaagtt ggataactta ttcagatctt actttgata taagtaacac aagtactcta    1080
aatattgggc gtgctgagca tgaactacta tttggtttac agtggttaaa aaataaaaga    1140
aataccctta tgtatcataa agggggagtc aagaaggcag actataatta tggctatttt    1200
cagccttatt atatgccttc tggacgccag tatacacaag cattttattt acaagatcaa    1260
ataaaaatggc agaatttcct ctttacagga gggataagat atgaccatat caataatata    1320
gggcagaaaa atttagcgcc acgatataat gatatctctg caggacatga ttatagccag    1380
aaaaattata atggttggtc ttattattta ggtcttaagt atgatgtaaa tcattattta    1440
agtttattta cgaattttag taaaacttgg cgagcccctg ttattgatga acagtatgag    1500
acacaatata gtcaagcttc tgtatctgcg acttctttaa atttagaaaa agaaatgatt    1560
aatcaaacca gagtgggtgg aattattact ctcaatcatc tatttcagga aaatgatgct    1620
tttcaattta gaactactta tttttacaat cgcggcaaga atgaaatctt caaaacgaga    1680
ggagttaatt gcgtagaaaa tgctttagat gttgataata gtgtttgtcc taaaattatt    1740
agtaattacc gtaatttacc tggttatgtt attcaaggag cggaattaga agcttattat    1800
caatcatcgt atttatttgg tggactgaca tattcttatg taaaaggaaa acgcgatact    1860
```

```
tcaccaagaa atccatggag taaaacatct acatggatcg cagaaacatc acctagaaaa   1920

gcaatcgcta ctttaggttt taatattccg gaatattatt ttacggcagg ttggcgtgct   1980

gagtttgtga gaaagcaaga tagatcacca ctatctaatg attctaaagc atcatattgg   2040

gcattacctt cttcaaaagg atatagccta catagtgtat tcttctcttg gagtcctaca   2100

aagattaaag gaatgaattt caaagttact gttgataatt tatttaaccg accctattat   2160

ccttacttag gagaattagc ttcaggaaca ggtaggaatg tcaaatttag cctgactcag   2220

caattttaa                                                           2229


<210> SEQ ID NO 14
<211> LENGTH: 742
<212> TYPE: PRT
<213> ORGANISM: Pasteurella multocida

<400> SEQUENCE: 14

Met Asp Lys Asn Leu Met Lys Gly Cys Val Phe Leu Ser Ile Val Gly
1               5                   10                  15

Cys Gly Ile Gln Ile Gly Leu Ala Ser Asn Pro Asn Pro Pro Asp Val
            20                  25                  30

Asp Glu Leu Leu Pro Ile Ile Val Asn Ala Asp Glu Asp Asn Lys Leu
        35                  40                  45

Pro Gly Arg Ser Val Leu Lys Gln Lys Asn Ile Asp Gln Gln Gln Ala
    50                  55                  60

Asp Asn Ala Ala Asp Leu Ile Asn Ile Leu Pro Gly Val Asn Met Ala
65                  70                  75                  80

Gly Gly Phe Arg Pro Ser Gly Gln Thr Leu Asn Ile Asn Gly Met Gly
                85                  90                  95

Asp Ala Glu Asp Val Arg Val Gln Leu Asp Gly Ala Thr Lys Ser Phe
            100                 105                 110

Glu Lys Tyr Gln Gln Gly Ser Ile Phe Ile Glu Pro Glu Leu Leu Arg
        115                 120                 125

Lys Val Thr Val Asp Lys Gly Asn Tyr Ser Pro Gln Tyr Gly Asn Gly
    130                 135                 140

Gly Phe Ala Gly Thr Val Lys Phe Glu Thr Lys Asp Ala Thr Asp Phe
145                 150                 155                 160

Leu Lys Glu Asn Gln Lys Ile Gly Gly Leu Phe Lys Tyr Gly Asn Asn
                165                 170                 175

Ser Asn Asn Asn Gln Lys Thr Tyr Ser Thr Ala Leu Val Leu Gln Asn
            180                 185                 190

Glu Gln Lys Asn Ile Asp Leu Leu Leu Phe Gly Ser Val Arg Asn Ala
        195                 200                 205

Ser Asn Tyr Thr Arg Pro Asp Lys Ser Lys Ile Leu Phe Ser Lys Asn
    210                 215                 220

Asn Gln Lys Ser Gly Leu Ile Lys Val Asn Trp Gln Ile Thr Pro Glu
225                 230                 235                 240

His Leu Leu Thr Leu Ser Ser Val Tyr Gly Ile His Lys Gly Trp Glu
                245                 250                 255

Pro Trp Ala Ala Lys Arg Asp Val Met Ser Arg Pro Thr Glu Thr Glu
            260                 265                 270

Ile Lys His Tyr Gly Ile Asp Val Ala Trp Lys Arg Lys Leu Val Tyr
        275                 280                 285

Arg Asp Gln Lys Asp Glu Ser Tyr Ser Leu Lys Tyr Arg Tyr Leu Pro
    290                 295                 300
```

```
Glu Asn Asn Lys Trp Ile Asn Leu Ser Val Gln Leu Ser Tyr Ser Lys
305                 310                 315                 320

Thr Glu Gln Asn Asp Thr Arg His Glu Lys Val Thr Ser Ser Phe Leu
                325                 330                 335

Gly Thr Leu Gly Asn Lys Ser Trp Ile Thr Tyr Ser Asp Leu Thr Phe
            340                 345                 350

Asp Ile Ser Asn Thr Ser Thr Leu Asn Ile Gly Arg Ala Glu His Glu
        355                 360                 365

Leu Leu Phe Gly Leu Gln Trp Leu Lys Asn Lys Arg Asn Thr Leu Met
    370                 375                 380

Tyr His Lys Gly Gly Val Lys Lys Ala Asp Tyr Asn Tyr Gly Tyr Phe
385                 390                 395                 400

Gln Pro Tyr Tyr Met Pro Ser Gly Arg Gln Tyr Thr Gln Ala Phe Tyr
                405                 410                 415

Leu Gln Asp Gln Ile Lys Trp Gln Asn Phe Leu Phe Thr Gly Gly Ile
            420                 425                 430

Arg Tyr Asp His Ile Asn Asn Ile Gly Gln Lys Asn Leu Ala Pro Arg
        435                 440                 445

Tyr Asn Asp Ile Ser Ala Gly His Asp Tyr Ser Gln Lys Asn Tyr Asn
    450                 455                 460

Gly Trp Ser Tyr Tyr Leu Gly Leu Lys Tyr Asp Val Asn His Tyr Leu
465                 470                 475                 480

Ser Leu Phe Thr Asn Phe Ser Lys Thr Trp Arg Ala Pro Val Ile Asp
                485                 490                 495

Glu Gln Tyr Glu Thr Gln Tyr Ser Gln Ala Ser Val Ser Ala Thr Ser
            500                 505                 510

Leu Asn Leu Glu Lys Glu Met Ile Asn Gln Thr Arg Val Gly Gly Ile
        515                 520                 525

Ile Thr Leu Asn His Leu Phe Gln Glu Asn Asp Ala Phe Gln Phe Arg
    530                 535                 540

Thr Thr Tyr Phe Tyr Asn Arg Gly Lys Asn Glu Ile Phe Lys Thr Arg
545                 550                 555                 560

Gly Val Asn Cys Val Glu Asn Ala Leu Asp Val Asp Asn Ser Val Cys
                565                 570                 575

Pro Lys Ile Ile Ser Asn Tyr Arg Asn Leu Pro Gly Tyr Val Ile Gln
            580                 585                 590

Gly Ala Glu Leu Glu Ala Tyr Tyr Gln Ser Ser Tyr Leu Phe Gly Gly
        595                 600                 605

Leu Thr Tyr Ser Tyr Val Lys Gly Lys Arg Asp Thr Ser Pro Arg Asn
    610                 615                 620

Pro Trp Ser Lys Thr Ser Thr Trp Ile Ala Glu Thr Ser Pro Arg Lys
625                 630                 635                 640

Ala Ile Ala Thr Leu Gly Phe Asn Ile Pro Glu Tyr Tyr Phe Thr Ala
                645                 650                 655

Gly Trp Arg Ala Glu Phe Val Arg Lys Gln Asp Arg Ser Pro Leu Ser
            660                 665                 670

Asn Asp Ser Lys Ala Ser Tyr Trp Ala Leu Pro Ser Ser Lys Gly Tyr
        675                 680                 685

Ser Leu His Ser Val Phe Phe Ser Trp Ser Pro Thr Lys Ile Lys Gly
    690                 695                 700

Met Asn Phe Lys Val Thr Val Asp Asn Leu Phe Asn Arg Pro Tyr Tyr
705                 710                 715                 720
```

```
Pro Tyr Leu Gly Glu Leu Ala Ser Gly Thr Gly Arg Asn Val Lys Phe
                725                 730                 735

Ser Leu Thr Gln Gln Phe
            740


<210> SEQ ID NO 15
<211> LENGTH: 968
<212> TYPE: PRT
<213> ORGANISM: Haemophilus influenzae

<400> SEQUENCE: 15

Val Leu Leu Met Leu Ser Gln Pro Thr Asn Gln Pro Thr Asn Gln Pro
1               5                   10                  15

Thr Asn Gln Asn Ser Asn Ala Ser Glu Gln Leu Glu Gln Ile Asn Val
            20                  25                  30

Leu Gly Ser Asp Asn Asn Asn Asp Asn Thr Pro Pro Lys Ile Ala Glu
        35                  40                  45

Thr Val Lys Thr Ala Ser Gln Leu Lys Arg Gln Gln Val Gln Asp Ser
    50                  55                  60

Arg Asp Leu Val Arg Tyr Glu Thr Gly Val Thr Val Val Glu Ala Gly
65                  70                  75                  80

Arg Phe Gly Ser Ser Gly Tyr Ala Ile Arg Gly Val Asp Glu Asn Arg
                85                  90                  95

Val Ala Ile Thr Val Asp Gly Leu His Gln Ala Glu Thr Leu Ser Ser
            100                 105                 110

Gln Gly Phe Lys Glu Leu Phe Glu Gly Tyr Gly Asn Phe Asn Asn Thr
        115                 120                 125

Arg Asn Ser Val Glu Ile Glu Thr Leu Lys Val Ala Lys Ile Ala Lys
    130                 135                 140

Gly Ala Asp Ser Val Lys Val Gly Ser Gly Ser Leu Gly Gly Ala Val
145                 150                 155                 160

Leu Phe Glu Thr Lys Asp Ala Arg Asp Phe Leu Thr Glu Lys Asp Trp
                165                 170                 175

His Ile Gly Tyr Lys Ala Gly Tyr Ser Thr Ala Asp Asn Gln Gly Leu
            180                 185                 190

Asn Ala Val Thr Leu Ala Gly Arg Tyr Gln Met Phe Asp Ala Leu Ile
        195                 200                 205

Met His Ser Lys Arg His Gly His Glu Leu Glu Asn Tyr Asp Tyr Lys
    210                 215                 220

Asn Gly Arg Asp Ile Gln Gly Lys Glu Arg Glu Lys Ala Asp Pro Tyr
225                 230                 235                 240

Thr Ile Thr Lys Glu Ser Thr Leu Val Lys Phe Ser Phe Ser Pro Thr
                245                 250                 255

Glu Asn His Arg Phe Thr Val Ala Ser Asp Thr Tyr Leu Gln His Ser
            260                 265                 270

Arg Gly His Asp Phe Ser Tyr Asn Leu Val Lys Thr Thr Tyr Ile Asn
        275                 280                 285

Lys Asp Glu Glu Glu Leu Arg His Thr Asn Asp Leu Thr Lys Arg Lys
    290                 295                 300

Asn Val Ser Phe Thr Tyr Glu Asn Tyr Thr Val Thr Pro Phe Trp Asp
305                 310                 315                 320

Thr Leu Lys Leu Ser Tyr Ser Gln Gln Arg Ile Thr Thr Arg Ala Arg
                325                 330                 335

Thr Glu Asp Tyr Cys Asp Gly Asn Glu Lys Cys Asp Ser Tyr Lys Asn
            340                 345                 350
```

-continued

```
Pro Leu Gly Leu Gln Leu Lys Asn Gly Gln Ile Val Asp Arg Asp Gly
        355                 360                 365

Asn Pro Val Asn Leu Lys Leu Ile Asn Gly Arg His Lys Val Val Asp
    370                 375                 380

Lys Asn Asn Lys Leu Phe Gly Leu Thr Asp Glu Asp Asn Asn Ala Ala
385                 390                 395                 400

Phe Asp Gly Lys Gln Leu Gly Leu Ser Gly Phe Trp Phe Asp Cys Thr
                405                 410                 415

Val Phe Asp Cys Asp Lys Pro Val Arg Thr Tyr Lys Tyr Lys Tyr Ser
            420                 425                 430

Ser Ser Asn Pro Ala Val Glu Asn Val Glu Leu Asn Lys Phe Met Gln
        435                 440                 445

Val Asn Gly Lys Arg Phe Ala Thr Tyr Glu Asp Lys Ile Gln Ser Ser
    450                 455                 460

Glu Lys Arg Tyr Val Ile Leu Pro Asn Ser Lys Gly Tyr Leu Pro Leu
465                 470                 475                 480

Asp Tyr Lys Glu Arg Asp Leu Asn Thr Lys Thr Lys Gln Ile Asn Leu
                485                 490                 495

Asp Leu Thr Lys Ala Phe Thr Leu Phe Glu Ile Glu Asn Glu Leu Ser
            500                 505                 510

Tyr Gly Gly Val Tyr Ala Lys Thr Thr Lys Glu Met Val Asn Lys Ala
        515                 520                 525

Gly Tyr Tyr Gly Arg Asn Pro Thr Trp Trp Ala Glu Arg Thr Leu Gly
    530                 535                 540

Gln Asp Leu Ser Gly Asn Gln His Asn Cys Asn Thr Asn Ser Ser Tyr
545                 550                 555                 560

Asn Gly Met Leu Cys Pro Arg His Glu Pro Leu Thr Ser Phe Leu Ile
                565                 570                 575

Pro Val Glu Ala Thr Thr Lys Ser Leu Tyr Phe Ser Asp Asn Ile Lys
            580                 585                 590

Leu His Asn Met Leu Ser Val Asp Leu Gly Tyr Arg Tyr Asp Asp Ile
        595                 600                 605

Lys Tyr Gln Pro Glu Tyr Ile Pro Gly Val Thr Pro Lys Ile Ala Asp
    610                 615                 620

Asp Met Val Lys Gly Ile Phe Ile Pro Leu Pro Lys Gly Glu Lys Ile
625                 630                 635                 640

Lys Ile Gly Asn Tyr Glu Thr Thr Lys Pro Leu Thr Pro Glu Gln Ile
                645                 650                 655

Arg Lys Asn Ala Glu Glu Asn Ile Ala Tyr Ile Ala Gln Glu Lys Arg
            660                 665                 670

Phe Lys Lys His Ser Tyr Ser Leu Gly Ala Thr Phe Asp Pro Leu Asn
        675                 680                 685

Phe Leu Arg Val Gln Val Lys Tyr Ser Lys Gly Phe Arg Ala Pro Thr
    690                 695                 700

Ser Asp Glu Leu Tyr Phe Thr Phe Lys His Pro Asp Phe Thr Ile Leu
705                 710                 715                 720

Pro Asn Pro Val Leu Lys Pro Glu Glu Ala Lys Asn Gln Glu Ile Ala
                725                 730                 735

Leu Thr Val His Asp Asn Trp Gly Phe Val Ser Thr Ser Val Phe Gln
            740                 745                 750

Thr Lys Tyr Arg His Phe Ile Asp Leu Ala Tyr Leu Gly Ser Arg Asn
        755                 760                 765
```

Leu Ser Asn Ser Val Gly Gly Gln Ala Gln Ala Arg Asp Phe Gln Val
770 775 780

Tyr Gln Asn Val Asn Val Asp Asn Ala Lys Val Lys Gly Leu Glu Ile
785 790 795 800

Asn Ala Arg Leu Asn Leu Gly Tyr Phe Trp His Val Leu Asp Gly Phe
805 810 815

Asn Thr Ser Tyr Lys Phe Thr Tyr Gln Arg Gly Arg Leu Asp Gly Asp
820 825 830

Arg Pro Met Asn Ala Ile Gln Pro Lys Ala Ser Val Phe Gly Leu Gly
835 840 845

Tyr Asp His Lys Glu Asn Lys Phe Gly Ala Asp Leu Tyr Ile Thr Arg
850 855 860

Val Ser Glu Lys Lys Ala Lys Asp Thr Tyr Asn Met Phe Tyr Lys Glu
865 870 875 880

Glu Lys Lys Lys Asp Ser Ala Ile His Trp Arg Ser Asp Asp Tyr Thr
885 890 895

Leu Val Asp Phe Val Thr Tyr Ile Lys Pro Val Lys Asn Val Thr Leu
900 905 910

Gln Phe Gly Ile Tyr Asn Leu Thr Asp Arg Lys Tyr Leu Thr Trp Glu
915 920 925

Ser Ala Arg Ser Ile Lys Pro Phe Gly Thr Ser Asn Leu Ile Asn Gln
930 935 940

Gln Thr Gly Ala Gly Ile Asn Arg Phe Tyr Ser Pro Gly Arg Asn Tyr
945 950 955 960

Lys Leu Ser Ala Glu Ile Thr Phe
965

<210> SEQ ID NO 16
<211> LENGTH: 968
<212> TYPE: PRT
<213> ORGANISM: Pasteurella multocida

<400> SEQUENCE: 16

Met Arg Thr Thr Thr Ile Lys Phe Ser Ala Ile Thr Leu Ala Leu Leu
1 5 10 15

Ser Tyr Cys Gly Ala Ile Leu Ala Asp Ser His Gln Glu Ala Thr Glu
20 25 30

Leu Asp Thr Ile Thr Val Ser Ser Gln Gln Asp Glu Met Asn Ile Lys
35 40 45

Glu Lys Lys Val Gly Glu Thr Val Lys Thr Ala Ser Gln Leu Lys Arg
50 55 60

Gln Gln Val Gln Asp Ser Arg Asp Leu Val Arg Tyr Glu Thr Gly Val
65 70 75 80

Thr Val Val Glu Ala Gly Arg Phe Gly Ser Ser Gly Tyr Ala Ile Arg
85 90 95

Gly Val Asp Glu Asn Arg Val Ala Ile Thr Val Asp Gly Leu His Gln
100 105 110

Ala Glu Thr Leu Ser Ser Gln Gly Phe Lys Glu Leu Phe Glu Gly Tyr
115 120 125

Gly Asn Phe Asn Asn Thr Arg Asn Ser Val Glu Ile Glu Thr Leu Lys
130 135 140

Val Ala Lys Ile Ala Lys Gly Ala Asp Ser Val Lys Val Gly Ser Gly
145 150 155 160

Ser Leu Gly Gly Ala Val Leu Phe Glu Thr Lys Asp Ala Arg Asp Phe
165 170 175

-continued

```
Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Asn Tyr Asp Tyr Lys Asn Gly Arg Asp Ile Gln Gly Lys Glu Arg
225                 230                 235                 240

Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Leu Gln His Ser Arg Gly His Asp Leu Ser Tyr Asn Leu Val
        275                 280                 285

Ala Thr Thr His Ile Gln Leu Asp Glu Lys Glu Ser Arg His Ala Asn
    290                 295                 300

Asp Leu Thr Lys Arg Lys Asn Val Ser Phe Thr Tyr Glu Asn Tyr Thr
305                 310                 315                 320

Val Thr Pro Phe Trp Asp Thr Leu Lys Leu Ser Tyr Ser Gln Gln Arg
                325                 330                 335

Ile Thr Thr Arg Ala Arg Thr Glu Asp Tyr Cys Asp Gly Asn Glu Lys
            340                 345                 350

Cys Asp Ser Tyr Lys Asn Pro Leu Gly Leu Gln Leu Lys Glu Gly Lys
        355                 360                 365

Ile Val Asp Arg Asn Gly Asp Pro Val Asn Leu Lys Leu Val Asp Gly
    370                 375                 380

Lys His Gln Val Val Asp Lys Ala Gly Lys Pro Phe Asp Val Ala Ser
385                 390                 395                 400

Gly Thr Asn Tyr Ala Ala Phe Ser Gly Lys Glu Leu Ser Pro Ser Ser
                405                 410                 415

Phe Trp Leu Asp Cys Ser Ile Phe Asp Cys Ser Lys Pro Ile Asn Thr
            420                 425                 430

Tyr Lys Tyr Arg Tyr Thr Ser Ser Glu Pro Thr Leu Gln Gln Ile Thr
        435                 440                 445

Leu Asn Lys Thr Met Glu Ile Asn Gly Lys Thr Phe Ala Thr Tyr Asp
    450                 455                 460

Gly Arg Gly His Tyr Ile Ile Leu Pro Asn Ser Lys Gly Tyr Leu Pro
465                 470                 475                 480

Leu Asp Tyr Lys Glu Arg Asp Leu Asn Thr Lys Thr Lys Gln Ile Asn
                485                 490                 495

Leu Asp Leu Thr Lys Ala Phe Thr Leu Phe Glu Ile Glu Asn Glu Leu
            500                 505                 510

Ser Tyr Gly Gly Val Tyr Ala Lys Thr Thr Lys Glu Met Val Asn Lys
        515                 520                 525

Ala Gly Tyr Tyr Gly Arg Asn Pro Thr Trp Trp Ala Glu Arg Thr Leu
    530                 535                 540

Gly Gln Ser Trp Gly Lys Leu Arg Glu Cys Lys Thr Ser Ser Ser Tyr
545                 550                 555                 560

Asn Gly Met Leu Cys Pro Arg His Glu Pro Leu Thr Ser Phe Leu Ile
                565                 570                 575

Pro Val Glu Ala Thr Thr Lys Ser Leu Tyr Phe Ala Asp Asn Ile Lys
            580                 585                 590
```

-continued

```
Leu His Asn Met Leu Ser Val Asp Leu Gly Tyr Arg Tyr Asp Asp Ile
        595                 600                 605

Lys Tyr Gln Pro Glu Tyr Ile Pro Gly Val Thr Pro Lys Ile Ala Asp
    610                 615                 620

Asp Met Val Lys Gly Leu Phe Ile Pro Leu Pro Glu Gly Glu Lys Val
625                 630                 635                 640

Thr Val Gly Thr Met Val Phe Thr Lys Pro Leu Thr Gln Ala Gln Ile
                645                 650                 655

Arg Lys Asn Ala Glu Glu Asn Ile Ala Tyr Ile Ala Gln Glu Lys Arg
            660                 665                 670

Phe Lys Lys His Ser Tyr Ser Leu Gly Ala Thr Phe Asp Pro Leu Asn
        675                 680                 685

Phe Leu Arg Val Gln Val Lys Tyr Ser Lys Gly Phe Arg Ala Pro Thr
    690                 695                 700

Ser Asp Glu Leu Tyr Phe Thr Phe Lys His Pro Asp Phe Thr Ile Leu
705                 710                 715                 720

Pro Asn Pro Val Leu Lys Pro Glu Glu Ala Lys Asn Gln Glu Ile Ala
                725                 730                 735

Leu Thr Val His Asp Asn Trp Gly Phe Val Ser Thr Ser Val Phe Gln
            740                 745                 750

Thr Lys Tyr Arg His Phe Ile Asp Leu Ala Tyr Leu Gly Ser Arg Asn
        755                 760                 765

Leu Ser Asn Ser Val Gly Gly Gln Ala Gln Ala Arg Asp Phe Gln Val
    770                 775                 780

Tyr Gln Asn Val Asn Val Asp Asn Ala Lys Val Lys Gly Leu Glu Ile
785                 790                 795                 800

Asn Ala Arg Leu Asn Leu Gly Tyr Phe Trp His Val Leu Asp Gly Phe
                805                 810                 815

Asn Thr Ser Tyr Lys Phe Thr Tyr Gln Arg Gly Arg Leu Asp Gly Asp
            820                 825                 830

Arg Pro Met Asn Ala Ile Gln Pro Lys Ala Ser Val Phe Gly Leu Gly
        835                 840                 845

Tyr Asp His Lys Glu Asn Lys Phe Gly Ala Asp Leu Tyr Ile Thr Arg
    850                 855                 860

Val Ser Glu Lys Lys Ala Lys Asp Thr Tyr Asn Met Phe Tyr Lys Glu
865                 870                 875                 880

Gln Gly Tyr Lys Asp Ser Ala Val Arg Trp Arg Ser Asp Asp Tyr Thr
                885                 890                 895

Leu Val Asp Ala Val Gly Tyr Ile Lys Pro Ile Lys Asn Leu Thr Leu
            900                 905                 910

Gln Phe Gly Val Tyr Asn Leu Thr Asp Arg Lys Tyr Leu Thr Trp Glu
        915                 920                 925

Ser Ala Arg Ser Ile Lys Pro Phe Gly Thr Ser Asn Leu Ile Asn Gln
    930                 935                 940

Lys Thr Gly Ala Gly Ile Asn Arg Phe Tyr Ser Pro Gly Arg Asn Phe
945                 950                 955                 960

Lys Phe Ser Ala Glu Ile Thr Phe
                965
```

<210> SEQ ID NO 17
<211> LENGTH: 971
<212> TYPE: PRT
<213> ORGANISM: Pasteurella multocida

<400> SEQUENCE: 17

```
Met Arg Thr Thr Thr Ile Lys Phe Ser Ala Ile Thr Leu Ala Leu Leu
1               5                   10                  15

Ser Tyr Cys Gly Val Ile Leu Ala Asp Ser His Gln Glu Ala Thr Glu
            20                  25                  30

Leu Asp Thr Ile Thr Val Ser Ser Gln Gln Asp Glu Met Asn Ile Lys
        35                  40                  45

Glu Lys Lys Val Gly Glu Thr Val Lys Thr Ala Ser Gln Leu Lys Arg
    50                  55                  60

Gln Gln Val Gln Asp Ser Arg Asp Leu Val Arg Tyr Glu Thr Gly Val
65                  70                  75                  80

Thr Val Val Glu Ala Gly Arg Phe Gly Ser Ser Gly Tyr Ala Ile Arg
                85                  90                  95

Gly Val Asp Glu Asn Arg Val Ala Ile Thr Val Asp Gly Leu His Gln
            100                 105                 110

Ala Glu Thr Leu Ser Ser Gln Gly Phe Lys Glu Leu Phe Glu Gly Tyr
        115                 120                 125

Gly Asn Phe Asn Asn Thr Arg Asn Ser Val Glu Ile Glu Thr Leu Lys
    130                 135                 140

Val Ala Lys Ile Ala Lys Gly Ala Asp Ser Val Lys Val Gly Ser Gly
145                 150                 155                 160

Ser Leu Gly Gly Ala Val Leu Phe Glu Thr Lys Asp Ala Arg Asp Phe
                165                 170                 175

Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Ile Tyr Asp Tyr Lys Asn Gly Arg Asp Ile Gln Gly Lys Glu Arg
225                 230                 235                 240

Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Leu Gln His Ser Arg Gly His Asp Leu Ser Tyr Asn Leu Val
        275                 280                 285

Ala Thr Thr Tyr Ile Gln Leu Asp Glu Lys Glu Ser Arg His Ala Asn
    290                 295                 300

Asp Leu Thr Lys Arg Lys Asn Val Ser Phe Thr Tyr Glu Asn Tyr Thr
305                 310                 315                 320

Val Thr Pro Phe Trp Asp Thr Leu Lys Leu Ser Tyr Ser Gln Gln Arg
                325                 330                 335

Ile Thr Thr Arg Ala Arg Thr Glu Asp Tyr Cys Asp Gly Asn Glu Lys
            340                 345                 350

Cys Asp Ser Tyr Lys Asn Pro Leu Gly Leu Gln Leu Lys Glu Gly Lys
        355                 360                 365

Ile Val Asp Arg Asn Gly Asp Pro Val Asn Leu Gln Leu Val Asp Gly
    370                 375                 380

Lys His Gln Val Val Asp Lys Ala Gly Lys Pro Phe Asp Val Thr Ser
385                 390                 395                 400

Gly Thr Asn Tyr Ala Ala Phe Ser Gly Lys Gln Leu Gly Pro Ser Tyr
                405                 410                 415
```

-continued

```
Phe Trp Leu Glu Cys Thr Val Phe Asp Cys Ser Lys Pro Val Thr Thr
            420                 425                 430

Tyr Lys Tyr Arg Tyr Ser Thr Glu Thr Pro Val Lys Glu Asp Ile Gln
        435                 440                 445

Leu Asn Lys Thr Met Glu Val Asn Gly Lys Thr Phe Ala Thr Tyr Asp
    450                 455                 460

Met Gly Arg Glu Arg Arg Tyr Ile Ile Leu Pro Asn Ser Gln Gly Tyr
465                 470                 475                 480

Leu Pro Leu Asp Tyr Lys Glu Arg Asp Leu Asn Thr Lys Thr Lys Gln
                485                 490                 495

Ile Asn Leu Asp Leu Thr Lys Ala Phe Thr Leu Phe Glu Ile Glu Asn
            500                 505                 510

Glu Leu Ser Tyr Gly Gly Val Tyr Ala Lys Thr Thr Asn Gly Val Val
        515                 520                 525

Asn Lys Ala Gly Tyr Tyr Gly Arg Asn Pro Thr Trp Trp Ala Glu Arg
    530                 535                 540

Thr Leu Gly Gln Ser Trp Asn Gly Thr Leu Arg Glu Cys Lys Thr Ser
545                 550                 555                 560

Ser Ser Tyr Asn Gly Met Leu Cys Pro Arg His Glu Pro Leu Thr Ser
                565                 570                 575

Phe Leu Ile Pro Val Glu Ala Thr Thr Lys Ser Leu Tyr Phe Ala Asp
            580                 585                 590

Asn Ile Lys Leu His Asn Met Leu Ser Val Asp Leu Gly Tyr Arg Tyr
        595                 600                 605

Asp Asp Ile Lys Tyr Gln Pro Glu Tyr Ile Pro Gly Val Thr Pro Lys
    610                 615                 620

Ile Ala Asp Asp Met Val Lys Gly Leu Phe Ile Pro Leu Pro Glu Gly
625                 630                 635                 640

Glu Lys Val Thr Val Gly Thr Val Val Phe Thr Lys Pro Leu Thr Pro
                645                 650                 655

Glu Gln Ile Arg Lys Asn Ala Glu Glu Asn Ile Ala Tyr Ile Ala Gln
            660                 665                 670

Gly Lys Arg Phe Lys Lys His Ser Tyr Ser Leu Gly Thr Thr Phe Asp
        675                 680                 685

Pro Leu Asn Phe Leu Arg Val Gln Val Lys Tyr Ser Lys Gly Phe Arg
    690                 695                 700

Ala Pro Thr Ser Asp Glu Leu Tyr Phe Thr Phe Lys His Pro Asp Phe
705                 710                 715                 720

Thr Ile Leu Pro Asn Pro Val Leu Lys Pro Glu Glu Ala Lys Asn Gln
                725                 730                 735

Glu Ile Ala Leu Thr Val His Asp Asn Trp Gly Phe Val Ser Thr Ser
            740                 745                 750

Val Phe Gln Thr Lys Tyr Arg His Phe Ile Asp Leu Ala Tyr Leu Gly
        755                 760                 765

Ser Arg Asn Leu Ser Asn Ser Val Gly Gly Gln Ala Gln Ala Arg Asp
    770                 775                 780

Phe Gln Val Tyr Gln Asn Val Asn Val Asp Asn Ala Lys Val Lys Gly
785                 790                 795                 800

Leu Glu Ile Asn Ala Arg Leu Asn Leu Gly Tyr Phe Trp His Val Leu
                805                 810                 815

Asp Gly Phe Asn Thr Ser Tyr Lys Phe Thr Tyr Gln Arg Gly Arg Leu
            820                 825                 830

Asp Gly Asp Arg Pro Met Asn Ala Ile Gln Pro Lys Ala Ser Val Phe
```

```
        835                 840                 845

Gly Leu Gly Tyr Asp His Lys Glu Asn Lys Phe Gly Ala Asp Leu Tyr
    850                 855                 860

Ile Thr Arg Val Ser Glu Lys Lys Ala Lys Asp Thr Tyr Asn Met Phe
865                 870                 875                 880

Tyr Lys Glu Gln Gly Tyr Lys Asp Ser Ala Ile Arg Trp Arg Ser Asp
                885                 890                 895

Asp Tyr Thr Leu Val Asp Ala Val Gly Tyr Ile Lys Pro Ile Lys Asn
            900                 905                 910

Leu Thr Leu Gln Phe Gly Val Tyr Asn Leu Thr Glu Arg Lys Tyr Leu
        915                 920                 925

Thr Trp Glu Ser Ala Arg Ser Ile Lys Pro Phe Gly Thr Ser Asn Leu
    930                 935                 940

Ile Asn Gln Lys Thr Gly Ala Gly Ile Asn Arg Phe Tyr Ser Pro Gly
945                 950                 955                 960

Arg Asn Phe Lys Phe Ser Ala Glu Ile Thr Phe
                965                 970


<210> SEQ ID NO 18
<211> LENGTH: 971
<212> TYPE: PRT
<213> ORGANISM: Pasteurella multocida

<400> SEQUENCE: 18

Met Arg Thr Thr Thr Ile Lys Phe Ser Ala Ile Thr Leu Ala Leu Leu
1               5                   10                  15

Ser Tyr Cys Gly Ala Ile Leu Ala Asp Ser His Gln Glu Ala Thr Glu
            20                  25                  30

Leu Asp Thr Ile Thr Val Ser Ser Gln Gln Asp Glu Met Asn Ile Lys
        35                  40                  45

Glu Lys Lys Val Gly Glu Thr Val Lys Thr Ala Ser Gln Leu Lys Arg
    50                  55                  60

Gln Gln Val Gln Asp Ser Arg Asp Leu Val Arg Tyr Glu Thr Gly Val
65                  70                  75                  80

Thr Val Val Glu Ala Gly Arg Phe Gly Ser Ser Gly Tyr Ala Ile Arg
                85                  90                  95

Gly Val Asp Glu Asn Arg Val Ala Ile Thr Val Asp Gly Leu His Gln
            100                 105                 110

Ala Glu Thr Leu Ser Ser Gln Gly Phe Lys Glu Leu Phe Glu Gly Tyr
        115                 120                 125

Gly Asn Phe Asn Asn Thr Arg Asn Ser Val Glu Ile Glu Thr Leu Lys
    130                 135                 140

Val Ala Lys Ile Ala Lys Gly Ala Asp Ser Val Lys Val Gly Ser Gly
145                 150                 155                 160

Ser Leu Gly Gly Ala Val Leu Phe Glu Thr Lys Asp Ala Arg Asp Phe
                165                 170                 175

Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Asn Tyr Asp Tyr Lys Asn Gly Arg Asp Ile Gln Gly Lys Glu Arg
225                 230                 235                 240
```

-continued

```
Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Leu Gln His Ser Arg Gly His Asp Leu Ser Tyr Asn Leu Val
        275                 280                 285

Ala Thr Thr His Ile Gln Leu Asp Glu Lys Glu Ser Arg His Ala Asn
    290                 295                 300

Asp Leu Thr Lys Arg Lys Asn Val Ser Phe Thr Tyr Glu Asn Tyr Thr
305                 310                 315                 320

Val Thr Pro Phe Trp Asp Thr Leu Lys Leu Ser Tyr Ser Gln Gln Arg
                325                 330                 335

Ile Thr Thr Arg Ala Arg Thr Glu Asp Tyr Cys Asp Gly Asn Glu Lys
            340                 345                 350

Cys Asp Ser Tyr Lys Asn Pro Leu Gly Leu Gln Leu Lys Glu Gly Lys
        355                 360                 365

Ile Val Asp Arg Asn Gly Asp Pro Val Asn Leu Gln Leu Val Asp Gly
    370                 375                 380

Lys His Gln Val Val Asp Lys Ala Gly Lys Pro Phe Asp Val Thr Ser
385                 390                 395                 400

Gly Thr Asn Tyr Ala Ala Phe Ser Gly Lys Gln Leu Gly Pro Ser Tyr
                405                 410                 415

Phe Trp Leu Asp Cys Thr Val Phe Asp Cys Ser Lys Pro Val Thr Thr
            420                 425                 430

Tyr Lys Tyr Arg Tyr Ser Thr Glu Thr Pro Val Lys Glu Asp Ile Gln
        435                 440                 445

Leu Asn Lys Thr Met Glu Val Asn Gly Lys Thr Phe Ala Thr Tyr Asp
    450                 455                 460

Met Gly Arg Glu Arg Arg Tyr Ile Ile Leu Pro Asn Ser Gln Gly Tyr
465                 470                 475                 480

Leu Pro Leu Asp Tyr Lys Glu Arg Asp Leu Asn Thr Lys Thr Lys Gln
                485                 490                 495

Ile Asn Leu Asp Leu Thr Lys Ala Phe Thr Leu Phe Glu Ile Glu Asn
            500                 505                 510

Glu Leu Ser Tyr Gly Gly Val Tyr Ala Lys Thr Thr Lys Glu Met Val
        515                 520                 525

Asn Lys Ala Gly Tyr Tyr Gly Arg Asn Pro Thr Trp Trp Ala Glu Arg
    530                 535                 540

Thr Leu Gly Gln Ser Trp Asn Gly Thr Leu Arg Glu Cys Lys Thr Ser
545                 550                 555                 560

Ser Ser Tyr Asn Gly Met Leu Cys Pro Arg His Glu Pro Leu Thr Ser
                565                 570                 575

Phe Leu Ile Pro Val Glu Ala Thr Thr Lys Ser Leu Tyr Phe Ala Asp
            580                 585                 590

Asn Ile Lys Leu His Asn Met Leu Ser Val Asp Leu Gly Tyr Arg Tyr
        595                 600                 605

Asp Asp Ile Lys Tyr Gln Pro Glu Tyr Ile Pro Gly Val Thr Pro Lys
    610                 615                 620

Ile Ala Asp Asp Met Val Lys Gly Leu Phe Ile Pro Leu Pro Glu Gly
625                 630                 635                 640

Glu Lys Val Thr Val Gly Thr Val Val Phe Thr Lys Pro Leu Thr Pro
                645                 650                 655

Glu Gln Ile Arg Lys Asn Ala Glu Glu Asn Ile Ala Tyr Ile Ala Gln
```

```
            660                 665                 670

Glu Lys Arg Phe Lys Lys His Ser Tyr Ser Leu Gly Ala Thr Phe Asp
        675                 680                 685

Pro Leu Asn Phe Leu Arg Val Gln Val Lys Tyr Ser Lys Gly Phe Arg
    690                 695                 700

Ala Pro Thr Ser Asp Glu Leu Tyr Phe Thr Phe Lys His Pro Asp Phe
705                 710                 715                 720

Thr Ile Leu Pro Asn Pro Val Leu Lys Pro Glu Glu Ala Lys Asn Gln
                725                 730                 735

Glu Ile Ala Leu Thr Val His Asp Asn Trp Gly Phe Val Ser Thr Ser
            740                 745                 750

Val Phe Gln Thr Lys Tyr Arg His Phe Ile Asp Leu Ala Tyr Leu Gly
        755                 760                 765

Ser Arg Asn Leu Ser Asn Ser Val Gly Gly Gln Ala Gln Ala Arg Asp
    770                 775                 780

Phe Gln Val Tyr Gln Asn Val Asn Val Asp Asn Ala Lys Val Lys Gly
785                 790                 795                 800

Leu Glu Ile Asn Ala Arg Leu Asn Leu Gly Tyr Phe Trp His Val Leu
                805                 810                 815

Asp Gly Phe Asn Thr Ser Tyr Lys Phe Thr Tyr Gln Arg Gly Arg Leu
            820                 825                 830

Asp Gly Asp Arg Pro Met Asn Ala Ile Gln Pro Lys Ala Ser Val Phe
        835                 840                 845

Gly Leu Gly Tyr Asp His Lys Glu Asn Lys Phe Gly Ala Asp Leu Tyr
    850                 855                 860

Ile Thr Arg Val Ser Glu Lys Lys Ala Lys Asp Thr Tyr Asn Met Phe
865                 870                 875                 880

Tyr Lys Glu Gln Gly Tyr Lys Asp Ser Ala Val Arg Trp Arg Ser Asp
                885                 890                 895

Asp Tyr Thr Leu Val Asp Ala Val Gly Tyr Ile Lys Pro Ile Lys Asn
            900                 905                 910

Leu Thr Leu Gln Phe Gly Val Tyr Asn Leu Thr Asp Arg Lys Tyr Leu
        915                 920                 925

Thr Trp Glu Ser Ala Arg Ser Ile Lys Pro Phe Gly Thr Ser Asn Leu
    930                 935                 940

Ile Asn Gln Lys Thr Gly Ala Gly Ile Asn Arg Phe Tyr Ser Pro Gly
945                 950                 955                 960

Arg Asn Phe Lys Leu Ser Ala Glu Ile Thr Phe
                965                 970


<210> SEQ ID NO 19
<211> LENGTH: 792
<212> TYPE: PRT
<213> ORGANISM: Pasteurella multocida subsp. multocida P1062

<400> SEQUENCE: 19

Met Glu Lys Ile Asp Met Glu Ser Ala Lys Asn Pro Leu Lys Lys Thr
1               5                   10                  15

Thr Leu Ala Leu Leu Cys Cys Ser Thr Ala Phe Ser Leu Ser Ala Lys
            20                  25                  30

Thr Asp Thr Asn Ala Asp Lys Asn His Phe Leu Thr Glu Ile Val Val
        35                  40                  45

Tyr Ala Asp Gln Asn Lys Ser Met Ser Ser Thr Gln Ser Val Thr Gln
    50                  55                  60
```

-continued

```
Asp Asp Met Lys Lys Ser Pro Val Thr Asn Gly Asn Ile Thr Asp Tyr
65                  70                  75                  80

Leu Arg Ser Asn Pro His Val Arg Tyr Glu Asn Ser Asp Gln Asn Gly
                85                  90                  95

Leu Gln Arg Gly Glu Ile Lys Pro Glu Asn Ile Ser Ile Asn Gly Ala
            100                 105                 110

Asp Tyr Gln Gln Thr Thr Phe Phe Val Asp Asn Val Asn Ile Asn Asn
        115                 120                 125

Asp Met Gly Phe Gly Ser Asp Leu Phe Asp Gly Thr Met Ala Thr Val
    130                 135                 140

Pro Phe Ala Asn His Ser Gln Gly Tyr Phe Phe Asp Ala Asn Leu Leu
145                 150                 155                 160

Ser Ser Ile Val Val His Asp Ser Asn Val Ser Ala Ser Leu Gly Gly
                165                 170                 175

Phe Ala Gly Gly Ala Val Val Ala Lys Thr Lys Gln Tyr Asp Gly Lys
            180                 185                 190

Asp Gln Leu Lys Phe Ser Tyr Arg Thr Thr Asp Ala Ser Trp Ala Lys
        195                 200                 205

Phe Lys Val Glu Asp Lys Asp Leu Glu Arg Phe Lys Asn Ala Ile Pro
    210                 215                 220

Glu Gly Ser Val Ala Glu Phe Gln Pro Lys Tyr Ser Lys His Phe Phe
225                 230                 235                 240

Asn Ile Thr Ala Glu Lys Gly Leu Ser Glu Asn Leu Gly Met Val Ile
                245                 250                 255

Gly Leu Ser Arg Arg Thr Ser Ser Ile Gln Gln Ser Arg Gln Ile Asn
            260                 265                 270

Pro Gln Gly Asp Arg Asp Lys Gln Thr His Thr Arg Arg Ser Asp Asn
        275                 280                 285

Ala Leu Leu Asn Phe Asn Leu Thr Pro Asn Asp Lys His Arg Phe Glu
    290                 295                 300

Leu Gly Phe Arg Tyr Ser Asn Tyr Arg Glu Arg Lys Phe Phe Asn Thr
305                 310                 315                 320

Asn Ile Asp Ser Asn Val Phe Asp Tyr His Arg Ala Tyr Gly Val Thr
                325                 330                 335

Phe Ser Trp Ile Asn Ala Leu Gln Ser Gly Ile Leu Thr Thr Thr Leu
            340                 345                 350

Ala Tyr Asp Asn Phe Asp Asp Thr Arg Lys Ser Ala Ser Thr Ser Met
        355                 360                 365

Lys Thr Ile Ile Glu Asp Glu Asn Asp Tyr Thr Leu Gly Gly Met Gly
    370                 375                 380

Asn Ser Gln Leu Asn Gln Lys Asn Ser His Phe Ser Leu Glu Tyr Ala
385                 390                 395                 400

Met Asn Ser Phe Asp Leu Ser His Ile Asn His Ser Ile Ser Leu Gly
                405                 410                 415

Ser Val Phe Gln His Thr Gln Tyr Arg Phe His Arg Glu Ser Asp Ala
            420                 425                 430

Glu Ala Glu Ile Ile Asn Arg Ile Asp Leu Glu Asn Glu Lys Ile Glu
        435                 440                 445

Ile Lys Ser Ser Asn Leu Ala Lys Lys Gly Thr Val Lys Thr Arg Tyr
    450                 455                 460

Gln Asn Ile Ala Leu Tyr Val Glu Asp Leu Met Thr Trp Lys Asn Leu
465                 470                 475                 480

Glu Phe Arg Ala Gly Leu Arg Leu Glu Arg Asp Asp Tyr Leu Lys Asn
```

```
                485                 490                 495

Thr Asn Leu Ala Pro Arg Thr Val Phe Arg Tyr Lys Pro Phe Glu Asp
            500                 505                 510

Thr Ala Phe Ser Val Gly Trp Asn Arg Tyr Tyr Gly Arg Ser Phe Ala
        515                 520                 525

Ser Met Lys Leu Ser Glu Gly Ile Phe Lys Leu Asp Gly His Asp Thr
    530                 535                 540

Phe Arg Tyr Lys Asp Leu Ser Gln Phe Lys Thr Pro Tyr Ser Asp Glu
545                 550                 555                 560

Leu Ser Phe Gly Val Glu Gln Tyr Val Ala Asn Leu Ala Phe His Leu
                565                 570                 575

Lys Tyr Ile Leu Arg Asp Asn Lys Gln Arg Ile Val Leu Gln Glu Glu
            580                 585                 590

Asp Val Met Leu Asn Gly Glu Lys Lys Lys Leu Arg Tyr Tyr Gln Arg
        595                 600                 605

Gly Lys Asp Tyr Lys Thr Asn Val Leu Thr Phe Gln Ile Asn Thr Gln
    610                 615                 620

Ala Pro Trp Glu Leu Gly Pro Thr Arg Trp Thr Ser Ala Val Ala Phe
625                 630                 635                 640

Asp Trp Leu Asp Ser Lys Ala Ile Asp His Gly Arg Gly Tyr Asn Gly
                645                 650                 655

Ser Thr Pro Val Ile Leu Asp Gly Lys Leu Met Thr Tyr Glu Gln Met
            660                 665                 670

Leu Lys Lys Val Asn Ala Tyr Lys Glu Thr Trp Gly Leu Arg Leu Asn
        675                 680                 685

Leu Asp Met Phe Val Pro Arg Phe Asp Leu Ser Trp Ala Asn Thr Ile
    690                 695                 700

Tyr Val Lys Pro Pro Thr Thr Leu Thr Glu Arg Val Ser Ser Asn Thr
705                 710                 715                 720

Pro Glu Val Tyr Arg Ser Tyr Asp Tyr Gly Thr Tyr Thr Gln Trp Asp
                725                 730                 735

Thr Ser Leu Arg Trp Gln Pro Thr Phe Ala Glu Lys His Arg Pro Tyr
            740                 745                 750

Ile Lys Leu Asp Val Leu Asn Val Leu Asn Lys Thr Arg Lys Gly Ala
        755                 760                 765

Gly Pro Asn Gly Gln Asp Leu Gly Ile Tyr Thr Pro Gly Arg Glu Phe
    770                 775                 780

Trp Leu Glu Val Gly Tyr Glu Phe
785                 790
```

<210> SEQ ID NO 20
<211> LENGTH: 794
<212> TYPE: PRT
<213> ORGANISM: Pasteurella multocida

<400> SEQUENCE: 20

```
Met Glu Ser Ala Lys Asn Pro Leu Lys Lys Thr Thr Leu Ala Leu Leu
1               5                   10                  15

Cys Cys Ser Thr Ala Phe Ser Leu Ser Ala Lys Thr Asp Thr Asp Ser
            20                  25                  30

Asp Lys Asn His Phe Leu Thr Glu Ile Val Val Tyr Ala Asp Gln Asn
        35                  40                  45

Lys Ser Met Ser Ser Thr Gln Ser Val Thr Gln Asp Asp Met Lys Lys
    50                  55                  60
```

Ser Pro Val Thr Asn Gly Asn Ile Thr Asp Tyr Leu Arg Ser Asn Pro
65 70 75 80

His Val Arg Tyr Glu Asn Ser Asp Gln Asn Gly Leu Gln Arg Gly Glu
85 90 95

Ile Lys Pro Glu Asn Ile Ser Ile Asn Gly Ala Asp Tyr Gln Gln Thr
100 105 110

Thr Phe Phe Val Asp Asn Val Asn Ile Asn Asn Asp Met Gly Phe Gly
115 120 125

Ser Asp Leu Phe Asp Gly Thr Met Ala Thr Val Pro Phe Ala Asn His
130 135 140

Ser Gln Gly Tyr Phe Phe Asp Ala Asn Leu Leu Ser Ser Ile Val Val
145 150 155 160

His Asp Ser Asn Val Ser Ala Ser Leu Gly Gly Phe Ala Gly Gly Ala
165 170 175

Val Val Ala Lys Thr Lys Gln Tyr Asp Gly Lys Asp Arg Leu Lys Phe
180 185 190

Ser Tyr Arg Thr Thr Asp Ala Ser Trp Ala Lys Phe Lys Val Glu Asp
195 200 205

Lys Asp Leu Glu Arg Phe Lys Asn Ala Ile Pro Glu Gly Ser Val Ala
210 215 220

Glu Phe Gln Pro Lys Tyr Ser Lys His Phe Phe Asn Ile Thr Ala Glu
225 230 235 240

Lys Gly Leu Ser Glu Asn Leu Gly Met Val Ile Gly Leu Ser Arg Arg
245 250 255

Thr Ser Ser Ile Gln Gln Ser Arg Gln Ile Asn Pro Gln Gly Asp Arg
260 265 270

Asp Lys Gln Thr His Thr Arg Arg Ser Asp Asn Ala Leu Leu Asn Phe
275 280 285

Asn Leu Thr Pro Asn Asp Lys His Arg Phe Glu Leu Gly Phe Arg Tyr
290 295 300

Ser Asn Tyr Arg Glu Arg Lys Phe Phe Asn Thr Asn Ile Asp Ser Asn
305 310 315 320

Val Phe Asp Tyr His Arg Ala Tyr Gly Val Thr Phe Ser Trp Ile Asn
325 330 335

Ala Leu Gln Ser Gly Ile Leu Thr Thr Thr Leu Ala Tyr Asp Asn Phe
340 345 350

Asp Asp Thr Arg Lys Ser Ala Ser Thr Tyr Met Lys Thr Thr Leu Thr
355 360 365

Asp Asp Gly Glu Glu Tyr Thr Glu Gly Gly Met Gly Asn Ser Gln Leu
370 375 380

Asn Gln Lys Asn Leu His Thr Ser Leu Glu Tyr Ala Met Asn Pro Phe
385 390 395 400

Asn Leu Gly Ser Ile Glu His Ser Val Ser Leu Gly Gly Ile Tyr Gln
405 410 415

Ala Thr Lys Tyr Arg Phe Thr Arg His Ser Asp Ala Val Gly Glu Leu
420 425 430

Tyr Thr Pro Asn Trp Leu Asp Asn Asn Ser Asn Asp Ile Tyr Asp Glu
435 440 445

Leu Thr Leu Ala Gln Arg Asn Ile Ala Lys Lys Gly Thr Val Lys Thr
450 455 460

Arg Tyr Gln Asn Ile Ala Leu Tyr Val Glu Asp Leu Met Thr Trp Lys
465 470 475 480

Asn Leu Glu Phe Arg Ala Gly Leu Arg Leu Glu Arg Asp Asp Tyr Leu 485 490 495

Lys Asn Thr Asn Leu Ala Pro Arg Thr Val Phe Arg Tyr Lys Pro Phe
500 505 510

Glu Asp Thr Ala Phe Ser Val Gly Trp Asn Arg Tyr Tyr Gly Arg Ser
515 520 525

Phe Ala Ser Met Lys Leu Ser Glu Gly Ile Phe Lys Leu Asp Gly His
530 535 540

Asp Thr Phe Arg Tyr Lys Asp Leu Ser Gln Phe Lys Thr Pro Tyr Ser
545 550 555 560

Asp Glu Leu Ser Phe Gly Val Glu Gln Tyr Val Ala Asn Leu Ala Phe
565 570 575

His Leu Lys Tyr Ile Leu His Asp Asn Lys Gln Arg Ile Val Leu Gln
580 585 590

Glu Glu Asp Val Met Leu Asn Gly Glu Lys Lys Lys Leu Arg Tyr Tyr
595 600 605

Gln Arg Gly Lys Asp Tyr Lys Thr Asn Val Leu Thr Phe Gln Ile Ser
610 615 620

Thr Gln Ala Pro Trp Glu Phe Gly Pro Thr Arg Trp Thr Ser Ala Leu
625 630 635 640

Ala Phe Asp Trp Leu Asp Ser Lys Ala Ile Asp His Gly Arg Gly Tyr
645 650 655

Asn Gly Ser Thr Pro Val Ile Leu Asp Gly Lys Leu Met Thr Tyr Glu
660 665 670

Gln Met Leu Lys Lys Val Asn Ala Tyr Lys Glu Thr Trp Gly Leu Arg
675 680 685

Leu Asn Leu Asp Met Phe Val Pro Lys Phe Asp Leu Ser Trp Ala Asn
690 695 700

Thr Ile Tyr Val Lys Pro Pro Thr Thr Leu Thr Glu Arg Val Ser Ser
705 710 715 720

Asn Thr Pro Glu Val Tyr Arg Ser Tyr Asp Tyr Gly Thr Tyr Thr Gln
725 730 735

Trp Asp Thr Ser Leu Arg Trp Gln Pro Thr Phe Ala Glu Lys His Arg
740 745 750

Pro Tyr Ile Lys Leu Asp Val Leu Asn Val Leu Asn Lys Thr Arg Lys
755 760 765

Gly Ala Gly Pro Asn Gly Gln Asp Leu Gly Ile Tyr Thr Pro Gly Arg
770 775 780

Glu Phe Trp Leu Glu Val Gly Tyr Glu Phe
785 790

<210> SEQ ID NO 21
<211> LENGTH: 790
<212> TYPE: PRT
<213> ORGANISM: Pasteurella multocida

<400> SEQUENCE: 21

Met Glu Tyr Ala Lys Asn Pro Leu Lys Lys Thr Thr Leu Ala Leu Leu
1 5 10 15

Cys Cys Ser Thr Ala Phe Ser Leu Ser Ala Lys Thr Asp Thr Asn Ala
20 25 30

Asp Lys Asn His Phe Leu Thr Glu Ile Val Val Tyr Ala Asp Gln Asn
35 40 45

Lys Ser Met Ser Ser Thr Gln Ser Val Thr Gln Glu Asp Met Lys Lys
50 55 60

-continued

```
Ser Pro Val Thr Asn Gly Asn Ile Thr Asp Tyr Leu Arg Ser Asn Pro
65                  70                  75                  80

His Val Arg Tyr Glu Asn Ser Asp Gln Asn Gly Leu Gln Arg Gly Glu
                85                  90                  95

Ile Lys Pro Glu Asn Ile Ser Ile Asn Gly Ala Asp Tyr Gln Gln Thr
            100                 105                 110

Thr Phe Phe Val Asp Asn Val Asn Ile Asn Asn Asp Met Gly Phe Gly
        115                 120                 125

Ser Asp Leu Phe Asp Gly Thr Met Ala Thr Val Pro Phe Ala Asn His
    130                 135                 140

Ser Gln Gly Tyr Phe Phe Asp Ala Asn Leu Leu Ser Ser Ile Val Val
145                 150                 155                 160

His Asp Ser Asn Val Ser Ala Ser Leu Gly Gly Phe Ala Gly Gly Ala
                165                 170                 175

Val Val Ala Lys Thr Lys Gln Tyr Asp Gly Lys Asp Arg Leu Lys Phe
            180                 185                 190

Ser Tyr Arg Thr Thr Asp Ala Ser Trp Ala Lys Phe Lys Val Glu Asp
        195                 200                 205

Lys Asp Leu Glu Arg Phe Lys Asn Ala Ile Pro Glu Gly Ser Val Ala
    210                 215                 220

Glu Phe Gln Pro Lys Tyr Ser Lys Arg Phe Phe Asn Ile Thr Ala Glu
225                 230                 235                 240

Lys Gly Leu Ser Glu Asn Leu Gly Met Val Ile Gly Leu Ser Arg Arg
                245                 250                 255

Thr Ser Ser Ile Gln Gln Ser Arg Gln Ile Asn Pro Gln Gly Asp Arg
            260                 265                 270

Asp Lys Gln Thr His Thr Arg Arg Ser Asp Asn Ala Leu Leu Asn Phe
        275                 280                 285

Asn Leu Thr Pro Asn Asp Lys His Arg Phe Glu Leu Gly Phe Arg Tyr
    290                 295                 300

Ser Asn Tyr Arg Glu Arg Lys Phe Phe Asn Thr Asn Ile Asp Ser Asn
305                 310                 315                 320

Val Phe Asp Tyr His Arg Ala Tyr Gly Val Thr Phe Ser Trp Ile Asn
                325                 330                 335

Ala Leu Gln Ser Gly Ile Leu Thr Thr Thr Leu Ala Tyr Asp Asn Phe
            340                 345                 350

Asp Asp Thr Arg Lys Ser Ala Ser Thr Tyr Met Lys Thr Thr Leu Thr
        355                 360                 365

Glu Glu Gly Glu Glu Tyr Thr Glu Gly Gly Met Gly Asn Ser Gln Leu
    370                 375                 380

Asn Gln Lys Asn Leu His Thr Ser Leu Glu Tyr Ala Met Asn Pro Phe
385                 390                 395                 400

Asn Leu Gly Ser Ile Glu His Ser Val Ser Leu Gly Gly Ile Tyr Gln
                405                 410                 415

Ala Thr Lys Tyr Arg Phe Thr Arg His Ser Asp Ala Val Gly Glu Leu
            420                 425                 430

Tyr Thr Pro Asp Trp Leu Asn Gly Asn Thr Asp Lys Leu Ile Leu Thr
        435                 440                 445

Gln Arg Asn Ile Ala Lys Lys Gly Thr Val Lys Thr Arg Tyr Gln Asn
    450                 455                 460

Ile Ala Leu Tyr Val Glu Asp Leu Met Thr Trp Lys Asn Leu Glu Phe
465                 470                 475                 480

Arg Ala Gly Leu Arg Leu Glu Arg Asp Asp Tyr Leu Lys Asn Thr Asn
```

```
                485                 490                 495

Leu Ala Pro Arg Thr Val Phe Arg Tyr Lys Pro Phe Glu Asp Thr Ala
            500                 505                 510

Phe Ser Val Gly Trp Asn Arg Tyr Tyr Gly Arg Ser Phe Ala Ser Met
        515                 520                 525

Lys Leu Ser Glu Gly Ile Phe Lys Leu Asp Gly His Asp Thr Phe Arg
    530                 535                 540

Tyr Lys Asp Leu Ser Gln Phe Lys Thr Pro Tyr Ser Asp Glu Leu Ser
545                 550                 555                 560

Phe Gly Val Glu Gln Tyr Val Ala Asn Leu Ala Phe His Leu Lys Tyr
                565                 570                 575

Ile Leu Arg Asp Asn Lys Gln Arg Ile Val Leu Gln Glu Glu Asp Val
            580                 585                 590

Met Leu Asn Gly Glu Arg Lys Lys Leu Arg Tyr Tyr Gln Arg Gly Lys
        595                 600                 605

Asp Tyr Lys Thr Asn Val Leu Thr Phe Gln Ile Asn Thr Gln Ala Pro
    610                 615                 620

Trp Glu Leu Gly Pro Thr Arg Trp Thr Ser Ala Val Ala Phe Asp Trp
625                 630                 635                 640

Leu Asp Ser Lys Ala Ile Asp His Gly Arg Gly Tyr Asn Gly Ser Thr
                645                 650                 655

Pro Val Ile Leu Asp Gly Lys Leu Met Thr Tyr Glu Gln Met Leu Lys
            660                 665                 670

Lys Val Asn Ala Tyr Lys Glu Thr Trp Gly Leu Arg Leu Asn Leu Asp
        675                 680                 685

Met Phe Val Pro Arg Phe Asp Leu Ser Trp Ala Asn Thr Ile Tyr Val
    690                 695                 700

Lys Pro Pro Thr Thr Leu Thr Glu Arg Val Ser Ser Asn Thr Pro Glu
705                 710                 715                 720

Val Tyr Arg Ser Tyr Asp Tyr Gly Thr Tyr Thr Gln Trp Asp Thr Ser
                725                 730                 735

Leu Arg Trp Gln Pro Thr Phe Ala Glu Lys His Arg Pro Tyr Ile Lys
            740                 745                 750

Leu Asp Val Leu Asn Val Leu Asn Lys Thr Arg Lys Gly Ala Gly Pro
        755                 760                 765

Asn Gly Gln Asp Leu Gly Ile Tyr Thr Pro Gly Arg Glu Phe Trp Leu
    770                 775                 780

Glu Val Gly Tyr Glu Phe
785                 790
```

<210> SEQ ID NO 22
<211> LENGTH: 790
<212> TYPE: PRT
<213> ORGANISM: Pasteurella multocida

<400> SEQUENCE: 22

```
Met Glu Ser Ala Lys Asn Pro Leu Lys Lys Thr Thr Leu Ala Leu Leu
1               5                   10                  15

Cys Cys Ser Thr Ala Phe Ser Leu Ser Ala Lys Thr Asp Thr Asn Ala
            20                  25                  30

Asp Lys Asn His Phe Leu Thr Glu Ile Val Val Tyr Ala Asp Gln Asn
        35                  40                  45

Lys Ser Met Ser Ser Thr Gln Ser Val Thr Gln Asp Asp Met Lys Lys
    50                  55                  60
```

-continued

```
Ser Pro Val Thr Asn Gly Asn Ile Thr Asp Tyr Leu Arg Ser Asn Pro
65                  70                  75                  80

His Val Arg Tyr Glu Asn Ser Asp Gln Asn Gly Leu Gln Arg Gly Glu
                85                  90                  95

Ile Lys Pro Glu Asn Ile Ser Ile Asn Gly Ala Asp Tyr Gln Gln Thr
            100                 105                 110

Thr Phe Phe Val Asp Asn Val Asn Ile Asn Asn Asp Met Gly Phe Gly
        115                 120                 125

Ser Asp Leu Phe Asp Gly Thr Met Ala Thr Val Pro Phe Ala Asn His
    130                 135                 140

Ser Gln Gly Tyr Phe Phe Asp Ala Asn Leu Leu Ser Ser Ile Val Val
145                 150                 155                 160

His Asp Ser Asn Val Ser Ala Ser Leu Gly Gly Phe Ala Gly Gly Ala
                165                 170                 175

Val Val Ala Lys Thr Lys Gln Tyr Asp Gly Lys Asp Arg Leu Lys Phe
            180                 185                 190

Ser Tyr Arg Thr Thr Asp Ala Ser Trp Ala Lys Phe Lys Val Glu Asp
        195                 200                 205

Lys Asp Leu Glu Arg Phe Lys Asn Ala Ile Pro Glu Gly Ser Val Ala
    210                 215                 220

Glu Phe Gln Pro Lys Tyr Ser Lys His Phe Phe Asn Ile Thr Ala Glu
225                 230                 235                 240

Lys Gly Leu Ser Glu Asn Leu Gly Met Val Ile Gly Leu Ser Arg Arg
                245                 250                 255

Thr Ser Ser Ile Gln Gln Ser Arg Gln Ile Asn Pro Gln Gly Asp Arg
            260                 265                 270

Asp Lys Gln Thr His Thr Arg Arg Ser Asp Asn Ala Leu Leu Asn Phe
        275                 280                 285

Asn Leu Thr Pro Asn Asp Lys His Arg Phe Glu Leu Gly Phe Arg Tyr
    290                 295                 300

Ser Asn Tyr Arg Glu Arg Lys Phe Phe Asn Thr Asn Ile Asp Ser Asn
305                 310                 315                 320

Val Phe Asp Tyr His Arg Ala Tyr Gly Val Thr Phe Ser Trp Ile Asn
                325                 330                 335

Ala Leu Gln Ser Gly Ile Leu Thr Thr Thr Leu Ala Tyr Asp Asn Phe
            340                 345                 350

Asp Asp Thr Arg Lys Ser Ala Ser Thr Tyr Met Lys Thr Thr Leu Thr
        355                 360                 365

Glu Glu Gly Glu Glu Tyr Thr Glu Gly Gly Met Gly Asn Ser Gln Leu
    370                 375                 380

Asn Gln Lys Asn Leu His Thr Ser Leu Glu Tyr Ala Met Asn Pro Phe
385                 390                 395                 400

Asn Leu Gly Ser Ile Glu His Ser Val Ser Leu Gly Gly Ile Tyr Gln
                405                 410                 415

Ala Thr Lys Tyr Arg Phe Thr Arg His Ser Asp Ala Val Gly Glu Leu
            420                 425                 430

Tyr Thr Pro Asp Trp Leu Asn Gly Asn Thr Asp Lys Leu Ile Leu Thr
        435                 440                 445

Gln Arg Asn Ile Ala Lys Lys Gly Thr Val Lys Thr Arg Tyr Gln Asn
    450                 455                 460

Ile Ala Leu Tyr Val Glu Asp Leu Met Thr Trp Lys Asn Leu Glu Phe
465                 470                 475                 480

Arg Ala Gly Leu Arg Leu Glu Arg Asp Asp Tyr Leu Lys Asn Thr Asn
```

485 490 495

Leu Ala Pro Arg Thr Val Phe Arg Tyr Lys Pro Phe Glu Asp Thr Ala
500 505 510

Phe Ser Val Gly Trp Asn Arg Tyr Tyr Gly Arg Ser Phe Ala Ser Met
515 520 525

Lys Leu Ser Glu Gly Ile Phe Lys Leu Asp Gly His Asp Thr Phe Arg
530 535 540

Tyr Lys Asp Leu Ser Gln Phe Lys Thr Pro Tyr Ser Asp Glu Leu Ser
545 550 555 560

Phe Gly Val Glu Gln Tyr Val Ala Asn Leu Ala Phe His Leu Lys Tyr
565 570 575

Ile Leu Arg Asp Asn Lys Gln Arg Ile Val Leu Gln Glu Glu Asp Val
580 585 590

Met Leu Asn Gly Glu Lys Lys Lys Leu Arg Tyr Tyr Gln Arg Gly Lys
595 600 605

Asp Tyr Lys Thr Asn Val Leu Thr Phe Gln Ile Asn Thr Gln Ala Pro
610 615 620

Trp Glu Leu Gly Pro Thr Arg Trp Thr Ser Ala Val Ala Phe Asp Trp
625 630 635 640

Leu Asp Ser Lys Ala Ile Asp His Gly Arg Gly Tyr Asn Gly Ser Thr
645 650 655

Pro Val Ile Leu Asp Gly Lys Leu Met Thr Tyr Glu Gln Met Leu Lys
660 665 670

Lys Val Asn Ala Tyr Lys Glu Thr Trp Gly Leu Arg Leu Asn Leu Asp
675 680 685

Met Phe Val Pro Arg Phe Asp Leu Ser Trp Ala Asn Thr Ile Tyr Val
690 695 700

Lys Pro Pro Thr Thr Leu Thr Glu His Val Ser Ser Ser Thr Pro Glu
705 710 715 720

Val Tyr Arg Ser Tyr Asp Tyr Gly Thr Tyr Thr Gln Trp Asp Thr Ser
725 730 735

Leu Arg Trp Gln Pro Thr Phe Ala Glu Lys His Arg Pro Tyr Ile Lys
740 745 750

Leu Asp Val Leu Asn Val Leu Asn Lys Thr Arg Lys Gly Ala Gly Pro
755 760 765

Asn Gly Gln Asp Leu Gly Ile Tyr Thr Pro Gly Arg Glu Phe Trp Leu
770 775 780

Glu Val Gly Tyr Glu Phe
785 790

<210> SEQ ID NO 23
<211> LENGTH: 730
<212> TYPE: PRT
<213> ORGANISM: Pasteurella multocida

<400> SEQUENCE: 23

Met Ser Phe Lys His Lys Thr Leu Ala Leu Phe Val Ala His Ala Cys
1 5 10 15

Cys Thr Ser Val Leu Ala Glu Asn Ala Ala Thr Thr Leu Glu Pro Ile
20 25 30

Val Val Ser Asp Leu Ser His Thr Thr Leu Asn Leu Asp Gln Asn Lys
35 40 45

Leu Glu Lys Glu Ser Pro Lys Asp Leu Lys Ala Ile Phe Ala Thr Thr
50 55 60

-continued

```
Pro Asn Ile Asn Val Ile His Thr Gly His Ala Gln Leu Gly Asp Ile
65                  70                  75                  80

Glu Ile Arg Gly Met Gly Ser Ser Arg Glu Ile Phe Ala Thr Gly Ala
                85                  90                  95

Asn Arg Val Thr Met Glu Leu Asp Gly Met Asp Ile Ser Pro Ser Phe
            100                 105                 110

Tyr Phe Gly His Ser Ser Arg His Gly Arg Gln Tyr Phe Asp Pro Ser
        115                 120                 125

Asp Leu Lys Arg Val Glu Val His Lys Gly Pro Asn Ser Gln Gly Val
    130                 135                 140

Ala Gly His Val Arg Phe Gln Thr Lys Asp Pro His Asp Tyr Leu Leu
145                 150                 155                 160

Pro Asn Gln Arg Thr Gly Ala Gln Leu Arg Ala Gly Tyr Leu Gly Asp
                165                 170                 175

Ser Asp Ala Tyr Tyr Val Gly Ile Thr Gly Ala Ala Leu Leu Asp Glu
            180                 185                 190

His Ser Ser Ala Leu Val Ser Tyr Thr Arg Arg Trp Phe Asn Glu Phe
        195                 200                 205

Asn Asn Lys Gly Gly Leu Asp Val Thr Gly Ser Gln Arg Thr Lys Ser
    210                 215                 220

Asn Pro Ser Ser Gly Tyr Ser Asn Ala Val Asn Ser Lys Leu Arg Tyr
225                 230                 235                 240

Ser Pro Asn Asp Arg His Lys Phe Thr Leu Asn Leu Gln His Tyr Asp
                245                 250                 255

Leu Lys Arg Thr Ala Tyr Leu Glu Asp Ser Leu Gly Thr Thr Thr Thr
            260                 265                 270

Arg Arg Gly Thr Lys Thr Val His His Asn Thr Asn Ile Gln Lys Asn
        275                 280                 285

Gln Arg His Ala Ile Ala Phe Ser His Asp Met Gln Gln Thr Asn His
    290                 295                 300

Ser Ile Phe Asp His Leu His Trp Gln Ile Ala Leu Gln Gln Thr Lys
305                 310                 315                 320

Ser Thr Ser Arg Asn Thr Gly Ala Val Thr Ser Thr Ser Gly Ser Pro
                325                 330                 335

Pro Pro Ser Thr Pro Lys Phe Ser Gln Glu Arg Ser Leu Asp Gly Phe
            340                 345                 350

Lys Thr Lys Thr Ile Ser Leu Lys Thr Glu Phe Asn Lys Ser Leu Gly
        355                 360                 365

Gln His Val Val His Glu Leu His Tyr Gly Leu Lys Leu Gln Tyr Ser
    370                 375                 380

Gln Met Gln Ala Leu Arg Gln Thr Gln Ser Leu Asn Glu Gln Gly Ser
385                 390                 395                 400

Asn Thr Arg Thr Ser Ala Phe Phe Pro Thr Gln Gln Gln Trp Gln Ser
                405                 410                 415

Lys Leu His Leu Ser Asp Arg Ile Ser Phe Gly Lys Ser Gly Leu Ser
            420                 425                 430

Leu Thr Pro Ser Ile His Leu Thr Gln Ile Arg Ile Lys Pro Lys Thr
        435                 440                 445

Glu Asn Val Ser Lys Lys Asn Arg Glu Gln Leu Phe Thr Tyr Lys Asp
    450                 455                 460

Thr Ala Ile Gly Tyr Gly Leu Arg Val Asp Tyr Ala Leu Asn Glu Ala
465                 470                 475                 480

Asn Leu Leu Ser Leu Asn Tyr Gln His Ala Thr Arg Leu Pro Gly Tyr
```

-continued

```
                485                 490                 495

Gly Glu Asn Asn Ala Gln Ser Tyr Gly His Trp Pro Ala Lys Pro Asn
            500                 505                 510

Pro His Leu Gln Pro Glu Thr Ser Asp Gly Ile Glu Leu Ser Trp Arg
        515                 520                 525

Ser Ala Gly Ala Ile Gly Gln Gln Thr Thr Thr Leu Phe Tyr Asn Arg
    530                 535                 540

Tyr Asn Asp Leu Ile Tyr Leu Asp Thr Thr Ala Cys Tyr Ala Asp Arg
545                 550                 555                 560

Thr Gly Gln Val Gln Val Pro Cys Asp Leu Ala Asn Glu Lys Gly Arg
                565                 570                 575

Ser Tyr Ser Tyr Gly Ile Glu Phe Asp Gly Lys Leu Asn Leu Asp Thr
            580                 585                 590

Ile Gly Phe Ala Gln Gly Thr Tyr Leu Asn Ala Gly Phe Ala Tyr Ser
        595                 600                 605

Lys Gly Lys Thr Ala Asn Lys Gln Pro Gln Gly Arg Leu Asp Pro Leu
    610                 615                 620

Thr Gly Phe Val Gly Leu Gly Tyr Gln Gln Pro Met Asp Val Trp Gly
625                 630                 635                 640

Ile Glu Gly Lys Leu Lys Phe Ala Ala Lys Lys Lys Thr Lys Asp Leu
                645                 650                 655

Pro Ala Asn Gln Gly Phe Glu Gly Leu Pro Gly Tyr Ala Val Val Asp
            660                 665                 670

Leu Thr Ala Tyr Tyr Asn Val Thr Lys Gln Leu Tyr Leu Gly Ile Gly
        675                 680                 685

Ile Tyr Asn Val Leu Asp Lys Lys Tyr Ala Arg Trp Ala Met Ala Arg
    690                 695                 700

Gly Asp Ile Lys His Gly Asn Tyr Asp Lys His Thr Glu Ala Gly Arg
705                 710                 715                 720

His Phe Gly Ala Asn Ile Arg Tyr His Phe
                725                 730


<210> SEQ ID NO 24
<211> LENGTH: 727
<212> TYPE: PRT
<213> ORGANISM: Pasteurella multocida

<400> SEQUENCE: 24

Met Ser Phe Lys His Lys Thr Leu Ala Leu Phe Val Ala His Ala Cys
1               5                   10                  15

Cys Thr Ser Ala Leu Ala Glu Asn Ala Ala Thr Thr Leu Glu Pro Ile
            20                  25                  30

Val Val Ser Glu Leu Ser His Thr Thr Leu Asn Leu Asp Gln Asn Lys
        35                  40                  45

Leu Glu Lys Glu Ser Pro Lys Asp Leu Lys Ala Ile Phe Thr Thr Thr
    50                  55                  60

Pro Asn Ile Asn Val Ile His Thr Gly His Ala Gln Leu Gly Asp Ile
65                  70                  75                  80

Glu Ile Arg Gly Met Gly Ser Ser Arg Glu Ile Phe Ala Thr Gly Ala
                85                  90                  95

Asn Arg Val Thr Met Glu Leu Asp Gly Met Asp Ile Ser Pro Ser Phe
            100                 105                 110

Tyr Phe Gly His Ser Ser Arg His Gly Arg Gln Tyr Phe Asp Pro Ser
        115                 120                 125
```

-continued

```
Asp Leu Lys Arg Val Glu Ile His Lys Gly Pro Asn Ser Gln Gly Val
    130                 135                 140

Ala Gly His Val Arg Phe Gln Thr Lys Asp Pro Arg Asp Tyr Leu Leu
145                 150                 155                 160

Pro Asn Gln Arg Thr Gly Ala Gln Leu Arg Ala Gly Tyr Leu Gly Asp
                165                 170                 175

Ser Asp Ala Tyr Tyr Val Gly Ile Thr Gly Ala Thr Leu Leu Asp Glu
            180                 185                 190

His Ser Ser Ala Leu Val Ser Tyr Thr Arg Arg Trp Phe Asn Glu Phe
        195                 200                 205

Asn Asn Lys Gly Gly Leu Asp Val Thr Gly Ser Gln Arg Thr Lys Ser
    210                 215                 220

Asn Pro Ser Ser Gly Tyr Ser Asn Ala Val Asn Ser Lys Leu Arg Tyr
225                 230                 235                 240

Ser Pro Asn Asp Arg His Lys Phe Thr Leu Asn Leu Gln His Tyr Asp
                245                 250                 255

Leu Lys Arg Thr Ala Tyr Leu Glu Asp Ser Leu Gly Thr Thr Thr Thr
            260                 265                 270

Arg Arg Gly Thr Lys Thr Val His His Asn Thr Asn Ile Gln Lys Asn
        275                 280                 285

Gln Arg His Ala Ile Ala Phe Ser His Asp Met Gln Gln Thr Thr Ala
    290                 295                 300

Phe Phe Asp His Leu His Trp Gln Ile Ala Leu Gln Gln Thr Lys Ser
305                 310                 315                 320

Thr Ser Arg Asn Thr Gly Thr Val Thr Ser Thr Ser Ala Pro Pro Pro
                325                 330                 335

Pro Ser Thr Pro Lys Phe Ser Gln Glu Arg Ser Phe Asp Gly Phe Lys
            340                 345                 350

Thr Lys Thr Ile Ser Leu Lys Thr Glu Phe Asn Lys Ser Leu Gly Gln
        355                 360                 365

His Val Val His Glu Leu His Tyr Gly Leu Lys Leu Gln Tyr Ser Gln
    370                 375                 380

Met Gln Ala Leu Arg Gln Thr Gln Ser Leu Asn Glu Gln Gly Ser Asn
385                 390                 395                 400

Thr Arg Thr Ser Ala Phe Phe Pro Thr Gln Gln Gln Trp Gln Ser Lys
                405                 410                 415

Phe His Leu Ser Asp Arg Ile Ser Phe Gly Lys Ser Gly Leu Ser Leu
            420                 425                 430

Thr Pro Ser Ile His Leu Thr Gln Ile Arg Ile Lys Pro Lys Thr Glu
        435                 440                 445

Asn Val Ser Lys Lys Asn Arg Glu Gln Leu Phe Thr Tyr Lys Asp Thr
    450                 455                 460

Ala Ile Gly Tyr Gly Leu Arg Val Asp Tyr Ala Leu Asn Glu Ala Asn
465                 470                 475                 480

Leu Leu Ser Leu Asn Tyr Gln His Ala Thr Arg Leu Pro Gly Tyr Gly
                485                 490                 495

Glu Asn Asn Ala Gln Ser Tyr Gly His Trp Pro Ala Lys Pro Asn Pro
            500                 505                 510

His Leu Gln Pro Glu Thr Ser Asp Gly Val Glu Leu Ser Trp Arg Ser
        515                 520                 525

Ala Gly Ala Ile Gly Gln Gln Thr Thr Thr Leu Phe Tyr Asn Arg Tyr
    530                 535                 540

Asn Asp Leu Ile Tyr Leu Asp Thr Thr Ala Cys Tyr Ala Asp Arg Thr
```

-continued

```
545                 550                 555                 560

Gly Gln Val Pro Cys Asp Leu Ala Asn Glu Lys Gly Arg Ser Tyr Ser
                565                 570                 575

Tyr Gly Ile Glu Phe Asp Gly Lys Leu Asn Leu Asp Thr Ile Gly Phe
            580                 585                 590

Ala Gln Gly Thr Tyr Leu Asn Ala Gly Phe Ala Tyr Ser Lys Gly Lys
        595                 600                 605

Thr Ala Asn Lys Gln Pro Gln Gly Arg Leu Asp Pro Leu Thr Gly Phe
    610                 615                 620

Val Gly Leu Gly Tyr Gln Gln Pro Met Asp Val Trp Gly Ile Glu Gly
625                 630                 635                 640

Lys Leu Lys Phe Ala Ala Lys Lys Lys Thr Lys Asp Leu Pro Ala Asn
                645                 650                 655

Gln Gly Phe Glu Gly Leu Pro Gly Tyr Ala Val Val Asp Leu Thr Ala
            660                 665                 670

Tyr Tyr Asn Val Thr Lys Gln Leu Tyr Leu Gly Ile Gly Ile Tyr Asn
        675                 680                 685

Val Leu Asp Lys Lys Tyr Ala Arg Trp Ala Met Ala Arg Gly Asp Ile
    690                 695                 700

Lys His Gly Asn Tyr Asp Lys His Thr Glu Ala Gly Arg His Phe Gly
705                 710                 715                 720

Ala Asn Ile Arg Tyr His Phe
                725


<210> SEQ ID NO 25
<211> LENGTH: 727
<212> TYPE: PRT
<213> ORGANISM: Pasteurella multocida

<400> SEQUENCE: 25

Met Ser Phe Lys His Lys Thr Leu Ala Leu Phe Val Ala His Ala Cys
1               5                   10                  15

Cys Thr Ser Ala Leu Ala Glu Asn Val Ala Thr Thr Leu Glu Pro Ile
            20                  25                  30

Val Val Ser Asp Leu Ser His Thr Thr Leu Asn Leu Asp Gln Asn Lys
        35                  40                  45

Leu Glu Lys Glu Ser Pro Lys Asp Leu Lys Ala Ile Phe Ala Thr Thr
    50                  55                  60

Pro Asn Ile Asn Val Ile His Thr Gly His Ala Gln Leu Gly Asp Ile
65                  70                  75                  80

Glu Ile Arg Gly Met Gly Ser Ser Arg Glu Ile Phe Ala Thr Gly Ala
                85                  90                  95

Asn Arg Val Thr Met Glu Leu Asp Gly Met Asp Ile Ser Pro Ser Phe
            100                 105                 110

Tyr Phe Gly His Ser Ser Arg His Gly Arg Gln Tyr Phe Asp Pro Ser
        115                 120                 125

Asp Leu Lys Arg Val Glu Ile His Lys Gly Pro Asn Ser Gln Gly Val
    130                 135                 140

Ala Gly His Val Arg Phe Gln Thr Lys Asp Pro Arg Asp Tyr Leu Leu
145                 150                 155                 160

Pro Asn Gln Arg Thr Gly Ala Gln Leu Arg Ala Gly Tyr Leu Gly Asp
                165                 170                 175

Ser Asp Ala Tyr Tyr Val Gly Ile Thr Gly Ala Thr Leu Leu Asp Glu
            180                 185                 190
```

```
His Ser Ser Ala Leu Val Ser Tyr Thr Arg Arg Trp Phe Asn Glu Phe
        195                 200                 205

Asn Asn Lys Gly Gly Leu Asp Val Thr Gly Ser Gln Arg Thr Lys Ser
    210                 215                 220

Asn Pro Ser Ser Gly Tyr Ser Asn Ala Val Asn Ser Lys Leu Arg Tyr
225                 230                 235                 240

Ser Pro Asn Asp Arg His Lys Phe Thr Leu Asn Leu Gln His Tyr Asp
                245                 250                 255

Leu Lys Arg Thr Ala Tyr Leu Glu Asp Ser Leu Gly Thr Thr Thr Thr
            260                 265                 270

Arg Arg Gly Thr Lys Thr Val His His Asn Thr Asn Ile Gln Lys Asn
        275                 280                 285

Gln Arg His Ala Ile Ala Phe Ser His Asp Met Gln Gln Thr Thr Ala
    290                 295                 300

Phe Phe Asp His Leu His Trp Gln Ile Ala Leu Gln Gln Thr Lys Ser
305                 310                 315                 320

Thr Ser Arg Asn Thr Gly Ala Val Thr Ser Thr Ser Ala Ser Pro Pro
                325                 330                 335

Pro Ser Thr Pro Lys Phe Ser Gln Glu Arg Ser Phe Asp Gly Phe Lys
            340                 345                 350

Thr Lys Thr Ile Ser Leu Lys Thr Glu Phe Asn Lys Ser Leu Gly Gln
        355                 360                 365

His Val Val His Glu Leu His Tyr Gly Leu Lys Leu Gln Tyr Ser Gln
    370                 375                 380

Met Gln Ala Leu Arg Gln Thr Gln Ser Leu Asn Glu Gln Gly Ser Asn
385                 390                 395                 400

Thr Arg Thr Ser Ala Phe Phe Pro Thr Gln Gln Gln Trp Gln Ser Lys
                405                 410                 415

Leu His Leu Ser Asp Arg Ile Ser Phe Gly Lys Ser Gly Leu Ser Leu
            420                 425                 430

Thr Pro Ser Ile His Leu Thr Gln Ile Arg Ile Lys Pro Lys Thr Glu
        435                 440                 445

Asn Val Ser Lys Lys Asn Arg Glu Gln Leu Phe Thr Tyr Lys Asp Thr
    450                 455                 460

Ala Ile Gly Tyr Gly Leu Arg Val Asp Tyr Ala Leu Asn Glu Ala Asn
465                 470                 475                 480

Leu Leu Ser Leu Asn Tyr Gln His Ala Thr Arg Leu Pro Gly Tyr Gly
                485                 490                 495

Glu Asn Asn Ala Gln Ser Tyr Gly His Trp Pro Ala Lys Pro Asn Pro
            500                 505                 510

His Leu Gln Pro Glu Thr Ser Asp Gly Ile Glu Leu Ser Trp Arg Ser
        515                 520                 525

Ala Gly Ala Ile Gly Gln Gln Thr Thr Thr Leu Phe Tyr Asn Arg Tyr
    530                 535                 540

Asn Asp Leu Ile Tyr Leu Asp Thr Thr Ala Cys Tyr Ala Asp Arg Thr
545                 550                 555                 560

Gly Gln Val Pro Cys Asp Leu Ala Asn Glu Lys Gly Arg Ser Tyr Ser
                565                 570                 575

Tyr Gly Ile Glu Phe Asp Gly Lys Leu Asn Leu Asp Thr Ile Gly Phe
            580                 585                 590

Ala Gln Gly Thr Tyr Leu Asn Ala Gly Phe Ala Tyr Ser Lys Gly Lys
        595                 600                 605

Thr Ala Asn Lys Gln Pro Gln Gly Arg Leu Glu Pro Leu Thr Gly Phe
```

610 615 620

Val Gly Leu Gly Tyr Gln Gln Pro Met Asp Val Trp Gly Ile Glu Gly
625 630 635 640

Lys Leu Lys Phe Ala Ala Lys Lys Lys Thr Lys Asp Leu Pro Ala Asn
645 650 655

Gln Gly Phe Glu Gly Leu Pro Gly Tyr Ala Val Val Asp Leu Thr Ala
660 665 670

Tyr Tyr Asn Val Thr Lys Gln Leu Tyr Leu Gly Ile Gly Ile Tyr Asn
675 680 685

Val Leu Asp Lys Lys Tyr Ala Arg Trp Ala Met Ala Arg Gly Asp Ile
690 695 700

Lys His Gly Asn Tyr Asp Lys His Thr Glu Ala Gly Arg His Phe Gly
705 710 715 720

Ala Asn Ile Arg Tyr His Phe
725

<210> SEQ ID NO 26
<211> LENGTH: 727
<212> TYPE: PRT
<213> ORGANISM: Pasteurella multocida subsp. multocida str. Anand1_goat

<400> SEQUENCE: 26

Met Ser Phe Lys His Lys Thr Leu Ala Leu Phe Val Ala His Ala Cys
1 5 10 15

Cys Thr Ser Ala Leu Ala Glu Asn Ala Ala Thr Thr Leu Glu Pro Ile
20 25 30

Val Val Ser Asp Leu Ser His Thr Thr Leu Asn Leu Asp Gln Asn Lys
35 40 45

Leu Glu Lys Glu Ser Pro Lys Asp Leu Lys Ala Ile Phe Ala Thr Thr
50 55 60

Pro Asn Ile Asn Val Ile His Thr Gly His Ala Gln Leu Gly Asp Ile
65 70 75 80

Glu Ile Arg Gly Met Gly Ser Ser Arg Glu Ile Phe Ala Thr Gly Ala
85 90 95

Asn Arg Val Thr Met Glu Leu Asp Gly Met Asp Ile Ser Pro Ser Phe
100 105 110

Tyr Phe Gly His Ser Ser Arg His Gly Arg Gln Tyr Phe Asp Pro Ser
115 120 125

Asp Leu Lys Arg Val Glu Ile His Lys Gly Pro Asn Ser Gln Gly Val
130 135 140

Ala Gly His Val Arg Phe Gln Thr Lys Asp Pro Arg Asp Tyr Leu Leu
145 150 155 160

Pro Asn Gln Arg Thr Gly Ala Gln Leu Arg Ala Gly Tyr Leu Gly Asp
165 170 175

Ser Asp Ala Tyr Tyr Val Gly Ile Thr Gly Ala Thr Leu Leu Asp Glu
180 185 190

His Ser Ser Ala Leu Met Ser Tyr Thr Arg Arg Trp Phe Asn Glu Phe
195 200 205

Asn Asn Lys Gly Gly Leu Asp Val Thr Gly Ser Gln Arg Thr Lys Ser
210 215 220

Asn Pro Ser Ser Gly Tyr Ser Asn Ala Val Asn Ser Lys Leu Arg Tyr
225 230 235 240

Ser Pro Asn Asp Arg His Lys Phe Thr Leu Asn Leu Gln His Tyr Asp
245 250 255

```
Leu Lys Arg Thr Ala Tyr Leu Glu Asp Ser Leu Gly Thr Thr Thr Thr
            260                 265                 270

Arg Arg Gly Thr Lys Thr Val His His Asn Thr Asn Ile Gln Lys Asn
        275                 280                 285

Gln Arg His Ala Ile Ala Phe Ser His Asp Met Gln Gln Thr Thr Ala
    290                 295                 300

Phe Phe Asp His Leu His Trp Gln Ile Ala Leu Gln Gln Thr Lys Ser
305                 310                 315                 320

Thr Ser Arg Asn Thr Gly Ala Val Thr Asn Thr Ser Ala Ser Pro Pro
                325                 330                 335

Pro Ser Thr Pro Lys Phe Ser Gln Glu Arg Ser Leu Asp Gly Phe Lys
            340                 345                 350

Thr Lys Thr Ile Ser Leu Lys Thr Glu Phe Asn Lys Ser Ile Gly Gln
        355                 360                 365

His Val Val His Glu Leu His Tyr Gly Leu Lys Leu Gln Tyr Ser Gln
    370                 375                 380

Met Gln Ala Leu Arg Gln Thr Gln Ser Leu Asn Glu Gln Gly Ser Asn
385                 390                 395                 400

Thr Arg Thr Ser Ala Phe Phe Pro Thr Gln Gln Gln Trp Gln Ser Lys
                405                 410                 415

Leu His Leu Ser Asp Arg Ile Ser Phe Gly Lys Ser Gly Leu Ser Leu
            420                 425                 430

Thr Pro Ser Ile His Leu Thr Gln Ile Arg Ile Lys Pro Lys Thr Glu
        435                 440                 445

Asn Val Ser Lys Lys Asn Arg Glu Gln Leu Phe Thr Tyr Lys Asp Thr
    450                 455                 460

Ala Ile Gly Tyr Gly Leu Arg Val Asp Tyr Ala Leu Asn Glu Ala Asn
465                 470                 475                 480

Leu Leu Ser Leu Asn Tyr Gln His Ala Thr Arg Leu Pro Gly Tyr Gly
                485                 490                 495

Glu Asn Asn Ala Gln Ser Tyr Gly His Trp Pro Ala Lys Pro Asn Pro
            500                 505                 510

His Leu Gln Pro Glu Thr Ser Asp Gly Ile Glu Leu Ser Trp Arg Ser
        515                 520                 525

Ala Gly Ala Ile Gly Gln Gln Thr Thr Thr Leu Phe Tyr Asn Arg Tyr
    530                 535                 540

Asn Asp Leu Ile Tyr Leu Asp Thr Thr Ala Cys Tyr Ala Asp Arg Thr
545                 550                 555                 560

Gly Gln Val Pro Cys Asp Leu Ala Asn Glu Lys Gly Arg Ser Tyr Ser
                565                 570                 575

Tyr Gly Ile Glu Phe Asp Gly Lys Leu Asn Leu Asp Thr Ile Gly Phe
            580                 585                 590

Ala Gln Gly Thr Tyr Leu Asn Ala Gly Phe Ala Tyr Ser Lys Gly Lys
        595                 600                 605

Thr Ala Asn Lys Gln Pro Gln Gly Arg Leu Asp Pro Leu Thr Gly Phe
    610                 615                 620

Val Gly Leu Gly Tyr Gln Gln Pro Met Asp Val Trp Gly Ile Glu Gly
625                 630                 635                 640

Lys Leu Lys Phe Ala Ala Lys Lys Lys Thr Lys Asp Leu Pro Ala Asn
                645                 650                 655

Gln Gly Phe Glu Gly Leu Pro Gly Tyr Ala Val Val Asp Leu Thr Ala
            660                 665                 670

Tyr Tyr Asn Val Thr Lys Gln Leu Tyr Leu Gly Ile Gly Ile Tyr Asn
```

```
        675                 680                 685

Val Leu Asp Lys Lys Tyr Ala Arg Trp Ala Met Ala Arg Gly Asp Ile
    690                 695                 700

Lys His Gly Asn Tyr Asp Lys His Thr Glu Ala Gly Arg His Phe Gly
705                 710                 715                 720

Ala Asn Ile Arg Tyr His Phe
                725


<210> SEQ ID NO 27
<211> LENGTH: 964
<212> TYPE: PRT
<213> ORGANISM: Pasteurella multocida

<400> SEQUENCE: 27

Met Arg Thr Thr Thr Ile Lys Phe Ser Ala Ile Thr Leu Ala Leu Leu
1               5                   10                  15

Ser Tyr Cys Gly Val Ile Leu Ala Asp Ser His Gln Glu Ala Thr Glu
            20                  25                  30

Leu Asp Thr Ile Thr Val Ser Ser Gln Gln Asp Glu Met Asn Ile Lys
        35                  40                  45

Glu Lys Lys Val Gly Glu Thr Val Lys Thr Ala Ser Gln Leu Lys Arg
    50                  55                  60

Gln Gln Val Gln Asp Ser Arg Asp Leu Val Arg Tyr Glu Thr Gly Val
65                  70                  75                  80

Thr Val Val Glu Ala Gly Arg Phe Gly Ser Ser Gly Tyr Ala Ile Arg
                85                  90                  95

Gly Val Asp Glu Asn Arg Val Ala Ile Thr Val Asp Gly Leu His Gln
            100                 105                 110

Ala Glu Thr Leu Ser Ser Gln Gly Phe Lys Glu Leu Phe Glu Gly Tyr
        115                 120                 125

Gly Asn Phe Asn Asn Thr Arg Asn Ser Val Glu Ile Glu Thr Leu Lys
    130                 135                 140

Val Ala Lys Ile Ala Lys Gly Ala Asp Ser Val Lys Val Gly Ser Gly
145                 150                 155                 160

Ser Leu Gly Gly Ala Val Leu Phe Glu Thr Lys Asp Ala Arg Asp Phe
                165                 170                 175

Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Asn Tyr Asp Tyr Lys Asn Gly Arg Asp Ile Gln Gly Lys Glu Arg
225                 230                 235                 240

Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Ile Gln Arg Ser Arg Gly His Asp Arg Ser Tyr Ser Leu Gln
        275                 280                 285

Pro Gln Ser Asn Tyr Phe Thr Tyr Asp Glu Lys Glu Ser Arg His Ala
    290                 295                 300

Asn Asp Leu Thr Lys Arg Lys Asn Val Ser Phe Thr Tyr Glu Asn Tyr
305                 310                 315                 320
```

```
Ser Val Thr Pro Phe Trp Asp Thr Leu Lys Leu Ser Tyr Ser Gln Gln
                325                 330                 335

Lys Ile Arg Thr Arg Ala Arg Thr Glu Asp Tyr Cys Asp Gly Asn Glu
            340                 345                 350

Lys Cys Asp Ser Tyr Lys Asn Pro Leu Gly Leu Gln Leu Lys Asp Gly
        355                 360                 365

Lys Ile Val Asp Pro Glu Gly Asn Gln Ile Thr Leu Lys Gly Thr Gly
    370                 375                 380

Phe Asn Thr Glu Ile Val Asp Lys Asn Gly Asn Pro Phe Pro Thr Thr
385                 390                 395                 400

Ser Gly Thr Asn Asn Ala Ala Phe Ser Asn Asn Ile Gln Leu Gly Pro
                405                 410                 415

Lys Glu Phe Trp Leu Asp Cys Ser Leu Phe Asp Cys Thr Gln Pro Phe
            420                 425                 430

Thr Val Tyr Asn Tyr Gln Asn Gly Gln Tyr Thr Pro Lys Gln Val Glu
        435                 440                 445

Leu Ser Glu Glu Ile Thr Val Asn Gly Lys Leu Tyr Lys Thr Ala Lys
    450                 455                 460

Glu Glu Arg Gly Val Arg Asn Tyr Leu Ile Leu Pro Asn Ser Lys Gly
465                 470                 475                 480

Tyr Leu Pro Tyr Asp Tyr Lys Glu Arg Asp Leu Asp Ser Asn Thr Lys
                485                 490                 495

Gln Ile Asn Leu Asp Leu Thr Lys Thr Phe Ser Thr Phe Asn Ile Glu
            500                 505                 510

Asn Glu Leu Leu Tyr Gly Ala Ile Tyr Ser Arg Thr Glu Lys Lys Met
        515                 520                 525

Val Asn Lys Ala Gly Tyr Asp Gly Arg Asn Pro Thr Trp Trp Ala Asp
    530                 535                 540

Arg Ile Leu Gly Lys Ser Thr Asn Cys Asn Tyr Asn Gly Leu Lys Cys
545                 550                 555                 560

Pro Arg His Glu Pro Leu Thr Ser Phe Leu Ile Pro Val Glu Ala Thr
                565                 570                 575

Thr Lys Ser Leu Tyr Phe Ser Asp Asn Ile Lys Leu His Asn Met Leu
            580                 585                 590

Ser Val Asp Leu Gly Tyr Arg Tyr Asp Asp Ile Lys Tyr Gln Pro Glu
        595                 600                 605

Tyr Ile Pro Gly Val Thr Pro Lys Ile Ala Asp Asp Met Val Lys Gly
    610                 615                 620

Ile Phe Ile Pro Leu Pro Lys Gly Glu Lys Val Thr Thr Pro Trp Gly
625                 630                 635                 640

Ala Glu Tyr Thr Lys Pro Leu Thr Gln Glu Gln Ile Arg Lys Asn Ala
                645                 650                 655

Glu Glu Asn Ile Ala Tyr Ile Ala Gln Glu Lys Arg Phe Lys Lys His
            660                 665                 670

Ser Tyr Ser Leu Gly Ala Thr Phe Asp Pro Leu Asn Phe Leu Arg Val
        675                 680                 685

Gln Val Lys Tyr Ser Lys Gly Phe Arg Ala Pro Thr Ser Asp Glu Leu
    690                 695                 700

Tyr Phe Thr Phe Lys His Pro Asp Phe Thr Ile Leu Pro Asn Pro Val
705                 710                 715                 720

Leu Lys Pro Glu Glu Ala Lys Asn Gln Glu Ile Ala Leu Thr Val His
                725                 730                 735

Asp Asn Trp Gly Phe Val Ser Thr Ser Val Phe Gln Thr Lys Tyr Arg
```

```
            740                 745                 750

His Phe Ile Asp Leu Ala Tyr Leu Gly Ser Arg Asn Leu Ser Asn Ser
        755                 760                 765

Val Gly Gly Gln Ala Gln Ala Arg Asp Phe Gln Val Tyr Gln Asn Val
    770                 775                 780

Asn Val Asp Asn Ala Lys Val Lys Gly Leu Glu Ile Asn Ala Arg Leu
785                 790                 795                 800

Asn Leu Gly Tyr Phe Trp His Val Leu Asp Gly Phe Asn Thr Ser Tyr
            805                 810                 815

Lys Phe Thr Tyr Gln Arg Gly Arg Leu Asp Gly Asp Arg Pro Met Asn
            820                 825                 830

Ala Ile Gln Pro Lys Ala Ser Val Phe Gly Leu Gly Tyr Asp His Lys
        835                 840                 845

Glu Asn Lys Phe Gly Ala Asp Leu Tyr Ile Thr Arg Val Ser Glu Lys
    850                 855                 860

Lys Ala Lys Asp Thr Tyr Asn Met Phe Tyr Lys Glu Gln Gly Tyr Lys
865                 870                 875                 880

Asp Ser Ala Ile Arg Trp Arg Ser Asp Asp Tyr Thr Leu Val Asp Ala
            885                 890                 895

Val Gly Tyr Ile Lys Pro Ile Lys Asn Leu Thr Leu Gln Phe Gly Val
            900                 905                 910

Tyr Asn Leu Thr Asp Arg Lys Tyr Leu Thr Trp Glu Ser Ala Arg Ser
        915                 920                 925

Ile Lys Pro Phe Gly Thr Ser Asn Leu Ile Asn Gln Lys Thr Gly Ala
    930                 935                 940

Gly Ile Asn Arg Phe Tyr Ser Pro Gly Arg Asn Phe Lys Phe Ser Ala
945                 950                 955                 960

Glu Ile Thr Phe


<210> SEQ ID NO 28
<211> LENGTH: 963
<212> TYPE: PRT
<213> ORGANISM: Pasteurella multocida

<400> SEQUENCE: 28

Met Arg Thr Thr Thr Ile Lys Phe Ser Ala Ile Thr Leu Ala Leu Leu
1               5                   10                  15

Ser Tyr Cys Gly Ala Ile Leu Ala Asp Ser His Gln Glu Ala Thr Glu
            20                  25                  30

Leu Asp Thr Ile Thr Val Ser Ser Gln Gln Asp Glu Met Asn Ile Lys
        35                  40                  45

Glu Lys Lys Val Gly Glu Thr Val Lys Thr Ala Ser Gln Leu Lys Arg
    50                  55                  60

Gln Gln Val Gln Asp Ser Arg Asp Leu Val Arg Tyr Glu Thr Gly Val
65                  70                  75                  80

Thr Val Val Glu Ala Gly Arg Phe Gly Ser Ser Gly Tyr Ala Ile Arg
            85                  90                  95

Gly Val Asp Glu Asn Arg Val Ala Ile Thr Val Asp Gly Leu His Gln
            100                 105                 110

Ala Glu Thr Leu Ser Ser Gln Gly Phe Lys Glu Leu Phe Glu Gly Tyr
        115                 120                 125

Gly Asn Phe Asn Asn Thr Arg Asn Ser Val Glu Ile Glu Thr Leu Lys
    130                 135                 140

Val Ala Lys Ile Ala Lys Gly Ala Asp Ser Val Lys Val Gly Ser Gly
```

-continued

```
145                 150                 155                 160

Ser Leu Gly Gly Ala Val Leu Phe Glu Thr Lys Asp Ala Arg Asp Phe
                165                 170                 175

Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Asn Tyr Asp Tyr Lys Asn Gly Arg Asp Ile Gln Gly Lys Glu Arg
225                 230                 235                 240

Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Ile Gln Arg Ser Arg Gly His Asp Arg Ser Tyr Ser Leu Gln
        275                 280                 285

Pro Gln Ser Asn Tyr Phe Thr Tyr Asp Glu Lys Glu Ser Arg His Ala
    290                 295                 300

Asn Asp Leu Thr Lys Arg Lys Asn Val Ser Phe Thr Tyr Glu Asn Tyr
305                 310                 315                 320

Ser Val Thr Pro Phe Trp Asp Thr Leu Lys Leu Ser Tyr Ser Gln Gln
                325                 330                 335

Lys Ile Arg Thr Arg Ala Arg Thr Glu Asp Tyr Cys Asp Gly Asn Glu
            340                 345                 350

Lys Cys Asp Ser Tyr Lys Asn Pro Leu Gly Leu Gln Leu Lys Asp Gly
        355                 360                 365

Lys Ile Val Asp Pro Ala Gly Asn Gln Ile Thr Leu Lys Gly Thr Gly
    370                 375                 380

Phe Asn Thr Glu Ile Val Asp Lys Asp Gly Lys Pro Phe Pro Thr Thr
385                 390                 395                 400

Ser Gly Thr Asn Asn Ala Ala Phe Ser Asn Asn Leu Gln Leu Ser Pro
                405                 410                 415

Thr Gly Phe Trp Leu Asp Cys Thr Ile Phe Asp Cys Thr Lys Pro Phe
            420                 425                 430

Thr Val Tyr Asn Tyr Lys Gln Asn Lys Tyr Glu Pro Arg Glu Val Met
        435                 440                 445

Leu Ser Glu Glu Ile Thr Ile Asp Gly Lys Leu Tyr Lys Thr Ala Lys
    450                 455                 460

Glu Glu Ser Gly Val Arg Asn Tyr Leu Ile Leu Pro Asn Ser Lys Gly
465                 470                 475                 480

Tyr Leu Pro Tyr Asp Tyr Lys Glu Arg Asp Leu Asp Ser Asn Thr Lys
                485                 490                 495

Gln Ile Asn Leu Asp Leu Thr Lys Thr Phe Ser Thr Phe Asn Ile Glu
            500                 505                 510

Asn Glu Leu Leu Tyr Gly Ala Ile Tyr Ser Arg Thr Glu Lys Lys Met
        515                 520                 525

Val Asn Lys Ala Gly Tyr Asp Gly Arg Asn Pro Thr Trp Trp Ala Asp
    530                 535                 540

Arg Ile Leu Gly Lys Ser Thr Asn Cys Asn Tyr Asn Gly Leu Lys Cys
545                 550                 555                 560

Pro Arg His Glu Pro Leu Thr Ser Phe Leu Ile Pro Val Glu Ala Thr
                565                 570                 575
```

Thr Lys Ser Leu Tyr Phe Ser Asp Asn Ile Lys Leu His Asn Met Leu
580 585 590

Ser Val Asp Leu Gly Tyr Arg Tyr Asp Asp Ile Lys Tyr Gln Pro Glu
595 600 605

Tyr Ile Pro Gly Val Thr Pro Lys Ile Ala Asp Asp Met Val Lys Gly
610 615 620

Ile Phe Ile Pro Leu Pro Lys Gly Glu Lys Ile Lys Ile Glu Asn Tyr
625 630 635 640

Glu Thr Thr Lys Pro Leu Thr Pro Glu Gln Ile Arg Lys Asn Ala Glu
645 650 655

Glu Asn Ile Ala Tyr Ile Ala Gln Glu Lys Arg Phe Lys Lys His Ser
660 665 670

Tyr Ser Leu Gly Ala Thr Phe Asp Pro Leu Asn Phe Leu Arg Val Gln
675 680 685

Val Lys Tyr Ser Lys Gly Phe Arg Ala Pro Thr Ser Asp Glu Leu Tyr
690 695 700

Phe Thr Phe Lys His Pro Asp Phe Thr Ile Leu Pro Asn Pro Val Leu
705 710 715 720

Lys Pro Glu Glu Ala Lys Asn Gln Glu Ile Ala Leu Thr Val His Asp
725 730 735

Asn Trp Gly Phe Val Ser Thr Ser Val Phe Gln Thr Lys Tyr Arg His
740 745 750

Phe Ile Asp Leu Ala Tyr Leu Gly Ser Arg Asn Leu Ser Asn Ser Val
755 760 765

Gly Gly Gln Ala Gln Ala Arg Asp Phe Gln Val Tyr Gln Asn Val Asn
770 775 780

Val Asp Asn Ala Lys Val Lys Gly Leu Glu Ile Asn Ala Arg Leu Asn
785 790 795 800

Leu Gly Tyr Phe Trp His Val Leu Asp Gly Phe Asn Thr Ser Tyr Lys
805 810 815

Phe Thr Tyr Gln Arg Gly Arg Leu Asp Gly Asp Arg Pro Met Asn Ala
820 825 830

Ile Gln Pro Lys Ala Ser Val Phe Gly Leu Gly Tyr Asp His Lys Glu
835 840 845

Asn Lys Phe Gly Ala Asp Leu Tyr Ile Thr Arg Val Ser Glu Lys Lys
850 855 860

Ala Lys Asp Thr Tyr Asn Met Phe Tyr Lys Glu Gln Gly Tyr Lys Asp
865 870 875 880

Ser Ala Ile Arg Trp Arg Ser Asp Asp Tyr Thr Leu Val Asp Ala Val
885 890 895

Gly Tyr Ile Lys Pro Ile Lys Asn Leu Thr Leu Gln Phe Gly Val Tyr
900 905 910

Asn Leu Thr Asp Arg Lys Tyr Leu Thr Trp Glu Ser Ala Arg Ser Ile
915 920 925

Lys Pro Phe Gly Thr Ser Asn Leu Ile Asn Gln Lys Thr Gly Ala Gly
930 935 940

Ile Asn Arg Phe Tyr Ser Pro Gly Arg Asn Phe Lys Phe Ser Ala Glu
945 950 955 960

Ile Thr Phe

<210> SEQ ID NO 29
<211> LENGTH: 963
<212> TYPE: PRT

<213> ORGANISM: Pasteurella multocida

<400> SEQUENCE: 29

```
Met Arg Thr Thr Thr Ile Lys Phe Ser Ala Ile Thr Leu Ala Leu Leu
1               5                   10                  15

Ser Tyr Cys Gly Ala Ile Leu Ala Asp Ser His Gln Glu Ala Thr Glu
            20                  25                  30

Leu Asp Thr Ile Thr Val Ser Ser Gln Gln Asp Glu Met Asn Ile Lys
        35                  40                  45

Glu Lys Lys Val Gly Glu Thr Val Lys Thr Ala Ser Gln Leu Lys Arg
    50                  55                  60

Gln Gln Val Gln Asp Ser Arg Asp Leu Val Arg Tyr Glu Thr Gly Val
65                  70                  75                  80

Thr Val Val Glu Ala Gly Arg Phe Gly Ser Ser Gly Tyr Ala Ile Arg
                85                  90                  95

Gly Val Asp Glu Asn Arg Val Ala Ile Thr Val Asp Gly Leu His Gln
            100                 105                 110

Ala Glu Thr Leu Ser Ser Gln Gly Phe Lys Glu Leu Phe Glu Gly Tyr
        115                 120                 125

Gly Asn Phe Asn Asn Thr Arg Asn Ser Val Glu Ile Glu Thr Leu Lys
    130                 135                 140

Val Ala Lys Ile Ala Lys Gly Ala Asp Ser Val Lys Val Gly Ser Gly
145                 150                 155                 160

Ser Leu Gly Gly Ala Val Leu Phe Glu Thr Lys Asp Ala Arg Asp Phe
                165                 170                 175

Leu Thr Glu Lys Asp Trp His Ile Gly Tyr Lys Ala Gly Tyr Ser Thr
            180                 185                 190

Ala Asp Asn Gln Gly Leu Asn Ala Val Thr Leu Ala Gly Arg Tyr Gln
        195                 200                 205

Met Phe Asp Ala Leu Ile Met His Ser Lys Arg His Gly His Glu Leu
    210                 215                 220

Glu Asn Tyr Asp Tyr Lys Asn Gly Arg Asp Ile Gln Gly Lys Glu Arg
225                 230                 235                 240

Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Ile Gln Arg Ser Arg Gly His Asp Arg Ser Tyr Ser Leu Gln
        275                 280                 285

Pro Gln Ser Asn Tyr Phe Thr Tyr Asp Glu Lys Glu Ser Arg His Ala
    290                 295                 300

Asn Asp Leu Thr Lys Arg Lys Asn Val Ser Phe Thr Tyr Glu Asn Tyr
305                 310                 315                 320

Ser Ile Thr Pro Phe Trp Asp Thr Leu Lys Leu Ser Tyr Ser Gln Gln
                325                 330                 335

Lys Ile Arg Thr Arg Ala Arg Thr Glu Asp Tyr Cys Asp Gly Asn Glu
            340                 345                 350

Lys Cys Asp Ser Tyr Lys Asn Pro Leu Gly Leu Gln Leu Lys Asp Gly
        355                 360                 365

Lys Ile Val Asp Pro Ala Gly Asn Gln Ile Thr Leu Lys Gly Thr Gly
    370                 375                 380

Phe Asn Thr Glu Ile Val Asp Lys Asp Gly Lys Pro Phe Pro Thr Thr
385                 390                 395                 400
```

```
Ser Gly Thr Asn Asn Ala Ala Phe Ser Asn Asn Leu Gln Leu Ser Pro
                405                 410                 415

Thr Gly Phe Trp Leu Asp Cys Thr Ile Phe Asp Cys Thr Lys Pro Phe
            420                 425                 430

Thr Val Tyr Asn Tyr Lys Gln Asn Lys Tyr Glu Pro Arg Glu Val Met
        435                 440                 445

Leu Ser Glu Glu Ile Thr Ile Asp Gly Lys Leu Tyr Lys Thr Ala Lys
    450                 455                 460

Glu Glu Ser Gly Val Arg Asn Tyr Leu Ile Leu Pro Asn Ser Lys Gly
465                 470                 475                 480

Tyr Leu Pro Tyr Asp Tyr Lys Glu Arg Asp Leu Asp Ser Asn Thr Lys
                485                 490                 495

Gln Ile Asn Leu Asp Leu Thr Lys Thr Phe Ser Thr Phe Asn Ile Glu
            500                 505                 510

Asn Glu Leu Leu Tyr Gly Ala Ile Tyr Ser Arg Thr Glu Lys Lys Met
        515                 520                 525

Val Asn Lys Ala Gly Tyr Asp Gly Arg Asn Pro Thr Trp Trp Ala Asp
    530                 535                 540

Arg Ile Leu Gly Lys Ser Thr Asn Cys Asn Tyr Asn Gly Leu Lys Cys
545                 550                 555                 560

Pro Arg His Glu Pro Leu Thr Ser Phe Leu Ile Pro Val Glu Ala Thr
                565                 570                 575

Thr Lys Ser Leu Tyr Phe Ser Asp Asn Ile Lys Leu His Asn Met Leu
            580                 585                 590

Ser Val Asp Leu Gly Tyr Arg Tyr Asp Asp Ile Lys Tyr Gln Pro Glu
        595                 600                 605

Tyr Ile Pro Gly Val Thr Pro Lys Ile Ala Asp Asp Met Val Lys Gly
    610                 615                 620

Ile Phe Ile Pro Leu Pro Lys Gly Glu Lys Ile Lys Ile Gly Asn Tyr
625                 630                 635                 640

Glu Thr Thr Lys Pro Leu Thr Pro Glu Gln Ile Arg Lys Asn Ala Glu
                645                 650                 655

Glu Asn Ile Ala Tyr Ile Ala Gln Glu Lys Arg Phe Lys Lys His Ser
            660                 665                 670

Tyr Ser Leu Gly Ala Thr Phe Asp Pro Leu Asn Phe Leu Arg Val Gln
        675                 680                 685

Val Lys Tyr Ser Lys Gly Phe Arg Ala Pro Thr Ser Asp Glu Leu Tyr
    690                 695                 700

Phe Thr Phe Lys His Pro Asp Phe Thr Ile Leu Pro Asn Pro Val Leu
705                 710                 715                 720

Lys Pro Glu Glu Ala Lys Asn Gln Glu Ile Ala Leu Thr Val His Asp
                725                 730                 735

Asn Trp Gly Phe Val Ser Thr Ser Val Phe Gln Thr Lys Tyr Arg His
            740                 745                 750

Phe Ile Asp Leu Ala Tyr Leu Gly Ser Arg Asn Leu Ser Asn Ser Val
        755                 760                 765

Gly Gly Lys Ala Gln Ala Arg Asp Phe Gln Val Tyr Gln Asn Val Asn
    770                 775                 780

Val Asp Asn Ala Lys Val Lys Gly Val Glu Ile Asn Ala Arg Leu Asn
785                 790                 795                 800

Leu Gly Tyr Phe Trp His Val Leu Asp Gly Phe Asn Thr Ser Tyr Lys
                805                 810                 815

Phe Thr Tyr Gln Arg Gly Arg Leu Asp Gly Asp Arg Pro Met Asn Ala
```

820 825 830

Ile Gln Pro Lys Ala Ser Val Phe Gly Leu Gly Tyr Asp His Lys Glu
835 840 845

Asn Lys Phe Gly Ala Asp Leu Tyr Ile Thr Arg Val Ser Glu Lys Lys
850 855 860

Ala Lys Asp Thr Tyr Asn Met Phe Tyr Lys Glu Gln Gly Tyr Lys Asp
865 870 875 880

Ser Ala Ile Arg Trp Arg Ser Asp Asp Tyr Thr Leu Ile Asp Ala Val
885 890 895

Gly Tyr Ile Lys Pro Ile Lys Asn Leu Thr Leu Gln Phe Gly Val Tyr
900 905 910

Asn Leu Thr Asp Arg Lys Tyr Leu Thr Trp Glu Ser Ala Arg Ser Ile
915 920 925

Lys Pro Phe Gly Thr Ser Asn Leu Ile Asn Gln Lys Thr Gly Ala Gly
930 935 940

Ile Asn Arg Phe Tyr Ser Pro Gly Arg Asn Phe Lys Leu Ser Ala Glu
945 950 955 960

Ile Thr Phe

<210> SEQ ID NO 30
<211> LENGTH: 971
<212> TYPE: PRT
<213> ORGANISM: Pasteurella multocida

<400> SEQUENCE: 30

Met Arg Thr Thr Thr Ile Lys Phe Ser Ala Ile Thr Leu Ala Leu Leu
1 5 10 15

Ser Tyr Cys Gly Val Ile Leu Ala Asp Ser His Gln Glu Ala Thr Glu
20 25 30

Leu Asp Thr Ile Thr Val Ser Ser Gln Gln Asp Glu Met Asn Ile Lys
35 40 45

Glu Lys Lys Val Gly Glu Thr Val Lys Thr Ala Ser Gln Leu Lys Arg
50 55 60

Gln Gln Val Gln Asp Ser Arg Asp Leu Val Arg Tyr Glu Thr Gly Val
65 70 75 80

Thr Val Val Glu Ala Gly Arg Phe Gly Ser Ser Gly Tyr Ala Ile Arg
85 90 95

Gly Val Asp Glu Asn Arg Val Ala Ile Thr Val Asp Gly Leu His Gln
100 105 110

Ala Glu Thr Leu Ser Ser Gln Gly Phe Lys Glu Leu Phe Glu Gly Tyr
115 120 125

Gly Asn Phe Asn Asn Thr Arg Asn Ser Val Glu Ile Glu Thr Leu Lys
130 135 140

Val Ala Lys Ile Ala Lys Gly Ala Asp Ser Val Lys Val Gly Ser Gly
145 150 155 160

Ser Leu Gly Gly Ala Val Leu Phe Glu Thr Lys Asp Ala Arg Asp Phe
165 170 175

Leu Thr Glu Lys Asp Trp His Ile Gly Tyr Lys Ala Gly Tyr Ser Thr
180 185 190

Ala Asp Asn Gln Gly Leu Asn Ala Val Thr Leu Ala Gly Arg Tyr Gln
195 200 205

Met Phe Asp Ala Leu Ile Met His Ser Lys Arg His Gly His Glu Leu
210 215 220

Glu Ile Tyr Asp Tyr Lys Asn Gly Arg Asp Ile Gln Gly Lys Glu Arg

-continued

```
225                 230                 235                 240

Glu Lys Ala Asp Pro Tyr Thr Ile Thr Lys Glu Ser Thr Leu Val Lys
                245                 250                 255

Phe Ser Phe Ser Pro Thr Glu Asn His Arg Phe Thr Val Ala Ser Asp
            260                 265                 270

Thr Tyr Leu Gln His Ser Arg Gly His Asp Leu Ser Tyr Asn Leu Val
        275                 280                 285

Ala Thr Thr Tyr Ile Gln Leu Asp Glu Lys Glu Ser Arg His Ala Asn
    290                 295                 300

Asp Leu Thr Lys Arg Lys Asn Val Ser Phe Thr Tyr Glu Asn Tyr Thr
305                 310                 315                 320

Val Thr Pro Phe Trp Asp Thr Leu Lys Leu Ser Tyr Ser Gln Gln Arg
                325                 330                 335

Ile Thr Thr Arg Ala Arg Thr Glu Asp Tyr Cys Asp Gly Asn Glu Lys
            340                 345                 350

Cys Asp Ser Tyr Lys Asn Pro Leu Gly Leu Gln Leu Lys Glu Gly Lys
        355                 360                 365

Ile Val Asp Arg Asn Gly Asp Pro Val Asn Leu Gln Leu Val Asp Gly
    370                 375                 380

Lys His Gln Val Val Asp Lys Ala Gly Lys Pro Phe Asp Val Thr Ser
385                 390                 395                 400

Gly Thr Asn Tyr Ala Ala Phe Ser Gly Lys Gln Leu Gly Pro Ser Tyr
                405                 410                 415

Phe Trp Leu Glu Cys Thr Val Phe Asp Cys Ser Lys Pro Val Thr Thr
            420                 425                 430

Tyr Lys Tyr Arg Tyr Ser Thr Glu Thr Pro Val Lys Glu Asp Ile Gln
        435                 440                 445

Leu Asn Lys Thr Met Glu Val Asn Gly Lys Thr Phe Ala Thr Tyr Asp
    450                 455                 460

Met Gly Arg Glu Arg Arg Tyr Ile Ile Leu Pro Asn Ser Gln Gly Tyr
465                 470                 475                 480

Leu Pro Leu Asp Tyr Lys Glu Arg Asp Leu Asn Thr Lys Thr Lys Gln
                485                 490                 495

Ile Asn Leu Asp Leu Thr Lys Ala Phe Thr Leu Phe Glu Ile Glu Asn
            500                 505                 510

Glu Leu Ser Tyr Gly Gly Val Tyr Ala Lys Thr Thr Asn Gly Val Val
        515                 520                 525

Asn Lys Ala Gly Tyr Tyr Gly Arg Asn Pro Thr Trp Trp Ala Glu Arg
    530                 535                 540

Thr Leu Gly Gln Ser Trp Asn Gly Thr Leu Arg Glu Cys Lys Thr Ser
545                 550                 555                 560

Ser Ser Tyr Asn Gly Met Leu Cys Pro Arg His Glu Pro Leu Thr Ser
                565                 570                 575

Phe Leu Ile Pro Val Glu Ala Thr Thr Lys Ser Leu Tyr Phe Ala Asp
            580                 585                 590

Asn Ile Lys Leu His Asn Met Leu Ser Val Asp Leu Gly Tyr Arg Tyr
        595                 600                 605

Asp Asp Ile Lys Tyr Gln Pro Glu Tyr Ile Pro Gly Val Thr Pro Lys
    610                 615                 620

Ile Ala Asp Asp Met Val Lys Gly Leu Phe Ile Pro Leu Pro Glu Gly
625                 630                 635                 640

Glu Lys Val Thr Val Gly Thr Val Val Phe Thr Lys Pro Leu Thr Pro
                645                 650                 655
```

-continued

```
Glu Gln Ile Arg Lys Asn Ala Glu Glu Asn Ile Ala Tyr Ile Ala Gln
            660                 665                 670

Gly Lys Arg Phe Lys Lys His Ser Tyr Ser Leu Gly Thr Thr Phe Asp
        675                 680                 685

Pro Leu Asn Phe Leu Arg Val Gln Val Lys Tyr Ser Lys Gly Phe Arg
    690                 695                 700

Ala Pro Thr Ser Asp Glu Leu Tyr Phe Thr Phe Lys His Pro Asp Phe
705                 710                 715                 720

Thr Ile Leu Pro Asn Pro Val Leu Lys Pro Glu Glu Ala Lys Asn Gln
                725                 730                 735

Glu Ile Ala Leu Thr Val His Asp Asn Trp Gly Phe Val Ser Thr Ser
            740                 745                 750

Val Phe Gln Thr Lys Tyr Arg His Phe Ile Asp Leu Ala Tyr Leu Gly
        755                 760                 765

Ser Arg Asn Leu Ser Asn Ser Val Gly Gly Gln Ala Gln Ala Arg Asp
    770                 775                 780

Phe Gln Val Tyr Gln Asn Val Asn Val Asp Asn Ala Lys Val Lys Gly
785                 790                 795                 800

Leu Glu Ile Asn Ala Arg Leu Asn Leu Gly Tyr Phe Trp His Val Leu
                805                 810                 815

Asp Gly Phe Asn Thr Ser Tyr Lys Phe Thr Tyr Gln Arg Gly Arg Leu
            820                 825                 830

Asp Gly Asp Arg Pro Met Asn Ala Ile Gln Pro Lys Ala Ser Val Phe
        835                 840                 845

Gly Leu Gly Tyr Asp His Lys Glu Asn Lys Phe Gly Ala Asp Leu Tyr
    850                 855                 860

Ile Thr Arg Val Ser Glu Lys Lys Ala Lys Asp Thr Tyr Asn Met Phe
865                 870                 875                 880

Tyr Lys Glu Gln Gly Tyr Lys Asp Ser Ala Ile Arg Trp Arg Ser Asp
                885                 890                 895

Asp Tyr Thr Leu Val Asp Ala Val Gly Tyr Ile Lys Pro Ile Lys Asn
            900                 905                 910

Leu Thr Leu Gln Phe Gly Val Tyr Asn Leu Thr Glu Arg Lys Tyr Leu
        915                 920                 925

Thr Trp Glu Ser Ala Arg Ser Ile Lys Pro Phe Gly Thr Ser Asn Leu
    930                 935                 940

Ile Asn Gln Lys Thr Gly Ala Gly Ile Asn Arg Phe Tyr Ser Pro Gly
945                 950                 955                 960

Arg Asn Phe Lys Phe Ser Ala Glu Ile Thr Phe
                965                 970


<210> SEQ ID NO 31
<211> LENGTH: 848
<212> TYPE: PRT
<213> ORGANISM: Pasteurella multocida

<400> SEQUENCE: 31

Met Gln Lys Ser Gln Pro Tyr Pro Ile His Leu Gly Ile Phe Leu Met
1               5                   10                  15

Leu Gly Leu Pro Thr Trp Ala Phe Ser Gln Ala Asn Leu Glu Lys Ser
            20                  25                  30

Thr Ile Asn Lys Leu Glu Thr Ile Leu Val Asn Glu Ser Glu Glu Lys
        35                  40                  45

Asn Lys Phe Asp Glu Asn Leu Ile Lys Thr Tyr Leu Ser Ser Gly Ser
```

-continued

```
    50                  55                  60

Tyr Ser Tyr Leu Ser Gln Ser Asp Ile Ser Thr Phe Arg Gly Ser Ser
65                  70                  75                  80

Val Gly Asp Phe Leu Ser Gly Val Pro Gly Val Ile Val Gly Asn Lys
                85                  90                  95

Arg Asn Ser Gly Ala Leu Ser Val Asn Ile Arg Gly Ile Ala Asn Glu
            100                 105                 110

Asn Arg Val Pro Val Trp Ile Asp Lys Gly Leu Gln Ser Val Pro Ser
        115                 120                 125

Tyr Gln Gly Tyr Ala Gly Ser Ser Thr Arg Thr Tyr Leu Asp Pro Asp
    130                 135                 140

Leu Ile Ser Gln Val Glu Ile Glu Lys Gly Pro Ser Leu Gln Met Asp
145                 150                 155                 160

Ala Thr Gly Ala Thr Gly Gly Val Val Arg Val Glu Thr Leu Arg Trp
                165                 170                 175

Gln Asp Ile Ile Pro Gln Gly Asn Lys Leu Gly Val Arg Leu Lys Leu
            180                 185                 190

Gly Thr Met Thr Asn Thr Val Ser Pro Pro Pro Tyr Tyr Thr Arg Gly
        195                 200                 205

Gly Tyr Gln Thr Lys Tyr Ile Ser Lys Cys Leu Ser Asn His Thr Gly
    210                 215                 220

Leu Cys Gln Thr Gln Thr Tyr Ala Pro Asn Ala Arg Tyr Ser Ser His
225                 230                 235                 240

Gly Phe Asp Leu Asn Ala Tyr Asn Tyr Ser Leu Ala Phe Ala Asn Lys
                245                 250                 255

Trp Ser Asn Ala Asp Leu Val Leu Ala Tyr Ala Lys Arg Lys Gln Gly
            260                 265                 270

Asn Tyr Phe Val Gly Arg His Gly Gln Thr Pro Val Ile Glu Ser Ile
        275                 280                 285

Glu Phe Glu Glu Asp Ser Val Glu Val Lys Glu Pro Arg Val His Glu
    290                 295                 300

Asp Val Glu Ile Gly Ser Leu Thr Phe Lys Glu Asn Arg Ser Thr Leu
305                 310                 315                 320

Tyr Arg Pro Gly Glu Glu Ala Leu Asn Thr Ser Gln Asp Asn Thr Ser
                325                 330                 335

Tyr Leu Ala Lys Ile Asn Val Tyr Asn Asp Val His Arg Leu Gly Leu
            340                 345                 350

Ala Tyr Arg His Tyr His Ser Arg Phe Gly Glu Ile Met Ser Ser Ile
        355                 360                 365

Leu Asn Phe Arg Ala Tyr Gly Ala Leu Gln Gly Glu Gly Thr Glu Val
    370                 375                 380

Lys Val Asp Ser Tyr His Ala Asn Tyr Ser Tyr Asn Pro Thr Thr Pro
385                 390                 395                 400

Tyr Val Asn Leu Ser Val Asn Ala Tyr Phe Thr Asp Ser Asp Ser Ser
                405                 410                 415

Asn Phe Thr Pro Phe Ile Glu Glu Tyr Gly Tyr Ser Leu Ser Ser Arg
            420                 425                 430

His Ala His Phe Leu Val Ser Lys Gln Lys Gly Leu Ser Ile Glu Asn
        435                 440                 445

Thr Ser Ile Phe Gln Leu Asn Asp Lys Pro Phe Thr Leu Lys Tyr Gly
    450                 455                 460

Leu Ala His Ser Tyr Glu Arg Ile Tyr Gln Pro Arg Asn Ala Gln Ala
465                 470                 475                 480
```

-continued

```
Arg Val Arg Ala Lys Gly Tyr Pro Glu Asp Ala Ile Gly Pro Leu Tyr
                485                 490                 495

Ile Arg Asp Gly Lys Arg Lys Glu Trp Ser Ala Phe Val Ala Ala Asn
            500                 505                 510

Tyr Pro Ile Thr Ser Trp Leu Lys Ala Asp Ile Gly Leu Arg Tyr Leu
        515                 520                 525

Gln Ser Thr Ile Tyr Asp Tyr Ile Val Arg Thr Glu Arg Val Asn Ile
    530                 535                 540

Gly Gly Ala Leu Val Pro Asn Pro Asn Gly Ser Gly Asn Ile Trp Val
545                 550                 555                 560

Glu Lys Tyr Lys Asp Val Val His Lys Gln Ala Pro Val Lys Asn Lys
                565                 570                 575

Gly Met Ser Pro Ile Val Met Phe Thr Phe Glu Pro Ile Asn Gly Val
            580                 585                 590

Gln Ile Tyr Thr Lys Tyr Ala Glu Ala Leu Arg Ser Pro Ser Leu Phe
        595                 600                 605

Gln Ala Thr Lys Gly Trp Ser Met Ser Ala Thr Glu Asp Asn Leu Glu
    610                 615                 620

Gln Leu Arg Pro Glu Arg Ala Lys Asn Trp Glu Ala Gly Ile Asn Leu
625                 630                 635                 640

Phe Tyr Glu Asn Leu Gly Gly Lys Asp Asn Ile Leu Gly Phe Lys Leu
                645                 650                 655

Ala Tyr Phe Asn Asn Arg Ile Lys Asp Tyr Leu Thr Arg Ser Tyr Ser
            660                 665                 670

Pro Lys Asp Lys Val Thr Gln Thr Ile Asn Ile Gln Ser Ala Gln Phe
        675                 680                 685

Lys Gly Ile Glu Leu Ser Ala Tyr Tyr Asp Met Gly Lys Phe Tyr Ala
    690                 695                 700

Lys Leu Ala Gly Thr Tyr Tyr Thr Lys Thr Lys Phe Cys Leu Thr Ala
705                 710                 715                 720

Glu Gln Ala Gly Lys Gly Glu Gln Cys Asn Ser Gly Tyr Val Tyr Arg
                725                 730                 735

Ser Asn Leu Asn Asn Ala Val Pro Pro Arg Leu Asn Leu His Ala Thr
            740                 745                 750

Leu Gly Thr Arg Leu Phe Glu Gln Lys Leu Asp Ile Gly Ala Arg Tyr
        755                 760                 765

Ser Tyr Tyr Ser Lys Arg Leu Val Pro Val Leu Ser Ala Glu Arg Phe
    770                 775                 780

Val Asn Thr Ser Ser Ile Glu Trp Ala Pro Tyr Ser Leu Val Asp Leu
785                 790                 795                 800

Tyr Ala Asn Tyr Asn Val Ser Asn Asn Leu Lys Leu Thr Met Thr Met
                805                 810                 815

Asp Asn Val Phe Asn Arg Tyr Tyr Leu Asp Ile Asn Asn Met Gly Leu
            820                 825                 830

Asn Thr Ala Pro Gly Arg Thr Leu His Leu Gly Leu Glu Tyr Arg Phe
        835                 840                 845
```

<210> SEQ ID NO 32
<211> LENGTH: 848
<212> TYPE: PRT
<213> ORGANISM: Pasteurella multocida subsp. multocida

<400> SEQUENCE: 32

```
Met Gln Lys Gln Gln Pro Tyr Pro Ile His Leu Gly Ile Phe Leu Met
```

-continued

```
1               5                   10                  15

Leu Gly Leu Pro Thr Trp Ala Phe Ser Gln Ala Asn Leu Glu Lys Ser
            20                  25                  30

Thr Ile Asn Lys Leu Glu Thr Ile Leu Val Asn Glu Ser Glu Glu Lys
        35                  40                  45

Asn Lys Phe Asp Glu Asn Leu Ile Lys Thr Tyr Leu Ser Ser Gly Ser
    50                  55                  60

Tyr Ser Tyr Leu Ser Gln Ser Asp Ile Ser Thr Phe Arg Gly Ser Ser
65                  70                  75                  80

Val Gly Asp Phe Leu Ser Gly Val Pro Gly Val Ile Val Gly Asn Lys
                85                  90                  95

Arg Asn Ser Gly Ala Leu Ser Val Asn Ile Arg Gly Ile Ala Asn Glu
            100                 105                 110

Asn Arg Val Pro Val Trp Ile Asp Lys Gly Leu Gln Ser Val Pro Ser
        115                 120                 125

Tyr Gln Gly Tyr Ala Gly Ser Ser Thr Arg Thr Tyr Leu Asp Pro Asp
    130                 135                 140

Leu Ile Ser Gln Val Glu Ile Glu Lys Gly Pro Ser Leu Gln Met Asp
145                 150                 155                 160

Ala Thr Gly Ala Thr Gly Gly Val Val Arg Val Glu Thr Leu Arg Trp
                165                 170                 175

Gln Asp Ile Ile Pro Gln Gly Lys Asn Trp Gly Val Arg Leu Lys Leu
            180                 185                 190

Gly Thr Met Ala Asn Thr Val Ser Pro Pro Pro Tyr Tyr Thr Arg Gly
        195                 200                 205

Gly Tyr Gln Thr Lys Tyr Ile Ser Lys Cys Leu Ser Asn His Thr Gly
    210                 215                 220

Leu Cys Gln Thr Gln Thr Tyr Ala Pro Asn Ala Arg Tyr Ser Ser His
225                 230                 235                 240

Gly Phe Asp Leu Asn Ala Tyr Asn Tyr Ser Leu Ala Phe Ala Asn Lys
                245                 250                 255

Trp Gln Asn Ala Asp Leu Val Leu Ala Tyr Ala Lys Arg Lys Gln Gly
            260                 265                 270

Asn Tyr Phe Val Gly Arg His Gly Gln Thr Pro Val Ile Glu Ser Ile
        275                 280                 285

Glu Phe Glu Glu Asp Ser Val Glu Val Lys Glu Pro Arg Val His Glu
    290                 295                 300

Asp Val Glu Ile Gly Ser Leu Thr Phe Lys Glu Asn Arg Ser Thr Leu
305                 310                 315                 320

Tyr Arg Pro Gly Glu Glu Ala Leu Asn Thr Ser Gln Asp Asn Thr Ser
                325                 330                 335

Tyr Leu Ala Lys Ile Asn Val Tyr Asn Asp Val His Arg Leu Gly Leu
            340                 345                 350

Ala Tyr Arg His Tyr His Ser Arg Phe Gly Glu Ile Met Ser Ser Ile
        355                 360                 365

Leu Asn Phe Arg Ala Tyr Gly Ala Leu Gln Gly Glu Gly Thr Glu Val
    370                 375                 380

Lys Val Asp Ser Tyr His Ala Asn Tyr Ser Tyr Asn Ser Thr Thr Pro
385                 390                 395                 400

Tyr Val Asn Leu Ser Val Asn Ala Tyr Phe Thr Asp Ser Asp Ser Ser
                405                 410                 415

Asn Phe Thr Pro Phe Ile Glu Glu Tyr Gly Tyr Ser Leu Ser Ser Arg
            420                 425                 430
```

-continued

```
His Ala His Phe Leu Val Ser Lys Gln Lys Gly Leu Ser Ile Glu Asn
        435                 440                 445

Thr Ser Ile Phe Gln Leu Asn Asp Lys Pro Phe Thr Leu Lys Tyr Gly
    450                 455                 460

Leu Ala His Ser Tyr Glu Arg Ile Tyr Gln Pro Arg Asn Ala Gln Ala
465                 470                 475                 480

Arg Val Arg Ala Lys Gly Tyr Pro Glu Asp Ala Ile Gly Pro Leu Tyr
                485                 490                 495

Ile Arg Asp Gly Lys Arg Lys Glu Trp Ser Ala Phe Val Ala Ala Asn
            500                 505                 510

Tyr Pro Ile Thr Ser Trp Leu Lys Ala Asp Ile Gly Leu Arg Tyr Leu
        515                 520                 525

Gln Ser Thr Ile Tyr Asp Tyr Ile Val Arg Thr Glu Arg Val Asn Ile
    530                 535                 540

Gly Gly Ala Leu Val Pro Asn Pro Asn Gly Ser Gly Asn Ile Trp Val
545                 550                 555                 560

Glu Lys Tyr Lys Asp Val Val His Lys Gln Ala Pro Val Lys Asn Lys
                565                 570                 575

Gly Met Ser Pro Ile Val Met Phe Thr Phe Glu Pro Ile Asn Gly Val
            580                 585                 590

Gln Ile Tyr Thr Lys Tyr Ala Glu Ala Leu Arg Ser Pro Ser Leu Phe
        595                 600                 605

Gln Ala Thr Lys Gly Trp Ser Met Ser Ala Thr Ala Asp Asn Leu Glu
    610                 615                 620

Gln Leu Arg Pro Glu Arg Ala Lys Asn Trp Glu Ala Gly Ile Asn Leu
625                 630                 635                 640

Phe Tyr Glu Asn Leu Gly Gly Lys Asp Asn Ile Leu Gly Phe Lys Leu
                645                 650                 655

Ala Tyr Phe Asn Asn Arg Ile Lys Asp Tyr Leu Thr Arg Ser Tyr Ser
            660                 665                 670

Pro Lys Asp Lys Val Thr Gln Thr Ile Asn Ile Gln Ser Ala Gln Phe
        675                 680                 685

Lys Gly Ile Glu Leu Ser Ala Tyr Tyr Asp Met Gly Lys Phe Tyr Ala
    690                 695                 700

Lys Leu Ala Gly Thr Tyr Tyr Thr Lys Thr Lys Phe Cys Leu Thr Ala
705                 710                 715                 720

Glu Gln Ala Gly Lys Gly Glu Gln Cys Asn Ser Gly Tyr Val Tyr Arg
                725                 730                 735

Ser Asn Leu Asn Asn Ala Val Pro Pro Arg Leu Asn Leu His Ala Thr
            740                 745                 750

Leu Gly Thr Arg Leu Phe Glu Gln Lys Leu Asp Ile Gly Ala Arg Tyr
        755                 760                 765

Ser Tyr Tyr Ser Lys Arg Leu Val Pro Val Leu Ser Ala Glu Arg Phe
    770                 775                 780

Val Asn Thr Ser Ser Ile Glu Trp Ala Pro Tyr Ser Leu Val Asp Leu
785                 790                 795                 800

Tyr Ala Asn Tyr Asn Val Ser Asn Asn Leu Lys Leu Thr Met Thr Met
                805                 810                 815

Asp Asn Val Phe Asn Arg Tyr Tyr Leu Asp Ile Asn Asn Thr Gly Leu
            820                 825                 830

Asn Thr Ala Pro Gly Arg Thr Leu His Leu Gly Leu Glu Tyr Arg Phe
        835                 840                 845
```

<210> SEQ ID NO 33
<211> LENGTH: 848
<212> TYPE: PRT
<213> ORGANISM: Pasteurella multocida subsp. gallicida str. Anand1_poultry

<400> SEQUENCE: 33

```
Met Gln Lys Gln Gln Pro Tyr Pro Ile His Leu Gly Ile Phe Leu Met
1               5                   10                  15

Leu Gly Leu Pro Thr Trp Ala Phe Ser Gln Ala Asn Leu Glu Lys Ser
            20                  25                  30

Thr Ile Asn Lys Leu Glu Thr Ile Leu Val Asn Glu Ser Glu Glu Lys
        35                  40                  45

Asn Lys Phe Asp Glu Asn Leu Ile Lys Thr Tyr Leu Ser Ser Gly Ser
    50                  55                  60

Tyr Ser Tyr Leu Ser Gln Ser Asp Ile Ser Thr Phe Arg Gly Ser Ser
65                  70                  75                  80

Val Gly Asp Phe Leu Ser Gly Val Pro Gly Val Ile Val Gly Asn Lys
                85                  90                  95

Arg Asn Ser Gly Ala Leu Ser Val Asn Ile Arg Gly Ile Ala Asn Glu
            100                 105                 110

Asn Arg Val Pro Val Trp Ile Asp Lys Gly Leu Gln Ser Val Pro Ser
        115                 120                 125

Tyr Gln Gly Tyr Ala Gly Ser Ser Thr Arg Thr Tyr Leu Asp Pro Asp
    130                 135                 140

Leu Ile Ser Gln Val Glu Ile Glu Lys Gly Pro Ser Leu Gln Met Asp
145                 150                 155                 160

Ala Thr Gly Ala Thr Gly Gly Val Val Arg Val Asp Thr Leu Arg Trp
                165                 170                 175

Gln Asp Ile Ile Pro Gln Gly Lys Asn Trp Gly Val Arg Leu Lys Leu
            180                 185                 190

Gly Thr Met Thr Asn Thr Val Ser Pro Pro Pro Tyr Tyr Thr Arg Gly
        195                 200                 205

Gly Tyr Gln Thr Lys Tyr Ile Ser Lys Cys Leu Ser Asn Asp Thr Gly
    210                 215                 220

Leu Cys Gln Thr Gln Thr Tyr Ala Pro Asn Ala Arg Tyr Ser Ser His
225                 230                 235                 240

Gly Phe Asp Leu Asn Ala Tyr Asn Tyr Ser Leu Ala Phe Ala Asn Lys
                245                 250                 255

Trp Gln Asn Ala Asp Leu Val Leu Ala Tyr Ala Lys Arg Lys Gln Gly
            260                 265                 270

Asn Tyr Phe Val Gly Arg His Gly Gln Thr Pro Val Ile Glu Ser Ile
        275                 280                 285

Lys Phe Glu Glu Asp Ser Val Glu Val Lys Glu Pro Arg Val His Glu
    290                 295                 300

Asp Val Glu Ile Gly Ser Leu Thr Phe Lys Glu Asn Arg Ser Thr Leu
305                 310                 315                 320

Tyr Arg Pro Gly Glu Glu Ala Leu Asn Thr Ser Gln Asp Asn Thr Ser
                325                 330                 335

Tyr Leu Ala Lys Ile Asn Val Tyr Asn Asp Val His Arg Leu Gly Leu
            340                 345                 350

Ala Tyr Arg His Tyr His Ser Arg Phe Gly Glu Ile Met Ser Ser Ile
        355                 360                 365

Leu Asn Phe Arg Ala Tyr Gly Ala Leu Gln Gly Glu Gly Thr Glu Val
```

-continued

```
    370                 375                 380

Lys Val Asp Ser Tyr His Ala Asn Tyr Ser Tyr Asn Pro Thr Thr Pro
385                 390                 395                 400

Tyr Val Asn Leu Asn Val Asn Ala Tyr Phe Thr Asp Ser Asp Ser Ser
                405                 410                 415

Asn Phe Thr Pro Phe Ile Glu Glu Tyr Gly Tyr Ser Leu Ser Ser Arg
                420                 425                 430

His Ala His Phe Leu Val Ser Lys Gln Lys Gly Leu Ser Ile Glu Asn
        435                 440                 445

Thr Ser Ile Phe Gln Leu Asn Asp Lys Pro Phe Thr Leu Lys Tyr Gly
    450                 455                 460

Leu Ala His Ser Tyr Glu Arg Ile Tyr Gln Pro Arg Asn Ala Gln Ala
465                 470                 475                 480

Arg Val Arg Ala Lys Gly Tyr Pro Glu Asp Ala Ile Gly Pro Leu Tyr
                485                 490                 495

Ile Arg Asp Gly Lys Arg Lys Glu Trp Ser Ala Phe Val Ala Ala Asn
                500                 505                 510

Tyr Pro Ile Asn Ser Trp Leu Lys Ala Asp Ile Gly Leu Arg Tyr Leu
        515                 520                 525

Gln Ser Thr Ile Tyr Asp Tyr Ile Val Arg Thr Glu Arg Val Asn Ile
    530                 535                 540

Gly Gly Ala Leu Val Pro Asn Pro Asn Gly Pro Gly Asn Ile Trp Val
545                 550                 555                 560

Glu Lys Tyr Lys Asp Val Val His Lys Gln Ala Pro Val Lys Asn Lys
                565                 570                 575

Gly Met Ser Pro Ile Val Met Leu Thr Phe Glu Pro Ile Asn Gly Val
                580                 585                 590

Gln Ile Tyr Thr Lys Tyr Ala Glu Ala Leu Arg Ser Pro Ser Leu Phe
        595                 600                 605

Gln Ala Thr Lys Gly Trp Ser Met Ser Ala Thr Ala Asp Asn Leu Glu
    610                 615                 620

Gln Leu Arg Pro Glu Arg Ala Lys Asn Trp Glu Ala Gly Ile Asn Leu
625                 630                 635                 640

Phe Tyr Glu Asn Leu Gly Gly Lys Asp Asn Ile Leu Gly Phe Lys Leu
                645                 650                 655

Ala Tyr Phe Asn Asn Arg Ile Lys Asp Tyr Leu Thr Arg Ser Tyr Ser
                660                 665                 670

Pro Lys Asp Lys Val Thr Gln Thr Ile Asn Ile Gln Ser Ala Gln Phe
        675                 680                 685

Lys Gly Ile Glu Leu Ser Ala Tyr Tyr Asp Met Gly Lys Phe Tyr Thr
    690                 695                 700

Lys Leu Ala Gly Thr Tyr Tyr Thr Lys Thr Lys Phe Cys Leu Thr Ala
705                 710                 715                 720

Glu Gln Ala Gly Lys Gly Glu Gln Cys Asn Ser Gly Tyr Val Tyr Arg
                725                 730                 735

Ser Asn Leu Asn Asn Ala Val Pro Pro Arg Leu Asn Leu His Ala Thr
                740                 745                 750

Leu Gly Thr Arg Leu Phe Glu Gln Lys Leu Asp Ile Gly Ala Arg Tyr
        755                 760                 765

Ser Tyr Tyr Ser Lys Arg Leu Val Pro Val Leu Ser Ala Glu Arg Phe
    770                 775                 780

Val Asn Thr Ser Ser Ile Glu Trp Ala Pro Tyr Ser Leu Val Asp Leu
785                 790                 795                 800
```

Tyr Ala Asn Tyr Asn Val Ser Asn Asn Leu Lys Leu Thr Met Thr Met
805 810 815

Asp Asn Val Phe Asn Arg Tyr Tyr Leu Asp Ile Asn Asn Met Gly Leu
820 825 830

Asn Thr Ala Pro Gly Arg Thr Leu His Leu Gly Leu Glu Tyr Arg Phe
835 840 845

<210> SEQ ID NO 34
<211> LENGTH: 848
<212> TYPE: PRT
<213> ORGANISM: Pasteurella multocida

<400> SEQUENCE: 34

Met Gln Lys Gln Gln Pro Tyr Pro Ile His Leu Gly Ile Phe Leu Met
1 5 10 15

Leu Gly Leu Pro Thr Trp Ala Phe Ser Gln Ala Asn Leu Glu Lys Ser
20 25 30

Thr Ile Asn Lys Leu Glu Thr Ile Leu Val Asn Glu Ser Glu Glu Lys
35 40 45

Asn Lys Phe Asp Glu Asn Leu Ile Lys Thr Tyr Leu Ser Ser Gly Ser
50 55 60

Tyr Ser Tyr Leu Ser Gln Ser Asp Ile Ser Thr Phe Arg Gly Ser Ser
65 70 75 80

Val Gly Asp Phe Leu Ser Gly Val Pro Gly Val Ile Ala Gly Asn Lys
85 90 95

Arg Asn Ser Gly Ala Leu Ser Val Asn Ile Arg Gly Ile Ala Asn Glu
100 105 110

Asn Arg Val Pro Val Trp Ile Asp Lys Gly Leu Gln Ser Val Pro Ser
115 120 125

Tyr Gln Gly Tyr Ala Gly Ser Ser Thr Arg Thr Tyr Leu Asp Pro Asp
130 135 140

Leu Ile Ser Gln Val Glu Ile Glu Lys Gly Pro Ser Leu Gln Met Asp
145 150 155 160

Ala Thr Gly Ala Thr Gly Gly Val Val Arg Val Glu Thr Leu Arg Trp
165 170 175

Gln Asp Ile Ile Pro Gln Gly Lys Asn Trp Gly Val Arg Leu Lys Leu
180 185 190

Gly Thr Met Thr Asn Thr Val Ser Pro Pro Pro Tyr Tyr Thr Arg Gly
195 200 205

Gly Tyr Gln Thr Lys Tyr Ile Ser Lys Cys Leu Ser Asn Asp Thr Gly
210 215 220

Leu Cys Gln Thr Gln Thr Tyr Ala Pro Asn Ala Arg Tyr Ser Ser His
225 230 235 240

Gly Phe Asp Leu Asn Ala Tyr Asn Tyr Ser Leu Ala Phe Ala Asn Lys
245 250 255

Trp Gln Asn Ala Asp Leu Val Leu Ala Tyr Ala Lys Arg Lys Gln Gly
260 265 270

Asn Tyr Phe Val Gly Arg His Gly Gln Thr Pro Val Ile Glu Ser Ile
275 280 285

Glu Phe Glu Glu Asp Ser Val Glu Val Lys Glu Pro Arg Val His Glu
290 295 300

Glu Val Glu Ile Gly Ser Leu Thr Phe Lys Glu Asn Arg Ser Thr Leu
305 310 315 320

Tyr Arg Pro Gly Glu Glu Ala Leu Asn Thr Ser Gln Asp Asn Thr Ser

```
                325                 330                 335

Tyr Leu Ala Lys Ile Asn Val Tyr Asn Asp Val His Arg Leu Gly Leu
            340                 345                 350

Ala Tyr Arg His Tyr His Ser Arg Phe Gly Glu Ile Met Ser Ser Ile
        355                 360                 365

Leu Asn Phe Arg Ala Tyr Gly Ala Leu Gln Gly Glu Gly Thr Glu Val
    370                 375                 380

Lys Val Asp Ser Tyr His Ala Asn Tyr Ser Tyr Asn Pro Thr Thr Pro
385                 390                 395                 400

Tyr Val Asn Leu Asn Val Asn Ala Tyr Phe Thr Asp Ser Asp Ser Ser
                405                 410                 415

Asn Phe Thr Pro Phe Ile Glu Glu Tyr Gly Tyr Ser Leu Ser Ser Arg
            420                 425                 430

His Ala His Phe Leu Val Ser Lys Gln Lys Gly Leu Ser Ile Glu Asn
        435                 440                 445

Thr Ser Ile Phe Gln Leu Asn Asp Lys Pro Phe Thr Leu Lys Tyr Gly
    450                 455                 460

Leu Ala His Ser Tyr Glu Arg Ile Tyr Gln Pro Arg Asn Ala Gln Ala
465                 470                 475                 480

Arg Val Arg Ala Lys Gly Tyr Pro Glu Asp Ala Ile Gly Pro Leu Tyr
                485                 490                 495

Ile Arg Asp Gly Lys Arg Lys Glu Trp Ser Ala Phe Val Ala Ala Asn
            500                 505                 510

Tyr Pro Ile Thr Ser Trp Leu Lys Ala Asp Ile Gly Leu Arg Tyr Leu
        515                 520                 525

Gln Ser Thr Ile Tyr Asp Tyr Ile Val Arg Thr Glu Arg Val Asn Ile
    530                 535                 540

Gly Gly Ala Leu Val Pro Asn Pro Asn Gly Ser Gly Asn Ile Trp Val
545                 550                 555                 560

Glu Lys Tyr Lys Asp Val Val His Lys Gln Ala Pro Val Lys Asn Lys
                565                 570                 575

Gly Met Ser Pro Ile Val Met Leu Thr Phe Glu Pro Ile Asn Gly Val
            580                 585                 590

Gln Ile Tyr Thr Lys Tyr Ala Glu Ala Leu Arg Ser Pro Ser Leu Phe
        595                 600                 605

Gln Ala Thr Lys Gly Trp Ser Met Ser Ala Thr Ala Asp Asn Leu Glu
    610                 615                 620

Gln Leu Arg Pro Glu Arg Ala Lys Asn Trp Glu Ala Gly Ile Asn Leu
625                 630                 635                 640

Phe Tyr Glu Asn Leu Gly Gly Lys Asp Asn Ile Leu Gly Phe Lys Leu
                645                 650                 655

Ala Tyr Phe Asn Asn Arg Ile Lys Asp Tyr Leu Thr Arg Ser Tyr Ser
            660                 665                 670

Pro Lys Asp Lys Val Thr Gln Thr Ile Asn Ile Gln Ser Ala Gln Phe
        675                 680                 685

Lys Gly Ile Glu Leu Ser Ala Tyr Tyr Asp Met Gly Lys Phe Tyr Thr
    690                 695                 700

Lys Leu Ala Gly Thr Tyr Tyr Thr Lys Thr Lys Phe Cys Leu Thr Ala
705                 710                 715                 720

Glu Gln Ala Gly Lys Gly Glu Gln Cys Asn Ser Gly Tyr Val Tyr Arg
                725                 730                 735

Ser Asn Leu Asn Asn Ala Val Pro Pro Arg Leu Asn Leu His Ala Thr
            740                 745                 750
```

```
Leu Gly Thr Arg Leu Phe Glu Gln Lys Leu Asp Ile Gly Ala Arg Tyr
        755                 760                 765

Ser Tyr Tyr Ser Lys Arg Leu Val Pro Val Leu Ser Ala Glu Arg Phe
    770                 775                 780

Val Asn Thr Ser Ser Ile Glu Trp Ala Pro Tyr Ser Leu Val Asp Leu
785                 790                 795                 800

Tyr Ala Asn Tyr Asn Val Ser Asn Asn Leu Lys Leu Thr Met Thr Met
                805                 810                 815

Asp Asn Val Phe Asn Arg Tyr Tyr Leu Asp Ile Asn Asn Met Gly Leu
            820                 825                 830

Asn Thr Ala Pro Gly Arg Thr Leu His Leu Gly Leu Glu Tyr Arg Phe
        835                 840                 845


<210> SEQ ID NO 35
<211> LENGTH: 784
<212> TYPE: PRT
<213> ORGANISM: Pasteurella multocida

<400> SEQUENCE: 35

Met Lys Tyr Pro Leu Ser Tyr Lys Asn Ile Ala Arg Ser Ile Pro Phe
1               5                   10                  15

Leu Ser Phe Ile Ala Phe Pro Leu Tyr Ala Gln Glu Thr Thr Glu Leu
            20                  25                  30

Glu Gln Ile Thr Val Gln Glu Ser Ala Thr Ala Glu Val Asn Lys Thr
        35                  40                  45

Ser Pro Thr Val Ile Ser Lys Ser Ala Thr Thr Ile Gln Asn Lys Met
    50                  55                  60

Ile Arg Asp Thr Arg Asp Leu Val Arg Tyr Thr Thr Asp Val Gly Ile
65                  70                  75                  80

Ser Asp Asn Gly Arg Phe Leu Lys Gly Phe Ala Met Arg Gly Val Glu
                85                  90                  95

Asp Asn Arg Val Gly Ile Ser Ile Asp Gly Val Ser Leu Pro Asp Ser
            100                 105                 110

Glu Glu Asn Ser Leu Tyr Ala Arg Tyr Gly Asn Phe Asn Asn Ser Arg
        115                 120                 125

Leu Ser Ile Asp Pro Glu Leu Ile Gln Thr Ile Asp Ile Val Arg Gly
    130                 135                 140

Ser Asp Ser Phe Asn Ala Gly Ser Gly Ser Leu Gly Gly Gly Val Asn
145                 150                 155                 160

Tyr Asn Thr Leu Asp Pro Gln His Ile Val Lys Ala Gly Asn Ser Val
                165                 170                 175

Gly Ala Leu Leu Arg Gly Ser Tyr Ala Ser Lys Asn Arg Glu Trp Val
            180                 185                 190

Arg Thr Leu Gly Ile Gly Tyr Val Gly Glu Lys Phe Asp Ala Leu Leu
        195                 200                 205

Met Tyr Ser Gln Arg Thr Gly His Glu Phe Lys Ser Arg Gly Ser Gly
    210                 215                 220

Pro Glu Phe Arg Tyr Ser Ser Ser Gln His Pro Asp Pro Val Thr Gln
225                 230                 235                 240

Arg Phe His Asn Tyr Leu Ala Lys Met Asn Tyr Gln Ile Asn Asp Asn
                245                 250                 255

Gln Arg Ile Gly Leu Thr Leu Asn Gly Gln Thr Gly Gly Arg Tyr Ile
            260                 265                 270

Asp Glu Arg Ser Tyr Thr Leu Met Gly Ser Gln Trp Arg Glu Ala Asp
```

-continued

```
        275                 280                 285

Asp Gln Asn Glu Arg Leu Asn Ala Asn Leu Tyr Tyr Ile Tyr Ala Pro
    290                 295                 300

Ser Thr Gly Trp Leu Ala Tyr Ser Lys Phe Asp Leu Asp Tyr Gln Lys
305                 310                 315                 320

Thr Asp Leu Ala Ala Val Asn Tyr Lys Gly Gly Arg His Phe Thr Thr
                325                 330                 335

Asp Ala Lys Glu Leu Asn Glu Ile Tyr Asp Arg Arg Met Lys Thr Val
            340                 345                 350

Phe Thr Arg Gly Ser Val Glu Leu Asn Ala Gln Pro Val His Phe Tyr
        355                 360                 365

Gly Glu His Thr Leu Thr Ile Lys Gly Tyr Val Ser Gln Arg Asp Phe
    370                 375                 380

Lys Asn Ile Asn Gln Asp Arg Ile Gly Ile Gly Thr Asn Tyr Asp Thr
385                 390                 395                 400

Gln Tyr His Tyr Thr Ile Gln Tyr Pro Ile Arg Thr Lys Gln Tyr Gly
                405                 410                 415

Leu Ser Leu Lys Asp His Val Arg Trp Asn Asp Thr Phe Ser Ser His
            420                 425                 430

Leu Gly Leu Arg Tyr Asp His Thr Lys Leu Lys Pro Lys Glu Leu Asn
        435                 440                 445

Ala Pro Cys Ser Lys Ala Cys Leu Glu Glu Gly Lys Pro Lys Pro Thr
    450                 455                 460

Arg Phe Ser Thr Val Ser Thr Phe Ala Gly Leu Glu Ala Gln Leu Ser
465                 470                 475                 480

Pro Ser Trp Met Leu Gly Tyr Asn Ile Ser Thr Gly Tyr Arg Val Pro
                485                 490                 495

Thr Ala Ser Glu Met Phe Phe Ser Phe Thr Asn Ala Tyr Gly Thr Trp
            500                 505                 510

Lys Ser Asn Pro Ser Leu Lys Pro Glu Lys Ser Ile Asn His Thr Leu
        515                 520                 525

Ser Leu Lys Gly Asn Ser Glu Lys Gly Leu Leu Asp Leu Thr Leu Tyr
    530                 535                 540

Gln Thr Asn Tyr Arg His Phe Leu Phe Glu Gln Glu Ser Leu Ile Gln
545                 550                 555                 560

Arg Thr Glu Ile Arg Tyr Gly Gln Pro Tyr Thr Tyr Gln Ser Gln Glu
                565                 570                 575

Gln Gln Met Val Asn Leu Asp Lys Ala Lys Ile Tyr Gly Val Glu Leu
            580                 585                 590

Lys Thr His Val Asn Leu Asp Gln Met Ile Ala Val Ile Pro Gln Gly
        595                 600                 605

Phe Lys Phe Tyr Ala Ala Leu Gly Tyr Ser Lys Gly Lys Leu Ser Asn
    610                 615                 620

Asn Ala Ser Leu Leu Ser Ile Gln Pro Leu Lys Ile Ile Leu Gly Leu
625                 630                 635                 640

Asp Tyr Glu Ala Thr Asn Gly Lys Trp Ala Ile Phe Asn Arg Leu Thr
                645                 650                 655

Tyr Leu Gly Glu Lys Arg Ala Ser Asp Ala Lys Val Tyr Glu Ile Lys
            660                 665                 670

Arg Arg Cys Thr Glu Phe Val Thr Glu Thr Asp Pro Trp Ser Gly Glu
        675                 680                 685

Gln Ile Thr His Cys Lys Lys Arg Glu Leu Tyr Pro Asp Leu Ser Thr
    690                 695                 700
```

```
Tyr Lys Tyr Leu Asn Lys Ser Ala Phe Val Phe Asp Thr Phe Gly Tyr
705                 710                 715                 720

Tyr Lys Ile Thr Asp Asp Ile Thr Phe Arg Ala Gly Ile Tyr Asn Leu
                725                 730                 735

Phe Asn Lys Lys Tyr His Thr Trp Asp Ala Leu Arg Gly Ile Asn Ala
            740                 745                 750

Asn Ser Thr Leu Asn Ser Val Asp Arg Glu Gly Lys Gly Leu Gln Arg
        755                 760                 765

Phe Tyr Ala Pro Gly Arg Asn Tyr Ala Ala Ser Leu Glu Ile Arg Phe
    770                 775                 780


<210> SEQ ID NO 36
<211> LENGTH: 784
<212> TYPE: PRT
<213> ORGANISM: Pasteurella multocida

<400> SEQUENCE: 36

Met Lys Tyr Pro Leu Ser Tyr Lys Asn Ile Ala Arg Ser Ile Pro Phe
1               5                   10                  15

Leu Ser Phe Ile Ala Phe Pro Leu Tyr Ala Gln Glu Thr Thr Glu Leu
            20                  25                  30

Glu Gln Ile Thr Val Gln Glu Ser Ala Thr Ala Glu Val Asn Lys Thr
        35                  40                  45

Ser Pro Thr Val Ile Ser Lys Ser Ala Thr Thr Ile Gln Asn Glu Met
    50                  55                  60

Ile Arg Asp Thr Arg Asp Leu Val Arg Tyr Thr Thr Asp Val Gly Ile
65                  70                  75                  80

Ser Asp Asn Gly Arg Phe Leu Lys Gly Phe Ala Met Arg Gly Val Glu
                85                  90                  95

Asp Asn Arg Val Gly Ile Ser Ile Asp Asp Val Ser Leu Pro Asp Ser
            100                 105                 110

Glu Glu Asn Ser Leu Tyr Ala Arg Tyr Gly Asn Phe Asn Asn Ser Arg
        115                 120                 125

Leu Ser Ile Asp Pro Glu Leu Ile Gln Thr Ile Asp Ile Val Arg Gly
    130                 135                 140

Ser Asp Ser Phe Asn Ala Gly Ser Gly Ser Leu Gly Gly Gly Val Asn
145                 150                 155                 160

Tyr Asn Thr Leu Asp Pro Gln His Ile Val Lys Ala Gly Asn Ser Val
                165                 170                 175

Gly Ala Leu Leu Arg Gly Ser Tyr Ala Ser Lys Asn Arg Glu Trp Val
            180                 185                 190

Arg Thr Leu Gly Ile Gly Tyr Val Gly Glu Lys Phe Asp Ala Leu Leu
        195                 200                 205

Met Tyr Ser Gln Arg Thr Gly His Glu Phe Lys Ser Arg Gly Ser Gly
    210                 215                 220

Pro Glu Phe Arg Tyr Ser Ser Ser Gln His Pro Asp Pro Val Thr Gln
225                 230                 235                 240

Arg Phe His Asn Tyr Leu Ala Lys Met Asn Tyr Gln Ile Asn Asp Asn
                245                 250                 255

Gln Arg Ile Gly Leu Thr Leu Asn Gly Gln Thr Gly Gly Arg Tyr Ile
            260                 265                 270

Asp Glu Arg Ser Tyr Thr Leu Met Gly Ser Gln Trp Arg Glu Ala Asp
        275                 280                 285

Asp Gln Asn Glu Arg Leu Asn Ala Asn Leu Tyr Tyr Ile Tyr Ala Pro
```

-continued

```
    290                 295                 300

Ser Thr Gly Trp Leu Ala Tyr Ser Lys Phe Asp Leu Asp Tyr Gln Lys
305                 310                 315                 320

Thr Asp Leu Ala Ala Val Asn Tyr Lys Gly Gly Arg His Phe Thr Thr
                325                 330                 335

Asp Ala Lys Glu Leu Asn Glu Ile Tyr Asp Arg Arg Met Lys Thr Val
            340                 345                 350

Phe Thr Arg Gly Ser Val Glu Leu Asn Ala Gln Pro Val His Phe Tyr
        355                 360                 365

Gly Glu His Thr Leu Thr Ile Lys Gly Tyr Val Ser Gln Arg Asp Phe
    370                 375                 380

Lys Asn Ile Asn Gln Asp Arg Ile Gly Ile Gly Thr Asn Tyr Asp Thr
385                 390                 395                 400

Gln Tyr His Tyr Thr Ile Gln Tyr Pro Ile Arg Thr Lys Gln Tyr Gly
                405                 410                 415

Leu Ser Leu Lys Asp His Val Arg Trp Asn Asp Thr Phe Ser Ser His
            420                 425                 430

Leu Gly Leu Arg Tyr Asp His Thr Lys Leu Lys Pro Lys Glu Leu Asn
        435                 440                 445

Ala Pro Cys Ser Asn Ala Cys Leu Glu Glu Gly Lys Pro Lys Pro Thr
    450                 455                 460

Arg Phe Ser Thr Val Ser Thr Phe Ala Gly Leu Glu Ala Gln Leu Ser
465                 470                 475                 480

Pro Ser Trp Met Leu Gly Tyr Asn Ile Ser Thr Gly Tyr Arg Val Pro
                485                 490                 495

Thr Ala Ser Glu Met Phe Phe Ser Phe Thr Asn Ala Tyr Gly Thr Trp
            500                 505                 510

Lys Ser Asn Pro Ser Leu Lys Pro Glu Lys Ser Ile Asn His Thr Leu
        515                 520                 525

Ser Leu Lys Gly Asn Ser Glu Lys Gly Leu Leu Asp Leu Thr Leu Tyr
    530                 535                 540

Gln Thr Asn Tyr Arg His Phe Leu Phe Glu Gln Glu Ser Leu Ile Gln
545                 550                 555                 560

Arg Thr Glu Met Arg Tyr Gly Arg Pro Tyr Thr Tyr Gln Ser Gln Glu
                565                 570                 575

Gln Gln Met Val Asn Leu Asp Lys Ala Lys Ile Tyr Gly Val Glu Leu
            580                 585                 590

Lys Thr His Val Asn Leu Asp Gln Met Ile Ala Val Ile Pro Gln Gly
        595                 600                 605

Phe Lys Phe Tyr Ala Ala Leu Gly Tyr Ser Lys Gly Lys Leu Ser Asn
    610                 615                 620

Asn Ala Ser Leu Leu Ser Ile Gln Pro Leu Lys Ile Ile Leu Gly Leu
625                 630                 635                 640

Asp Tyr Glu Ala Thr Asn Gly Lys Trp Ala Ile Phe Asn Arg Leu Thr
                645                 650                 655

Tyr Leu Gly Glu Lys Arg Ala Ser Asp Ala Lys Val Tyr Glu Ile Lys
            660                 665                 670

Arg Arg Cys Thr Glu Phe Val Thr Glu Thr Asp Pro Trp Ser Gly Glu
        675                 680                 685

Gln Ile Thr Arg Cys Lys Lys Arg Glu Leu Tyr Pro Asp Leu Ser Thr
    690                 695                 700

Tyr Lys His Leu Asn Lys Ser Ala Phe Val Phe Asp Thr Phe Gly Tyr
705                 710                 715                 720
```

```
Tyr Lys Ile Thr Asp Asp Ile Thr Phe Arg Ala Gly Ile Tyr Asn Leu
                725                 730                 735

Phe Asn Lys Lys Tyr His Thr Trp Asp Ala Leu Arg Gly Ile Asn Ala
            740                 745                 750

Asn Ser Thr Leu Asn Ser Val Asp Arg Glu Gly Lys Gly Leu Gln Arg
        755                 760                 765

Phe Tyr Ala Pro Gly Arg Asn Tyr Ala Ala Ser Leu Glu Ile Arg Phe
    770                 775                 780


<210> SEQ ID NO 37
<211> LENGTH: 784
<212> TYPE: PRT
<213> ORGANISM: Pasteurella multocida

<400> SEQUENCE: 37

Met Lys Tyr Pro Leu Ser Tyr Lys Asn Ile Ala Arg Ser Ile Pro Phe
1               5                   10                  15

Leu Ser Phe Ile Ala Phe Pro Leu Tyr Ala Gln Glu Thr Thr Glu Leu
            20                  25                  30

Glu Gln Ile Thr Val Gln Glu Ser Ala Thr Ala Glu Val Asn Lys Thr
        35                  40                  45

Ser Pro Thr Val Ile Ser Lys Ser Ala Thr Thr Ile Gln Asn Glu Met
    50                  55                  60

Ile Arg Asp Thr Arg Asp Leu Val Arg Tyr Thr Thr Asp Val Gly Ile
65                  70                  75                  80

Ser Asp Asn Gly Arg Phe Leu Lys Gly Phe Ala Met Arg Gly Val Glu
                85                  90                  95

Asp Asn Arg Val Gly Ile Ser Ile Asp Gly Val Ser Leu Pro Asp Ser
            100                 105                 110

Glu Glu Asn Ser Leu Tyr Ala Arg Tyr Gly Asn Phe Asn Asn Ser Arg
        115                 120                 125

Leu Ser Ile Asp Pro Glu Leu Ile Gln Thr Ile Asp Ile Val Arg Gly
    130                 135                 140

Ser Asp Ser Phe Asn Ala Gly Ser Gly Ser Leu Gly Gly Gly Val Asn
145                 150                 155                 160

Tyr Asn Thr Leu Asp Pro Gln His Ile Val Lys Ala Gly Asn Ser Val
                165                 170                 175

Gly Ala Leu Leu Arg Gly Ser Tyr Ala Ser Lys Asn Arg Glu Trp Val
            180                 185                 190

Arg Thr Leu Gly Ile Gly Tyr Val Gly Glu Lys Phe Asp Ala Leu Leu
        195                 200                 205

Met Tyr Ser Gln Arg Thr Gly His Glu Phe Lys Ser Arg Gly Ser Gly
    210                 215                 220

Pro Glu Phe Arg Tyr Ser Ser Ser Gln His Pro Asp Pro Val Thr Gln
225                 230                 235                 240

Arg Phe His Asn Tyr Leu Ala Lys Met Asn Tyr Gln Ile Asn Asp Lys
                245                 250                 255

Gln Arg Ile Gly Leu Thr Leu Asn Gly Gln Thr Gly Gly Arg Tyr Ile
            260                 265                 270

Asp Glu Arg Ser Tyr Thr Leu Met Gly Ser Gln Trp Arg Glu Ala Asp
        275                 280                 285

Asp Gln Asn Glu Arg Leu Asn Ala Asn Leu Tyr Tyr Ile Tyr Ala Pro
    290                 295                 300

Ser Thr Gly Trp Leu Ala Tyr Ser Lys Phe Asp Leu Asp Tyr Gln Lys
```

-continued 305 310 315 320

Thr Asp Leu Ala Ala Val Asn Tyr Lys Gly Gly Arg His Phe Thr Thr
325 330 335

Asp Ala Lys Glu Leu Asn Glu Ile Tyr Asp Arg Arg Met Lys Thr Val
340 345 350

Phe Thr Arg Gly Ser Val Glu Leu Asn Ala Gln Pro Val His Phe Tyr
355 360 365

Gly Glu His Thr Leu Thr Ile Lys Gly Tyr Val Ser Gln Arg Asp Phe
370 375 380

Lys Asn Ile Asn Gln Asp Arg Ile Gly Ile Gly Thr Asn Tyr Asp Thr
385 390 395 400

Gln Tyr His Tyr Thr Ile Gln Tyr Pro Ile Arg Thr Lys Gln Tyr Gly
405 410 415

Leu Ser Leu Lys Asp His Val Arg Trp Asn Asp Thr Phe Ser Ser His
420 425 430

Leu Gly Leu Arg Tyr Asp His Thr Lys Leu Lys Pro Lys Glu Leu Asn
435 440 445

Ala Pro Cys Ser Lys Ala Cys Leu Glu Glu Gly Lys Pro Lys Pro Thr
450 455 460

Arg Phe Ser Thr Val Ser Thr Phe Ala Gly Phe Glu Ala Gln Leu Ser
465 470 475 480

Pro Ser Trp Met Leu Gly Tyr Asn Ile Ser Thr Gly Tyr Arg Val Pro
485 490 495

Thr Ala Ser Glu Met Phe Phe Ser Phe Thr Asn Ala Tyr Gly Thr Trp
500 505 510

Lys Ser Asn Pro Ser Leu Lys Pro Glu Lys Ser Ile Asn His Thr Leu
515 520 525

Ser Leu Lys Gly Asn Ser Glu Lys Gly Leu Leu Asp Leu Thr Leu Tyr
530 535 540

Gln Thr Asn Tyr Arg His Phe Leu Phe Glu Gln Glu Ser Leu Ile Gln
545 550 555 560

Arg Thr Glu Met Arg Tyr Gly Arg Pro Tyr Thr Tyr Gln Ser Gln Glu
565 570 575

Gln Gln Met Val Asn Leu Asp Lys Ala Lys Ile Tyr Gly Val Glu Leu
580 585 590

Lys Thr His Val Asn Leu Asp Gln Met Ile Ala Val Ile Pro Gln Gly
595 600 605

Phe Lys Phe Tyr Ala Ala Leu Gly Tyr Ser Lys Gly Lys Leu Ser Asn
610 615 620

Asn Ala Ser Leu Leu Ser Ile Gln Pro Leu Lys Ile Ile Leu Gly Leu
625 630 635 640

Asp Tyr Glu Ala Thr Asn Gly Lys Trp Ala Ile Phe Asn Arg Leu Thr
645 650 655

Tyr Leu Gly Glu Lys Arg Ala Ser Asp Ala Lys Val Tyr Glu Ile Lys
660 665 670

Arg Arg Cys Thr Glu Phe Val Thr Glu Thr Asp Pro Trp Ser Gly Glu
675 680 685

Gln Ile Thr Arg Cys Lys Lys Arg Glu Leu Tyr Pro Asp Leu Ser Thr
690 695 700

Tyr Lys His Leu Asn Lys Ser Ala Phe Val Phe Asp Thr Phe Gly Tyr
705 710 715 720

Tyr Lys Ile Thr Asp Asp Ile Thr Phe Arg Ala Gly Ile Tyr Asn Leu
725 730 735

```
Phe Asn Lys Lys Tyr His Thr Trp Asp Ala Leu Arg Gly Ile Asn Ala
            740                 745                 750

Asn Ser Thr Leu Asn Ser Val Asp Arg Glu Gly Lys Gly Leu Gln Arg
        755                 760                 765

Phe Tyr Ala Pro Gly Arg Asn Tyr Ala Ala Ser Leu Glu Ile Arg Phe
    770                 775                 780


<210> SEQ ID NO 38
<211> LENGTH: 784
<212> TYPE: PRT
<213> ORGANISM: Pasteurella multocida

<400> SEQUENCE: 38

Met Lys Tyr Pro Leu Ser Tyr Lys Asn Ile Ala Arg Ser Ile Pro Phe
1               5                   10                  15

Leu Ser Phe Ile Ala Phe Pro Leu Tyr Ala Gln Glu Thr Thr Glu Leu
            20                  25                  30

Glu Gln Ile Thr Val Gln Glu Ser Ala Thr Ala Glu Val Asn Lys Thr
        35                  40                  45

Ser Pro Thr Val Ile Ser Lys Ser Ala Thr Thr Ile Gln Asn Glu Met
    50                  55                  60

Ile Arg Asp Thr Arg Asp Leu Val Arg Tyr Thr Thr Asp Val Gly Ile
65                  70                  75                  80

Ser Asp Asn Gly Arg Phe Leu Lys Gly Phe Ala Met Arg Gly Val Glu
                85                  90                  95

Asp Asn Arg Val Gly Ile Ser Ile Asp Gly Val Ser Leu Pro Asp Ser
            100                 105                 110

Glu Glu Asn Ser Leu Tyr Ala Arg Tyr Gly Asn Phe Asn Asn Ser Arg
        115                 120                 125

Leu Ser Ile Asp Pro Glu Leu Ile Gln Thr Ile Asp Ile Val Arg Gly
    130                 135                 140

Ser Asp Ser Phe Asn Ala Gly Ser Gly Ser Leu Gly Gly Gly Val Asn
145                 150                 155                 160

Tyr Asn Thr Leu Asp Pro Gln His Ile Val Lys Ala Gly Asn Ser Val
                165                 170                 175

Gly Ala Leu Leu Arg Gly Ser Tyr Ala Ser Lys Asn Arg Glu Trp Val
            180                 185                 190

Arg Thr Leu Gly Ile Gly Tyr Val Gly Glu Lys Phe Asp Ala Leu Leu
        195                 200                 205

Met Tyr Ser Gln Arg Thr Gly His Glu Phe Lys Ser Arg Gly Ser Gly
    210                 215                 220

Pro Glu Phe Arg Tyr Ser Ser Ser Gln His Pro Asp Pro Val Thr Gln
225                 230                 235                 240

Arg Phe His Asn Tyr Leu Ala Lys Met Asn Tyr Gln Ile Asn Asp Asn
                245                 250                 255

Gln Arg Ile Gly Leu Thr Leu Asn Gly Gln Thr Gly Gly Arg Tyr Ile
            260                 265                 270

Asp Glu Arg Ser Tyr Thr Leu Met Gly Ser Gln Trp Arg Glu Ala Asp
        275                 280                 285

Asp Gln Asn Glu Arg Leu Asn Ala Asn Leu Tyr Tyr Ile Tyr Ala Pro
    290                 295                 300

Ser Thr Gly Trp Leu Ala Tyr Ser Lys Phe Asp Leu Asp Tyr Gln Lys
305                 310                 315                 320

Thr Asp Leu Ala Ala Val Asn Tyr Lys Gly Gly Arg His Phe Thr Thr
```

-continued

```
                325                 330                 335

Asp Ala Lys Glu Leu Asn Glu Ile Tyr Asp Arg Arg Met Lys Thr Val
            340                 345                 350

Phe Thr Arg Gly Ser Val Glu Leu Asn Ala Gln Pro Val His Phe Tyr
        355                 360                 365

Gly Glu His Thr Leu Thr Ile Lys Gly Tyr Val Ser Gln Arg Asp Phe
    370                 375                 380

Lys Asn Ile Asn Gln Asp Arg Ile Gly Ile Gly Thr Asn Tyr Asp Thr
385                 390                 395                 400

Gln Tyr His Tyr Thr Ile Gln Tyr Pro Ile Arg Thr Lys Gln Tyr Gly
                405                 410                 415

Leu Ser Leu Lys Asp His Val Arg Trp Asn Asp Thr Phe Ser Ser His
            420                 425                 430

Leu Gly Leu Arg Tyr Asp His Thr Lys Leu Lys Pro Lys Glu Leu Asn
        435                 440                 445

Ala Pro Cys Ser Lys Ala Cys Leu Glu Glu Gly Lys Pro Lys Pro Thr
    450                 455                 460

Arg Phe Ser Thr Val Ser Thr Phe Ala Gly Leu Glu Ala Gln Leu Ser
465                 470                 475                 480

Pro Ser Trp Met Leu Gly Tyr Asn Ile Ser Thr Gly Tyr Arg Val Pro
                485                 490                 495

Thr Ala Ser Glu Met Phe Phe Ser Phe Thr Asn Ala Tyr Gly Thr Trp
            500                 505                 510

Lys Ser Asn Pro Ser Leu Lys Pro Glu Lys Ser Ile Asn His Thr Leu
        515                 520                 525

Ser Leu Lys Gly Asn Ser Glu Lys Gly Leu Leu Asp Leu Thr Leu Tyr
    530                 535                 540

Gln Thr Asn Tyr Arg His Phe Leu Phe Glu Gln Glu Ser Leu Ile Gln
545                 550                 555                 560

Arg Thr Glu Met Arg Tyr Gly Arg Pro Tyr Thr Tyr Gln Ser Gln Glu
                565                 570                 575

Gln Gln Met Val Asn Leu Asp Lys Ala Lys Ile Tyr Gly Val Glu Leu
            580                 585                 590

Lys Thr His Val Asn Leu Asp Gln Met Ile Ala Val Ile Pro Gln Gly
        595                 600                 605

Phe Lys Phe Tyr Ala Ala Leu Gly Tyr Ser Lys Gly Lys Leu Ser Asn
    610                 615                 620

Asn Ala Ser Leu Leu Ser Ile Gln Pro Leu Lys Ile Ile Leu Gly Leu
625                 630                 635                 640

Asp Tyr Glu Ala Thr Asn Gly Lys Trp Ala Ile Phe Asn Arg Leu Thr
                645                 650                 655

Tyr Leu Gly Glu Lys Arg Ala Ser Asp Ala Lys Val Tyr Glu Ile Lys
            660                 665                 670

Arg Arg Cys Thr Glu Phe Val Thr Glu Thr Asp Pro Trp Ser Gly Glu
        675                 680                 685

Gln Ile Thr Arg Cys Lys Lys Arg Glu Leu Tyr Pro Asp Leu Ser Thr
    690                 695                 700

Tyr Lys His Leu Asn Lys Ser Ala Phe Val Phe Asp Thr Phe Gly Tyr
705                 710                 715                 720

Tyr Lys Ile Thr Asp Asp Ile Thr Phe Arg Ala Gly Ile Tyr Asn Leu
                725                 730                 735

Phe Asn Lys Lys Tyr His Thr Trp Asp Ala Leu Arg Gly Ile Asn Ala
            740                 745                 750
```

Asn Ser Thr Leu Asn Ser Val Asp Arg Glu Gly Lys Gly Leu Gln Arg
        755                 760                 765

Phe Tyr Ala Pro Gly Arg Asn Tyr Ala Ala Ser Leu Glu Ile Arg Phe
    770                 775                 780

<210> SEQ ID NO 39
<211> LENGTH: 745
<212> TYPE: PRT
<213> ORGANISM: Haemophilus influenzae

<400> SEQUENCE: 39

Met Asn Ile Ile Ile Asn Lys Arg Ile Phe Leu Leu Val Thr Phe Val
1               5                   10                  15

Gly Ile Gln Leu Asn Val Thr Ala Lys Gln Asn Ser Ser Asn Ser Asn
            20                  25                  30

Arg Glu Glu Leu Leu Pro Ile Ile Val Asn Thr Asp Glu Asp Ser Asn
        35                  40                  45

Lys Leu Pro Gly Arg Ser Val Leu Lys Gln Lys Asn Ile Glu Gln Gln
    50                  55                  60

Gln Ala Asp Asn Ala Ala Asn Leu Ile Asn Ile Leu Pro Gly Val Asn
65                  70                  75                  80

Met Ala Gly Gly Phe Arg Pro Gly Gly Gln Thr Leu Asn Ile Asn Gly
                85                  90                  95

Met Gly Asp Ala Glu Asp Val Arg Val Gln Leu Asp Gly Ala Thr Lys
            100                 105                 110

Ser Phe Glu Lys Tyr Gln Gln Gly Ser Ile Phe Ile Glu Pro Glu Leu
        115                 120                 125

Leu Arg Lys Val Thr Val Asp Lys Gly Asn Tyr Ser Pro Gln Tyr Gly
    130                 135                 140

Asn Gly Gly Phe Ala Gly Thr Val Lys Phe Glu Thr Arg Asp Ala Arg
145                 150                 155                 160

Asp Phe Leu Lys Glu Asn Gln Lys Ile Gly Gly Leu Leu Lys Tyr Gly
                165                 170                 175

Asn Asn Ser Asn Asn Asn Gln Lys Thr Tyr Ser Thr Ala Leu Val Leu
            180                 185                 190

Gln Asn Glu Gln Lys Asn Ile Asp Leu Leu Leu Phe Gly Ser Val Arg
        195                 200                 205

Asn Ala Gly Asp Tyr Lys Arg Pro Asp Asn Ser Lys Ile Leu Phe Ser
    210                 215                 220

Lys Asn Asn Gln Lys Thr Gly Leu Ile Lys Val Asn Trp Gln Ile Thr
225                 230                 235                 240

Pro Glu His Leu Leu Thr Leu Ser Ser Val Tyr Gly Ile His Lys Gly
                245                 250                 255

Trp Glu Pro Trp Ala Ala Lys Arg Asp Val Thr Ser Arg Pro Thr Glu
            260                 265                 270

Thr Glu Ile Lys Arg Tyr Gly Ile Asp Val Ala Trp Lys Arg Lys Leu
        275                 280                 285

Val Tyr Arg Asp Gln Lys Asp Glu Ser Tyr Ser Leu Lys Tyr Arg Tyr
    290                 295                 300

Leu Pro Glu Asn Asn Lys Trp Ile Asn Leu Ser Val Gln Leu Ser Tyr
305                 310                 315                 320

Ser Lys Thr Glu Gln Asn Asp Thr Arg His Glu Lys Val Thr Ser Ser
                325                 330                 335

Phe Leu Gly Thr Leu Gly Asn Lys Ser Trp Ile Thr Tyr Ser Asp Leu 340 345 350

Thr Phe Asp Ile Ser Asn Thr Ser Thr Leu Asn Ile Gly Arg Ala Glu
355 360 365

His Glu Leu Leu Phe Gly Leu Gln Trp Leu Lys Asn Thr Arg Asn Thr
370 375 380

Leu Met Tyr His Lys Gly Lys Met Asn Asp Lys Thr Tyr Asn Tyr Gly
385 390 395 400

Tyr Phe Gln Pro Tyr Tyr Met Pro Ser Gly Arg Gln Tyr Thr Gln Ala
405 410 415

Phe Tyr Leu Gln Asp Gln Ile Lys Trp Lys Asn Ile Ile Phe Ser Thr
420 425 430

Gly Ala Arg Tyr Asp His Ile Asn Asn Ile Gly Gln Lys Asn Leu Ala
435 440 445

Pro Gln Tyr Asn Asp Ile Ser Ala Gly His Asn Tyr Ser Gln Lys Asn
450 455 460

Tyr Asn Gly Trp Ser Tyr Tyr Leu Gly Leu Lys Tyr Asp Val Asn His
465 470 475 480

Tyr Leu Ser Leu Phe Thr Asn Phe Ser Arg Thr Trp Arg Ala Pro Val
485 490 495

Ile Asp Glu Gln Tyr Glu Thr Gln Tyr Ser Lys Ala Ser Val Pro Ala
500 505 510

Thr Ser Leu Asn Leu Glu Lys Glu Met Ile Ser Gln Thr Arg Gly Gly
515 520 525

Gly Ile Val Thr Leu Asn Asn Leu Phe Gln Glu Asp Asp Thr Phe Gln
530 535 540

Phe Arg Ala Thr Tyr Phe Tyr His Arg Gly Lys Asn Glu Ile Phe Lys
545 550 555 560

Thr Arg Gly Val Asn Cys Val Gly Asn Ala Leu Asp Val Asp Asn Lys
565 570 575

Ile Cys Pro Lys Ile Ile Ser Asn Tyr Arg Asn Leu Pro Gly Tyr Val
580 585 590

Ile Gln Gly Ala Glu Leu Glu Ala Tyr Tyr Gln Ser Thr Tyr Leu Phe
595 600 605

Gly Glu Leu Thr Tyr Ser Tyr Val Lys Gly Lys Arg Asp Thr Ser Pro
610 615 620

Arg Asn Pro Trp Gly Lys Thr Ser Thr Trp Ile Ala Glu Ile Pro Pro
625 630 635 640

Arg Lys Ala Thr Ala Thr Leu Gly Phe Asn Val Pro Lys Tyr Tyr Leu
645 650 655

Thr Val Gly Trp Arg Ala Glu Phe Val Arg Arg Gln Asp Arg Ser Pro
660 665 670

Ser Ser Arg Asp Pro Lys Ala Ser Tyr Tyr Leu Ser Leu Pro Ala Ser
675 680 685

Arg Gly Tyr Ser Leu His Asn Leu Phe Leu Ser Trp Thr Pro Glu Lys
690 695 700

Ile Lys Gly Met Asn Ile Lys Ile Thr Val Asp Asn Leu Phe Asn Arg
705 710 715 720

Ala Tyr Asn Pro Tyr Leu Gly Glu Leu Ala Ser Gly Thr Gly Arg Asn
725 730 735

Ile Lys Phe Ser Leu Ser Gln Lys Phe
740 745

<210> SEQ ID NO 40

<211> LENGTH: 742
<212> TYPE: PRT
<213> ORGANISM: Pasteurella multocida

<400> SEQUENCE: 40

```
Met Asp Lys Asn Leu Met Lys Gly Cys Val Phe Leu Leu Ile Val Gly
1               5                   10                  15

Cys Gly Ile Gln Ile Gly Leu Ala Ser Asn Pro Asn Pro Pro Asp Val
            20                  25                  30

Asp Glu Leu Leu Pro Ile Ile Val Asn Ala Asp Glu Asp Asn Lys Leu
        35                  40                  45

Pro Gly Arg Ser Val Leu Lys Gln Lys Asn Ile Asp Gln Gln Gln Ala
    50                  55                  60

Asp Asn Ala Ala Asp Leu Ile Asn Ile Leu Pro Gly Val Asn Met Ala
65                  70                  75                  80

Gly Gly Phe Arg Pro Gly Gly Gln Thr Leu Asn Ile Asn Gly Met Gly
                85                  90                  95

Asp Ala Glu Asp Val Arg Val Gln Leu Asp Gly Ala Thr Lys Ser Phe
            100                 105                 110

Glu Lys Tyr Gln Gln Gly Ser Ile Phe Ile Glu Pro Glu Leu Leu Arg
        115                 120                 125

Lys Val Thr Val Asp Lys Gly Asn Tyr Ser Pro Gln Tyr Gly Asn Gly
    130                 135                 140

Ser Phe Ala Gly Thr Val Lys Phe Glu Thr Lys Asp Ala Thr Asp Phe
145                 150                 155                 160

Leu Lys Glu Asn Gln Lys Ile Gly Gly Leu Phe Lys Tyr Gly Asn Asn
                165                 170                 175

Ser Asn Asn Asn Gln Lys Thr Tyr Ser Thr Ala Leu Val Leu Gln Asn
            180                 185                 190

Glu Gln Lys Asn Ile Asp Leu Leu Leu Phe Gly Ser Val Arg Asn Ala
        195                 200                 205

Ser Asn Tyr Thr Arg Pro Asp Lys Ser Lys Ile Leu Phe Ser Lys Asn
    210                 215                 220

Asn Gln Lys Ser Gly Leu Ile Lys Val Asn Trp Gln Ile Thr Pro Glu
225                 230                 235                 240

His Leu Leu Thr Leu Ser Ser Val Tyr Gly Ile His Lys Gly Trp Glu
                245                 250                 255

Pro Trp Ala Ala Lys Arg Asp Val Met Ser Arg Pro Thr Glu Lys Glu
            260                 265                 270

Ile Lys Arg Tyr Gly Ile Asp Val Ala Trp Lys Arg Lys Leu Val Tyr
        275                 280                 285

Arg Asp Gln Lys Asp Glu Ser Tyr Ser Leu Lys Tyr Arg Tyr Leu Pro
    290                 295                 300

Glu Asn Asn Lys Trp Ile Asn Leu Ser Val Gln Leu Ser Tyr Ser Lys
305                 310                 315                 320

Thr Glu Gln Asn Asp Thr Arg His Glu Lys Val Thr Ser Ser Phe Leu
                325                 330                 335

Gly Thr Leu Gly Asn Lys Ser Trp Ile Thr Tyr Ser Asp Leu Thr Phe
            340                 345                 350

Asp Ile Ser Asn Thr Ser Thr Leu Asn Ile Gly Arg Ala Glu His Glu
        355                 360                 365

Leu Leu Phe Gly Leu Gln Trp Leu Lys Asn Lys Arg Asn Thr Leu Met
    370                 375                 380

Tyr His Lys Glu Gly Val Lys Lys Ala Asp Tyr Asn Tyr Gly Tyr Phe
```

-continued

```
385                 390                 395                 400

Gln Pro Tyr Tyr Met Pro Ser Gly Arg Gln Tyr Thr Gln Ala Phe Tyr
                405                 410                 415

Leu Gln Asp Gln Ile Lys Trp Gln Asn Phe Leu Phe Thr Gly Gly Ile
            420                 425                 430

Arg Tyr Asp His Ile Asn Asn Ile Gly Gln Lys Asn Leu Ala Pro Arg
        435                 440                 445

Tyr Asn Asp Ile Ser Ala Gly His Asp Tyr Ser Gln Lys Asn Tyr Asn
    450                 455                 460

Gly Trp Ser Tyr Tyr Leu Gly Leu Lys Tyr Asp Val Asn His Tyr Leu
465                 470                 475                 480

Ser Leu Phe Thr Asn Phe Ser Lys Thr Trp Arg Ala Pro Val Ile Asp
                485                 490                 495

Glu Gln Tyr Glu Thr Gln Tyr Ser Gln Ala Ser Val Ser Ala Thr Ser
            500                 505                 510

Leu Asn Leu Glu Lys Glu Met Ile Asn Gln Thr Arg Val Gly Gly Ile
        515                 520                 525

Ile Thr Leu Asn His Leu Phe Gln Glu Asn Asp Ala Phe Gln Phe Arg
    530                 535                 540

Thr Thr Tyr Phe Tyr Asn Arg Gly Lys Asn Glu Ile Phe Lys Thr Arg
545                 550                 555                 560

Gly Val Asn Cys Val Glu Asn Ala Leu Asp Val Asp Asn Ser Val Cys
                565                 570                 575

Pro Lys Ile Ile Ser Asn Tyr Arg Asn Leu Pro Gly Tyr Val Ile Gln
            580                 585                 590

Gly Ala Glu Leu Glu Ala Tyr Tyr Gln Ser Ser Tyr Leu Phe Gly Gly
        595                 600                 605

Leu Thr Tyr Ser Tyr Val Lys Gly Lys Arg Asp Thr Ser Pro Arg Asn
    610                 615                 620

Pro Trp Ser Lys Thr Ser Thr Trp Ile Ala Glu Thr Pro Pro Arg Lys
625                 630                 635                 640

Ala Thr Ala Thr Leu Gly Phe Asn Ile Pro Glu Tyr Tyr Phe Thr Ala
                645                 650                 655

Gly Trp Arg Ala Glu Phe Val Arg Lys Gln Asp Arg Ser Pro Leu Ser
            660                 665                 670

Asn Asp Ser Lys Ala Ser Tyr Trp Ala Leu Pro Ser Ser Lys Gly Tyr
        675                 680                 685

Ser Leu His Ser Val Phe Phe Ser Trp Ser Pro Thr Lys Ile Lys Gly
    690                 695                 700

Met Asn Phe Lys Val Thr Val Asp Asn Leu Phe Asn Arg Pro Tyr Tyr
705                 710                 715                 720

Pro Tyr Leu Gly Glu Leu Ala Ser Gly Thr Gly Arg Asn Val Lys Phe
                725                 730                 735

Ser Leu Thr Gln Gln Phe
            740


<210> SEQ ID NO 41
<211> LENGTH: 742
<212> TYPE: PRT
<213> ORGANISM: Pasteurella multocida

<400> SEQUENCE: 41

Met Asp Lys Asn Leu Met Lys Gly Cys Val Phe Leu Ser Ile Val Gly
1               5                   10                  15
```

-continued

```
Cys Gly Ile Gln Ile Gly Leu Ala Ser Asn Pro Asn Pro Pro Asp Val
            20                  25                  30

Asp Glu Leu Leu Pro Ile Ile Val Asn Ala Asp Glu Asp Asn Lys Leu
        35                  40                  45

Pro Gly Arg Ser Val Leu Lys Gln Lys Asn Ile Asp Gln Gln Gln Ala
    50                  55                  60

Asp Asn Ala Ala Asp Leu Ile Asn Ile Leu Pro Gly Val Asn Met Ala
65                  70                  75                  80

Gly Gly Phe Arg Pro Gly Gly Gln Thr Leu Asn Ile Asn Gly Met Gly
                85                  90                  95

Asp Ala Glu Asp Val Arg Val Gln Leu Asp Gly Ala Thr Lys Ser Phe
            100                 105                 110

Glu Lys Tyr Gln Gln Gly Ser Ile Phe Ile Glu Pro Glu Leu Leu Arg
        115                 120                 125

Lys Val Thr Val Asp Lys Gly Asn Tyr Ser Pro Gln Tyr Gly Asn Gly
    130                 135                 140

Gly Phe Ala Gly Thr Val Lys Phe Glu Thr Lys Asp Ala Thr Asp Phe
145                 150                 155                 160

Leu Lys Glu Asn Gln Lys Ile Gly Gly Leu Phe Lys Tyr Gly Asn Asn
                165                 170                 175

Ser Asn Asn Asn Gln Lys Thr Tyr Ser Thr Ala Leu Val Leu Gln Asn
            180                 185                 190

Glu Gln Lys Asn Ile Asp Leu Leu Leu Phe Gly Ser Val Arg Asn Ala
        195                 200                 205

Ser Asn Tyr Thr Arg Pro Asp Lys Ser Lys Ile Leu Phe Ser Lys Asn
    210                 215                 220

Asn Gln Lys Ser Gly Leu Ile Lys Val Asn Trp Gln Ile Thr Pro Glu
225                 230                 235                 240

His Leu Leu Thr Leu Ser Ser Val Tyr Gly Ile His Lys Gly Trp Glu
                245                 250                 255

Pro Trp Ala Ala Lys Arg Asp Val Met Ser Arg Pro Thr Glu Thr Glu
            260                 265                 270

Ile Lys Arg Tyr Gly Ile Asp Val Ala Trp Lys Arg Lys Leu Val Tyr
        275                 280                 285

Arg Asp Gln Lys Asp Glu Ser Tyr Ser Leu Lys Tyr Arg Tyr Leu Pro
    290                 295                 300

Glu Asn Asn Lys Trp Ile Asn Leu Ser Val Gln Leu Ser Tyr Ser Lys
305                 310                 315                 320

Thr Glu Gln Asn Asp Thr Arg His Glu Lys Val Thr Ser Ser Phe Leu
                325                 330                 335

Gly Thr Leu Gly Asn Lys Ser Trp Ile Thr Tyr Ser Asp Leu Thr Phe
            340                 345                 350

Asp Ile Ser Asn Thr Ser Thr Leu Asn Ile Gly Arg Ala Glu His Glu
        355                 360                 365

Leu Leu Phe Gly Leu Gln Trp Leu Lys Asn Lys Arg Asn Thr Leu Met
    370                 375                 380

Tyr His Lys Glu Gly Val Lys Lys Ala Asp Tyr Asn Tyr Gly Tyr Phe
385                 390                 395                 400

Gln Pro Tyr Tyr Met Pro Ser Gly Arg Gln Tyr Thr His Ala Phe Tyr
                405                 410                 415

Leu Gln Asp Gln Ile Lys Trp Gln Asn Phe Leu Phe Thr Gly Gly Ile
            420                 425                 430

Arg Tyr Asp His Ile Asn Asn Ile Gly Gln Lys Asn Leu Ala Pro Arg
```

```
        435                 440                 445

Tyr Asn Asp Ile Ser Ala Gly His Asp Tyr Ser Gln Lys Asn Tyr Asn
    450                 455                 460

Gly Trp Ser Tyr Tyr Leu Gly Leu Lys Tyr Asp Val Asn His Tyr Leu
465                 470                 475                 480

Ser Leu Phe Thr Asn Phe Ser Lys Thr Trp Arg Ala Pro Val Ile Asp
                485                 490                 495

Glu Gln Tyr Glu Thr Gln Tyr Ser Gln Ala Ser Val Ser Ala Thr Ser
            500                 505                 510

Leu Asn Leu Glu Lys Glu Met Ile Asn Gln Thr Arg Val Gly Gly Ile
        515                 520                 525

Ile Thr Leu Asn His Leu Phe Gln Glu Asn Asp Ala Phe Gln Phe Arg
    530                 535                 540

Thr Thr Tyr Phe Tyr Asn Arg Gly Lys Asn Glu Ile Phe Lys Thr Arg
545                 550                 555                 560

Gly Val Asn Cys Val Glu Asn Ala Leu Asp Val Asp Asn Ser Val Cys
                565                 570                 575

Pro Lys Ile Ile Ser Asn Tyr Arg Asn Leu Pro Gly Tyr Val Ile Gln
            580                 585                 590

Gly Ala Glu Leu Glu Ala Tyr Tyr Gln Ser Ser Tyr Leu Phe Gly Gly
        595                 600                 605

Leu Thr Tyr Ser Tyr Val Lys Gly Lys Arg Asp Thr Ser Pro Arg Asn
    610                 615                 620

Pro Trp Ser Lys Thr Ser Thr Trp Ile Ala Glu Thr Pro Pro Arg Lys
625                 630                 635                 640

Ala Thr Ala Thr Leu Gly Phe Asn Ile Pro Glu Tyr Tyr Phe Thr Ala
                645                 650                 655

Gly Trp Arg Ala Glu Phe Val Arg Lys Gln Asp Arg Ser Pro Leu Ser
            660                 665                 670

Asn Asp Ser Lys Ala Ser Tyr Trp Ala Leu Pro Ser Ser Lys Gly Tyr
        675                 680                 685

Ser Leu His Ser Val Phe Phe Ser Trp Ser Pro Thr Lys Ile Lys Gly
    690                 695                 700

Met Asn Phe Lys Val Thr Val Asp Asn Leu Phe Asn Arg Pro Tyr Tyr
705                 710                 715                 720

Pro Tyr Leu Gly Glu Leu Ala Ser Gly Thr Gly Arg Asn Val Lys Phe
                725                 730                 735

Ser Leu Thr Gln Gln Phe
            740


<210> SEQ ID NO 42
<211> LENGTH: 742
<212> TYPE: PRT
<213> ORGANISM: Pasteurella multocida

<400> SEQUENCE: 42

Met Asp Lys Asn Leu Met Lys Gly Cys Val Phe Leu Ser Ile Val Gly
1               5                   10                  15

Cys Gly Ile Gln Ile Gly Leu Ala Ser Asn Pro Asn Pro Pro Asp Val
            20                  25                  30

Asp Glu Leu Leu Pro Ile Ile Val Asn Ala Asp Glu Asp Asn Lys Leu
        35                  40                  45

Pro Gly Arg Ser Val Leu Lys Gln Lys Asn Ile Asp Gln Gln Gln Ala
    50                  55                  60
```

-continued

```
Asp Asn Ala Ala Asp Leu Ile Asn Ile Leu Pro Gly Val Asn Met Ala
65                  70                  75                  80

Gly Gly Phe Arg Pro Gly Gly Gln Thr Leu Asn Ile Asn Gly Met Gly
                85                  90                  95

Asp Ala Glu Asp Val Arg Val Gln Leu Asp Gly Ala Thr Lys Ser Phe
            100                 105                 110

Glu Lys Tyr Gln Gln Gly Ser Ile Phe Ile Glu Pro Glu Leu Leu Arg
        115                 120                 125

Lys Val Thr Val Asp Lys Gly Asn Tyr Ser Pro Gln Tyr Gly Asn Gly
    130                 135                 140

Gly Phe Ala Gly Thr Val Lys Phe Glu Thr Lys Asp Ala Thr Asp Phe
145                 150                 155                 160

Leu Lys Glu Asn Gln Lys Ile Gly Gly Leu Phe Lys Tyr Gly Asn Asn
                165                 170                 175

Ser Asn Asn Asn Gln Lys Thr Tyr Ser Thr Ala Leu Val Leu Gln Asn
            180                 185                 190

Glu Gln Lys Asn Ile Asp Leu Leu Leu Phe Gly Ser Val Arg Asn Ala
        195                 200                 205

Ser Asn Tyr Thr Arg Pro Asp Lys Ser Lys Ile Leu Phe Ser Lys Asn
    210                 215                 220

Asn Gln Lys Ser Gly Leu Ile Lys Val Asn Trp Gln Ile Thr Pro Glu
225                 230                 235                 240

His Leu Leu Thr Leu Ser Ser Val Tyr Gly Ile His Lys Gly Trp Glu
                245                 250                 255

Pro Trp Ala Ala Lys Arg Asp Val Met Ser Arg Pro Thr Glu Thr Glu
            260                 265                 270

Ile Lys His Tyr Gly Ile Asp Val Ala Trp Lys Arg Lys Leu Val Tyr
        275                 280                 285

Arg Asp Gln Lys Asp Glu Ser Tyr Ser Leu Lys Tyr Arg Tyr Leu Pro
    290                 295                 300

Glu Asn Asn Lys Trp Ile Asn Leu Ser Val Gln Leu Ser Tyr Ser Lys
305                 310                 315                 320

Thr Glu Gln Asn Asp Thr Arg His Glu Lys Val Thr Ser Ser Phe Leu
                325                 330                 335

Gly Thr Leu Gly Asn Lys Ser Trp Ile Thr Tyr Ser Asp Leu Thr Phe
            340                 345                 350

Asp Ile Ser Asn Thr Ser Thr Leu Asn Ile Gly Arg Ala Glu His Glu
        355                 360                 365

Leu Leu Phe Gly Leu Gln Trp Leu Lys Asn Lys Arg Asn Thr Leu Met
    370                 375                 380

Tyr His Lys Gly Gly Val Lys Lys Ala Asp Tyr Asn Tyr Gly Tyr Phe
385                 390                 395                 400

Gln Pro Tyr Tyr Met Pro Ser Gly Arg Gln Tyr Thr Gln Ala Phe Tyr
                405                 410                 415

Leu Gln Asp Gln Ile Lys Trp Gln Asn Phe Leu Phe Thr Gly Gly Ile
            420                 425                 430

Arg Tyr Asp His Ile Asn Asn Ile Gly Gln Lys Asn Leu Ala Pro Arg
        435                 440                 445

Tyr Asn Asp Ile Ser Ala Gly His Asp Tyr Ser Gln Lys Asn Tyr Asn
    450                 455                 460

Gly Trp Ser Tyr Tyr Leu Gly Leu Lys Tyr Asp Val Asn His Tyr Leu
465                 470                 475                 480

Ser Leu Phe Thr Asn Phe Ser Lys Thr Trp Arg Ala Pro Val Ile Asp
```

-continued

```
                485                 490                 495

Glu Gln Tyr Glu Thr Gln Tyr Ser Arg Ala Ser Val Ser Ala Thr Ser
            500                 505                 510

Leu Asn Leu Glu Lys Glu Met Ile Asn Gln Thr Arg Val Gly Gly Ile
        515                 520                 525

Ile Thr Leu Asn His Leu Phe Gln Glu Asn Asp Ala Phe Gln Phe Arg
    530                 535                 540

Thr Thr Tyr Phe Tyr Asn Arg Gly Lys Asn Glu Ile Phe Lys Thr Arg
545                 550                 555                 560

Gly Val Asn Cys Val Glu Asn Ala Leu Asp Val Asp Asn Ser Val Cys
                565                 570                 575

Pro Lys Ile Ile Ser Asn Tyr Arg Asn Leu Pro Gly Tyr Val Ile Gln
            580                 585                 590

Gly Ala Glu Leu Glu Ala Tyr Tyr Gln Ser Ser Tyr Leu Phe Gly Gly
        595                 600                 605

Leu Thr Tyr Ser Tyr Val Lys Gly Lys Arg Asp Thr Ser Pro Arg Asn
    610                 615                 620

Pro Trp Ser Lys Thr Ser Thr Trp Ile Ala Glu Thr Pro Pro Arg Lys
625                 630                 635                 640

Ala Thr Ala Thr Leu Gly Phe Asn Ile Pro Glu Tyr Tyr Phe Thr Ala
                645                 650                 655

Gly Trp Arg Ala Glu Phe Val Arg Lys Gln Asp Arg Ser Pro Leu Ser
            660                 665                 670

Asn Asp Ser Lys Ala Ser Tyr Trp Ala Leu Pro Ser Ser Lys Gly Tyr
        675                 680                 685

Ser Leu His Ser Val Phe Phe Ser Trp Ser Pro Thr Lys Ile Lys Gly
    690                 695                 700

Met Asn Phe Lys Val Thr Val Asp Asn Leu Phe Asn Arg Pro Tyr Tyr
705                 710                 715                 720

Pro Tyr Leu Gly Glu Leu Ala Ser Gly Thr Gly Arg Asn Val Lys Phe
                725                 730                 735

Ser Leu Thr Gln Gln Phe
            740


<210> SEQ ID NO 43
<211> LENGTH: 2418
<212> TYPE: DNA
<213> ORGANISM: Pasteurella multocida

<400> SEQUENCE: 43

atgatttcaa gaggttgtaa agtaaataaa ttttttgctg ttttgatgat gtgttgcatt      60

ccgcaagtag tttgggcaaa tacagaaaag aagcaaattg tttttttaga tgaaattagt     120

gtggagtcga aaggtgctgc ttttcgtagc gatccccttt ccggcttacc aaaacaaaat     180

gacattttag tcagtaagca aaaattaaaa acaggatcca gtacattagg taatgcgtta     240

gcgggtgaac tcagtgtaca tagtaatcaa tttggtggtg gatccagtgc acctgtcgtt     300

cgaggacagg aaggcgtgcg tttaaaaatc ttacaaaatg gttctgatgt cattgatatg     360

tctcaacttt ctcctgacca tgcgattggt gtcgatacgt tattggcaga gcaagtcgaa     420

attgtacgtg gtgcctcaac attgttatat gccaatgcgt cacctgctgg tgtgattaat     480

gtagtagata aacgcattcc aacacagctt cctcaaaagg gctatgaagt ggatttcaac     540

acgcgttata acacgaatag tcatgaaaaa ttggtaacgg ctgcactgac tttcgggtta     600

ggtaagcaca ttgctttacg ggtagaagaa ctgttacgtg gctcaaataa ttaccatgtg     660
```

ccagcattta agctagacaa aacattaaat tatgtccccg atactcaaaa taaaacgaag 720
tcaggtaact atggtgtggc ttttatcggt gagcgaggtt atgtcggttt tgcctacaat 780
cttcgtcgtg agaaatatgg gttaccggga cataaccata agctagatag ttgtgctgcg 840
catatttggg gtggcaatgt acgtaatgac tattatttag ggctttatcc tcatttaatg 900
catgatacgg atctagtaaa tacgcatttc cattgtggat caaatcatga catggatgga 960
aaacacagtc atgatcatcc gtacggtcac gatcatgacc attctattgc cggtccattg 1020
attgattctt atgctaaacg ttatgacata cgtgctgaag tcaaacagcc gatgaaagcg 1080
attgagaaaa tcaaactcag ttattcggaa acccgttata aacacgatga aaaagatggc 1140
aatatcgccg tgaatttatt taaaaataac ggatataacc tgcgcgtaga aattttccat 1200
acgcccatag cggggttgag tggcgttata ggggcgcagt atcaaacaca aaccagcagt 1260
gcgaatattc cgcgtattgc accatgctca aataatgcaa gcgatccttg tcataagaaa 1320
aagcaacgcg atccgtccaa aatcactaag ggtgatcgta agtcatgggc attgattgaa 1380
aatactcaat cacaaatgag tttttttgct atagaacaat tgcgttggca agatttttta 1440
tttgaaattg gtgtacgtac ggaaaaacaa cgcattgata ttgaatatga tcgcgcttgg 1500
ctgtttaaag taaagcgaaa gctagaaggc tgtgatccga attcgttctt ttatagccca 1560
tcaggatgtc gtcaaggcag ttatccagca cctgattttg cctcttatca tgatcgcgcg 1620
acctcttatt ctggtgctat cagttggaat atgacgcctg actacaccct ttctttgact 1680
tactcacata acgaacgtca cccaacaccg atggaattgt attaccacgg caaacattta 1740
gcgacggtgt catttgaaca tggcaatcgt aatctgaaaa aagaagtttc tgataactgg 1800
gaagtcggtc ttgcgtatct tggtgacaag ctaagttata aagtgaatgt atattacaat 1860
gattttaaaa atcggatttt taatcaaaca ttgaacaaat ccggtaattt atctttgaat 1920
cgttataatc aatccaaagc gaaatattat ggtgtggaag ggcgtattga ctatgcgttg 1980
acacctgaac tgcacatggg actttttggt gattatgtgc gtggaaaact gtatgattta 2040
ccgccaacgt accgtgtcga tcatgtggcg aatagcttag aacccgttcc tcaacctgat 2100
caagacgcac cacgtgtccc gccaatgcgt ttaggctttc gtgtgaatat ggagatgact 2160
gagagtttaa caagttcact cgaatacact tacgtttatc aacaaaagaa agtagcgccg 2220
ttagaaaatc aaacggctgc atatagttta ttaaatatcg gagtggatta ttcacgccaa 2280
atagctgggg taaattatca attatttgtt caagcaaata atgtgttaaa ccgtaaagtt 2340
tattctcata cttctttttt accctttgta ccgcagatgg ggcgtaatgt gactttagga 2400
ttaaacatcc atttctaa 2418

<210> SEQ ID NO 44
<211> LENGTH: 805
<212> TYPE: PRT
<213> ORGANISM: Pasteurella multocida

<400> SEQUENCE: 44

Met Ile Ser Arg Gly Cys Lys Val Asn Lys Phe Phe Ala Val Leu Met
1 5 10 15

Met Cys Cys Ile Pro Gln Val Val Trp Ala Asn Thr Glu Lys Lys Gln
20 25 30

Ile Val Phe Leu Asp Glu Ile Ser Val Glu Ser Lys Gly Ala Ala Phe
35 40 45

Arg Ser Asp Pro Leu Ser Gly Leu Pro Lys Gln Asn Asp Ile Leu Val

-continued

```
    50                  55                  60

Ser Lys Gln Lys Leu Lys Thr Gly Ser Ser Thr Leu Gly Asn Ala Leu
65                  70                  75                  80

Ala Gly Glu Leu Ser Val His Ser Asn Gln Phe Gly Gly Gly Ser Ser
                85                  90                  95

Ala Pro Val Val Arg Gly Gln Glu Gly Val Arg Leu Lys Ile Leu Gln
            100                 105                 110

Asn Gly Ser Asp Val Ile Asp Met Ser Gln Leu Ser Pro Asp His Ala
        115                 120                 125

Ile Gly Val Asp Thr Leu Leu Ala Glu Gln Val Glu Ile Val Arg Gly
    130                 135                 140

Ala Ser Thr Leu Leu Tyr Ala Asn Ala Ser Pro Ala Gly Val Ile Asn
145                 150                 155                 160

Val Val Asp Lys Arg Ile Pro Thr Gln Leu Pro Gln Lys Gly Tyr Glu
                165                 170                 175

Val Asp Phe Asn Thr Arg Tyr Asn Thr Asn Ser His Glu Lys Leu Val
            180                 185                 190

Thr Ala Ala Leu Thr Phe Gly Leu Gly Lys His Ile Ala Leu Arg Val
        195                 200                 205

Glu Glu Leu Leu Arg Gly Ser Asn Asn Tyr His Val Pro Ala Phe Lys
    210                 215                 220

Leu Asp Lys Thr Leu Asn Tyr Val Pro Asp Thr Gln Asn Lys Thr Lys
225                 230                 235                 240

Ser Gly Asn Tyr Gly Val Ala Phe Ile Gly Glu Arg Gly Tyr Val Gly
                245                 250                 255

Phe Ala Tyr Asn Leu Arg Arg Glu Lys Tyr Gly Leu Pro Gly His Asn
            260                 265                 270

His Lys Leu Asp Ser Cys Ala Ala His Ile Trp Gly Gly Asn Val Arg
        275                 280                 285

Asn Asp Tyr Tyr Leu Gly Leu Tyr Pro His Leu Met His Asp Thr Asp
    290                 295                 300

Leu Val Asn Thr His Phe His Cys Gly Ser Asn His Asp Met Asp Gly
305                 310                 315                 320

Lys His Ser His Asp His Pro Tyr Gly His Asp His Asp His Ser Ile
                325                 330                 335

Ala Gly Pro Leu Ile Asp Ser Tyr Ala Lys Arg Tyr Asp Ile Arg Ala
            340                 345                 350

Glu Val Lys Gln Pro Met Lys Ala Ile Glu Lys Ile Lys Leu Ser Tyr
        355                 360                 365

Ser Glu Thr Arg Tyr Lys His Asp Glu Lys Asp Gly Asn Ile Ala Val
    370                 375                 380

Asn Leu Phe Lys Asn Asn Gly Tyr Asn Leu Arg Val Glu Ile Phe His
385                 390                 395                 400

Thr Pro Ile Ala Gly Leu Ser Gly Val Ile Gly Ala Gln Tyr Gln Thr
                405                 410                 415

Gln Thr Ser Ser Ala Asn Ile Pro Arg Ile Ala Pro Cys Ser Asn Asn
            420                 425                 430

Ala Ser Asp Pro Cys His Lys Lys Lys Gln Arg Asp Pro Ser Lys Ile
        435                 440                 445

Thr Lys Gly Asp Arg Lys Ser Trp Ala Leu Ile Glu Asn Thr Gln Ser
    450                 455                 460

Gln Met Ser Phe Phe Ala Ile Glu Gln Leu Arg Trp Gln Asp Phe Leu
465                 470                 475                 480
```

```
Phe Glu Ile Gly Val Arg Thr Glu Lys Gln Arg Ile Asp Ile Glu Tyr
                485                 490                 495

Asp Arg Ala Trp Leu Phe Lys Val Lys Arg Lys Leu Glu Gly Cys Asp
            500                 505                 510

Pro Asn Ser Phe Phe Tyr Ser Pro Ser Gly Cys Arg Gln Gly Ser Tyr
        515                 520                 525

Pro Ala Pro Asp Phe Ala Ser Tyr His Asp Arg Ala Thr Ser Tyr Ser
    530                 535                 540

Gly Ala Ile Ser Trp Asn Met Thr Pro Asp Tyr Thr Leu Ser Leu Thr
545                 550                 555                 560

Tyr Ser His Asn Glu Arg His Pro Thr Pro Met Glu Leu Tyr Tyr His
                565                 570                 575

Gly Lys His Leu Ala Thr Val Ser Phe Glu His Gly Asn Arg Asn Leu
            580                 585                 590

Lys Lys Glu Val Ser Asp Asn Trp Glu Val Gly Leu Ala Tyr Leu Gly
        595                 600                 605

Asp Lys Leu Ser Tyr Lys Val Asn Val Tyr Tyr Asn Asp Phe Lys Asn
    610                 615                 620

Arg Ile Phe Asn Gln Thr Leu Asn Lys Ser Gly Asn Leu Ser Leu Asn
625                 630                 635                 640

Arg Tyr Asn Gln Ser Lys Ala Lys Tyr Tyr Gly Val Glu Gly Arg Ile
                645                 650                 655

Asp Tyr Ala Leu Thr Pro Glu Leu His Met Gly Leu Phe Gly Asp Tyr
            660                 665                 670

Val Arg Gly Lys Leu Tyr Asp Leu Pro Pro Thr Tyr Arg Val Asp His
        675                 680                 685

Val Ala Asn Ser Leu Glu Pro Val Pro Gln Pro Asp Gln Asp Ala Pro
    690                 695                 700

Arg Val Pro Pro Met Arg Leu Gly Phe Arg Val Asn Met Glu Met Thr
705                 710                 715                 720

Glu Ser Leu Thr Ser Ser Leu Glu Tyr Thr Tyr Val Tyr Gln Gln Lys
                725                 730                 735

Lys Val Ala Pro Leu Glu Asn Gln Thr Ala Ala Tyr Ser Leu Leu Asn
            740                 745                 750

Ile Gly Val Asp Tyr Ser Arg Gln Ile Ala Gly Val Asn Tyr Gln Leu
        755                 760                 765

Phe Val Gln Ala Asn Asn Val Leu Asn Arg Lys Val Tyr Ser His Thr
    770                 775                 780

Ser Phe Leu Pro Phe Val Pro Gln Met Gly Arg Asn Val Thr Leu Gly
785                 790                 795                 800

Leu Asn Ile His Phe
                805


<210> SEQ ID NO 45
<211> LENGTH: 87
<212> TYPE: PRT
<213> ORGANISM: Mannheimia haemolytica

<400> SEQUENCE: 45

Ser Lys Arg Arg Asp Asn Tyr Gly Leu Pro Gly His Asn His Lys Phe
1               5                   10                  15

Asp Phe Cys Thr Gly His Ile Tyr Gly Asn Lys Arg Asp Lys Tyr Ala
            20                  25                  30

Tyr Thr Tyr Leu Tyr Pro His Leu Ile Gly Glu Glu Asn Ile Gly Ser
```

```
        35                  40                  45

Asn Pro His Phe His Cys Gly Thr Asn His Ala Glu Asp Gly Thr His
    50                  55                  60

Ser His Asp Asn Pro Phe Gly His Ala His Asp His Thr His Lys Gly
65                  70                  75                  80

Pro Trp Val Asp Leu Glu Ser
                85


<210> SEQ ID NO 46
<211> LENGTH: 790
<212> TYPE: PRT
<213> ORGANISM: Bibersteinia trehalosi USDA-ARS-USMARC-188

<400> SEQUENCE: 46

Met Phe Asn Lys Lys Leu Leu Ala Val Leu Ile Ser Ala Gln Phe Ser
1               5                   10                  15

Pro Leu Val Trp Ala Asn Asn Asn Asp Val Ala Val Leu Asp Glu Val
            20                  25                  30

Ser Val Val Gly Ser Thr Pro Ser Ile Ser Gln Gly Ser Glu Val Thr
        35                  40                  45

Leu Leu Lys Val Ser Asp Lys Ile Ile Ala Gly Lys Glu Phe Lys Lys
    50                  55                  60

Arg Ser Ala Thr Leu Gly Asn Ala Leu Ala Ala Glu Leu Gly Val His
65                  70                  75                  80

Ser Asn Pro Phe Gly Gly Gly Ala Ser Lys Pro Ile Ile Arg Gly Gln
                85                  90                  95

Glu Gly Ala Arg Ile Arg Ile Leu Gln Asn Gly Ser Asp Val Ile Asp
            100                 105                 110

Met Ser Asn Leu Ser Pro Asp His Ala Val Val Ala Asp Ser Leu Leu
        115                 120                 125

Ala Lys Gln Val Glu Ile Leu Arg Gly Ser Ser Thr Leu Leu Tyr Ala
    130                 135                 140

Ser Ser Ser Pro Ala Gly Ile Val Asn Val Val Asp Lys Arg Ile Pro
145                 150                 155                 160

Thr Glu Ile Pro Glu Lys Gly Tyr Glu Val Glu Leu Asn Ser Arg Phe
                165                 170                 175

Asp Thr Ala Ala Lys Glu Lys Val Gly Ala Leu Gly Ala Thr Phe Gly
            180                 185                 190

Ile Gly Lys His Ile Ala Val Arg Ala Glu Gly Leu Thr Arg His Ser
        195                 200                 205

Asp Asn Tyr Arg Val Pro Gly Ile Asn Leu Gly Glu Arg Leu Asn Tyr
    210                 215                 220

Val Pro Asp Thr Tyr Asn Lys Ser Lys Val Gly Thr Leu Gly Leu Ser
225                 230                 235                 240

Phe Val Gly Glu Gln Gly Tyr Ile Gly Ala Ser Tyr Ser Lys Arg Arg
                245                 250                 255

Asp Asn Tyr Gly Leu Pro Gly His Asn His Lys Phe Asp Phe Cys Thr
            260                 265                 270

Gly His Ile Tyr Gly Asn Lys Arg Asp Lys Tyr Ala Tyr Thr Tyr Leu
        275                 280                 285

Tyr Pro His Leu Ile Gly Glu Glu Asn Ile Gly Ser Asn Pro His Phe
    290                 295                 300

His Cys Gly Thr Asn His Ala Glu Asp Gly Thr His Ser His Asp Asn
305                 310                 315                 320
```

-continued

Pro Phe Gly His Asp His Asp His Thr His Pro Gly Pro Trp Val Asp
325 330 335

Leu Glu Ser Lys Arg Phe Asp Val Lys Ala Glu Leu Arg Gln Pro Phe
340 345 350

Lys Gly Ile Asp Lys Ile Lys Val Ser Tyr Ala Asp Ala Asp Tyr Tyr
355 360 365

His Asp Glu Lys Asp Ala Gly Val Leu Ala Thr Arg Tyr His Lys Gln
370 375 380

Leu Lys Lys Asp Gln Asp Tyr Gly Lys Pro Val Asn Ile Phe Lys Asn
385 390 395 400

Arg Gly Lys Asn Ala Arg Leu Glu Ile Tyr His Ala Pro Leu Asp Gly
405 410 415

Leu Thr Gly Val Trp Gly Val Gln Tyr Gln Thr Gln Lys Ser Ser Met
420 425 430

His Ala Pro Lys Asp Arg Glu Val Lys Phe Pro Leu Val Glu Asn Thr
435 440 445

Asn Lys Gln Met Ser Leu Phe Gly Ile Glu Gln Tyr Met Trp Asp Asn
450 455 460

Phe Ala Leu Glu Phe Ala Gly Arg Val Glu Lys Gln Lys Ile Glu Ile
465 470 475 480

Glu Tyr Asp Arg Asn Glu Ile Lys Arg Leu Gln Asp His Tyr Arg Ile
485 490 495

Ser Gly Gly Lys Gln Val Glu Pro Asp Leu Ser Pro Tyr Asn Gln Asn
500 505 510

Ala Tyr Ala Tyr Ser Gly Thr Leu Asn Trp Phe Phe His Pro Asp Tyr
515 520 525

Gln Leu Ser Phe Thr Ala Ser His Asn Glu Arg Phe Pro Thr Pro Met
530 535 540

Glu Leu Tyr Tyr His Gly Gln His Ile Ala Thr Asn Ser Phe Glu Tyr
545 550 555 560

Gly Asn Lys Asp Leu Lys Lys Glu Gln Ser Asn Asn Val Glu Leu Gly
565 570 575

Leu Gly Tyr Gln Thr Glu Arg Val Gly Tyr Lys Val Asn Val Tyr Tyr
580 585 590

Asn His Phe Lys Asn Tyr Ile Tyr Asn Glu Asn Leu Phe Arg Glu Asn
595 600 605

Gln Leu Phe Met Arg Arg Tyr Asn Gln Ala Lys Ala Arg Phe Tyr Gly
610 615 620

Ile Glu Ala Glu Ala Ser Tyr Arg Phe Asn Asn Lys Tyr Gln Ala Thr
625 630 635 640

Ile Phe Gly Asp Met Val Arg Gly Trp Leu Thr Asn Leu Pro Pro Leu
645 650 655

Thr Val Asn Ser Asp Tyr Ser Val Phe Lys Asp Tyr Leu Pro Lys Asp
660 665 670

Ala Lys Pro Gly Glu Asp Tyr Leu Ile Tyr Arg Ala Asp Gln Asn Thr
675 680 685

Pro Arg Thr Pro Pro Val Arg Leu Gly Phe Arg Phe Asn Ala Glu Phe
690 695 700

Thr Pro Asn Trp Ser Gly Asp Leu Glu Leu Ile Arg Thr Phe Thr Gln
705 710 715 720

Arg Arg Thr Ser Gln Leu Glu Tyr Ile Thr Glu Gly Asn Thr Met Leu
725 730 735

Asn Ile Gly Val Ala Tyr Ser Asn Lys Trp Lys Asp Leu Asp Tyr Lys

```
            740                 745                 750

Ile Ser Leu Asn Gly Thr Asn Leu Leu Asn Gln Pro Val Tyr Ile His
        755                 760                 765

Thr Ser Tyr His Gln Phe Val Pro Gln Met Gly Arg Asn Phe Ile Leu
    770                 775                 780

Gly Met Glu Met Lys Phe
785                 790


<210> SEQ ID NO 47
<211> LENGTH: 782
<212> TYPE: PRT
<213> ORGANISM: Actinobacillus pleuropneumoniae

<400> SEQUENCE: 47

Met Leu Ile Ser Ala Gln Phe Ser Pro Leu Val Trp Ala Asn Asn Asn
1               5                   10                  15

Asp Val Ala Val Leu Asp Glu Val Ser Val Val Gly Ser Thr Pro Ser
            20                  25                  30

Ile Ser Gln Gly Ser Glu Val Thr Leu Leu Lys Val Ser Asp Lys Ile
        35                  40                  45

Ile Ala Gly Lys Glu Phe Lys Lys Arg Ser Ala Thr Leu Gly Asn Ala
    50                  55                  60

Leu Ala Ala Glu Leu Gly Val His Ser Asn Pro Phe Gly Gly Gly Ala
65                  70                  75                  80

Ser Lys Pro Ile Ile Arg Gly Gln Glu Gly Ala Arg Ile Arg Ile Leu
                85                  90                  95

Gln Asn Gly Ser Asp Val Ile Asp Met Ser Asn Leu Ser Pro Asp His
            100                 105                 110

Ala Val Val Ala Asp Ser Leu Leu Ala Lys Gln Val Glu Ile Leu Arg
        115                 120                 125

Gly Ser Ser Thr Leu Leu Tyr Ala Ser Ser Ser Pro Ala Gly Ile Val
    130                 135                 140

Asn Val Val Asp Lys Arg Ile Pro Thr Glu Ile Pro Glu Lys Gly Tyr
145                 150                 155                 160

Glu Val Glu Leu Asn Ser Arg Phe Asp Thr Ala Ala Lys Glu Lys Val
                165                 170                 175

Gly Ala Leu Gly Ala Thr Phe Gly Ile Gly Lys His Ile Ala Val Arg
            180                 185                 190

Ala Glu Gly Leu Thr Arg His Ser Asp Asn Tyr Arg Val Pro Gly Ile
        195                 200                 205

Asn Leu Gly Glu Arg Leu Asn Tyr Val Pro Asp Thr Tyr Asn Lys Ser
    210                 215                 220

Lys Val Gly Thr Leu Gly Leu Ser Phe Val Gly Glu Gln Gly Tyr Ile
225                 230                 235                 240

Gly Ala Ser Tyr Ser Lys Arg Arg Asp Asn Tyr Gly Leu Pro Gly His
                245                 250                 255

Asn His Lys Phe Asp Phe Cys Ile Gly His Ile Tyr Gly Asn Lys Gln
            260                 265                 270

Gly Lys Tyr Ala Tyr Thr Tyr Leu Tyr Pro His Leu Ile Gly Glu Glu
        275                 280                 285

Asn Ile Gly Ser Asn Pro His Phe His Cys Gly Thr Asp His Ala Glu
    290                 295                 300

Asp Gly Thr His Ser His Asp Asn Pro Phe Gly His Asp His Asp His
305                 310                 315                 320
```

-continued

```
Thr His Pro Gly Pro Trp Val Asp Leu Glu Ser Lys Arg Phe Asp Val
                325                 330                 335

Lys Ala Glu Leu Arg Gln Pro Phe Lys Gly Ile Asp Lys Ile Lys Val
            340                 345                 350

Ser Tyr Ala Asp Ala Asp Tyr Tyr His Asp Glu Lys Asp Ala Gly Val
        355                 360                 365

Leu Ala Thr Arg Tyr His Lys Gln Leu Lys Lys Asp Gln Asp Tyr Gly
    370                 375                 380

Lys Pro Val Asn Ile Phe Lys Asn Arg Gly Lys Asn Ala Arg Leu Glu
385                 390                 395                 400

Ile Tyr His Ala Pro Leu Gly Gly Leu Thr Gly Val Trp Gly Val Gln
                405                 410                 415

Tyr Gln Thr Gln Lys Ser Ser Met His Ala Pro Lys Asp Arg Glu Val
            420                 425                 430

Lys Phe Pro Leu Val Glu Asn Thr Asn Lys Gln Met Ser Leu Phe Gly
        435                 440                 445

Ile Glu Gln Tyr Met Trp Asp Asn Phe Ala Leu Glu Phe Ala Gly Arg
    450                 455                 460

Val Glu Lys Gln Lys Ile Glu Ile Glu Tyr Asp Arg Asn Glu Ile Lys
465                 470                 475                 480

Arg Leu Gln Asp His Tyr Arg Ile Ser Gly Gly Lys Gln Val Glu Pro
                485                 490                 495

Asp Leu Ser Pro Tyr Asn Gln Asn Ala Tyr Ala Tyr Ser Ser Thr Leu
            500                 505                 510

Asn Trp Phe Phe His Pro Asp Tyr Gln Leu Ser Phe Thr Ala Ser His
        515                 520                 525

Asn Glu Arg Phe Pro Thr Pro Met Glu Leu Tyr Tyr His Gly Gln His
    530                 535                 540

Ile Ala Thr Asn Ser Phe Glu Tyr Gly Asn Lys Asp Leu Lys Lys Glu
545                 550                 555                 560

Gln Ser Asn Asn Val Glu Leu Gly Leu Gly Tyr Gln Thr Glu Arg Val
                565                 570                 575

Gly Tyr Lys Val Asn Val Tyr Tyr Asn His Phe Lys Asn Tyr Ile Tyr
            580                 585                 590

Asn Glu Asn Leu Phe Arg Glu Asn Gln Leu Phe Met Arg Arg Tyr Asn
        595                 600                 605

Gln Ala Lys Ala Arg Phe Tyr Gly Ile Glu Ala Glu Ala Ser Tyr Arg
    610                 615                 620

Phe Asn Asn Lys Tyr Gln Ala Thr Ile Phe Gly Asp Met Val Arg Gly
625                 630                 635                 640

Trp Leu Thr Asn Leu Pro Pro Leu Thr Val Asn Ser Asp Tyr Ser Val
                645                 650                 655

Phe Lys Asp Tyr Leu Pro Lys Asp Ala Lys Pro Gly Glu Asp Tyr Leu
            660                 665                 670

Ile Tyr Arg Ala Asp Gln Asn Thr Pro Arg Thr Pro Pro Val Arg Leu
        675                 680                 685

Gly Phe Arg Phe Asn Ala Glu Phe Thr Pro Asn Trp Ser Gly Asp Leu
    690                 695                 700

Glu Leu Ile Arg Thr Phe Thr Gln Arg Arg Thr Ser Gln Leu Glu Tyr
705                 710                 715                 720

Ile Thr Glu Gly Asn Thr Met Leu Asn Ile Gly Val Ala Tyr Ser Asn
                725                 730                 735

Lys Trp Lys Asp Leu Asp Tyr Lys Ile Ser Leu Asn Gly Thr Asn Leu
```

```
            740                 745                 750

Leu Asn Gln Pro Val Tyr Ile His Thr Ser Tyr His Gln Phe Val Pro
        755                 760                 765

Gln Thr Gly Arg Asn Phe Ile Leu Val Val Asn Val Lys Phe
    770                 775                 780


<210> SEQ ID NO 48
<211> LENGTH: 790
<212> TYPE: PRT
<213> ORGANISM: Mannheimia granulomatis

<400> SEQUENCE: 48

Met Thr Asn Lys Thr Ile Leu Ala Leu Leu Ile Ser Ala His Leu Ser
1               5                   10                  15

Ser Leu Ala Leu Ala Gln Thr Lys Glu Asp Ile Ala Val Leu Glu Glu
            20                  25                  30

Val Ser Val Ile Gly Asn Ser Asp Thr Pro Val Val Ala Gln Gly Ser
        35                  40                  45

Glu Val Thr Ile Leu Lys Val Ser Asp Lys Ile Ile Asp Gly Lys Glu
    50                  55                  60

Phe Lys Lys Arg Ser Ala Thr Leu Gly Asn Ala Leu Ala Ala Glu Leu
65                  70                  75                  80

Gly Val His Ser Asn Pro Phe Gly Gly Gly Ala Ser Lys Pro Ile Ile
                85                  90                  95

Arg Gly Gln Glu Gly Ala Arg Ile Lys Ile Leu Gln Asn Gly Ala Glu
            100                 105                 110

Val Val Asp Met Ser Ser Leu Ser Pro Asp His Ala Val Val Ala Asp
        115                 120                 125

Ser Leu Leu Ala Ser Lys Val Glu Val Leu Arg Gly Ser Ser Thr Leu
    130                 135                 140

Leu Tyr Thr Ser Ser Ser Pro Ala Gly Val Val Asn Val Val Asp Lys
145                 150                 155                 160

Arg Ile Pro Thr Ser Ile Pro Glu Lys Gly Tyr Glu Val Glu Leu Asn
                165                 170                 175

Ser Arg Phe Asp Thr Val Ser Lys Glu Arg Leu Gly Val Ile Gly Ala
            180                 185                 190

Thr Val Gly Leu Gly Gln His Val Ala Leu Arg Val Glu Gly Leu Asn
        195                 200                 205

Arg His Ser Asp Asn Tyr Arg Val Lys Ser Leu Gln Leu Gly Glu Ser
    210                 215                 220

Leu Asn Tyr Val Pro Asp Thr Tyr Asn Arg Ser Arg Val Gly Thr Met
225                 230                 235                 240

Gly Ile Ser Phe Ile Gly Glu Arg Gly Tyr Ile Gly Ala Ala Tyr Ser
                245                 250                 255

His Arg Lys Asp Thr Tyr Gly Leu Pro Gly His Asn His Lys Phe Asp
            260                 265                 270

Phe Cys Thr Gly His Ile Tyr Gly Val Asp Arg Asp Lys His Ala His
        275                 280                 285

Thr Tyr Leu Tyr Pro His Leu Leu Thr Asn Glu Leu Ile Ser Glu Asn
    290                 295                 300

Pro His Phe His Cys Gly Ser Asp His Gly Leu Asp His Asn His Ser
305                 310                 315                 320

His Asp Asn Pro Tyr Gly His Lys His Asp His Thr His Lys Gly Pro
                325                 330                 335
```

```
Trp Val Asp Leu Arg Ser Lys Arg Leu Asp Leu Lys Met Glu Leu Lys
            340                 345                 350

Gln Pro Phe Ser Gly Ile Glu Lys Leu Arg Leu Ser His Thr Asp Val
        355                 360                 365

Asn Tyr Tyr His Asp Glu Lys Asp Ala Gly Val Leu Leu Thr Phe Leu
    370                 375                 380

His Lys Gln Leu Lys Lys Asp Lys Asp Tyr Gly Lys Pro Val Asn Ile
385                 390                 395                 400

Tyr Lys Asn Arg Gly Lys Asn Ser Arg Leu Glu Phe Tyr His Thr Pro
                405                 410                 415

Val Gly Gly Leu Thr Gly Val Trp Gly Leu Gln Tyr Gln Thr Gln Lys
            420                 425                 430

Ser Ser Met Asn Ala Pro Lys Asp Arg Glu Val Arg Phe Pro Leu Ile
        435                 440                 445

Glu Asn Asn Asn Lys Gln Leu Ser Leu Phe Gly Ile Glu Gln Tyr Met
    450                 455                 460

Trp Asp Asn Phe Ala Val Glu Leu Ala Gly Arg Ile Glu Lys Gln Lys
465                 470                 475                 480

Ile Glu Ile Asp Tyr Asp Leu Asn Glu Ile Lys Arg Leu Gln Asp Phe
                485                 490                 495

Tyr Arg Ile Ser Gly Gly Ala Gln Val Glu Pro Asp Leu Ser Pro Tyr
            500                 505                 510

Asn Lys Thr Ala Tyr Ala Tyr Ser Gly Thr Leu Asn Trp Phe Phe His
        515                 520                 525

Pro Asn Tyr Gln Leu Ser Phe Thr Ala Ser His Asn Glu Arg His Pro
    530                 535                 540

Thr Pro Met Glu Leu Tyr Tyr His Gly Gln His Leu Ala Thr Ser Ser
545                 550                 555                 560

Phe Glu Tyr Gly Asn Lys Asp Leu Lys Lys Glu Gln Ser Asn Asn Val
                565                 570                 575

Glu Leu Gly Leu Gly Tyr Gln Gly Glu Lys Phe Gly Tyr Lys Thr Thr
            580                 585                 590

Val Tyr Tyr Asn His Phe Lys Asn Tyr Ile Phe Asn Glu Asn Leu Tyr
        595                 600                 605

Arg Glu Asn Gln Leu Phe Met Arg Arg Tyr Ser Gln Ala Lys Ala Arg
    610                 615                 620

Phe Tyr Gly Leu Glu Ala Glu Met Ser Tyr Arg Phe Asn Asp Lys Tyr
625                 630                 635                 640

Gln Ala Thr Leu Phe Gly Asp Met Val Arg Gly Trp Leu Thr Asp Leu
                645                 650                 655

Pro Pro Val Lys Val Gly Gly Ile His Lys Glu His Leu Pro Lys Asp
            660                 665                 670

Ala Lys Pro Gly Glu Thr Tyr Leu Leu Tyr Arg Ala Asp Met Asn Thr
        675                 680                 685

Pro Arg Thr Pro Pro Val Arg Leu Gly Leu Arg Leu Asn Ala Gln Phe
    690                 695                 700

Asn Glu Asn Trp Ala Gly Glu Ala Glu Phe Tyr Arg Met Phe Ser Gln
705                 710                 715                 720

Arg Arg Leu Ser Gln Leu Glu Tyr Pro Thr Asn Gly His Ser Met Leu
                725                 730                 735

Asn Leu Gly Leu Ser Tyr Ser Asn Lys Phe Lys Asn Ala Glu Tyr Lys

            740                 745                 750

Ile Ser Leu Asn Gly Thr Asn Leu Leu Asn Gln Ala Val Tyr Ile His
```

755 760 765

Thr Ser Tyr His Gln Phe Val Ser Gln Pro Gly Arg Asn Phe Ile Leu
770 775 780

Gly Leu Glu Met Lys Phe
785 790

<210> SEQ ID NO 49
<211> LENGTH: 790
<212> TYPE: PRT
<213> ORGANISM: Mannheimia sp. USDA-ARS-USMARC-1261

<400> SEQUENCE: 49

Met Thr Asn Lys Thr Leu Leu Ala Val Leu Ile Ser Ala His Leu Ser
1 5 10 15

Thr Leu Ala Leu Ala Gln Thr Asn Glu Asp Val Ala Val Leu Asp Glu
20 25 30

Val Ser Val Ile Gly Asn Thr Ala Thr Pro Val Ile Ala Gln Gly Ser
35 40 45

Glu Val Thr Leu Leu Lys Val Ser Asp Lys Ile Ile Glu Gly Lys Glu
50 55 60

Phe Lys Lys Arg Ser Ala Thr Leu Gly Asn Ala Leu Ser Ala Glu Leu
65 70 75 80

Gly Val His Ser Asn Pro Phe Gly Gly Gly Ala Ser Lys Pro Ile Ile
85 90 95

Arg Gly Gln Glu Gly Ala Arg Ile Lys Ile Leu Gln Asn Gly Ser Asp
100 105 110

Val Val Asp Met Ser Ser Leu Ser Pro Asp His Ala Val Val Ala Asp
115 120 125

Ser Leu Leu Ala Ser Gln Val Glu Val Leu Arg Gly Ser Ser Thr Leu
130 135 140

Leu Tyr Thr Ser Ser Ser Pro Ala Gly Val Val Asn Val Val Asp Lys
145 150 155 160

Arg Ile Pro Thr Ile Val Pro Glu Lys Gly Tyr Glu Val Glu Leu Asn
165 170 175

Ser Arg Phe Asp Thr Ala Ser Lys Glu Arg Leu Gly Val Leu Gly Ala
180 185 190

Thr Leu Gly Leu Gly Gln His Val Ala Leu Arg Val Glu Gly Leu Ala
195 200 205

Arg His Ser Asp Asn Tyr Arg Val Lys Ser Leu Gln Leu Gly Glu Arg
210 215 220

Leu Asn Tyr Val Pro Asp Thr Tyr Asn Arg Ser Arg Val Gly Thr Val
225 230 235 240

Gly Leu Ser Phe Val Gly Glu Arg Gly Tyr Ile Gly Ala Ala Tyr Asn
245 250 255

Glu Arg Thr Asp Thr Tyr Gly Leu Pro Gly His Asn His Lys Phe Asp
260 265 270

Glu Cys Ile Gly His Ile Tyr Asn Glu Val Arg Asp Lys Tyr Ala Tyr
275 280 285

Thr Tyr Lys Tyr Pro His Leu Leu Asp Glu Asp Leu Ile Ser His Gly
290 295 300

Pro His Phe His Cys Gly Thr Asp His Glu Met Asp Ala Gly His Ser
305 310 315 320

His Asp Asn Pro Tyr Gly His Thr His Asp His Thr His Lys Gly Pro
325 330 335

```
Trp Val Asp Leu Lys Ser Lys Arg Ile Asp Val Lys Gly Glu Leu Leu
            340                 345                 350

Lys Pro Phe Arg Gly Leu Asp Lys Ile Arg Ala Ser Tyr Thr Asp Val
        355                 360                 365

Asn Tyr Tyr His Asp Glu Lys Asp Ala Gly Ser Val Ser Thr Phe Val
    370                 375                 380

Asn Lys Gln Leu Lys Lys Asp Gln Asn Tyr Gly Lys Pro Val Asn Ile
385                 390                 395                 400

Tyr Lys Asn Arg Gly Lys Asn Ser Arg Leu Glu Phe Tyr His Ser Pro
                405                 410                 415

Ile Gly Gly Leu Thr Gly Val Trp Gly Val Gln Tyr Gln Thr Gln Lys
            420                 425                 430

Ser Ser Met Asn Ala Pro Asn Asp Arg Glu Val Arg Phe Pro Leu Val
        435                 440                 445

Glu Asn Asn Asn Lys Gln Leu Ser Leu Phe Ala Ile Glu Gln Tyr Met
    450                 455                 460

Trp Asp Asn Phe Ala Leu Glu Leu Ala Gly Arg Ile Glu Lys Gln Lys
465                 470                 475                 480

Ile Glu Ile Asp Tyr Asp Leu Glu Glu Ile Arg Arg Leu Gln Lys Phe
                485                 490                 495

Tyr Ser Glu Ser Gly Gly Arg Gln Val Glu Pro Asp Leu Ser Pro Tyr
            500                 505                 510

Asp Lys Thr Ala Tyr Ala Tyr Ser Gly Thr Phe Asn Trp Phe Phe His
        515                 520                 525

Pro Asp Tyr Gln Leu Ser Phe Thr Val Ser His Asn Glu Arg His Pro
    530                 535                 540

Thr Pro Met Glu Leu Tyr Tyr His Gly Pro His Leu Ala Thr Ser Ser
545                 550                 555                 560

Phe Glu Tyr Gly Asn Lys Asp Leu Lys Lys Glu Gln Ser Asn Asn Val
                565                 570                 575

Glu Leu Gly Leu Ser Tyr Gln Gly Glu Lys Phe Gly Tyr Lys Thr Thr
            580                 585                 590

Val Tyr Tyr Asn His Phe Lys Asn Tyr Ile Phe Asn Glu Asn Leu Tyr
        595                 600                 605

Arg Glu Asn Gln Leu Phe Met Arg Arg Tyr Ser Gln Ala Lys Ala Arg
    610                 615                 620

Phe Tyr Gly Leu Glu Ala Glu Met Ser Tyr Arg Phe Asn Glu Gln Tyr
625                 630                 635                 640

Gln Ala Thr Ile Phe Gly Asp Met Val Arg Gly Trp Leu Thr Asp Leu
                645                 650                 655

Pro Pro Val Lys Val Gly Gly Ile His Lys His His Leu Pro Lys Asp
            660                 665                 670

Ala Lys Pro Gly Glu Thr Tyr Leu Leu Tyr Arg Ala Asp Met Asn Thr
        675                 680                 685

Pro Arg Thr Pro Pro Leu Arg Leu Gly Leu Arg Val Asn Ala Gln Phe
    690                 695                 700

Asn Glu Asn Trp Ala Gly Glu Ala Glu Phe Tyr Arg Met Phe Ser Gln
705                 710                 715                 720

Arg Arg Leu Ser Gln Leu Glu Tyr Pro Thr Lys Gly His Ser Met Leu
                725                 730                 735

Asn Leu Gly Leu Ser Tyr Ser Asn Lys Phe Lys Asn Ala Glu Tyr Lys
            740                 745                 750

Ile Ser Leu Asn Gly Thr Asn Leu Leu Asn Gln Pro Ile Tyr Ile His
```

```
        755                 760                 765

Thr Ser Tyr His Pro Phe Val Ser Gln Pro Gly Arg Asn Phe Ile Leu
    770                 775                 780

Gly Val Glu Val Lys Phe
785                 790


<210> SEQ ID NO 50
<211> LENGTH: 817
<212> TYPE: PRT
<213> ORGANISM: Haemophilus parasuis

<400> SEQUENCE: 50

Met Ile Asn Asn Arg Thr Thr Glu Gln Gln Asn Asn Arg Thr Thr Glu
1               5                   10                  15

Gln Gln Asn Asn Arg Thr Thr Ala Phe Ser Leu Ala Phe Ser Leu Leu
            20                  25                  30

Leu Cys Cys Leu Gly Ile Asn Ala Glu Gln Leu Glu Leu Asp Glu Ile
        35                  40                  45

Ser Val Met Gly Lys Val Pro Glu Gly Asn Ser Ile Ser Phe Leu Lys
    50                  55                  60

Val Ser Asp Ala Ile Ile Asp Gly Glu Lys Phe Lys Asn Arg Ser Ala
65                  70                  75                  80

Thr Leu Gly Asn Ala Leu Ser Ser Glu Leu Gly Val His Ser Thr Pro
                85                  90                  95

Phe Gly Gly Gly Ala Ser Ala Pro Ile Ile Arg Gly Gln Glu Gly Val
            100                 105                 110

Arg Val Lys Ile Leu Gln Asn Asn Ala Asp Val Val Asp Met Ser Asn
        115                 120                 125

Ile Ser Pro Asp His Ala Ile Thr Ala Asp Thr Leu Leu Ala Asn Gln
    130                 135                 140

Val Glu Ile Leu Arg Gly Ala Ser Thr Leu Leu Tyr Ala Ser Ser Ser
145                 150                 155                 160

Pro Ala Gly Ile Val Asn Ile Val Asp Gln Arg Ile Pro Asn Lys Met
                165                 170                 175

Pro Lys Lys Gly Tyr Glu Val Thr Leu Ser Ser Arg Phe Asp Thr Ala
            180                 185                 190

Ser Lys Glu Lys Val Tyr Ala Leu Gly Thr Thr Ile Gly Ile Gly Lys
        195                 200                 205

His Leu Ala Leu Arg Leu Glu Gly Leu Asp Arg Gln Ser Gln Asn Tyr
    210                 215                 220

Lys Val Pro Gln Ile Lys Leu Gly Glu Thr Leu Asn Tyr Val Pro Asp
225                 230                 235                 240

Thr Tyr His Gln Ser Lys Val Gly Thr Ile Gly Leu Ser Phe Ile Gly
                245                 250                 255

Glu Lys Gly Tyr Leu Gly Ala Ser Tyr Asn Gln Arg Lys Asp Arg Tyr
            260                 265                 270

Gly Leu Pro Gly His Asn His Lys Phe Asp Thr Cys Ile Ala His Ile
        275                 280                 285

Tyr Asp Met Arg Leu Gln Gly Lys His Ser Tyr Thr Asn Leu Tyr Pro
    290                 295                 300

His Leu Met Ser Asp Glu Met Val Thr Glu Asn Pro His Phe His Cys
305                 310                 315                 320

Gly Thr Asp Tyr Asp Leu Asp Pro Ser His Ser His Asp His Pro Tyr
                325                 330                 335
```

-continued

```
Gly His Asp His Asp His Thr His Ile Gly Pro Trp Val Asp Leu His
            340                 345                 350

Ser Lys Arg Ile Asp Ile Lys Gly Glu Ile Lys Gln Pro Leu Pro Met
        355                 360                 365

Leu Asp Lys Ile Gln Leu Ser Tyr Ala Gln Thr Asp Tyr Tyr His Asp
    370                 375                 380

Glu Lys Asp Ala Gly Lys Ser Gly Asp Thr Ile Asn Pro Asn Arg Val
385                 390                 395                 400

Asp Lys Ser Lys Asp Phe Gly Lys Pro Val Asn Ile Phe Lys Asn Gln
                405                 410                 415

Gly Lys Asn Ala Arg Leu Glu Phe Phe His Thr Pro Ile Gly Gly Leu
            420                 425                 430

Thr Gly Met Phe Gly Val Gln Tyr Gln Thr Leu Gln Ser Ser Ala Asn
        435                 440                 445

Thr Pro Ser Asn Arg Glu Val Gln Trp Pro Leu Val Asp Asn Arg Asn
    450                 455                 460

Lys Gln Ile Ser Leu Phe Ala Leu Glu Gln Tyr Ala Trp Asp Asn Phe
465                 470                 475                 480

Ala Ile Glu Leu Gly Leu Arg Thr Glu Lys Gln Asn Ile His Ile Asp
                485                 490                 495

Tyr Asp Leu Ala Lys Ile Gln Lys Gln Gln Lys Phe Asn Glu Arg Thr
            500                 505                 510

Tyr Gly Lys Gln Val Asp Pro Asp Leu Ser Asp Tyr Asp Glu Lys Ala
        515                 520                 525

Ile Ser Tyr Thr Gly Ala Phe Asn Trp Phe Phe His Pro Asp Tyr Gln
    530                 535                 540

Leu Ser Phe Thr Ala Ser His Asn Glu Arg Leu Pro Thr Pro Met Glu
545                 550                 555                 560

Leu Tyr Tyr His Gly Gln His Leu Ala Thr Asn Ser Phe Glu Tyr Gly
                565                 570                 575

Asn Lys Asp Leu Lys Lys Glu Ile Ser Asn Asn Phe Glu Leu Gly Leu
            580                 585                 590

Gly Tyr His Thr Glu Lys Leu Asp Tyr Lys Leu Ser Thr Tyr Tyr Asn
        595                 600                 605

Asn Phe Asp Asn Tyr Ile Tyr Asn Glu Thr Leu Tyr Arg Ser Asn Asn
    610                 615                 620

Leu Phe Met Arg Arg Tyr Asn Gln Ala Lys Ala Thr Phe Tyr Gly Leu
625                 630                 635                 640

Glu Gly Ile Ile Asn Tyr Arg Phe Thr Pro Asp Tyr Gln Phe Ser Val
                645                 650                 655

Phe Gly Asp Met Val Lys Gly Lys Leu Lys Gln Leu Pro Asp Ile Lys
            660                 665                 670

Gly Leu Asn Asp Val Tyr Gly Glu Pro Ile Leu Asn Pro Asp Tyr Asp
        675                 680                 685

Pro Glu Tyr Asp Glu Pro Glu Asp Gln Tyr Tyr Arg Pro Tyr Leu Gly
    690                 695                 700

Lys Glu Met Ile Lys Gln Ala Asp Arg Val Ser Pro Arg Leu Pro Pro
705                 710                 715                 720

Ile Arg Leu Gly Ala Arg Phe Asn Ala Gln Leu Thr Glu Asn Leu Ser
                725                 730                 735

Gly Ser Val Glu Trp Met Lys Val Phe Thr Gln Asn Lys Val Ser Lys
            740                 745                 750

Leu Glu Ser Ser Thr Lys Gly Tyr Gln Leu Leu Asn Ala Ser Leu Asn
```

```
        755                 760                 765

Tyr Arg Arg Gln Ile Lys Gly Val Glu Tyr Thr Val Ser Leu Thr Gly
    770                 775                 780

Asn Asn Leu Leu Asn Gln Ala Val Tyr Ile His Asn Ser Tyr His Pro
785                 790                 795                 800

Tyr Val Pro Gln Met Gly Arg Asn Phe Ile Leu Gly Leu Asp Leu Ser
                805                 810                 815

Phe


<210> SEQ ID NO 51
<211> LENGTH: 825
<212> TYPE: PRT
<213> ORGANISM: Moraxella boevrei

<400> SEQUENCE: 51

Met Ala Val Leu Ala Ser Ser Ser Met Ser Val Phe Ala Asn Asp Ser
1               5                   10                  15

Ser Pro Glu Thr Thr Leu Asp Thr Ile Val Ile Glu Ala Thr Ser Ala
            20                  25                  30

Asn Lys Val Asn Ser Leu Ala Phe Ala Glu Ser Gln Lys Ala Ser Asp
        35                  40                  45

Met Val Ile Ser Lys Glu Arg Leu Lys Ser Lys Ser Ala Thr Leu Gly
    50                  55                  60

Asn Ala Leu Ala Gly Glu Ser Gly Ile His Ser Asn Pro Phe Gly Gly
65                  70                  75                  80

Gly Ala Ser Ala Pro Val Ile Arg Gly Gln Glu Gly Val Arg Val Lys
                85                  90                  95

Ile Leu Gln Asn Gly Ser Ala Val Ala Asp Met Ser Thr Val Ser Pro
            100                 105                 110

Asp His Val Val Ala Val Asp Thr Leu Leu Ala Ser Arg Val Glu Val
        115                 120                 125

Val Arg Gly Ala Ser Thr Leu Met His Ala Asn Ala Ser Pro Ala Gly
    130                 135                 140

Val Ile Asn Val Val Asp Gly Arg Ile Pro Asp Lys Met Pro Thr Gly
145                 150                 155                 160

Ile Thr Gly Glu Thr Met Leu Arg Phe Asn Ser Gly Ser Asp Glu Lys
                165                 170                 175

Leu Ala Thr Ala Gly Ile Ser Ala Pro Leu Asn Asp Asn Phe Val Leu
            180                 185                 190

Arg Leu Glu Ala Met Gly Arg Asp Ala Asn Pro Tyr Asn Val Pro Ala
        195                 200                 205

Ile Asn Phe Gly Glu Val Leu Asn Tyr Leu Pro Asp Ser Tyr Asn Lys
    210                 215                 220

Ser Thr Val Gly Thr Leu Gly Leu Ser Tyr Ile Gly Asn Gln Gly His
225                 230                 235                 240

Ile Gly Leu Ala Tyr Ser Glu Arg Arg Asp Lys Tyr Gly Leu Val Gly
                245                 250                 255

His Asn His Lys Phe Asp Asn Cys Glu Gly His Ala Phe Asn Thr Ser
            260                 265                 270

Arg Gly Leu Trp Gly Pro Glu Arg Arg Tyr Leu Ile Pro Tyr Pro His
        275                 280                 285

Leu Met Ser Asp Glu Asp Met Ile Thr Ser Leu His Phe His Cys Gly
    290                 295                 300

Thr Asn Tyr Asp Leu Asp Pro Ser His Ser His Glu His Val Tyr Gly
```

-continued

```
305                 310                 315                 320

His Lys His Asp His Thr Gln Lys Gly Pro Trp Val Asp Met Thr Ser
                325                 330                 335

Lys Thr Phe Ser Leu Gln Gly Glu Ile Asn Gln Pro Ile Pro Ser Ile
            340                 345                 350

Asp Lys Ile Arg Leu Thr Ala Ser His Ser Asn Tyr Glu His Gln Glu
        355                 360                 365

Tyr Asp Asp Gly Lys Gln Ile Pro Asp Pro Ser Lys Gly Lys Ile Phe
    370                 375                 380

Val Lys Gly Asn Thr Ser Tyr Trp Asp Asn Gln Gly Leu Ser Ser Lys
385                 390                 395                 400

Leu Ser Ile Tyr Gln Ser Pro Thr Asp Arg Leu Ser Phe Val Trp Gly
                405                 410                 415

Phe Asp Asn Gln Arg Asn Lys Thr His Ala Leu Ile Pro Ser Pro Asn
            420                 425                 430

Glu Lys Ala Gly Asn Arg Arg Leu Leu Val Lys Asn Thr Gln Lys Thr
        435                 440                 445

His Ser Ile Phe Gly Leu Ser Glu Tyr Lys Ile Gly Asn Val Lys Leu
    450                 455                 460

His Thr Ala Leu Arg Gln Glu Arg Thr Arg Ile Pro Val Glu Tyr Asn
465                 470                 475                 480

Met Asp Glu Ile Lys Ala Gln Leu Ala Asn Gly Ile Gly Thr Gln Glu
                485                 490                 495

Leu Pro Asp Leu Thr Pro Tyr Lys Ser Asn Ala Thr Ser Tyr Ala Met
            500                 505                 510

Gly Ala Ile Trp Asp Ile Asn Pro Lys Leu Arg Leu Asp Thr Thr Phe
        515                 520                 525

Ser His Asn Glu Arg Thr Pro Thr Pro Met Glu Leu Tyr Tyr His Gly
    530                 535                 540

Lys His Leu Ala Thr Asn Ser Phe Leu Tyr Gly Asn Lys Asp Leu Asn
545                 550                 555                 560

Lys Glu Lys Ser Asp Asn Gly Glu Leu Gly Leu Thr Phe Lys Gly Asp
                565                 570                 575

Lys Trp Arg Val Lys Gly Ser Ile Tyr Ala Asn Lys Phe Asp Asn Tyr
            580                 585                 590

Ile His Pro Glu Asn Leu Tyr Lys Ser Gly Asn Leu Thr Met Arg Arg
        595                 600                 605

Phe Thr Gln Ser Lys Ala Lys Leu Arg Gly Ala Glu Leu Glu Ile Gly
    610                 615                 620

Tyr Gln Phe Asn Pro Asn Leu Asn Val Ser Leu Phe Gly Asp Met Val
625                 630                 635                 640

Arg Gly Lys Leu Tyr Gly Phe Ser Pro Ile Thr Gly Gly Asn Leu Tyr
                645                 650                 655

Glu Lys Val Lys Val Ile Asp Pro Asn Cys Asp Leu Glu Lys Asp Asp
            660                 665                 670

Pro Asp Tyr Glu Asp Phe Cys Ile Asp Ile Glu Asn Lys Val Val Gly
        675                 680                 685

Lys Asp Thr Ile Thr Arg Pro Asp Arg Thr Pro Pro Arg Leu Ser Pro
    690                 695                 700

Asp Arg Ile Gly Met Arg Ile Asn Gly Glu Tyr Gly Asn Phe Ser Pro
705                 710                 715                 720

Ser Leu Glu Phe Ile Arg Val Phe Asp Gln Asn Arg Thr Ser Asn Ser
                725                 730                 735
```

```
Val Ala Ala Lys Tyr Asn Ser Glu Cys Thr His His Gln Tyr Gly Asn
            740                 745                 750

Glu Arg Leu Cys Pro Ile Phe Ile Gln Glu Asp Ala Thr Lys Gly Tyr
        755                 760                 765

Asn Leu Leu Asn Val Gly Leu Asp Tyr His Asn Tyr Phe Lys Gly Leu
    770                 775                 780

Gln Tyr Thr Val Ser Leu Asn Ala Asn Asn Leu Leu Asn Glu Lys Val
785                 790                 795                 800

Tyr Ile His Asn Ser Phe Leu Pro Phe Val Pro Gln Gln Gly Arg Asn
                805                 810                 815

Phe Ser Leu Ala Leu Thr Thr Lys Phe
            820                 825


<210> SEQ ID NO 52
<211> LENGTH: 869
<212> TYPE: PRT
<213> ORGANISM: Psychrobacter phenylpyruvicus

<400> SEQUENCE: 52

Met Lys Ile Lys Pro Leu Ser Tyr Ala Val Ser Ala Ile Met Leu Ser
1               5                   10                  15

Tyr Leu Ser His Thr Pro Met Ala Gln Ala Ala Val Ser Ser Lys Thr
            20                  25                  30

Val Thr Asp Thr Gln Asp Gln Lys Gln Thr Pro Ser Gln Gln Ala Ser
        35                  40                  45

Glu Thr Asp Ser Thr Pro Asp Ser Ala Ser Asn Pro Ile Ala Ile Phe
    50                  55                  60

Asp Thr Ile Thr Val Pro Pro Ser Ser Thr His Val Pro Ser Ser Leu
65                  70                  75                  80

Ala Phe Asp Asn Ala Gln Lys Ala Ser Asp Val Val Ile Asp Asn Glu
                85                  90                  95

Lys Leu Arg His Arg Ser Ala Thr Leu Gly Asn Ala Leu Ala Asp Glu
            100                 105                 110

Leu Gly Val His Ser Asn Pro Phe Gly Gly Gly Ser Ser Ala Pro Val
        115                 120                 125

Val Arg Gly Gln Glu Gly Val Arg Val Lys Ile Leu Gln Asn Gly Met
    130                 135                 140

Asp Ala Ile Asp Met Ser Thr Leu Ser Pro Asp His Val Val Gly Val
145                 150                 155                 160

Asp Thr Leu Leu Ala Asp Lys Val Glu Leu Ile Arg Gly Ala Ser Thr
                165                 170                 175

Leu Leu Tyr Ser Asn Ala Ser Pro Ala Gly Val Ile Asn Val Val Asp
            180                 185                 190

Gly Arg Ile Pro Thr Glu Val Pro Glu Gly Tyr Thr Gly Glu Ala Thr
        195                 200                 205

Leu Arg Phe Asn Glu Asn Asn Asp Glu Arg Val Ala Thr Ala Gly Ile
    210                 215                 220

Thr Phe Gly Leu Thr Asp Asn Val Ala Leu Arg Val Glu Gly Leu Thr
225                 230                 235                 240

Arg Lys Ala Asn Glu Tyr Glu Val Pro Glu Ile Asn Leu Gly Asp Lys
                245                 250                 255

Leu Asn Tyr Leu Pro Asp Ser Gln Asn Lys Ser Asn Val Gly Thr Ile
            260                 265                 270

Gly Leu Ser Tyr Val Gly Glu Arg Gly His Ile Gly Val Ala Tyr Ser
```

-continued

```
        275                 280                 285

Glu Arg Glu Asp Lys Tyr Gly Leu Val Gly His Asn His Lys Leu Asp
    290                 295                 300

Gly Cys Tyr Gly His Val Val Tyr Pro Gln Lys Asn Tyr Lys Asn Lys
305                 310                 315                 320

Pro Tyr Leu Ala Ala Tyr Pro His Leu Met Gly Asp Glu Asp Leu Ala
                325                 330                 335

Glu Ser Phe His Phe His Cys Asp Ser Asp His Asn Glu Asp Glu Pro
            340                 345                 350

His Ser His Asp Asn Pro Tyr Gly His Asp His Asp His Thr Gln Gly
        355                 360                 365

Gly Pro Trp Val Asp Met Asn Ser Lys Ser Tyr Tyr Leu Gln Gly Glu
    370                 375                 380

Leu Leu Glu Pro Ile Pro Ala Ile Glu Lys Val Arg Leu Asn Val Ala
385                 390                 395                 400

Tyr His Asp Tyr His His Glu Glu His Asp His Gly Lys Thr Ile Pro
                405                 410                 415

Asp Pro Ala Lys Gly Glu Arg Phe Val Lys Ala Gln Pro Ser Tyr Phe
            420                 425                 430

Asp Asn Gln Gly Tyr Asn Ala Lys Leu Glu Ala Tyr His Thr Pro Thr
        435                 440                 445

Glu His Leu Gln Gly Val Trp Gly Ile Gln Ser Gln Ser His Lys Ser
    450                 455                 460

Ser Ala Leu Ile Pro Ser Lys Glu Glu His Pro Gln Asn Arg Arg Pro
465                 470                 475                 480

Leu Val Glu Asn Lys His Arg Gln Phe Ser Val Phe Gly Val Glu Gln
                485                 490                 495

Tyr Lys Leu Asn Asp Trp Leu Phe Glu Ala Gly Leu Arg Tyr Glu His
            500                 505                 510

Ser Lys Ile Pro Val Thr Tyr Asn Leu Asp Glu Ile Glu Ala Gln Asn
        515                 520                 525

Lys Ile Leu Gly Gln Leu Leu Lys Pro Glu Gln Pro Asp Leu Thr Pro
    530                 535                 540

Tyr Gln Glu Ser Ala Phe Ser Tyr Ala Leu Gly Ala Ile Trp Asp Met
545                 550                 555                 560

Thr Pro Glu Tyr Arg Leu Asp Met Ser Tyr Ser His Asn Glu Arg Leu
                565                 570                 575

Pro Thr Pro Met Glu Leu Tyr Tyr His Gly Lys Asn Leu Ala Thr Asn
            580                 585                 590

Ser Phe Leu Tyr Gly Asn Lys Asp Leu Asp Lys Glu Glu Ser Asp Asn
        595                 600                 605

Phe Glu Leu Gly Ile Gln Phe Thr Gly Asp Lys Trp Arg Tyr Lys Ala
    610                 615                 620

Ser Ala Tyr Ser Asn His Phe Asp Asn Tyr Val His Ala Glu Asn Leu
625                 630                 635                 640

His Lys Asp Gly Asn Leu Tyr Met Arg Arg Met Thr Gln Ser Lys Ala
                645                 650                 655

Lys Ile Gln Gly Leu Glu Ala Glu Val Gly Tyr Glu Tyr Leu Pro Gly
            660                 665                 670

His Ser Ala Thr Leu Phe Gly Asp Tyr Val Arg Gly Lys Leu Tyr Gly
        675                 680                 685

Phe Ala Pro Val Tyr Gly Asn Glu Ile Lys Ser Gln Asn Glu Val Ile
    690                 695                 700
```

Lys Tyr Met Pro Pro Glu Glu Cys Gly Ala Ser Pro Gly Asp Asp Val
705 710 715 720

Tyr Glu Glu Trp Cys Gly Tyr Pro Asp Tyr Glu Val Ile Gly Ile Asp
725 730 735

Lys Val Glu Arg Pro Glu Arg Asn Ala Pro Arg Met Ser Pro Leu Arg
740 745 750

Leu Gly Leu Arg Leu Asn Asn Glu Tyr Asn Asp Asn Trp Ser Thr Ser
755 760 765

Leu Asp Phe Thr Arg Val Phe Ala Gln Asn Lys Thr Ser Thr Ala Thr
770 775 780

Val Val Asn Ile Pro Arg Asp Glu Ser Arg Leu Lys Val Thr Glu Val
785 790 795 800

Pro Glu Asp Ser Thr Ser Gly Tyr Ser Leu Leu Asn Val Gly Val Asp
805 810 815

Tyr Lys Asn Thr Trp Asp Asn Ala Lys His Pro Val Asp Tyr Thr Leu
820 825 830

Ser Leu Arg Ala Asn Asn Leu Leu Asp Glu Tyr Ile Tyr Val His Asn
835 840 845

Ser Phe Leu Pro Tyr Val Pro Gln Met Gly Arg Asn Phe Met Leu Ser
850 855 860

Leu Asn Val Glu Phe
865

<210> SEQ ID NO 53
<211> LENGTH: 805
<212> TYPE: PRT
<213> ORGANISM: Pasteurella multocida

<400> SEQUENCE: 53

Met Ile Ser Arg Gly Cys Lys Val Asn Lys Phe Phe Ala Val Leu Met
1 5 10 15

Met Cys Cys Ile Pro Gln Val Val Trp Ala Asn Thr Glu Lys Lys Gln
20 25 30

Ile Val Phe Leu Asp Glu Ile Ser Val Glu Ser Lys Gly Ala Ala Phe
35 40 45

Arg Ser Asp Pro Leu Ser Gly Leu Pro Lys Gln Asn Asp Ile Leu Val
50 55 60

Ser Lys Gln Lys Leu Lys Thr Gly Ser Ser Thr Leu Gly Asn Ala Leu
65 70 75 80

Ala Gly Glu Leu Ser Val His Ser Asn Gln Phe Gly Gly Gly Ser Ser
85 90 95

Ala Pro Val Val Arg Gly Gln Glu Gly Val Arg Leu Lys Ile Leu Gln
100 105 110

Asn Gly Ser Asp Val Ile Asp Met Ser Gln Leu Ser Pro Asp His Ala
115 120 125

Ile Gly Val Asp Thr Leu Leu Ala Glu Gln Val Glu Ile Val Arg Gly
130 135 140

Ala Ser Thr Leu Leu Tyr Ala Asn Ala Ser Pro Ala Gly Val Ile Asn
145 150 155 160

Val Val Asp Lys Arg Ile Pro Thr Gln Leu Pro Gln Lys Gly Tyr Glu
165 170 175

Val Asp Phe Asn Thr Arg Tyr Asn Thr Asn Ser His Glu Lys Leu Val
180 185 190

Thr Ala Ala Leu Thr Phe Gly Leu Gly Lys His Ile Ala Leu Arg Val

```
        195                 200                 205

Glu Glu Leu Leu Arg Gly Ser Asn Asn Tyr His Val Pro Ala Phe Lys
    210                 215                 220

Leu Asp Lys Thr Leu Asn Tyr Val Pro Asp Thr Gln Asn Lys Thr Lys
225                 230                 235                 240

Ser Gly Asn Tyr Gly Val Ala Phe Ile Gly Glu Arg Gly Tyr Val Gly
                245                 250                 255

Phe Ala Tyr Asn Leu Arg Arg Glu Lys Tyr Gly Leu Pro Gly His Asn
            260                 265                 270

His Lys Leu Asp Ser Cys Ala Ala His Ile Trp Gly Gly Asn Val Arg
        275                 280                 285

Asn Asp Tyr Tyr Leu Glu Leu Tyr Pro His Leu Met His Asp Thr Asp
    290                 295                 300

Leu Val Asn Thr His Phe His Cys Gly Ser Asn His Asp Met Asp Gly
305                 310                 315                 320

Lys His Ser His Asp His Pro Tyr Gly His Asp His Asp His Ser Ile
                325                 330                 335

Ala Gly Pro Leu Ile Asp Ser Tyr Ala Lys Arg Tyr Asp Ile Arg Ala
            340                 345                 350

Glu Val Lys Gln Pro Met Lys Ala Ile Glu Lys Ile Lys Leu Ser Tyr
        355                 360                 365

Ser Glu Thr Arg Tyr Lys His Asp Glu Lys Asp Gly Asn Ile Ala Val
    370                 375                 380

Asn Leu Phe Lys Asn Asn Gly Tyr Asn Leu Arg Val Glu Ile Phe His
385                 390                 395                 400

Thr Pro Ile Ala Gly Leu Ser Gly Val Ile Gly Ala Gln Tyr Gln Thr
                405                 410                 415

Gln Thr Ser Ser Ala Asn Ile Pro Arg Ile Ala Leu Cys Ser Asn Asn
            420                 425                 430

Ala Ser Asp Pro Cys His Lys Lys Lys Gln Arg Asp Pro Ser Lys Ile
        435                 440                 445

Thr Lys Gly Asp Arg Lys Ser Trp Ala Leu Ile Glu Asn Thr Gln Ser
    450                 455                 460

Gln Met Ser Phe Phe Ala Ile Glu Gln Leu Arg Trp Gln Asp Phe Leu
465                 470                 475                 480

Phe Glu Ile Gly Val Arg Thr Glu Lys Gln Arg Ile Asp Ile Glu Tyr
                485                 490                 495

Asp Arg Ala Trp Leu Phe Lys Val Lys Arg Lys Leu Glu Gly Cys Asp
            500                 505                 510

Pro Asn Ser Phe Phe Tyr Ser Pro Ser Gly Cys Arg Gln Gly Ser Tyr
        515                 520                 525

Pro Ala Pro Asp Phe Ala Ser Tyr His Asp Arg Ala Thr Ser Tyr Ser
    530                 535                 540

Gly Ala Ile Ser Trp Asn Met Thr Pro Asp Tyr Thr Leu Ser Leu Thr
545                 550                 555                 560

Tyr Ser His Asn Glu Arg His Pro Thr Pro Met Glu Leu Tyr Tyr His
                565                 570                 575

Gly Lys His Leu Ala Thr Val Ser Phe Glu His Gly Asn Arg Asn Leu
            580                 585                 590

Lys Lys Glu Val Ser Asp Asn Trp Glu Val Gly Leu Ala Tyr Leu Gly
        595                 600                 605

Asp Lys Leu Ser Tyr Lys Val Asn Val Tyr Tyr Asn Asp Phe Lys Asn
    610                 615                 620
```

-continued

Arg Ile Phe Asn Gln Thr Leu Asn Lys Ser Gly Asn Leu Ser Leu Asn
625 630 635 640

Arg Tyr Asn Gln Ser Lys Ala Lys Tyr Tyr Gly Val Glu Gly Arg Ile
645 650 655

Asp Tyr Ala Leu Thr Pro Glu Leu His Met Gly Leu Phe Gly Asp Tyr
660 665 670

Val Arg Gly Lys Leu Tyr Asp Leu Pro Pro Thr Tyr Arg Val Asp His
675 680 685

Val Ala Asn Ser Leu Glu Pro Val Pro Gln Pro Asp Gln Asp Ala Pro
690 695 700

Arg Val Pro Pro Met Arg Leu Gly Phe Arg Val Asn Met Glu Met Thr
705 710 715 720

Glu Ser Leu Thr Ser Ser Leu Glu Tyr Thr Tyr Val Tyr Gln Gln Lys
725 730 735

Lys Val Ala Pro Leu Glu Asn Gln Thr Ala Ala Tyr Ser Leu Leu Asn
740 745 750

Ile Arg Val Asp Tyr Ser Arg Gln Ile Ala Gly Val Asn Tyr Gln Leu
755 760 765

Phe Val Gln Ala Asn Asn Val Leu Asn Arg Lys Val Tyr Ser His Thr
770 775 780

Ser Phe Leu Pro Phe Val Pro Gln Met Gly Arg Asn Val Thr Leu Gly
785 790 795 800

Leu Asn Ile His Phe
805

<210> SEQ ID NO 54
<211> LENGTH: 826
<212> TYPE: PRT
<213> ORGANISM: Moraxella bovoculi 237

<400> SEQUENCE: 54

Met Val Asn Leu Tyr Ser Arg Pro Thr Val Leu Ala Leu Ser Ile Ala
1 5 10 15

Leu Val Ser Leu Ser Ala His Ala Asp Asp Thr Ala Thr Lys Thr Glu
20 25 30

Val Thr Leu Asp Thr Leu Asn Ala Val Val Lys Gly Gly Met Gln Thr
35 40 45

Thr Ser Thr Leu Lys Lys Pro Ser Asp Met Ile Ile Arg Arg Asp Thr
50 55 60

Leu Gln Gln Arg Ser Ala Thr Leu Gly Asn Ala Leu Ala Gly Glu Leu
65 70 75 80

Gly Ile His Ser Asn Pro Phe Gly Gly Gly Ala Ser Lys Pro Ile Ile
85 90 95

Arg Gly Gln Asp Gly Val Arg Val Lys Ile Leu Gln Asn Gly Thr Asp
100 105 110

Val Ile Asp Met Ser Ala Leu Ser Pro Asp His Val Val Ala Ala Asp
115 120 125

Thr Leu Leu Ala Ser Arg Val Glu Leu Val Arg Gly Ala Gly Thr Leu
130 135 140

Leu Tyr Gly Thr Ala Ser Gln Ala Gly Val Val Asn Val Ile Asp Glu
145 150 155 160

Arg Ile Pro Ser Arg Met Pro Gln Gly Asn Ile Lys Glu Lys Ile Glu
165 170 175

Gly Glu Thr Leu Leu Arg Tyr Asn Thr Gly Ser Asn Glu Lys Val Val

```
            180                 185                 190

Thr Ala Ser Leu Asn Met Gly Val Gly Gln Asn Val Ala Val Arg Val
        195                 200                 205

Glu Gly Leu Thr Arg Arg Ala Asp Asp Tyr Glu Val Pro Gly Phe Gln
    210                 215                 220

Ser Asp Val Met Leu Asp Tyr Leu Pro Asp Ser His Asn Lys Ser Thr
225                 230                 235                 240

Val Gly Thr Val Gly Val Ser Tyr Ile Gly Asp Lys Gly His Ile Gly
                245                 250                 255

Val Ser Tyr Ser Arg Arg Gln Asp Lys Tyr Gly Ile Pro Gly His Asn
            260                 265                 270

His Ala Tyr Asp Asn Cys Ile Ala His Val Leu Thr Pro Glu Ala Ser
        275                 280                 285

Ile Ser Arg Tyr Tyr Leu Lys Ala Tyr Pro His Leu Ile Gln Asn Met
    290                 295                 300

Asp Phe Ser Ser Ser Ala His Phe His Cys Gly Thr Asp His Ala His
305                 310                 315                 320

Asp Pro Gly Gln Ser His Glu His Pro Leu Gly Tyr Glu His Asp His
                325                 330                 335

Thr His Pro Gly Pro Trp Ile Asp Met Glu Ser Glu Arg Ile Asp Val
            340                 345                 350

Arg Ala Gln Trp Glu Lys Pro Phe Lys Gly Leu Asp Lys Ile Ala Leu
        355                 360                 365

Ser Phe Thr Ser Ser Asp Tyr Tyr His Glu Glu Asn Asp His Glu Val
    370                 375                 380

Glu Lys Leu Asp Lys Tyr Thr Gly Arg Leu Gln Thr Ile Asn Asn Lys
385                 390                 395                 400

Pro Gly Tyr Phe Gly Asn Gln Gly Lys Asn Val Arg Val Glu Phe His
                405                 410                 415

His Thr Pro Val Lys Asp Val Ser Gly Leu Trp Gly Met Gln Trp Gln
            420                 425                 430

Lys Gln Glu Ser Phe Ala His Leu Pro His Glu Arg Glu Glu Gly Gln
        435                 440                 445

Arg Tyr Pro Leu Ile Ala Asn Thr Asn Lys Gln Val Ser Val Phe Gly
    450                 455                 460

Leu Glu Arg Trp Gln Ala Asn Asp Lys Trp Ala Phe Glu Phe Gly Thr
465                 470                 475                 480

Arg Phe Glu Lys Gln Ser Ile Pro Ile Asp Tyr Ser Glu Asp Lys Leu
                485                 490                 495

Asp Arg Tyr Arg Pro Lys Pro Glu Cys Trp Asp Trp Gly Phe Ser Ser
            500                 505                 510

Gly Cys Leu Pro Ala Pro Asn Tyr Glu Glu Pro Asp Leu Thr Thr Tyr
        515                 520                 525

Lys Glu Lys Ala Thr Ser Tyr Ser Ile Gly Thr Thr Trp Asp Phe Lys
    530                 535                 540

Pro Asp Tyr Arg Leu Ser Ala Thr Tyr Ser His Asn Glu Arg Leu Pro
545                 550                 555                 560

Thr Pro Met Glu Leu Tyr Tyr His Gly Lys His Leu Ala Thr His Ser
                565                 570                 575

Phe Glu Phe Gly Asn Ile Gly Leu Asp Lys Glu Lys Ser Asn Asn Leu
            580                 585                 590

Asp Leu Gly Ile Ser Phe Ser Gly Asp Lys Trp Ser Tyr Ala Val Asn
        595                 600                 605
```

Ala Tyr His Ser Arg Phe Lys Asn Tyr Ile Tyr Asn Glu Asn Val Tyr
610 615 620

Arg Glu Gly Asn Leu Phe Met Arg Arg His Asn Gln Ala Lys Ala Asp
625 630 635 640

Phe Tyr Gly Leu Glu Gly Met Val Thr Tyr Asn Met Asp Asn His Ala
645 650 655

Ile Ser Leu Phe Gly Asp Leu Val Arg Gly Lys Leu Lys Asp Leu Pro
660 665 670

Asn Ala Tyr Ala Lys Ala Tyr Tyr Cys Asp Gly Ala Tyr Thr Thr Thr
675 680 685

Lys Pro Glu Asp Thr Glu Glu Asn Met Gln Arg Cys Asn Tyr Asn Tyr
690 695 700

Phe Thr Asp Asp Phe Asn Tyr Ser Tyr Glu Pro Ile Ile Ala Gln Pro
705 710 715 720

Asn Met Pro Thr Pro Arg Leu Pro Pro Ala Arg Leu Gly Leu Arg Trp
725 730 735

Gln Gly Asp Leu Ser Ala Asn Trp Ser Ala Asp Ala Glu Tyr Met His
740 745 750

Val Phe Gly Gln Asn Arg Ile Ser Lys Leu Glu Ser Ala Thr Ala Ser
755 760 765

Tyr Asp Met Leu Asn Leu Gly Leu Gly Tyr His Asn His Trp Gly Asn
770 775 780

Val Asp Tyr Thr Leu Ser Leu Arg Ala Asn Asn Val Leu Asp Glu Lys
785 790 795 800

Val Tyr Ile His Asn Ser Phe Leu Pro Phe Val Pro Gln Met Gly Arg
805 810 815

Asn Phe Ser Leu Ser Ala Asn Phe Lys Phe
820 825

<210> SEQ ID NO 55
<211> LENGTH: 850
<212> TYPE: PRT
<213> ORGANISM: Conchiformibius steedae

<400> SEQUENCE: 55

Met Phe Ser Arg Met Leu Ile Leu Pro Leu Leu Leu Gly Leu Gly Ala
1 5 10 15

Asn Ala Ala Tyr Ala Glu Gln Asn Thr Ser Pro Ala Lys Pro Ala Thr
20 25 30

Glu Asp Asn Glu Gly Lys Thr Leu Pro Ala Met Gln Gly Val Gly Lys
35 40 45

Arg Arg Asp Thr Ala Gln Pro Phe Ser Gly Asn Arg Lys Ala Ser Asp
50 55 60

Met Val Ile Ser Gln Glu Lys Leu Lys Ser Arg Ser Ala Asn Leu Gly
65 70 75 80

Glu Ala Leu Ala Gly Glu Leu Gly Ile His Gly Asn Pro Phe Gly Gly
85 90 95

Gly Ala Ser Ala Pro Val Ile Arg Gly Gln Glu Gly Val Arg Val Lys
100 105 110

Ile Leu Gln Gly Gly Ser Asp Val Val Asp Met Ser Ala Leu Ser Pro
115 120 125

Asp His Ala Val Ala Ala Asp Thr Leu Leu Ala Gln Gln Val Glu Val
130 135 140

Leu Arg Gly Thr Ser Thr Leu Ala Tyr Ala Ala Ala Ser Pro Ala Gly

-continued

```
145                 150                 155                 160

Val Ile Asn Ile Thr Asp Lys Arg Ile Pro Asp Arg Leu Pro Ala Lys
                165                 170                 175

Gly Trp Glu Ala Glu Thr Gly Val Arg Phe Asp Thr Ala Ala Lys Glu
            180                 185                 190

Lys Ala Leu Thr Ala Gly Ala Thr Phe Gly Ile Gly Lys His Phe Ala
        195                 200                 205

Val Arg Ala Glu Gly Leu Glu Arg Lys Ser Asp Asp Tyr Arg Val Pro
    210                 215                 220

Gly Ile Asn Leu Gly Glu Thr Leu Lys Tyr Val Pro Asp Thr Tyr Asn
225                 230                 235                 240

Arg Ser His Thr Gly Thr Leu Gly Val Ser Trp Val Gly Gln Asn Gly
                245                 250                 255

His Leu Gly Val Ser Tyr Ser His Arg Lys Asp Arg Tyr Gly Leu Pro
            260                 265                 270

Gly His Asn His Met Leu Asp Asn Cys Ser Gly His Val Phe Asp Val
        275                 280                 285

Thr Thr Ala Ser Ala Val Lys Arg Asn Tyr Leu Leu Pro Tyr Pro His
    290                 295                 300

Leu Ile Gly Asp Glu Asp Val Asn Leu Ser Gln His Phe His Cys His
305                 310                 315                 320

Thr Glu His Ser Ser Asn Ala Lys His Ser His Asp Asn Val Tyr Gly
                325                 330                 335

His Lys His Asp His Gly Glu Pro Gly Pro Trp Ile Asp Met Arg Val
            340                 345                 350

Arg Arg Tyr Asp Val Arg Gly Glu Trp Arg Thr Gln Leu Pro Phe Leu
        355                 360                 365

Glu Lys Ile Arg Leu Thr Ser Ala Tyr Thr Asp Tyr Tyr His Asp Glu
    370                 375                 380

Lys Asn Asp Gly Lys Val Tyr Ile Ser Pro Asp Asp Pro Glu Gly Trp
385                 390                 395                 400

Arg Glu Arg Lys Leu Lys Asp Ala Ala Ala Arg Lys Gly Lys Pro Asp
                405                 410                 415

Ile Ile Leu Lys Asn Lys Gly Leu Asn Thr Arg Leu Glu Phe Phe His
            420                 425                 430

Arg Phe Gly Ser Val Trp Asn Gly Met Ala Gly Val Gln Tyr Gln Thr
        435                 440                 445

Gln Arg Ser Ser Ala Arg Arg Val Met Pro Pro Met Ile Gly Gly Glu
    450                 455                 460

Arg Tyr Ile Asn Glu Arg Asn Pro Leu Val Asp Asn Thr Asn Lys Gln
465                 470                 475                 480

Leu Ser Leu Phe Ala Leu Gln Gln Tyr Arg Arg Gly Asn Trp Leu Ala
                485                 490                 495

Glu Gly Gly Val Arg Trp Glu Lys Gln Arg Ile Pro Ile Arg Tyr Asp
            500                 505                 510

His Asp Leu Leu Ala Gln Tyr Val Lys Pro Gly Thr Gln Gln Pro Asp
        515                 520                 525

Leu Lys Pro Tyr Ser Gln Lys Ala Leu Ser Tyr Ser Gly Ser Leu Leu
    530                 535                 540

Trp Asp Phe Lys Pro Gly Tyr Arg Leu Ser Leu Thr Ala Ser His Asn
545                 550                 555                 560

Glu Arg Leu Pro Thr Pro Met Glu Leu Tyr Tyr His Gly Lys His Leu
                565                 570                 575
```

-continued

```
Ala Thr Asn Ser Phe Glu Tyr Gly Asn Lys Asp Leu Lys Lys Glu Arg
            580                 585                 590

Ser Asn Asn Tyr Glu Ile Gly Leu Arg Tyr Phe Gly Asp Lys Trp Asp
        595                 600                 605

Tyr Lys Leu Ser Val Tyr His Asn Arg Phe Lys Asn Tyr Ile Tyr Asn
    610                 615                 620

Glu Asn Leu Tyr Arg Ser Gly Asn Leu Phe Ile Arg Arg Asn Thr Gln
625                 630                 635                 640

Ala Gln Gly Arg Phe His Gly Val Glu Gly Glu Val Ser Tyr Arg Phe
                645                 650                 655

Lys Pro Thr His Gln Val Thr Leu Phe Gly Asp Met Val Arg Gly Arg
            660                 665                 670

Leu Phe Gly Leu Ser Pro Val Tyr Gly Asp Lys Ile Tyr Arg Glu Tyr
        675                 680                 685

Glu Cys Val Asp Glu Asp Gly Leu Glu Asp Thr Cys Phe Glu Val Val
    690                 695                 700

Gly Arg Glu Lys Ile Glu Arg Pro Asp Arg His Ala Pro Arg Val Pro
705                 710                 715                 720

Pro Thr Arg Leu Gly Leu Arg Leu Asn Ser Gln Trp Gly Asp Asn Trp
                725                 730                 735

Thr Ala Ser Leu Glu Tyr Ala Arg Val Trp Ala Gln Asn Arg Thr Ala
            740                 745                 750

Val Ser Gln Phe Pro Arg Glu Arg Asp Asp Glu Asp Asp Glu Asp Glu
        755                 760                 765

Asp Glu Gly Asn Pro Lys Pro Arg Gln Gln Lys Leu Tyr Ala Glu Pro
    770                 775                 780

Val Leu Glu Asp Pro Thr Ser Gly Tyr His Leu Leu Asn Ala Gly Ile
785                 790                 795                 800

Ala Tyr Arg Lys Arg Ile Gly Lys Ala Asp Tyr Arg Val Ser Leu Asp
                805                 810                 815

Ala Phe Asn Leu Leu Asn Lys Lys Val Tyr Ile His Asn Ser His Leu
            820                 825                 830

Pro Tyr Val Pro Arg Pro Gly Arg Asn Phe Val Phe Gly Val Asn Val
        835                 840                 845

Ser Phe
    850
```